(12) United States Patent
Hipsley

(10) Patent No.: US 11,026,837 B2
(45) Date of Patent: Jun. 8, 2021

(54) SYSTEMS AND METHODS FOR OCULAR LASER SURGERY AND THERAPEUTIC TREATMENTS

(71) Applicant: AnnMarie Hipsley, Silver Lake, OH (US)

(72) Inventor: AnnMarie Hipsley, Silver Lake, OH (US)

(73) Assignee: ACE VISION GROUP, INC., Silver Lake, OH (US)

( * ) Notice: Subject to any disclaimer, the term of this patent is extended or adjusted under 35 U.S.C. 154(b) by 270 days.

(21) Appl. No.: 15/942,513

(22) Filed: Mar. 31, 2018

(65) Prior Publication Data
US 2019/0105200 A1 Apr. 11, 2019

Related U.S. Application Data

(60) Provisional application No. 62/480,294, filed on Mar. 31, 2017.

(51) Int. Cl.
*A61F 9/008* (2006.01)
*A61F 9/00* (2006.01)
(Continued)

(52) U.S. Cl.
CPC .......... *A61F 9/00802* (2013.01); *A61F 9/008* (2013.01); *A61F 9/0017* (2013.01); *A61F 9/00825* (2013.01); *A61F 9/00838* (2013.01); *A61B 18/203* (2013.01); *A61B 2018/00577* (2013.01); *A61B 2018/00613* (2013.01); *A61B 2018/00642* (2013.01);
(Continued)

(58) Field of Classification Search
CPC .... A61F 9/00802; A61F 9/0017; A61F 9/008; A61F 9/00825; A61F 9/00838; A61F 2009/00846; A61F 2009/00851; A61F 2009/00865; A61F 2009/00878; A61F 2009/0088; A61F 2009/00882; A61F 2009/00895; A61F 2009/00897; A61B 2018/20355; A61B 2018/20359; A61B 2018/00577; A61B 2018/00613; A61B 2018/00642; A61B 2018/00785; A61B 2018/00904
USPC .......................................................... 606/4
See application file for complete search history.

(56) References Cited

U.S. PATENT DOCUMENTS

| | | |
|---|---|---|
| 5,472,699 A | 12/1995 | Duffy et al. |
| 7,871,404 B2 | 1/2011 | Hipsley |

(Continued)

OTHER PUBLICATIONS

PCT/US2018/025608 ISR and Written Opinion dated Jun. 25, 2018.
(Continued)

*Primary Examiner* — Mallika D Fairchild
*Assistant Examiner* — Minh Duc G Pham
(74) *Attorney, Agent, or Firm* — One LLP; Joey Liu

(57) ABSTRACT

Systems, devices and methods are provided to deliver microporation medical treatments to improve biomechanics, wherein the system includes a laser for generating a beam of laser radiation on a treatment-axis not aligned with a patient's visual-axis, operable for use in subsurface ablative medical treatments to create an array pattern of micropores that improves biomechanics. The array pattern of micropores is at least one of a radial pattern, a spiral pattern, a phyllotactic pattern, or an asymmetric pattern.

15 Claims, 132 Drawing Sheets

Posterior Scleral Rejuvenation for IOP and Ocular Nerve Head Decompression

(51) Int. Cl.
    A61B 18/00    (2006.01)
    A61B 18/20    (2006.01)
(52) U.S. Cl.
    CPC .............. A61B 2018/00785 (2013.01); A61B
           2018/00904 (2013.01); A61B 2018/20355
           (2017.05); A61B 2018/20359 (2017.05); A61F
                    2009/0088 (2013.01); A61F 2009/00846
           (2013.01); A61F 2009/00851 (2013.01); A61F
                    2009/00865 (2013.01); A61F 2009/00878
           (2013.01); A61F 2009/00882 (2013.01); A61F
                    2009/00895 (2013.01); A61F 2009/00897
                                                 (2013.01)

(56)                 References Cited

U.S. PATENT DOCUMENTS 8,348,932  B2    1/2013   Hipsley
 2007/0016175  A1    1/2007   Hipsley
 2008/0058779  A1    3/2008   Hipsley et al.
 2011/0190798  A1    8/2011   Hipsley
 2014/0163597  A1    6/2014   Hipsley
 2014/0316388  A1*  10/2014   Hipsley ............... A61F 9/00802
                                                             606/4
 2015/0157406  A1    6/2015   Hipsley
 2016/0183961  A1    6/2016   Hipsley
 2017/0231697  A1    8/2017   Hipsley
 2018/0000339  A1    1/2018   Hipsley
 2018/0052972  A1    2/2018   Hipsley et al.

OTHER PUBLICATIONS

Biology Online, "Nuclear Pore definition", retrieved from http://www.biology-online.org/dictionary/Nuclear_pore.
The Free Dictionary, "Pore definition", retrieved from http://www.thefreedictionary.com/pore.
Cooper, Geoffrey M., "The Cell: A Molecular Approach", 2nd edition, Sunderland, MA, Sinauer Associates, 2000, retrieved from https://www.ncbi.nlm.nih.gov/books/NBK9839/.
Polarz, Sebastian et al. "Nanoporous Materials". Journal of Nanoscience and Nanotechnology, v.2, 581-612 (2002). Available from https://www.researchgate.net/publication/27264580_Nanoporous_materials.
Levenston, M.E. et al. "Variationally derived 3-field finite element formulations for quasistatic poroelastic analysis of hydrated biological tissues". Computer Methods in Applied Mechanics and Engineering. vol. 156, Issues 1-4, Apr. 14, 1998, pp. 231-246. Available from https://www.sciencedirect.com/science/article/pii/S0045782597002089.
Cowin, Stephen C. et al. "Hierarchical poroelasticity: movement of interstitial fluid between porositylevels in bones". Philosophical Transactions of the Royal A Society. 2009. pp. 3401-3444. Available from https://royalsocietypublishing.org/doi/pdf/10.1098/rsta.2009.0099.
Dathe, Annette et al. "The relationship between fractal properties of solid matrix and pore space in porous media". Geoderma. 2005. pp. 279-290. Available from http://soilandwater.bee.cornell.edu/publicatio ns/DatheG05.pdf.
Booth, James W. et al. "Explaining glomerular pores with fiber matrices A visualization study based on computer modeling". Membrane Biology Group and Department of Medicine. University of Toronto, Toronto, Canada. Available from https://www.ncbi.nlm.nih.gov/pmc/articles/PMC1262507/pdf.biophysj00087-0079.pdf.
Millodot, M. "Dictionary of Optometry and Visual Science". Elsevier Health Sciences, 2014.
Richdale K. et al., "Quantification of Age-Related and per Diopter Accommodative Changes of the Lens and Ciliary Muscle in the Emmetropic Human Eye: Lens and Ciliary Muscle with Age and Accommodation," *Investigative Ophthalmology & Visual Science*, vol. 54, No. 2, pp. 1095-1105, 2013.

Croft, M. A. et al., "Extralenticular and Lenticular Aspects of Accommodation and Presbyopia in Human Versus Monkey Eyes," *Investigative Ophthalmology and Visual Science*, vol. 54, No. 7, pp. 5035-5048, 2013.
Croft, M. A. et al., "Accommodative Movements of the Vitreous Membrane, Choroid, and Sclera in Young and Presbyopic Human and Nonhuman Primate Eyes," *Investigative Ophthalmology & Visual Science*, vol. 54, No. 7, pp. 5049-5058, 2013.
Lütjen-Drecoll, E. et al., "Morphology and Accommodative Function of the Vitreous Zonule in Human and Monkey Eyes," *Investigative Ophthalmology and Visual Science*, vol. 51, No. 3, pp. 1554-1564, 2010.
Nankivil, D. et al., "Effect of Anterior Zonule Transection on the Change in Lens Diameter and Power in Cynomolgus Monkeys during Simulated Accommodation," *Investigative Ophthalmology & Visual Science*, vol. 50, No. 8, pp. 4017-4021, 2009.
Croft, M. A. et al., "Accommodative Ciliary Body and Lens Function in Rhesus Monkeys, I: Normal Lens, Zonule and Ciliary Process Configuration in the Iridectomized Eye," *Investigative Ophthalmology & Visual Science*, vol. 47, No. 3, pp. 1076-1086, 2006.
Strenk, S. A., "Magnetic resonance imaging of the anteroposterior position and thickness of the aging, accommodating, phakic, and pseudophakic ciliary muscle," *Journal of Cataract & Refractive Surgery*, vol. 36, No. 2, pp. 235-241, 2010.
Goldberg, D. B., "Computer-animated model of accommodation and presbyopia," *Journal of Cataract & Refractive Surgery*, vol. 41, No. 2, pp. 437-445, 2015.
Hipsley, A. et al., "VisioDynamics Theory: A Biomechanical Model for the Aging Ocular Organ," *Step by Step Innovations in Presbyopia Management*, pp. 269-315, 2006.
Swartz, T. S. et al., "Restoration of accommodation: new perspectives," *Arquivos Brasileiros de Oftalmologia*, vol. 77, No. 1, pp. V-VII, 2014.
Ethier, C. R. et al., "Ocular Biomechanics and Biotransport," *Annu. Rev. Biomed. Eng.*, vol. 6, pp. 249-273, 2004.
Fung, Y. C., *Biomechanics: Mechanical Properties of Living Tissues*, Springer Science & Business Media, 2013.
Girard, M. J. et al., "Translating Ocular Biomechanics into Clinical Practice: Current State and Future Prospects," *Current Eye Research*, vol. 40, No. 1, pp. 1-18, 2015.
Roberts, C., "The Cornea is Not a Piece of Plastic," *Journal of Refractive Surgery*, vol. 16, No. 4, pp. 407-413, 2000.
Greene, P. R., "Mechanical Considerations in Myopia: Relative Effects of Accommodation, Convergence, Intraocular Pressure, and the Extraocular Muscles," *Optometry & Vision Science*, vol. 57, No. 12, pp. 902-914, 1980.
Yablonski, M. E. et al., "A Fluorophotometric Study of the Effect of Topical Timolol on Aqueous Humor Dynamics," *Experimental eye research*, vol. 27, No. 2, pp. 135-142, 1978.
Toris, C. B. et al., "Aqueous Humor Dynamics in the Aging Human Eye," *American Journal of Ophthalmology*, vol. 127, No. 4, pp. 407-412, 1999.s.
May, C. A. et al., "Immunohistochemical Classification and Functional Morphology of Human Choroidal Ganglion Cells," *Investigative Ophthalmology & Visual Science*, vol. 45, No. 2, pp. 361-367, 2004.
Detorakis, E. T. et al., "Ocular rigidity: biomechanical role, in vivo measurements and clinical significance," *Clinical & Experimental Ophthalmology*, vol. 41, No. 1, pp. 73-81, 2013.
Pallikaris, I. G. et al., "Ocular Rigidity in Patients with Age-related Macular Degeneration," *American Journal of Ophthalmology*, vol. 141, No. 4, pp. 611-615, 2006.
Glasser, A. et al., "Presbyopia and the Optical Changes in the Human Crystalline Lens with Age," *Vision Research*, vol. 38, No. 2, pp. 209-229, 1998.
Glasser, A. et al., "On the potential causes of presbyopia," *Vision Research*, vol. 39, No. 7, pp. 1267-1272, 1999.
Fisher R. F., "Presbyopia and the Changes with Age in the Human Crystalline Lens," *The Journal of physiology*, vol. 228, No. 3, pp. 765-779, 1973.
Koretz, J. F. et al., "Aging of the human lens: changes in lens shape at zero-diopter accommodation," *JOSA A*, vol. 18, No. 2, pp. 265-272, 2001.

(56) References Cited

OTHER PUBLICATIONS

Wilde, G. S., "Measurement of Human Lens Stiffness for Modelling Presbyopia Treatments (Doctoral Dissertation, Oxford University)," 2011.

Pallikaris, I. G. et al., "Ocular Rigidity in Living Human Eyes," *Investigative Ophthalmology & Visual Science*, vol. 46, No. 2, pp. 409-414, 2005.

Dastiridou, A. I. et al., "Ocular Rigidity, Outflow Facility, Ocular Pulse Amplitude, and Pulsatile Ocular Blood Flow in Open-Angle Glaucoma: A Manometric Study," *Investigative Ophthalmology & Visual Science*, vol. 54, No. 7, pp. 4571-4577, 2013.

Grytz, R., et al., "Age- and Race-Related Differences in Human Scleral Material Properties—Scleral Material Property Changes With Age and Race," *Investigative Ophthalmology & Visual Science*, vol. 55, No. 12, pp. 8163-8172, 2014.

Flügel-Koch, C. M. et al., "Anteriorly located zonular fibres as a tool for fine regulation in accommodation," *Ophthalmic and Physiological Optics*, vol. 36, No. 1, pp. 13-20, 2016.

Helmholtz, H. Von, "Mechanism of Accommodation," *Helmholtz's treatise on physiological optics, vol. 1, Trans. from the 3rd German ed.*, pp. 143-172, 1924.

Vilupuru, A. S. et al., "Spatially variant changes in lens power during ocular accommodation in a rhesus monkey eye," *Journal of Vision*, vol. 4, No. 4, pp. 299-309, 2004.

Artal, P. et al., "Compensation of corneal aberrations by the internal optics in the human eye," *Journal of Vision*, vol. 1, No. 1, pp. 1-1, 2001.

Schachar, R. A., "Zonular function: a new hypothesis with clinical implications," *Annals of Ophthalmology*, vol. 26, No. 2, pp. 36-38, 1993.

Schachar, R. A., "Pathophysiology of Accommodation and Presbyopia. Understanding the Clinical Implications," *The Journal of the Florida Medical Association*, vol. 81, No. 4, pp. 268-268, 1994.

Schachar, R. A., "Cause and Treatment of Presbyopia with a Method for Increasing the Amplitude of Accommodation," *Annals of Ophthalmology*, vol. 24, No. 12, pp. 445-445, 1992.

Schachar, R. A. et al., "The Mechanism of Ciliary Muscle Function," *Annals of Ophthalmology*, vol. 27, No. 3, pp. 126-132, 1995.

Strenk, S. A. et al., "Age-Related Changes in Human Ciliary Muscle and Lens: A Magnetic Resonance Imaging Study," *Investigative Ophthalmology & Visual Science*, vol. 40, No. 6, pp. 1162-1169, 1999.

Fyodorov, S. N., "Operation of Dosaged Dissection of Corneal Circular Ligament in Cases of Myopia of Mild Degree," *Annals of Ophthalmology*, vol. 11, No. 12, pp. 1885-1890, 1979.

Thornton, S. P., "Anterior Ciliary Sclerotomy (ACS), A Procedure to Reverse Presbyopia," *Surgery for Hyperopia and Presbyopia*, pp. 33-36, 1997.

Hamilton, D. R. et al., "Anterior Ciliary Sclerotomy for Treatment of Presbyopia: A Prospective Controlled Study," *Ophthalmology*, vol. 109, No. 11, pp. 1970-1976, 2002.

Lin, J. T. et al., "The New Mechanism of Laser Presbyopia Reversal (LAPR) and Accommodation," in, SLACK, Thorofare, NJ, 2002.

Lin, J. T. et al., "Treatment of Presbyopia by Infrared Laser Radial Sclerectomy," *Journal of Refractive Surgery*, vol. 19, No. 4, pp. 465-467, 2003.

Davidson, R. S. et al., "Surgical correction of presbyopia," *Journal of Cataract & Refractive Surgery*, vol. 42, No. 6, pp. 920-930, 2016.

Glasser, A., "Restoration of accommodation: surgical options for correction of presbyopia," *Clinical and Experimental Optometry*, vol. 91, No. 3, pp. 279-295, 2008.

Malecaze, F. J. et al., "Scleral Expansion Bands for Presbyopia," *Ophthalmology*, vol. 108, No. 12, pp. 2165-2171, 2001.

Coleman, D. J., "Unified Model for Accommodative Mechanism," *American Journal of Ophthalmology*, vol. 69, No. 6, pp. 1063-1079, 1970.

Coleman, D. J., "Presbyopia, Accommodation, and the Mature Catenary," *Ophthalmology*, vol. 108, No. 9, pp. 1544-1551, 2001.

Coleman, D. J., "On the Hydraulic Suspension Theory of Accommodation," *Transactions of the American Ophthalmological Society*, vol. 84, pp. 846, 1986.

Fincham, E. F., *The mechanism of accommodation*, G. Pulman & Sons, Limited, 1937.

Tscherning, M. H. E., *Physiologic Optics: Dioptrics of the Eye, Functions of the Retina Ocular Movements and Binocular Vision*, Keystone Publishing Company, 1920.

Read, S. A. et al., "Changes in intraocular pressure and ocular pulse amplitude with accommodation," *British Journal of Ophthalmology*, vol. 94, No. 3, pp. 332-335, 2010.

Crawford, K. et al., "Pilocarpine Antagonizes Prostaglandin F2α-Induced Ocular Hypotension in Monkeys: Evidence for Enhancement of Uveoscleral Outflow by Prostaglandin F2α, " *Archives of Ophthalmology*, vol. 105, No. 8, pp. 1112-1116, 1987.

Croft, M. A. et al., "Accommodation and presbyopia: The cillary neuromuscular view," *Ophthalmology Clinics*, vol. 19, No. 1, pp. 13-24, 2006.

Grierson, I. et al., "Effects of pilocarpine on the morphology of the human outflow apparatus," *British Journal of Ophthalmology*, vol. 62, No. 5, pp. 302-313, 1978.

Goel, M., et al., "Aqueous Humor Dynamics: A Review," *The open ophthalmology journal*, vol. 4, No. 1, 2010.

Ehlers, N. et al., "Applanation Tonometry and Central Corneal Thickness," *Acta ophthalmologica*, vol. 53, No. 1, pp. 34-43, 1975.

Goldmann, H., "Applanation Tonometry," in *Glaucoma; Transactions of the Second Conference*, pp. 220, 1956.

Friberg, T. R. et al., "A Comparison of the Elastic Properties of Human Choroid and Sclera," *Experimental eye research*, vol. 47, No. 3, pp. 429-436, 1988.

Dastiridou, A. I. et al., "Ocular Rigidity, Ocular Pulse Amplitude, and Pulsatile Ocular Blood Flow: The Effect of Intraocular Pressure," *Investigative Ophthalmology & Visual Science*, vol. 50, No. 12, pp. 5718-5722, 2009.

Ravalico, G. et al., "Age-Related Ocular Blood Flow Changes," *Investigative Ophthalmology & Visual Science*, vol. 37, No. 13, pp. 2645-2650, 1996.

Hommer, A. et al., "Estimation of Ocular Rigidity Based on Measurement of Pulse Amplitude Using Pneumotonometry and Fundus Pulse Using laser Interferometry in Glaucoma," *Investigative Ophthalmology & Visual Science*, vol. 49, No. 9, pp. 4046-4050, 2008.

Wang, J. et al., "Estimation of Ocular Rigidity in Glaucoma Using Ocular Pulse Amplitude and Pulsatile Choroidal Blood Flow" *Investigative Ophthalmology & Visual Science*, vol. 54, No. 3, pp. 1706-1711, 2013.

Lakes, R. S., *Viscoelastic materials*, Cambridge University Press, 2009.

Diamant, J. et al., "Collagen; ultrastructure and its relation to mechanical properties as a function of ageing," *Proceedings of the Royal Society of London B: Biological Sciences*, vol. 180, No. 1060, pp. 293-315, 1972.

Watson, P. G. et al., "Scleral structure, organisation and disease. A review," *Experimental eye research*, vol. 78, No. 3, pp. 609-623, 2004.

Bailey, A. J., "Molecular mechanisms of ageing in connective tissues," *Mechanisms of ageing and development*, vol. 122, No. 7, pp. 735-755, 2001.

Schofield, J. D. et al., "New knowledge of connective tissue ageing," *Journal of Clinical Pathology*, vol. 3, No. 1, pp. 174-190, 1978.

Scharffetter-Kochanek, K., "Photoaging of the Connective Tissue of Skin: Its Prevention and Therapy," *Advances in Pharmacology*, vol. 38, pp. 639-655, 1996.

Fisher, R., "The Force of Contraction of the Human Ciliary Muscle During Accommodation," *The Journal of physiology*, vol. 270, No. 1, pp. 51, 1977.

Swegmark, G., "Studies with Impedance Cyclography on Human Ocular Accommodation at Different Ages," *Acta ophthalmologica*, vol. 47, No. 5-6, pp. 1186-1206, 1969.

Tamm, E. et al., "Posterior Attachment of Ciliary Muscle in Young, Accommodating Old, Presbyopic Monkeys," *Investigative Ophthalmology & Visual Science*, vol. 32, No. 5, pp. 1678-1692, 1991.

(56) References Cited

OTHER PUBLICATIONS

Shephard, R. J. et al., "Physiology and Biochemistry of Exercise," *Journal of Occupational and Environmental Medicine*, vol. 24, No. 6, pp. 440, 1982.
Buckwalter, J., "Maintaining and Restoring Mobility in Middle and Old Age: The Importance of the Soft Tissues," *Instructional course lectures*, vol. 46, pp. 459-469, 1996.
Sigal, I. A. et al., "Finite Element Modeling of Optic Nerve Head Biomechanics," *Investigative Ophthalmology & Visual Science*, vol. 45, No. 12, pp. 4378-4387, 2004.
Yamauchi, M. et al., "Aging and Cross-Linking of Skin Collagen," *Biochemical and biophysical research communications*, vol. 152, No. 2, pp. 898-903, 1988.
Dale, W. C., "A composite materials analysis of the structure, mechanical properties, and aging of collagenous tissues," in, Ph. D. thesis, Case Western Reserve University, 1974.
Battaglioli, J. L. et al., "Measurements of the Compressive Properties of Scleral Tissue," *Investigative Ophthalmology & Visual Science*, vol. 25, No. 1, pp. 59-65, 1984.
Fung, Y.-C., "Stress-strain-history relations of soft tissues in simple elongation," in *Biomechanics: Its foundations and objectives*, N. P. Y. C. Fung, and M. Anliker., Ed., pp. 181-208, Englewood Clifts, New Jersey, Prentice-Hall, 1972.
Curtin, B. J., "Physiopathologic Aspects of Scleral Stress-Strain," *Transactions of the American Ophthalmological Society*, vol. 67, pp. 417, 1969.
Waring IV, G.O. et al., "Advances in the Surgical Correction of Presbyopia," *International Ophthalmology Clinics*, vol. 53, No. 1, pp. 129-152, 2013.
Hipsley, A. et al., *Laser scleral matrix microexcisions (LaserACE/erbium YAG laser)*, Slack Incorporated New Jersey, 2012.
Vincent, J., *Structural biomaterials*, Princeton University Press, 2012.
Wang, Y.-C. et al., "Stable extremely-high-damping discrete viscoelastic systems due to negative stiffness elements," *Applied Physics Letters*, vol. 84, No. 22, pp. 4451-4453, 2004.
Hipsley, A. et al, "Novel method using collagen CCL to evaluate ability of laser anterior ciliary excision procedure to decrease ocular rigidity for restoring accommodation," in *American Society of Cataract and Refractive Surgery*, ASCRS, 2013.
Asejczyk-Widlicka, M. et al., "The elasticity and rigidity of the outer coats of the eye," *British Journal of Ophthalmology*, vol. 92, No. 10, pp. 1415-1418, 2008.
Pierscionek, B. K. et al., "The effect of changing intraocular pressure on the corneal and scleral curvatures in the fresh porcine eye," *British Journal of Ophthalmology*, vol. 91, No. 6, pp. 801-803, 2007.
Friedenwald, J., "Clinical significance of ocular rigidity in relation to the tonometric measurement," *Transactions—American Academy of Ophthalmology and Otolaryngology.*, vol. 53, pp. 262-264, 1948.
Hipsley A, et al., "Visual outcomes 24 months after LaserACE," *Eye and Vision*. 2017;4:15.
Knott, R., "Fibonacci Numbers and Nature", Maths Surrey, available from http://www.maths.surrey.ac.uk/hosted-sites/R.Knott/Fibonacci/fibnat.html#seeds.
Walsh J. T., et al, "Er: YAG Laser Ablation of Tissue: Effect of Pulse Duration and Tissue Type on Thermal Damage" Lasers in Surgery and Medicine 9:314-326. 1989. Available from http://research.vuse.vanderbilt.edu/srdesign/2010/group20/docs/1900090403_ftp.pdf.
Tseng S.-H., et al., "Chromophore concentrations, absorption and scattering properties of human skin in-vivo" National Institutes of Health. Available from https://www.ncbi.nlm.nih.gov/pmc/articles/PMC2754563/.

\* cited by examiner

Posterior Scleral Rejuvenation for IOP and Ocular Nerve Head Decompression

Plurality of Treatment Zones in posterior globe

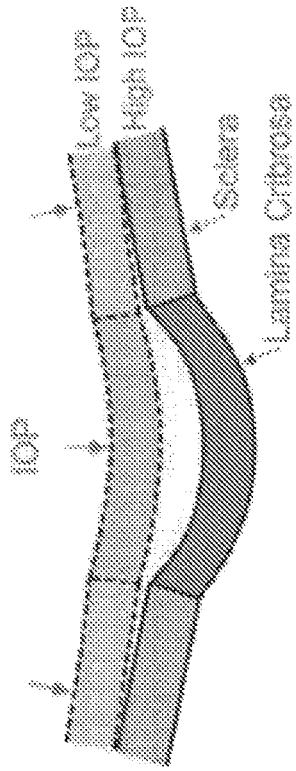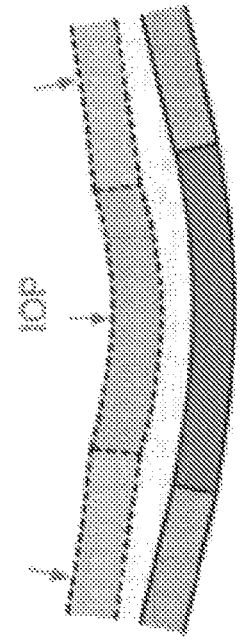
FIG. 1A-6

Mechanism of Action Scleral Rejuvenation to decrease IOP and improve efficient hydrodynamics of physiological functions in the anterior segment

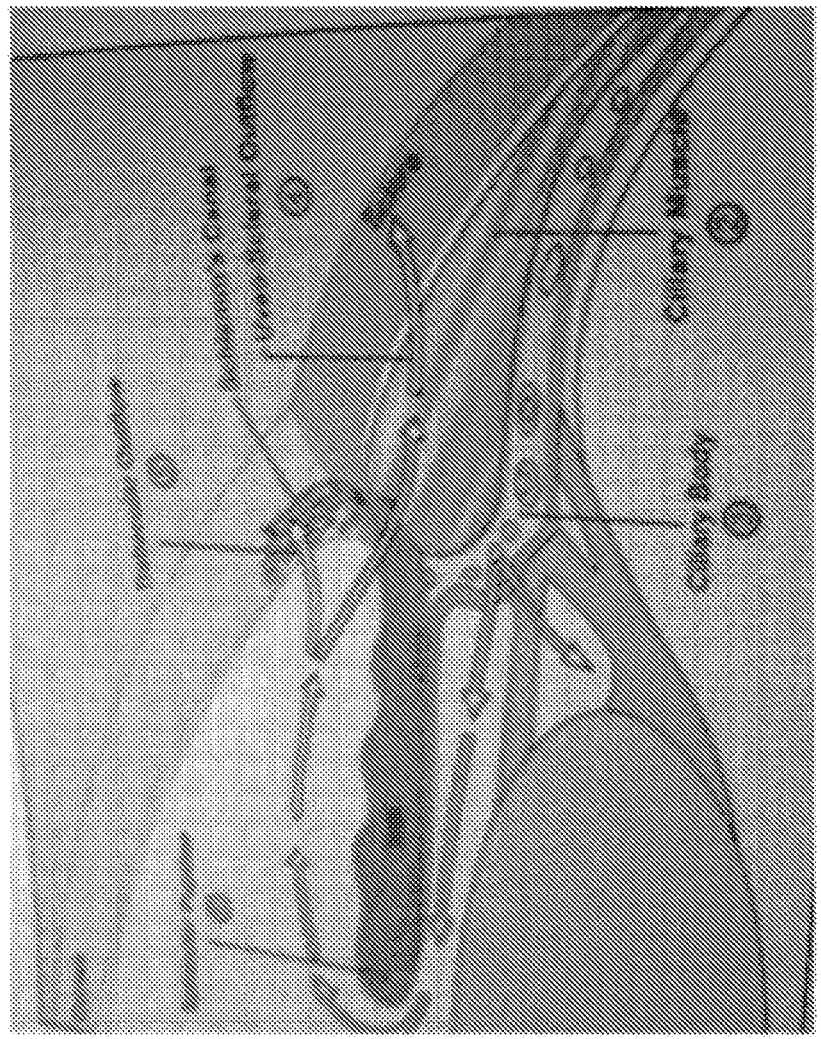

In Closed Angle: Scleral Rejuvenation improves compliance and allows pulling of the iris opening of the angle In open Angle: increased contraction of the longitudinal Ciliary muscle improves drainage of aqueous.

FIG. 1A-7

Coagulation Zones based on Pulse width

In order to find out these coagulation zones we use in 25W laser with the pulse lengths 100, (125), 150 and 200 microsec at 100Hz and then roughly the same fluence for all spots 250, 325 and 425 microns. Then we extrapoloid the curve down to 50 microsec that might give us info on the approx. coag zone

- @ 20 J/cm² for 250 um: 90 us
- @ 20 J/cm² for 325 um: 125 us
- @ 20 J/cm² for 425 um: 160 us Laser Profile optimized for lower Thermal Damage Zone to surrounding tissues is low

| eye | position 1/a/b/c/d | density / % of pulses | number of pulses | Setup according to WP3 |
|---|---|---|---|---|
| 1 | 5/7/10/13 | | 5 | S1 |
| 2 | | | 40 | |
| 3 | | | 10 | S3 |
| 4 | | | 10 | S3 + pressure on pupil |
| 5 | | | 50 | S4 |
| 6 | | | 10 | S3 |
| 7 | | | 30 | S6 |
| 8 | | | 30 | S6 |
| 9 | | | 50 | S4 |
| 10 | 10/13/5/7 | 10/10/30/30 | | S3/S3/S6/S6 |
| 11 | 10/13/5/7 | 10/10/30/30 | | S3/S3/S6/S6 |

FIG. 1G-1

Protocol: Diamond Pattern                                               All dimensions in mm

| Given: | | | |
|---|---|---|---|
| | 0.60 | Sclera Thickness | |
| | 0.60 | Hole Diameter | |
| | 0.40 | Hole Depth | |
| | 1.63 | Hole C-C spacing (along square edge) | |
| | 9 | Number of Holes (Diamond Pattern) | |
| | 1 | # Holes in Zone 1 | |
| | 7 | # Holes in Zone 2 | |
| | 1 | # Holes in Zone 3 | |
| Compute: | | | |
| | 0.28 | Hole Surface Area ($mm^2$, single hole) | |
| | 0.11 | Hole Volume ($mm^3$, single hole) | |
| | 10.6 | % Open Area | |

FIG. 2K-1-A

Protocol: Diamond Pattern                                All dimensions in mm

| | Sclera | | Hole | | %Hole | |
|---|---|---|---|---|---|---|
| | Area (mm²) | Volume (mm³) | | | | |
| Zone 1 | 23.4 | 5.3 | | | | |
| Zone 2 | 189.4 | 73.1 | | | | |
| Zone 3 | 66.5 | 36.6 | | | | |

| | Sclera | | Hole | | %Hole | |
|---|---|---|---|---|---|---|
| | Area (mm²) | Volume (mm³) | Area (mm²) | Volume (mm³) | Area | Volume |
| Zone 1 | 5.8 | 5.3 | 0.28 | 0.11 | 4.8% | 8.5% |
| Zone 2 | 47.4 | 73.1 | 1.98 | 0.79 | 4.2% | 4.3% |
| Zone 3 | 16.6 | 36.6 | 0.28 | 0.11 | 1.7% | 1.2% |
| Total: | 69.8 | 28.8 | 2.5 | 1.018 | 3.6% | 3.5% |

FIG. 2K-1-B

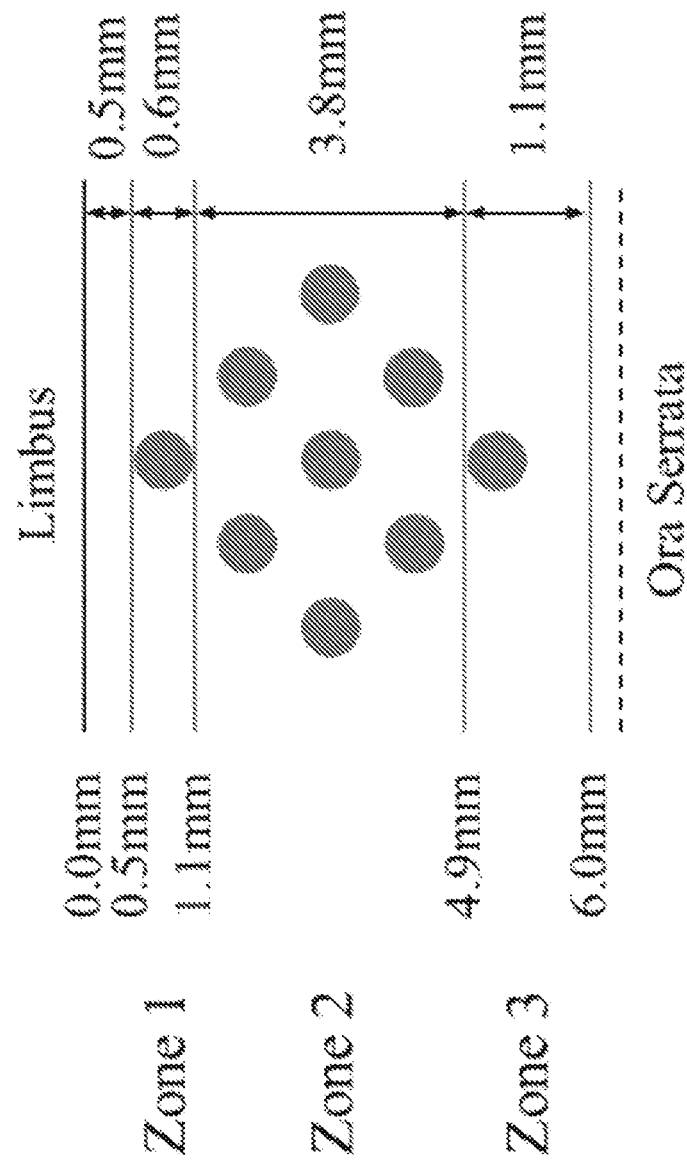
FIG. 2K-1-C

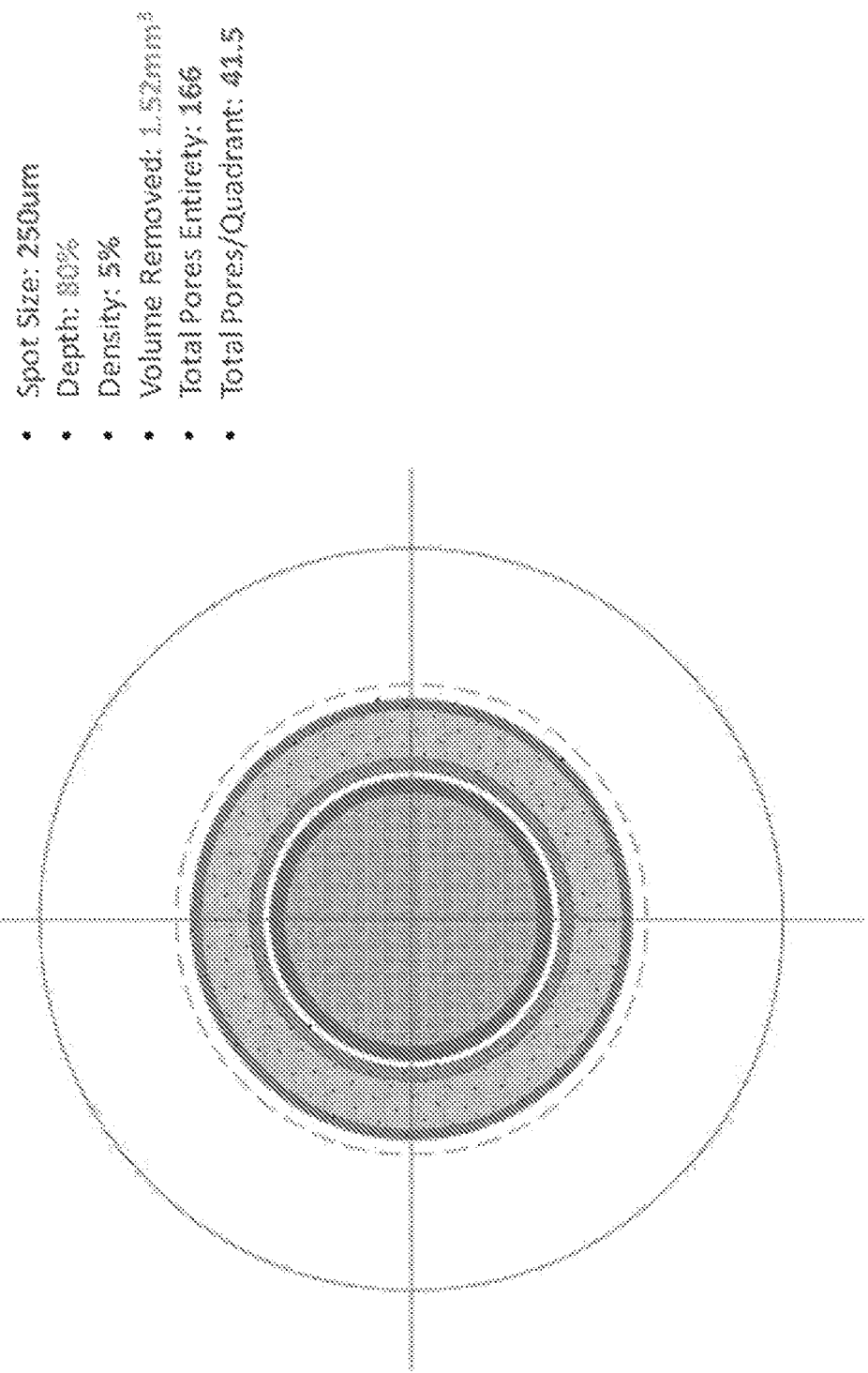

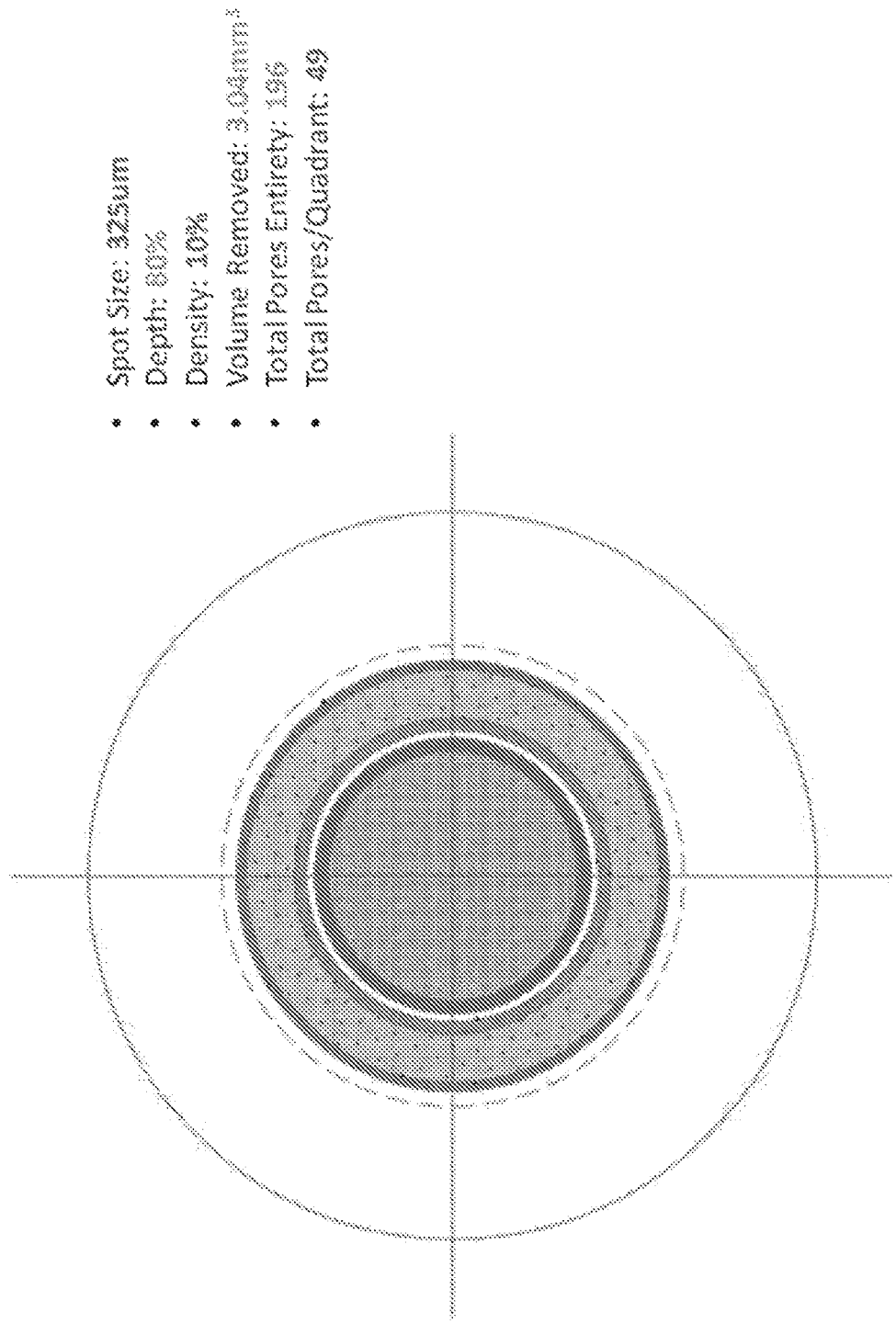

Protocol 4.4: 425um (115 Total Pores @ 10% = 28.75 Pores/Quadrant: Validated) (0273 and 0274)

- Spot Size: 425um
- Depth: 80%
- Density: 10%
- Volume Removed: 3.04mm³
- Total Pores Entirety: 115
- Total Pores/Quadrant: 28.75

Dimensions of Scleral Microporation & Lens zones.

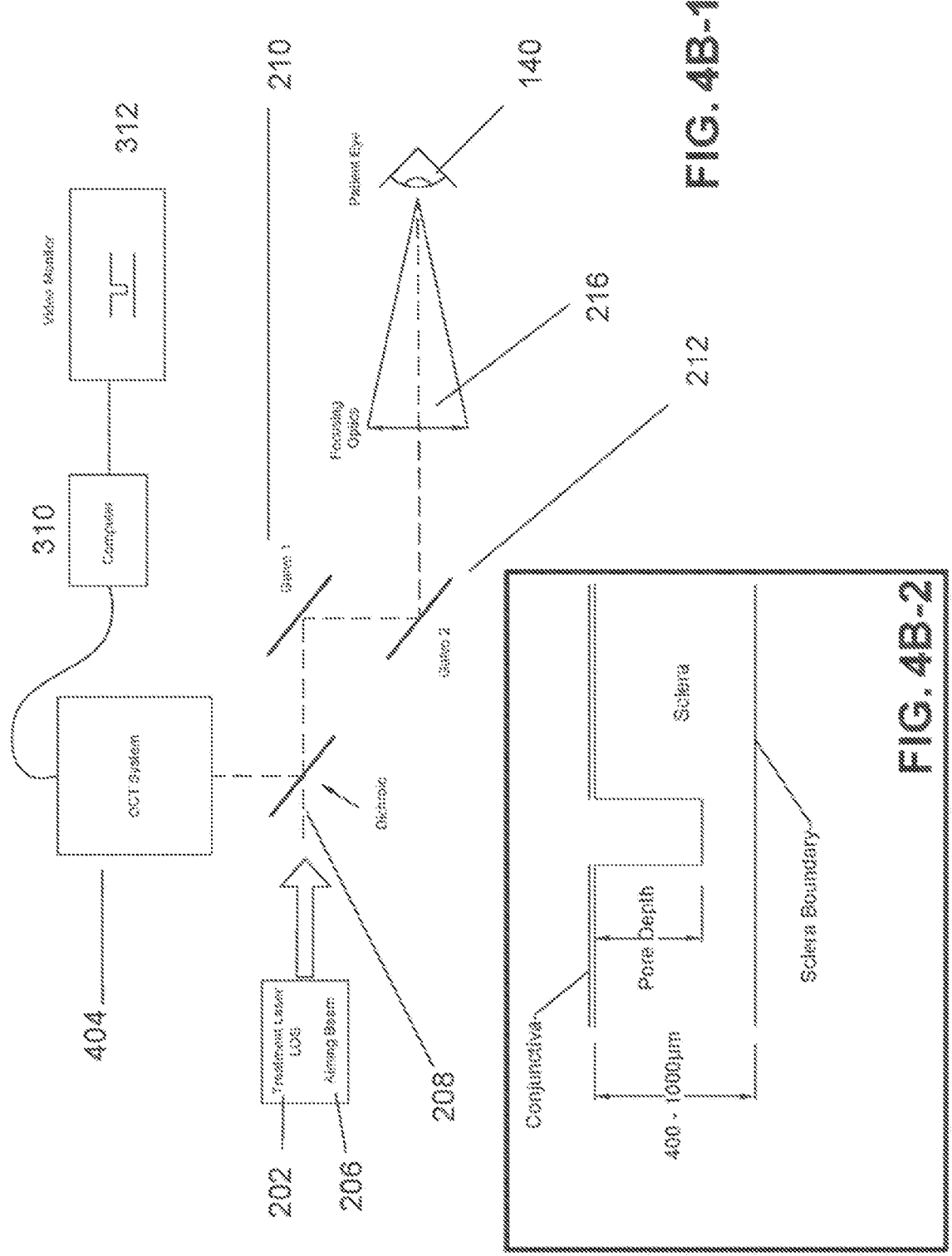

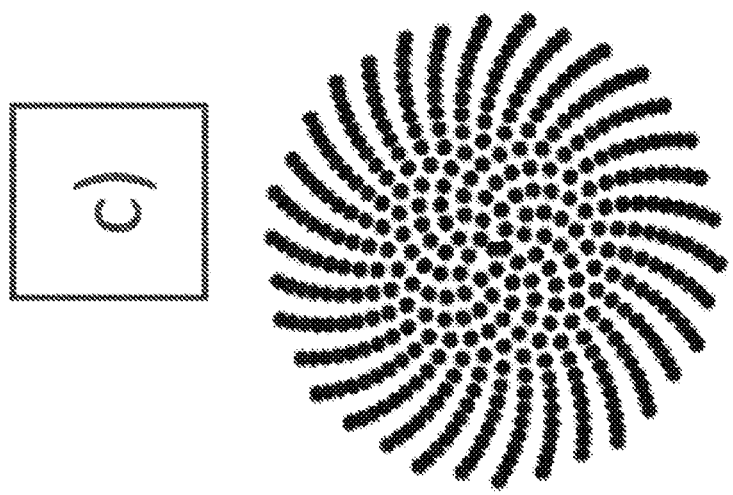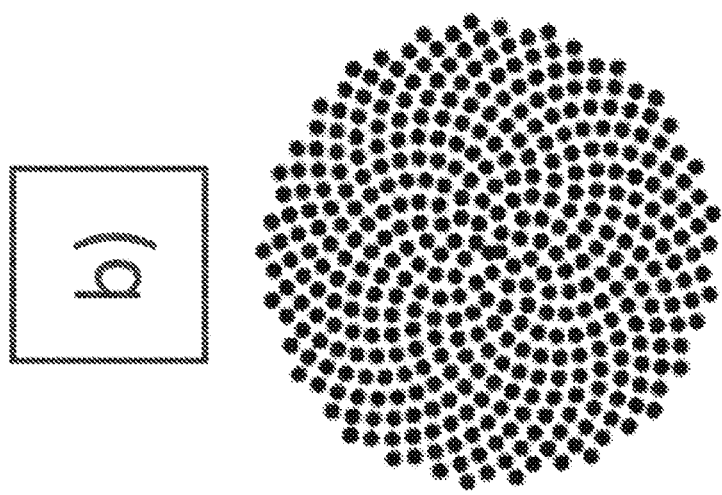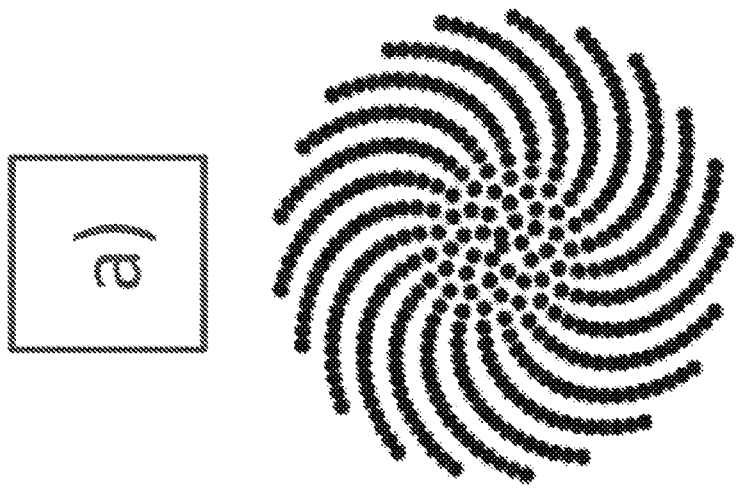
FIG. 14E

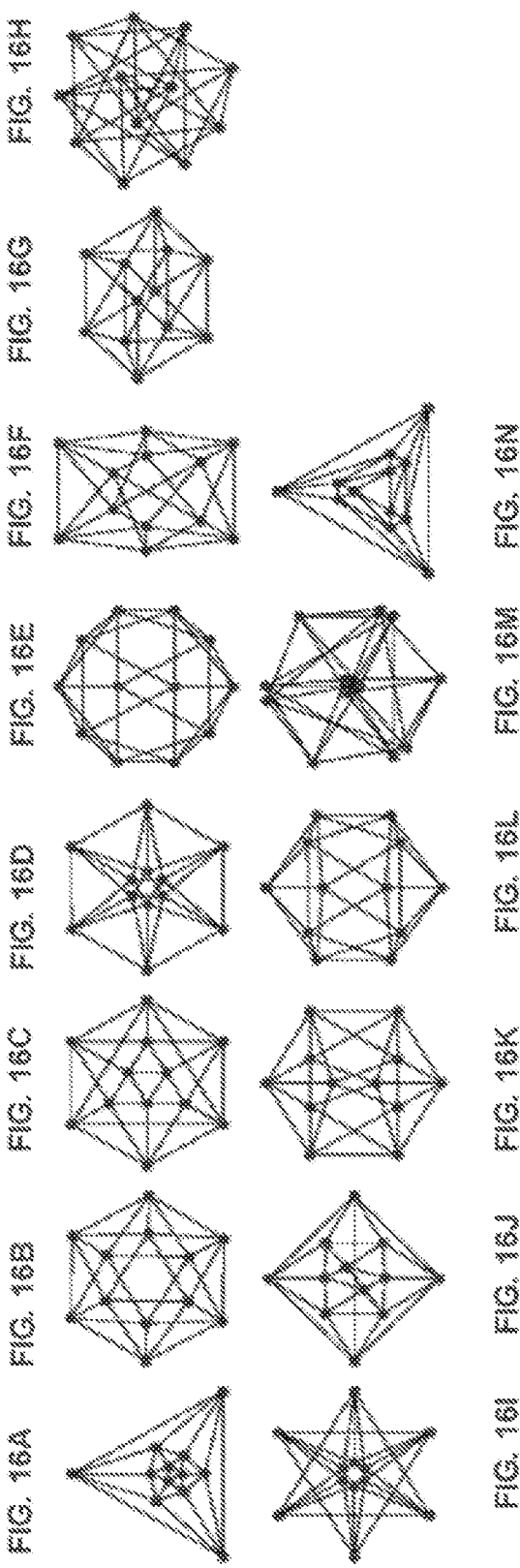

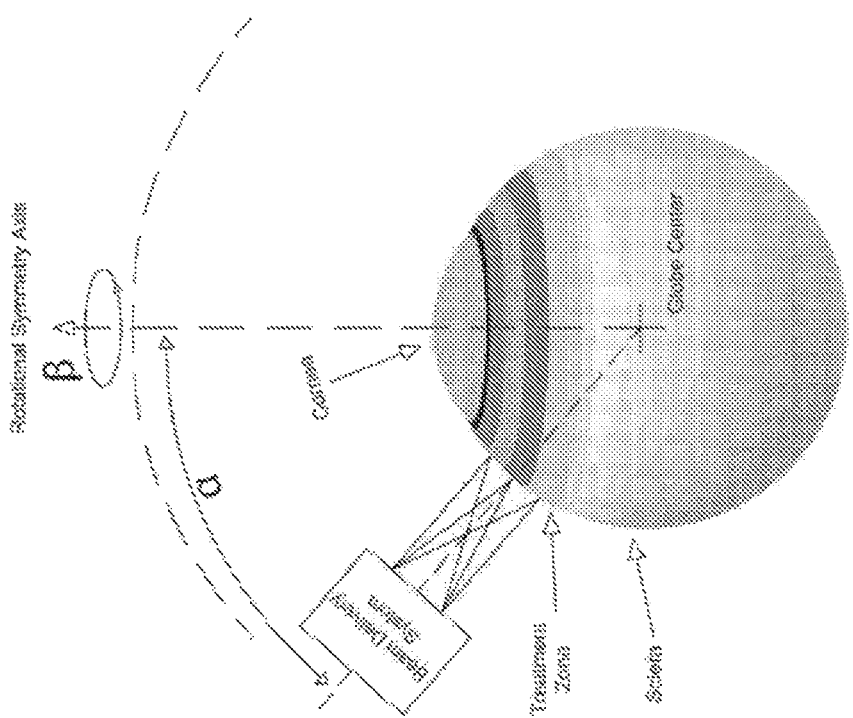

(#2) Entire Laser Head C/L Moves, NO Mirrors

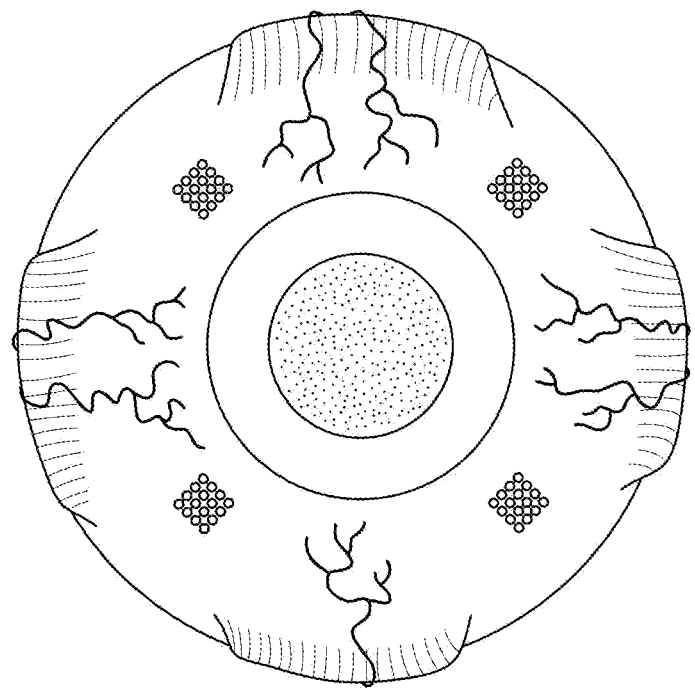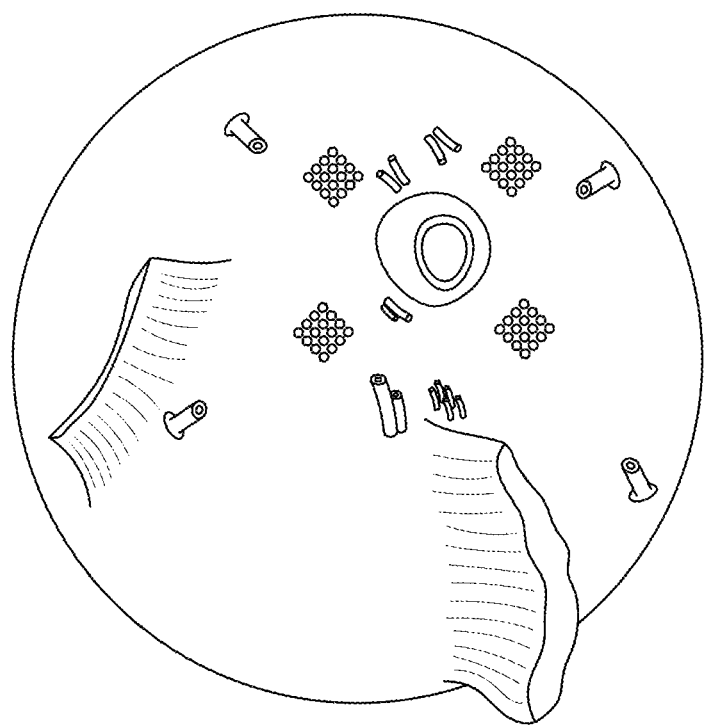
FIG. 20O ciliary muscle (CM)
elastic (EL)
Schlemm's canal (SC)
inner wall (IW)

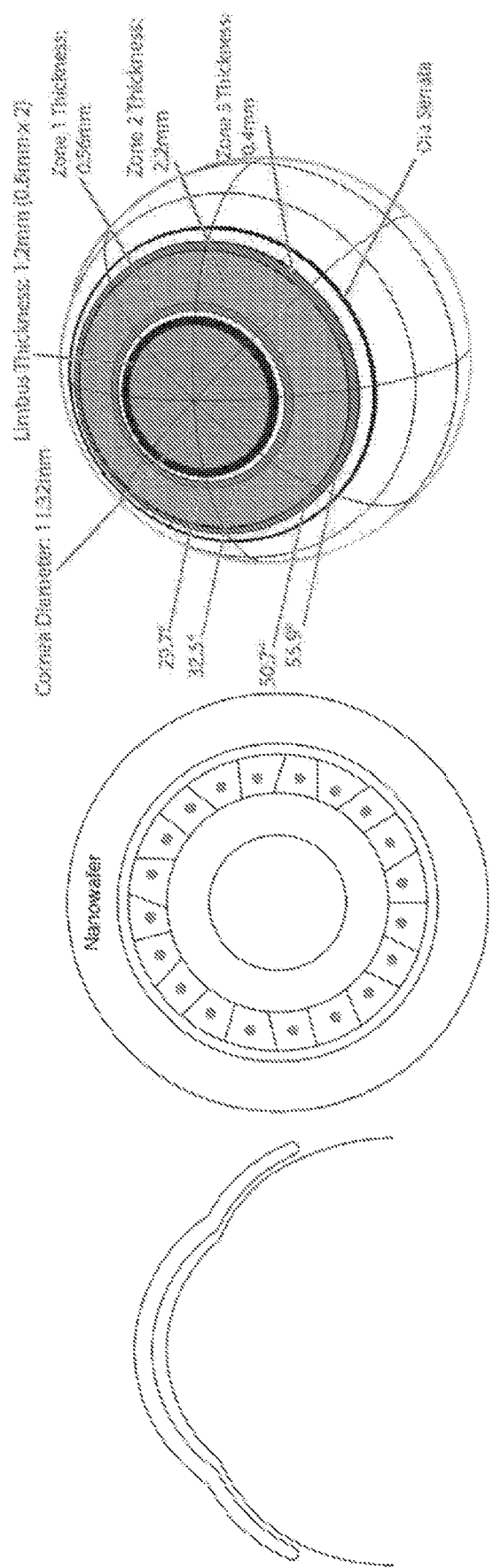

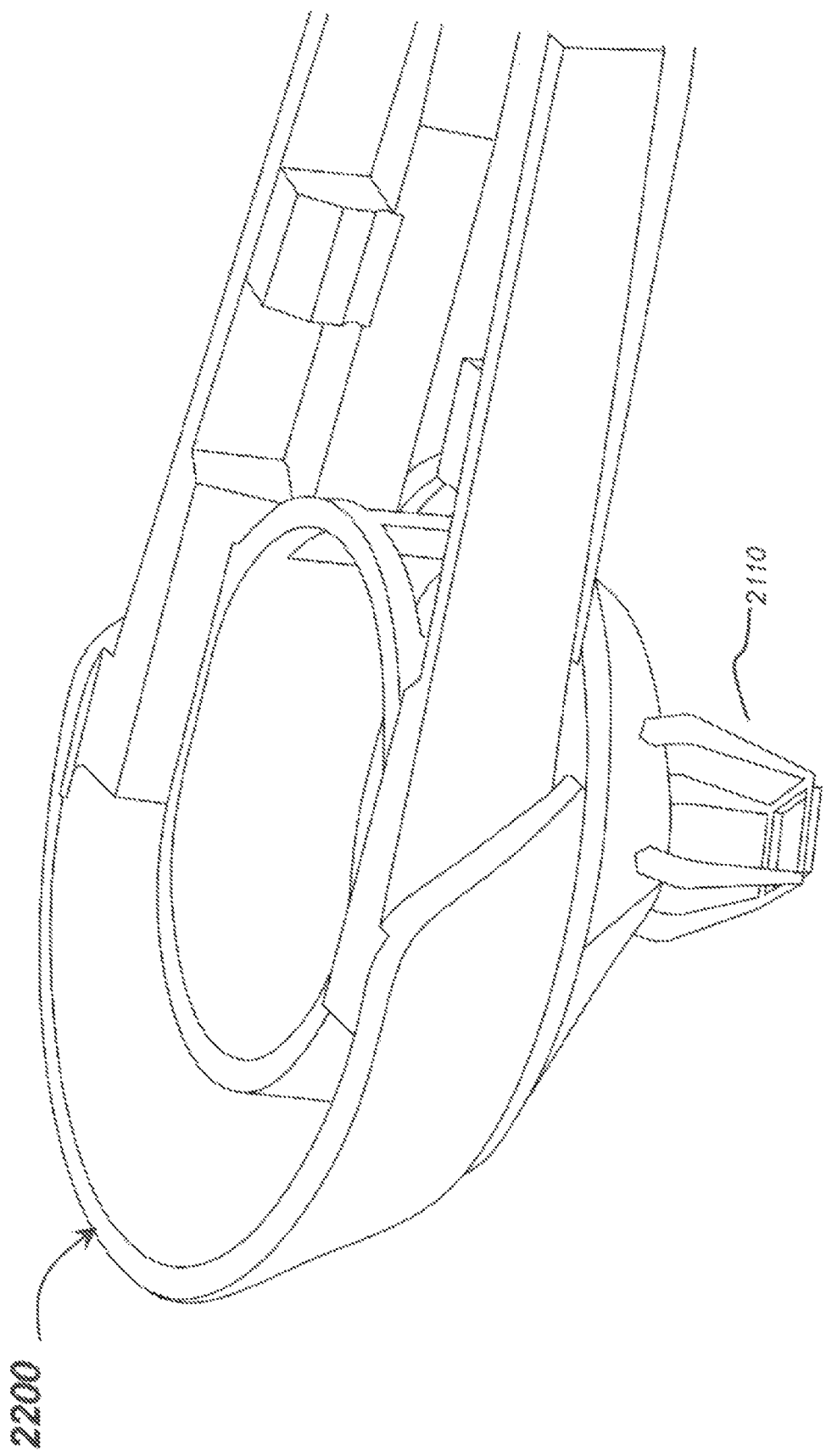

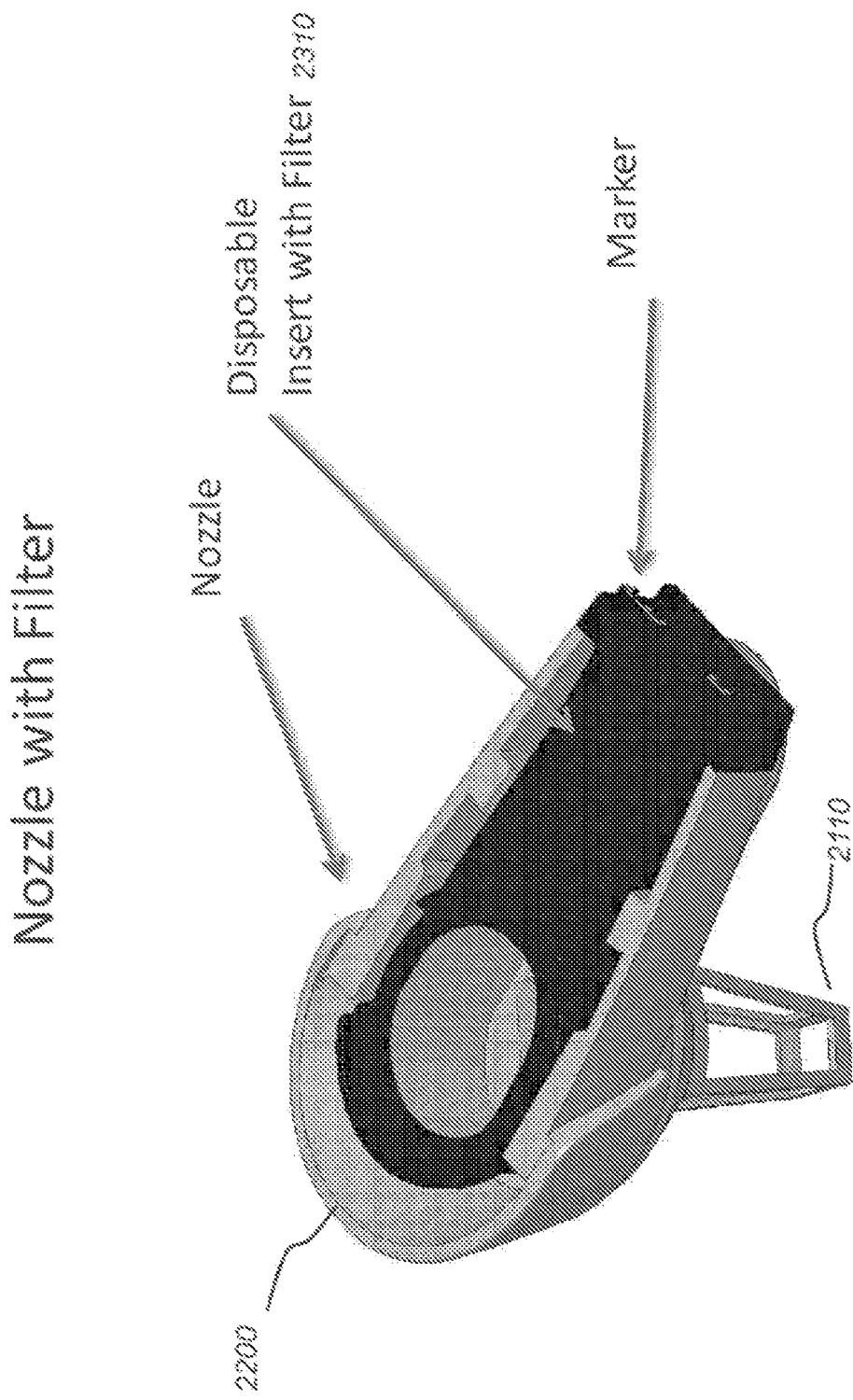

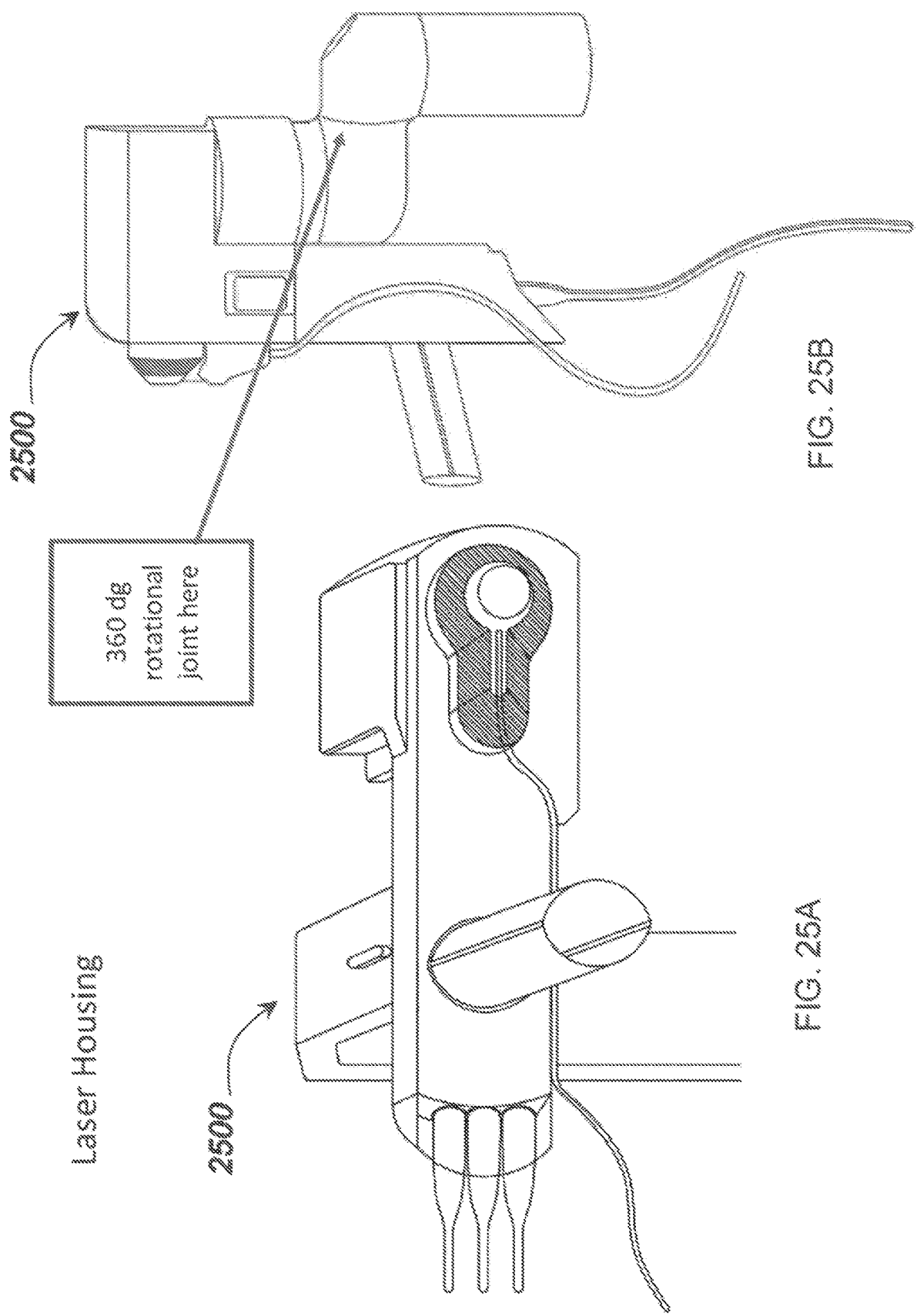

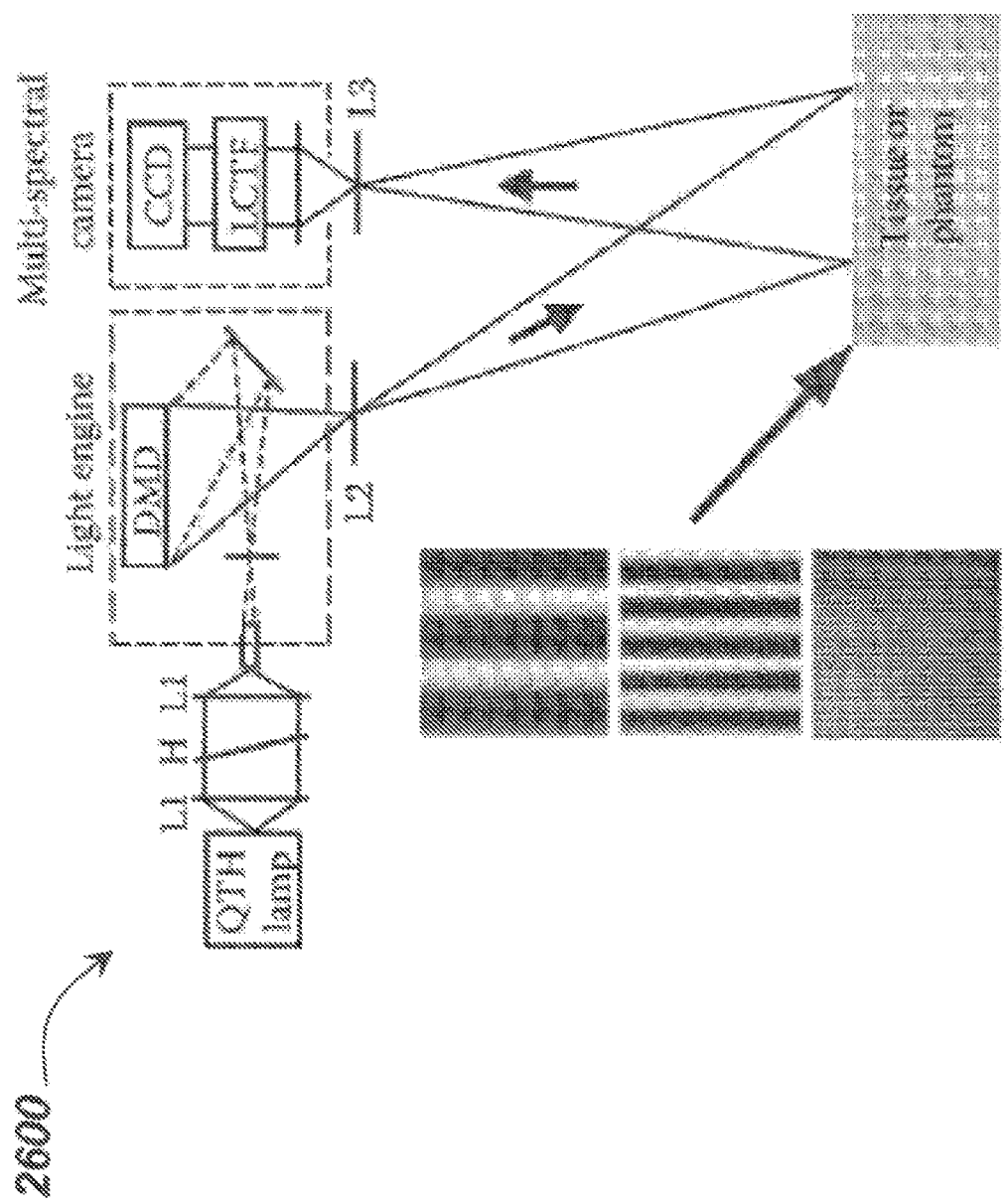
FIG. 26-A

CCD Camera with Nozzle
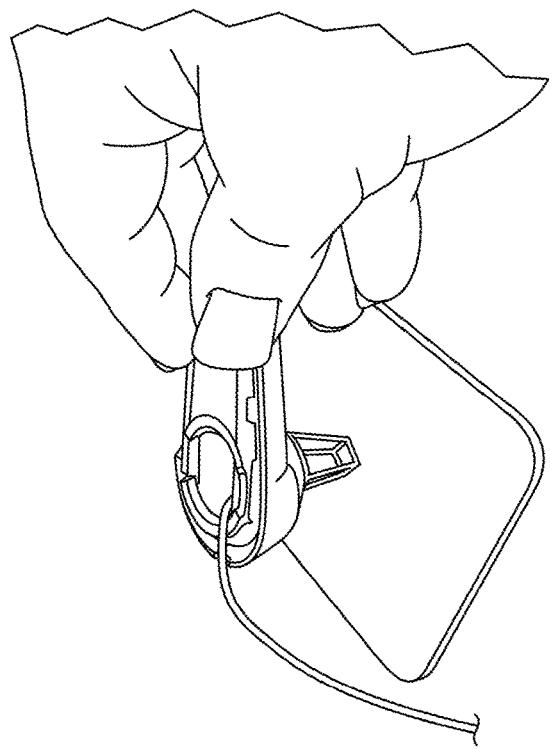
FIG. 26-B
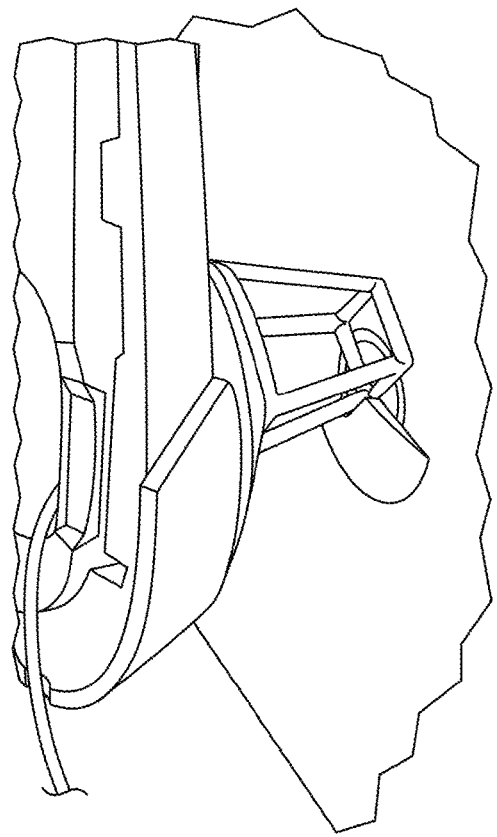
FIG. 26-C

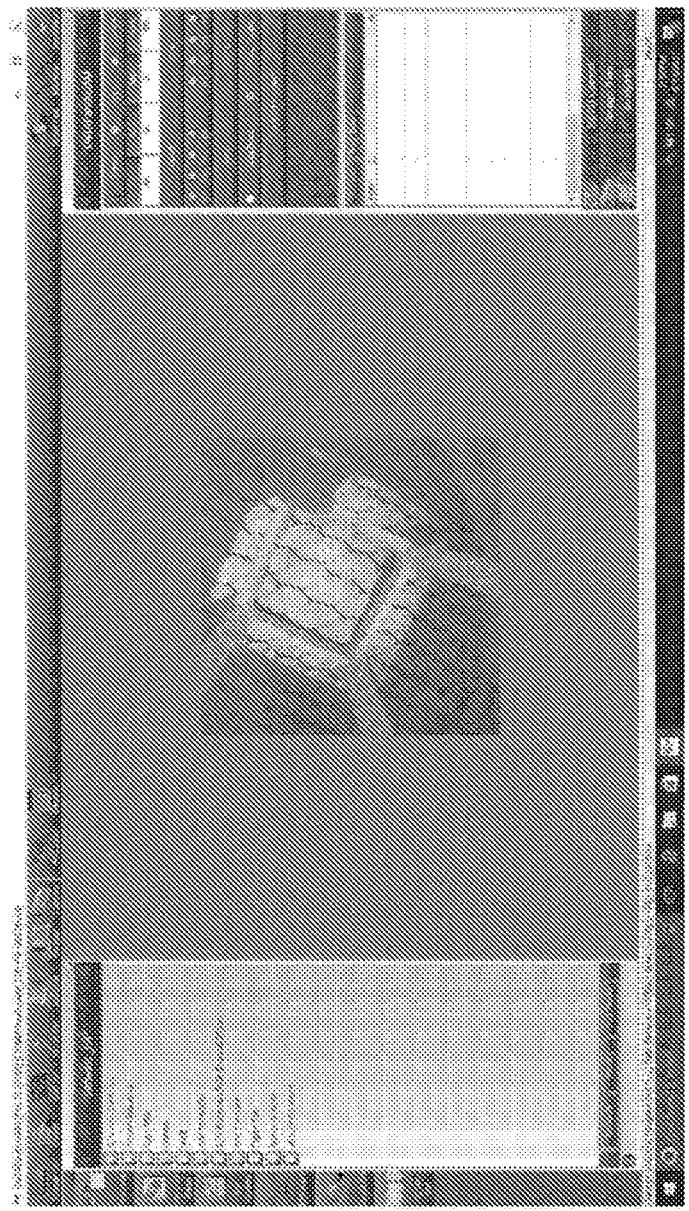
FIG. 26-D

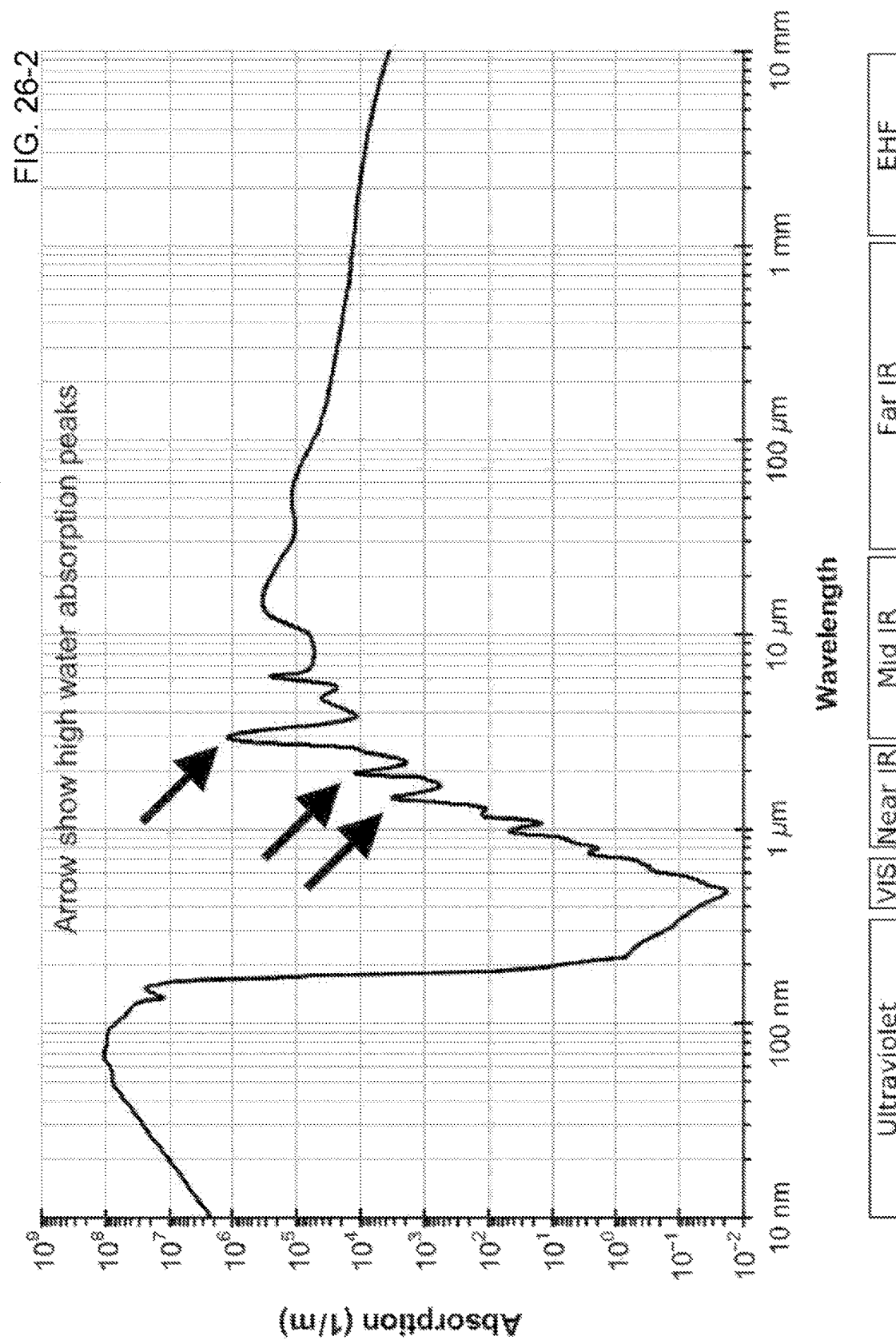

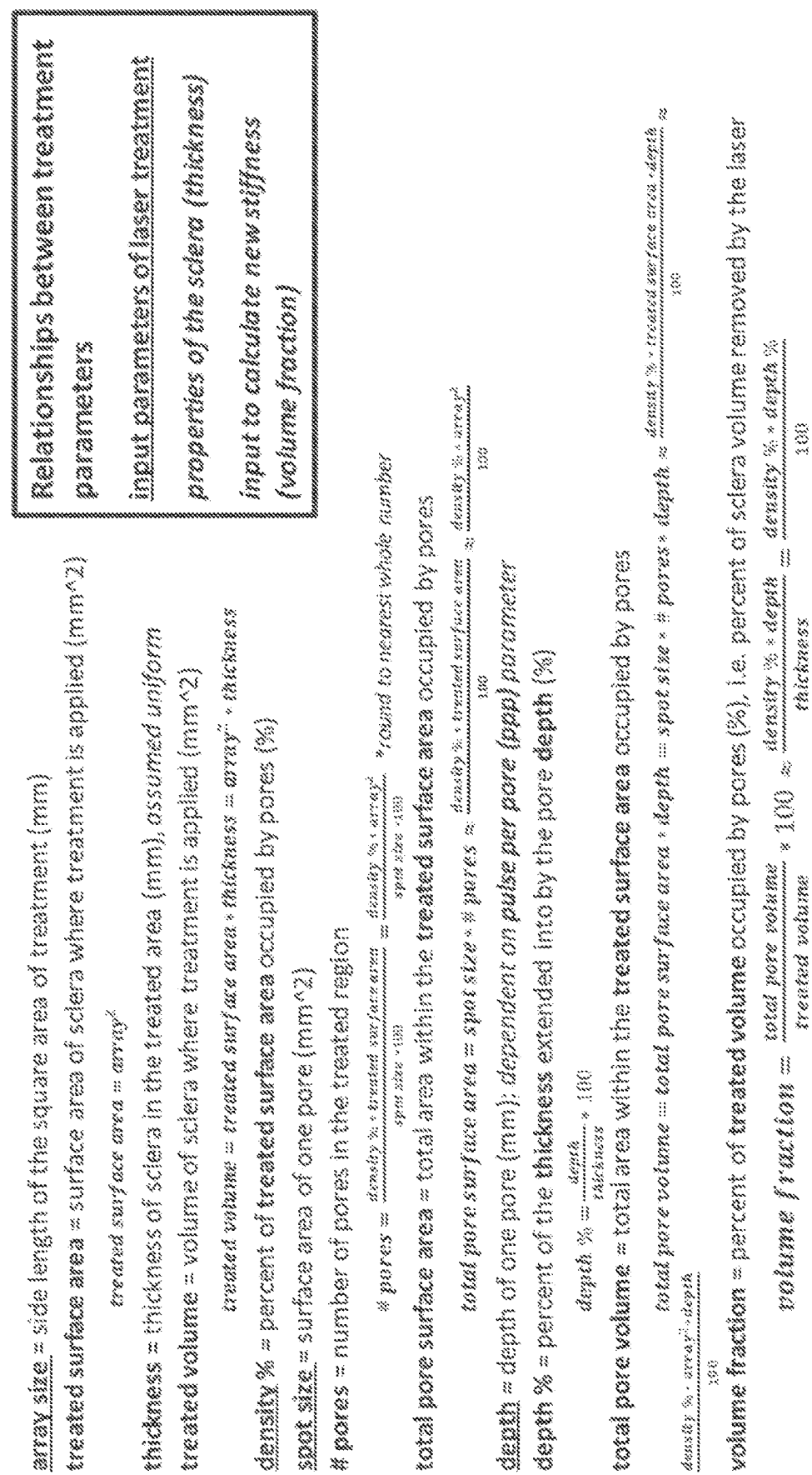
FIG. 26-3A1 calculating new stiffness of sclera in the treated region volume fraction = percent of treated volume occupied by pores (%), i.e. percent of sclera volume removed by the laser $$volume\ fraction = \frac{total\ pore\ volume}{treated\ volume} * 100 = \frac{density\ \% * depth}{thickness} = \frac{density\ \% * depth}{100}$$

stiffness = modulus of elasticity of sclera before treatment (MPa)

treated stiffness = modulus of elasticity of sclera after treatment (MPa); estimated from microscale mixture model $$treated\ stiffness = \left(1 - \frac{volume\ fraction}{100}\right) * stiffness = \left(1 - \frac{density\ \% * depth}{thickness * 100}\right) * stiffness = \left(1 - \frac{density\ \% * depth}{10000}\right) * stiffness$$

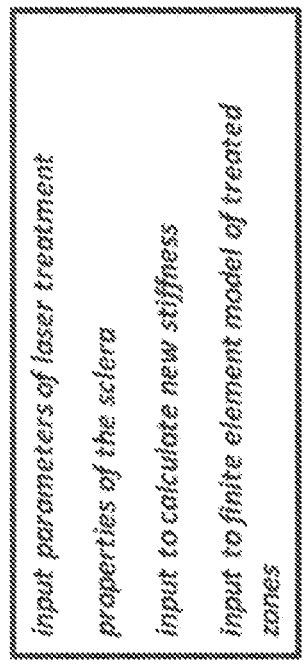

- input parameters of laser treatment
- properties of the sclera
- input to calculate new stiffness
- input to finite element model of treated zones

FIG. 26-3A2

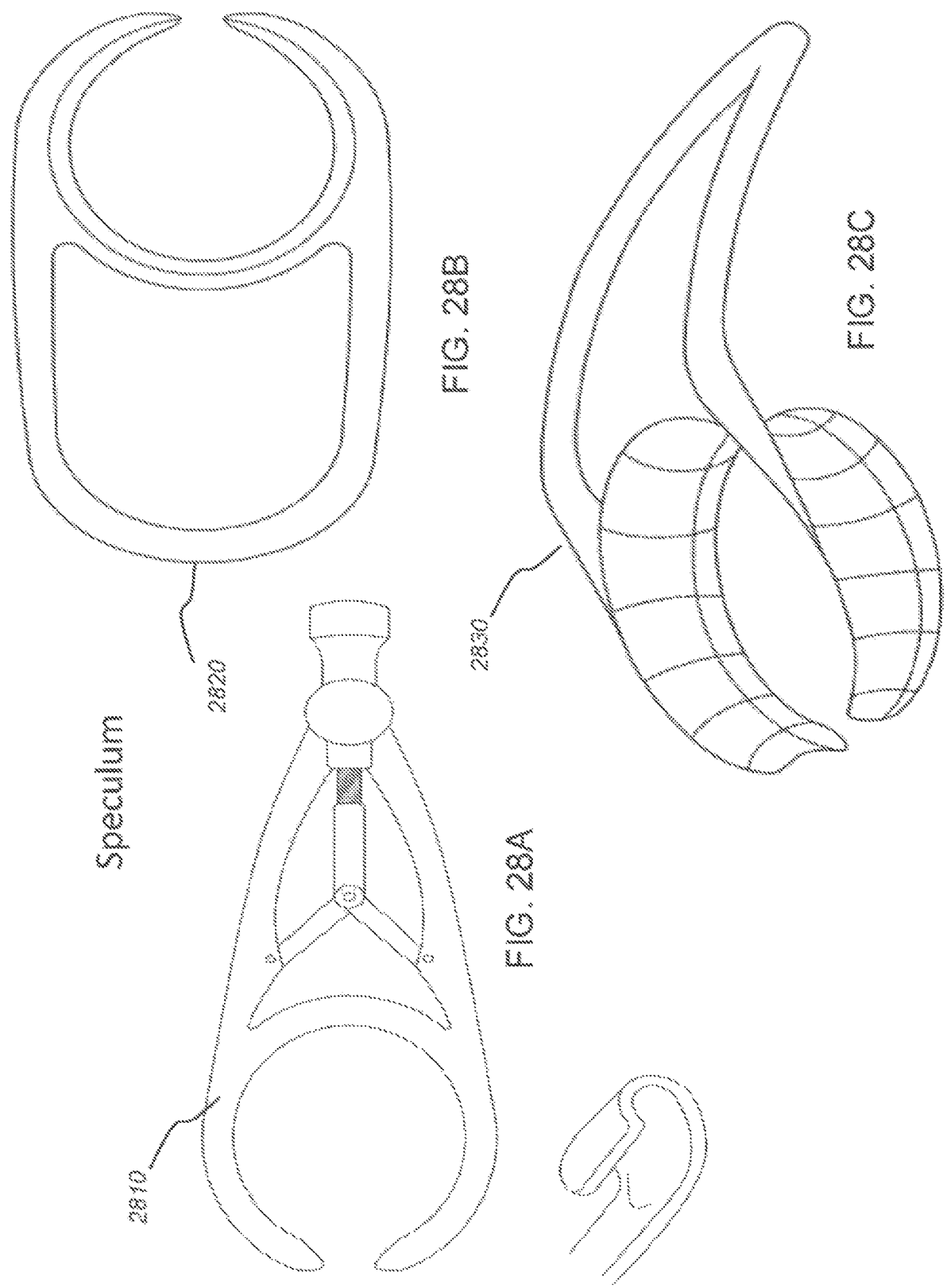

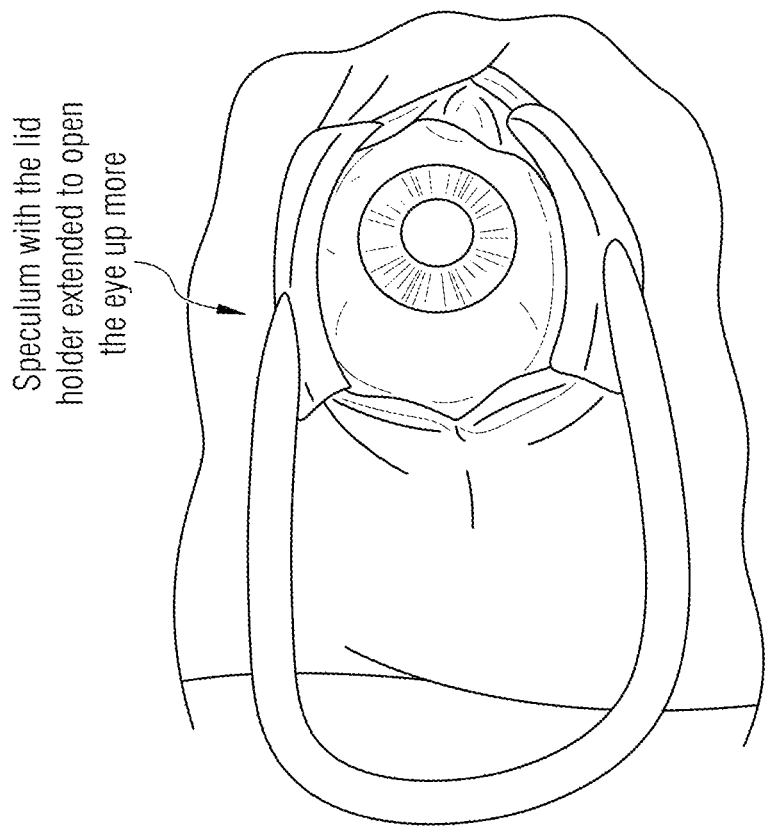
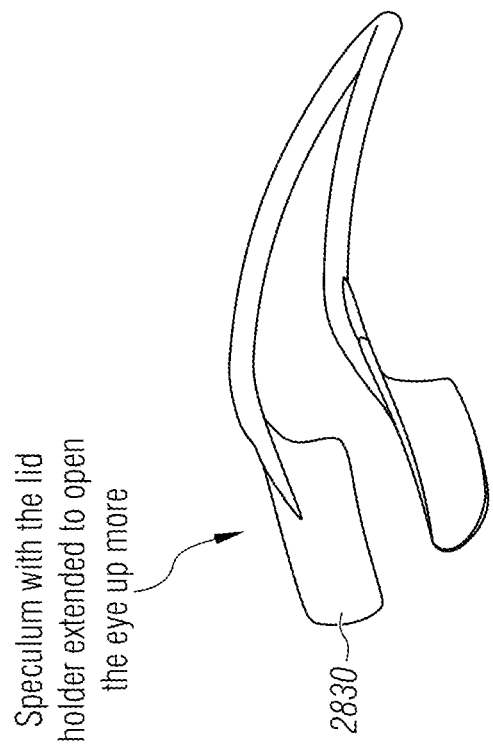
FIG. 29A
FIG. 29B therapy simulation methods: macro results baseline simulation: original model of healthy accommodation with "old" sclera

- stiff baseline sclera: modulus of elasticity (E) = 2.85 MPa, equivalent to ~50 years old
- tight attachment between the sclera and the ciliary/choroid
- All other parameters changed (ciliary activation, stiffness of other components, etc.)

zone treatment simulations: baseline model with sclera stiffness and attachment tightness altered in individual full zones

- treated combinations of zones (with & w/o changing attachment): individually: 0, 1, 2, 3, 4; combined: 1+2+3, 1+2+3+4, 0+1+2+3+4
- effective stiffness: modulus of elasticity (E) = 1.61 MPa, equivalent to ~30 years old*
- loose attachment between the sclera and the ciliary/choroid*

*values in original accommodation model

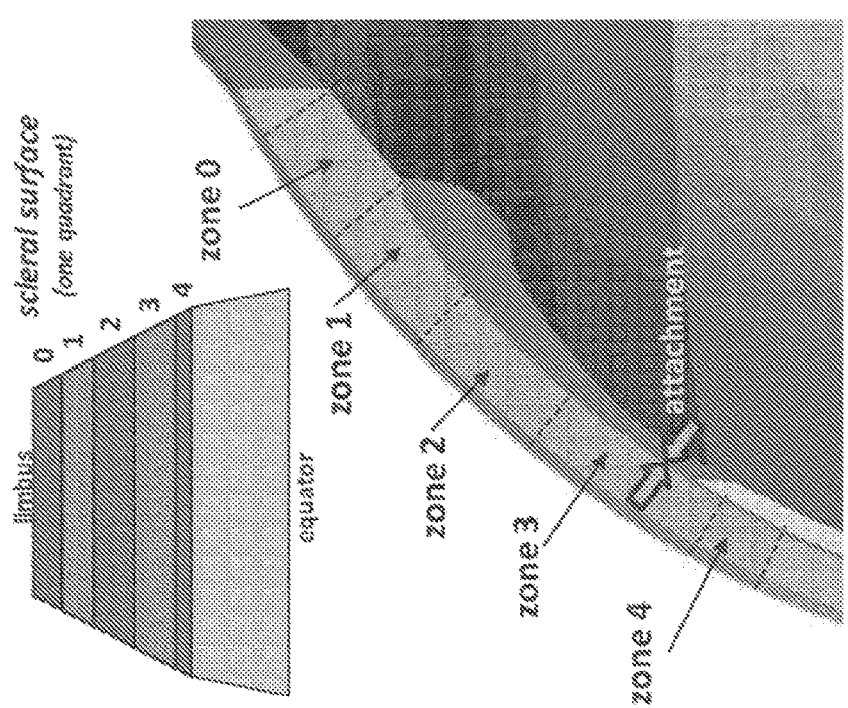

FIG. 35

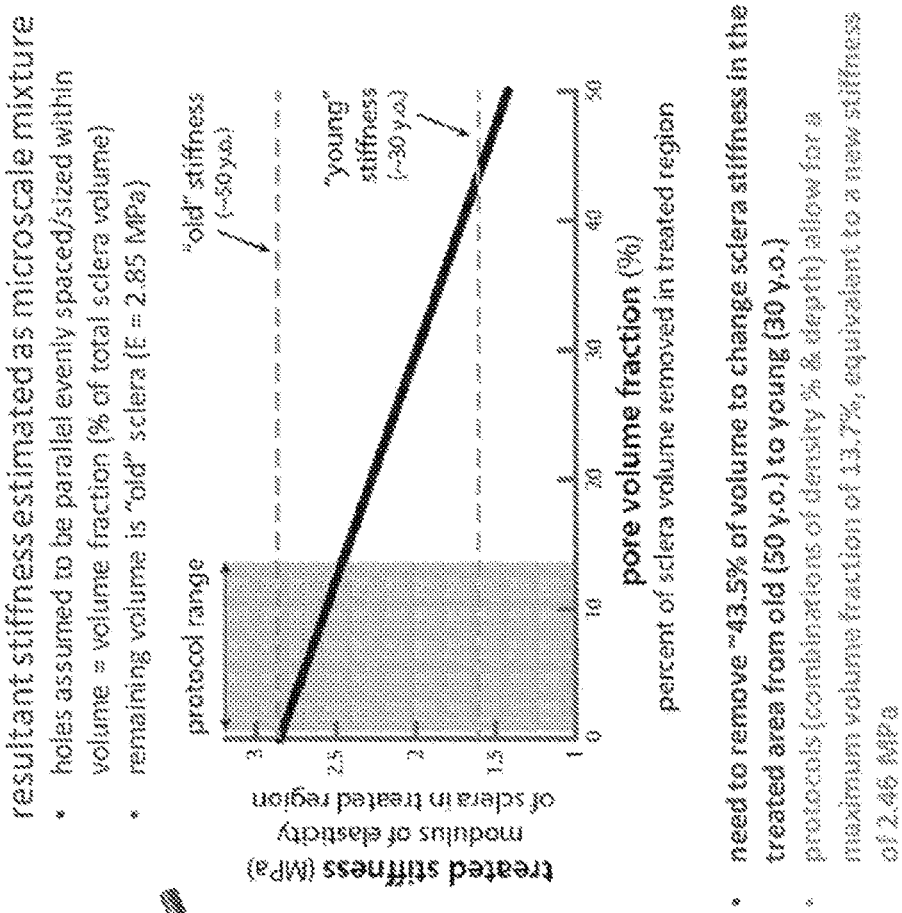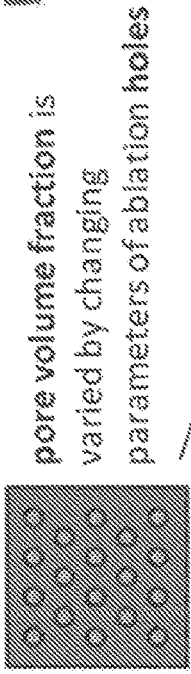
FIG. 36

Contact/eye mask w apertures Custom Nozzle fitted to Docking Station: Nozzle Guard Diagram onto Patch

Model outcomes: proposed protocol comparison

| | proposed protocol 1 | proposed protocol 2 | proposed protocol 3 | proposed protocol 4 | proposed protocol 5 |
|---|---|---|---|---|---|
| treatment shape | wedge 3 | wedge 2 | wedge 1 | 7x7 array | wedge 3 |
| density | 15% | 20% | 30% | 25% | 25% |
| depth % | 80% | 80% | 50% | 100% | 80% |
| spot diameter | 0.225 mm | 0.225 mm | 0.225 mm | 0.225 mm | 0.225 mm |
| lifeform (thickness) | monkey (0.2 mm) | monkey (0.2 mm) | monkey (0.2 mm) | monkey (0.2 mm) | monkey (0.2 mm) |
| apex thickening (mm) | 0.08962 | 0.08952 | 0.08960 | 0.08945 | 0.08962 |
| length shortening (mm) | 0.08831 | 0.08817 | 0.08784 | 0.08839 | 0.08831 |
| accommodation recovery (%) | 13.95 | 11.31 | 11.94 | 10.48 | 24.57 |
| accommodation (D) | 1.116 | 0.905 | 0.955 | 0.838 | 1.966 |

FIG. 41

SYSTEMS AND METHODS FOR OCULAR LASER SURGERY AND THERAPEUTIC TREATMENTS

CROSS REFERENCE TO RELATED APPLICATIONS

This application claims priority to U.S. Appl. No. 62/480,294, filed Mar. 31, 2017 and titled "SYSTEMS AND METHODS FOR OCULAR LASER SURGERY AND THERAPEUTIC TREATMENTS," the entire contents and disclosure of which is hereby incorporated by reference.

This application is related to the subject matter disclosed in U.S. Appl. No. 61/798,379, filed Mar. 15, 2013; U.S. Appl. No. 60/662,026, filed Mar. 15, 2005; U.S. application Ser. No. 11/376,969, filed Mar. 15, 2006; U.S. Appl. No. 60/842,270, filed Sep. 5, 2006; U.S. Appl. No. 60/865,314, filed Nov. 10, 2006; U.S. Appl. No. 60/857,821, filed Nov. 10, 2006; U.S. application Ser. No. 11/850,407, filed Sep. 5, 2007; U.S. application Ser. No. 11/938,489, filed Nov. 12, 2007; U.S. application Ser. No. 12/958,037, filed Dec. 1, 2010; U.S. application Ser. No. 13/342,441, filed Jan. 3, 2012; U.S. application Ser. No. 14/526,426, filed Oct. 28, 2014; U.S. application Ser. No. 14/861,142, filed Sep. 22, 2015; U.S. application Ser. No. 11/850,407, filed Sep. 5, 2007; U.S. application Ser. No. 14/213,492, filed Mar. 14, 2014; and to U.S. Appl. No. 62/356,457, filed Jun. 29, 2016; U.S. Appl. No. 62/356,467, filed Jun. 29, 2016, each of which is incorporated herein by reference in its entirety.

FIELD OF THE INVENTION

The subject matter described herein relates generally to systems, methods, therapies and devices for laser scleral microporation, and more particularly for to systems, methods and devices for laser scleral microporation rejuvenation of tissue of the eye, specifically regarding aging of connective tissue, rejuvenation of connective tissue by ocular or scleral rejuvenation.

BACKGROUND OF THE INVENTION

The eye is a biomechanical structure, a complex sense organ that contains complex muscular, drainage, and fluid mechanisms responsible for visual function and ocular biotransport. The accommodative system is the primary moving system in the eye organ, facilitating many physiological and visual functions in the eye. The physiological role of the accommodation system is to move aqueous, blood, nutrients, oxygen, carbon dioxide, and other cells, around the eye organ. In general, the loss of accommodative ability in presbyopes has many contributing lenticular, as well as extralenticular and physiological factors that are affected by increasing age. Increasing ocular rigidity with age produces stress and strain on these ocular structures and can affect accommodative ability which can impact the eye in the form of decreased biomechanical efficiency for physiological processes including visual accommodation, aqueous hydrodynamics, vitreous hydrodynamics and ocular pulsatile blood flow to name a few. Current procedures only manipulate optics through some artificial means such as by refractive laser surgery, adaptive optics, or corneal or intraocular implants which exchange power in one optic of the eye and ignore the other optic and the importance of preserving the physiological functions of the accommodative mechanism.

Additionally, current implanting devices in the sclera obtain the mechanical effect upon accommodation. They do not take into account effects of 'pores', 'micropores', or creating a matrix array of pores with a central hexagon, or polygon in 3D tissue. As such, current procedures and devices fail to restore normal ocular physiological functions.

Accordingly, there is a need for systems and methods for restoring normal ocular physiological functions taking into account effects of 'pores' or creating a lattice or matrix array of pores with a central hexagon or polygon in three dimensional (3D) tissue.

SUMMARY OF THE INVENTION

Disclosed are systems, devices and methods for laser scleral microporation for rejuvenation of tissue of the eye, specifically regarding aging of connective tissue, rejuvenation of connective tissue by scleral rejuvenation. The systems, devices and methods disclosed herein restore physiological functions of the eye including restoring physiological accommodation or physiological pseudo-accommodation through natural physiological and biomechanical phenomena associated with natural accommodation of the eye.

In some embodiments, a system is provided to deliver microporation medical treatments to improve biomechanics, wherein the system includes a laser for generating a beam of laser radiation on a treatment-axis not aligned with a patient's visual-axis, operable for use in subsurface ablative medical treatments to create an array or lattice pattern of micropores that improves biomechanics. The system includes a housing, a controller within the housing, in communication with the laser and operable to control dosimetry of the beam of laser radiation in application to a target tissue. The system also includes a lens operable to focus the beam of laser radiation onto a target tissue, and an automated off-axis subsurface anatomy tracking, measuring, and avoidance system. The array pattern of micropores is at least one of a radial pattern, a spiral pattern, a phyllotactic pattern, or an asymmetric pattern.

In some embodiments, the array pattern of micropores is a spiral pattern of an Archimedean spiral, a Euler spiral, a Fermat's spiral, a hyperbolic spiral, a lituus, a logarithmic spiral, a Fibonacci spiral, a golden spiral, a Bravais lattice, a non Bravais lattice, or combinations thereof.

In some embodiments, the array pattern of micropores has a controlled asymmetry which is an at least partial rotational asymmetry about the center of the array pattern. The at least partial rotational asymmetry may extend to at least 51 percent of the micropores of the array pattern. The at least partial rotational asymmetry may extend to at least 20 micropores of the array pattern. In some embodiments, the array pattern of micropores has a random asymmetry.

In some embodiments, the array pattern of micropores has a controlled symmetry which is an at least partial rotational symmetry about the center of the array pattern. The at least partial rotational symmetry may extend to at least 51 percent of the micropores of the array pattern. The at least partial rotational symmetry may extend to at least 20 micropores of the array pattern. In some embodiments, the array pattern of micropores may have a random symmetry.

In some embodiments, the array pattern has a number of clockwise spirals and a number of counter-clock wise spirals. The number of clockwise spirals and the number of counterclockwise spirals may be Fibonacci numbers or multiples of Fibonacci numbers, or they may be in a ratio that converges on the golden ratio.

In some embodiments, a method is provided for delivering microporation medical treatments to improve biomechanics. The method includes generating, by a laser, a treatment beam on a treatment-axis not aligned with a patient's visual-axis in a subsurface ablative medical treatment to create an array of micropores that improves biomechanics; controlling, by a controller in electrical communication with the laser, dosimetry of the treatment beam in application to a target tissue; focusing, by a lens, the treatment beam onto the target tissue; monitoring, by an automated off-axis subsurface anatomy tracking, measuring, and avoidance system, an eye position for application of the treatment beam; and wherein the array pattern of micropores is at least one of a radial pattern, a spiral pattern, a phyllotactic pattern, or an asymmetric pattern.

BRIEF DESCRIPTION OF THE DRAWING(S)

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely. Illustrated in the accompanying drawing(s) is at least one of the best mode embodiments of the present invention.

FIGS. 1A-4 to 1A-5 illustrate exemplary posterior scleral rejuvenation and treatment zones, according to an embodiment of the disclosure.

FIGS. 1A-6-1A-7 illustrate exemplary posterior scleral rejuvenation and ocular nerve head decompression, according to an embodiment of the disclosure.

FIG. 1E-1 illustrates exemplary coagulation zones, according to an embodiment of the disclosure.

FIG. 1E-2 illustrates an exemplary pattern speed calculation, according to an embodiment of the disclosure.

Figures 1, 1A:
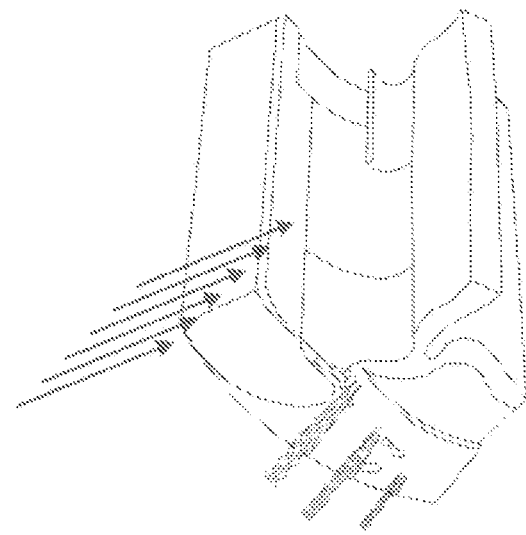
FIGS. 1A-1 to 1A-3 illustrate exemplary scleral laser rejuvenation of viscoelasticity, according to an embodiment of the disclosure.
Figures 1, 1A, 2, 3:
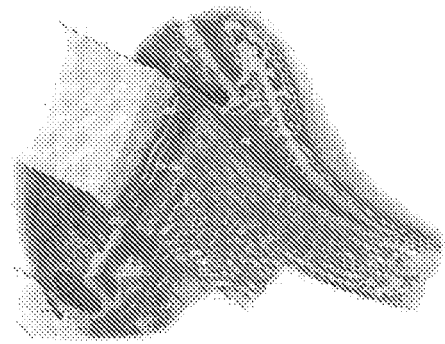
Figures 1, 1A, 2:
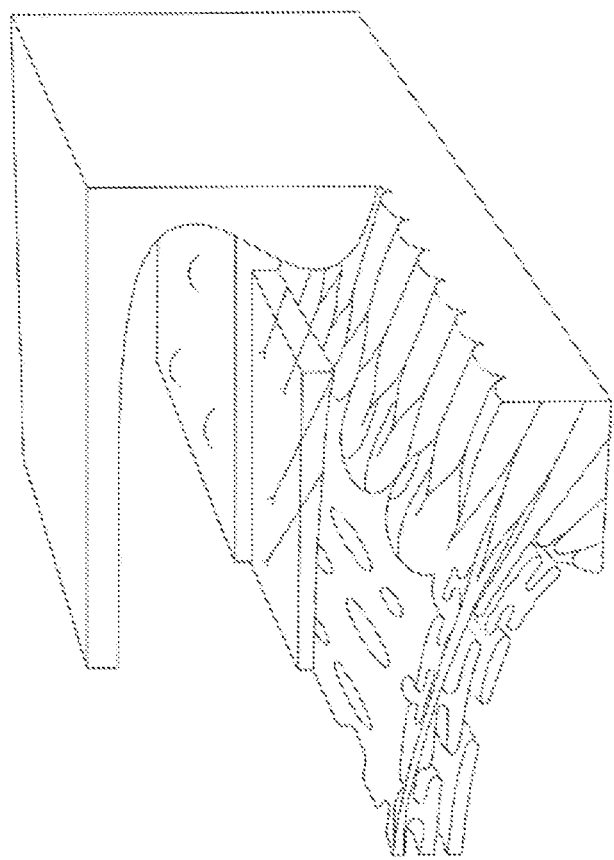
Figures 1, 1A, 2, 3, 4, 5:
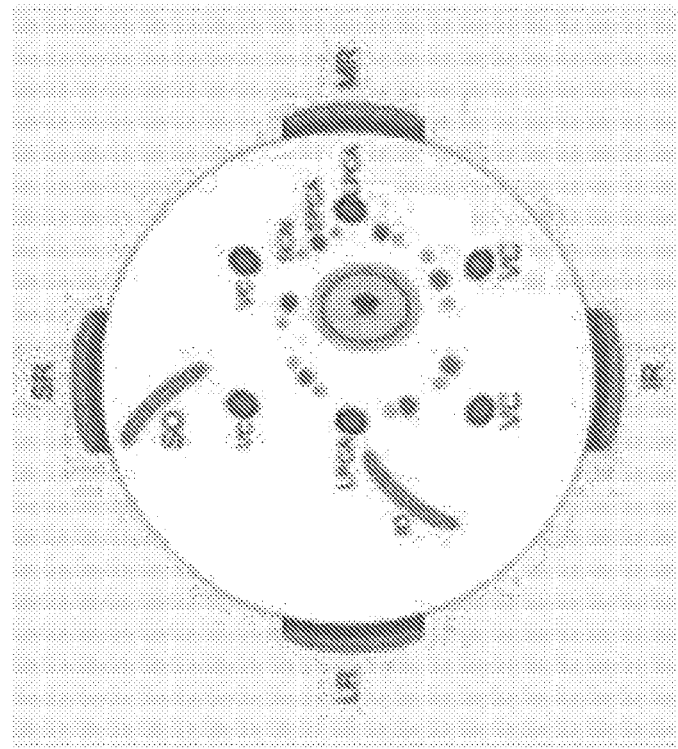
Figures 1, 1A, 2, 3, 4:
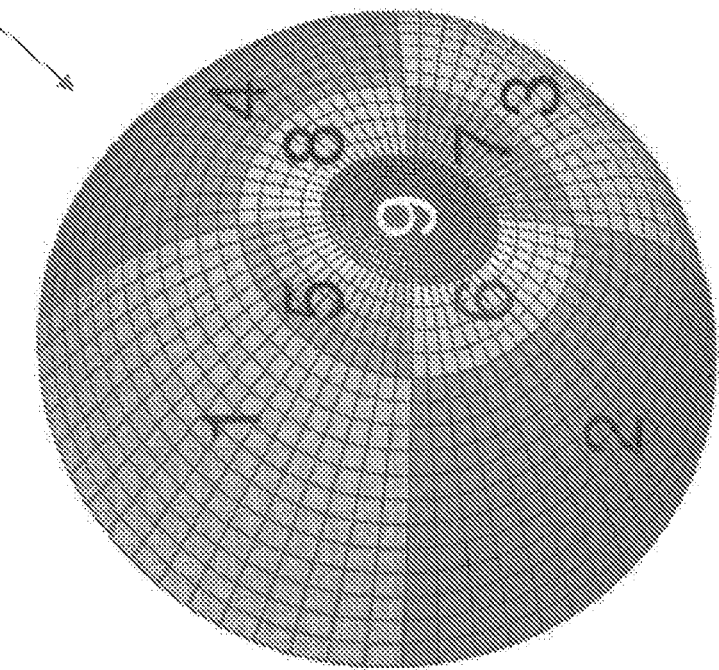
Figure 1C:
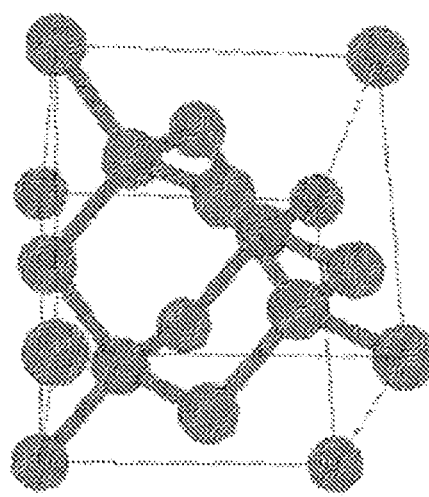
FIGS. 1B to 1E illustrate exemplary pore matrix arrays, according to an embodiment of the disclosure.
Figure 1E:
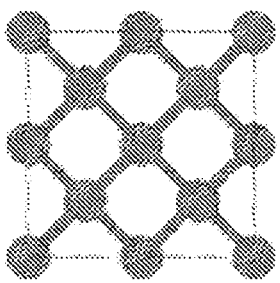
Figure 1B:
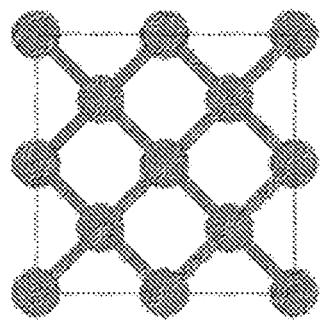
Figure 1D:
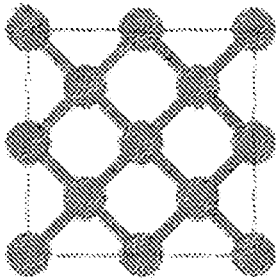
Figures 1, 1E:
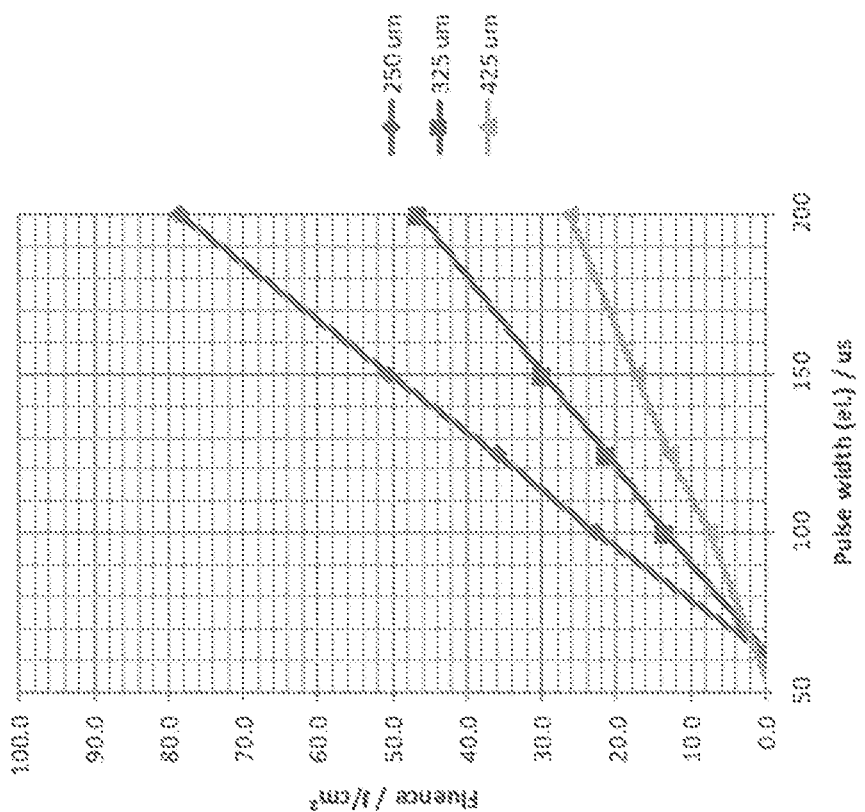
Figures 1, 1E, 2:
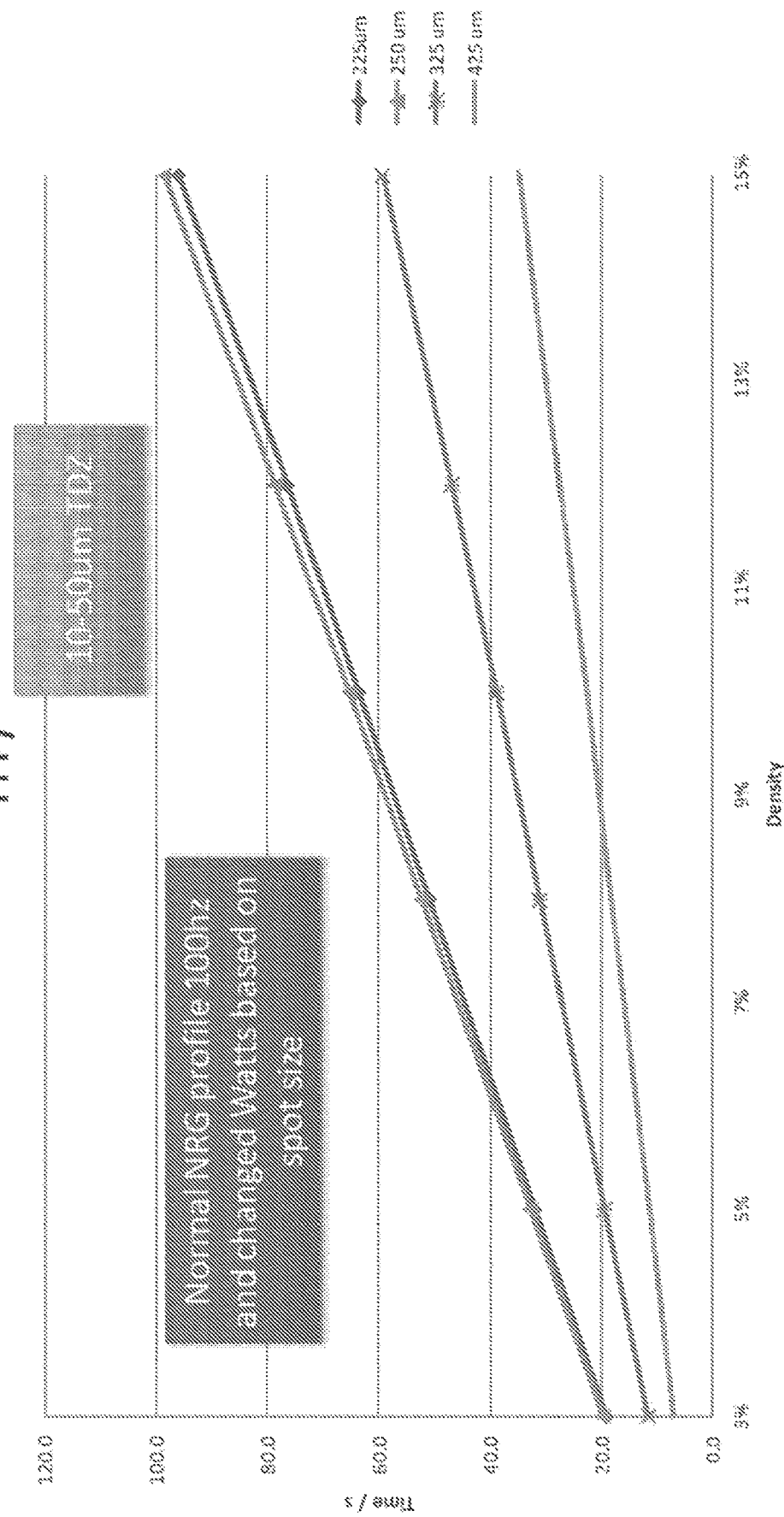
Figure 1F:
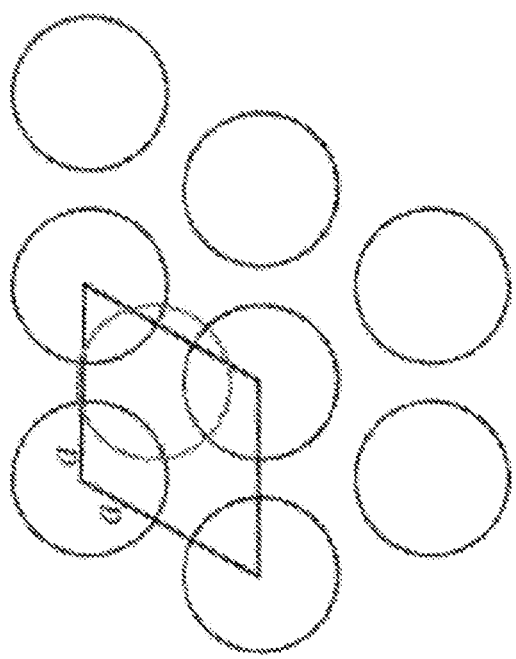
Figure 1F:
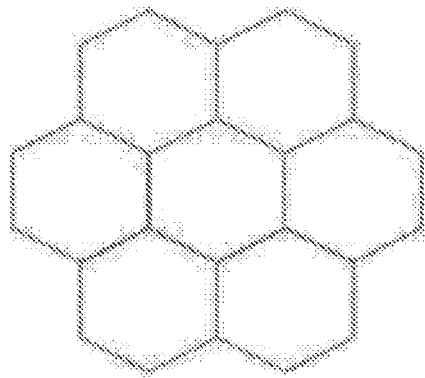
Figure 1F:
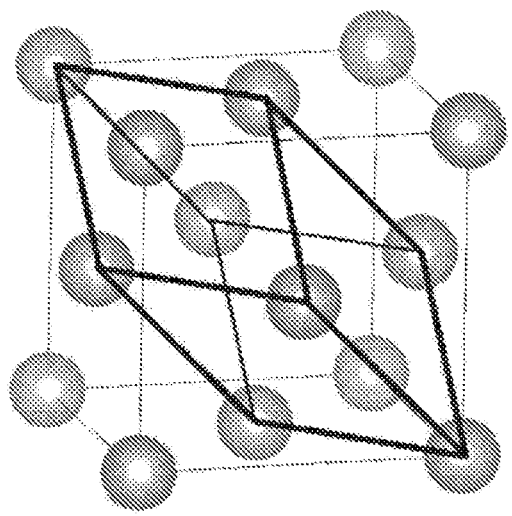
Figures 1, 1G, 2:
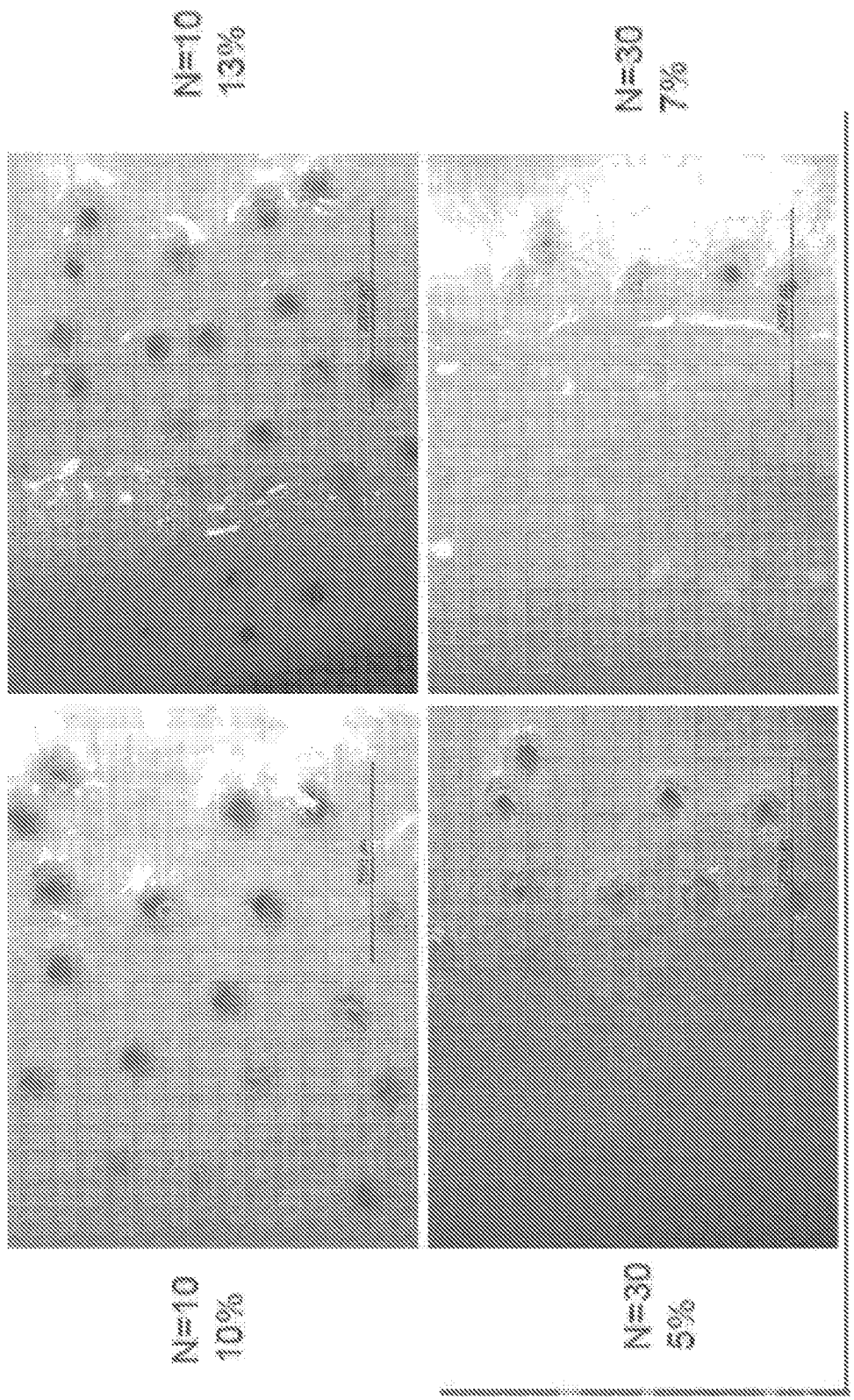
Figures 1, 1G, 2, 3:
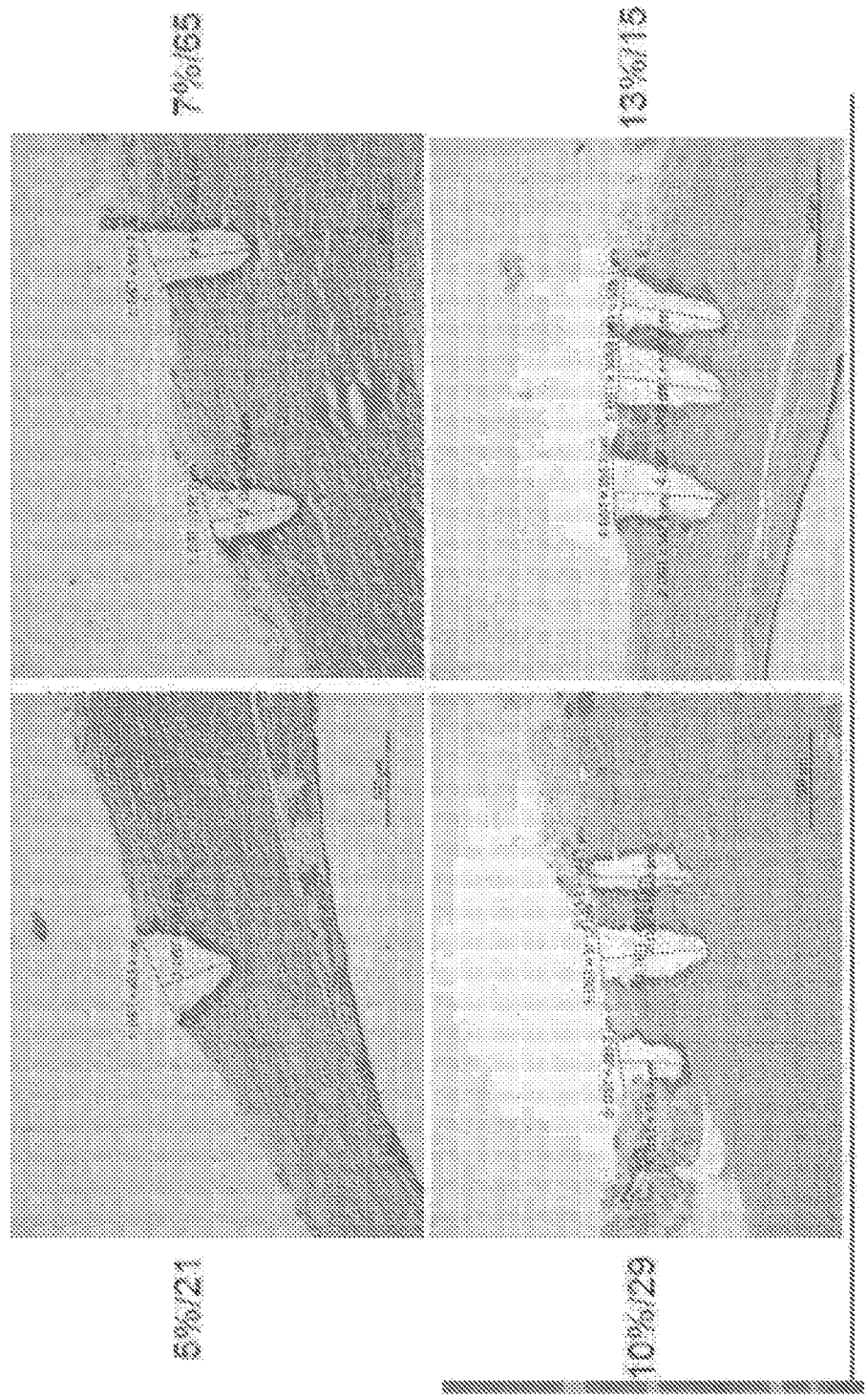
Figures 1, 1G, 2, 3, 4:
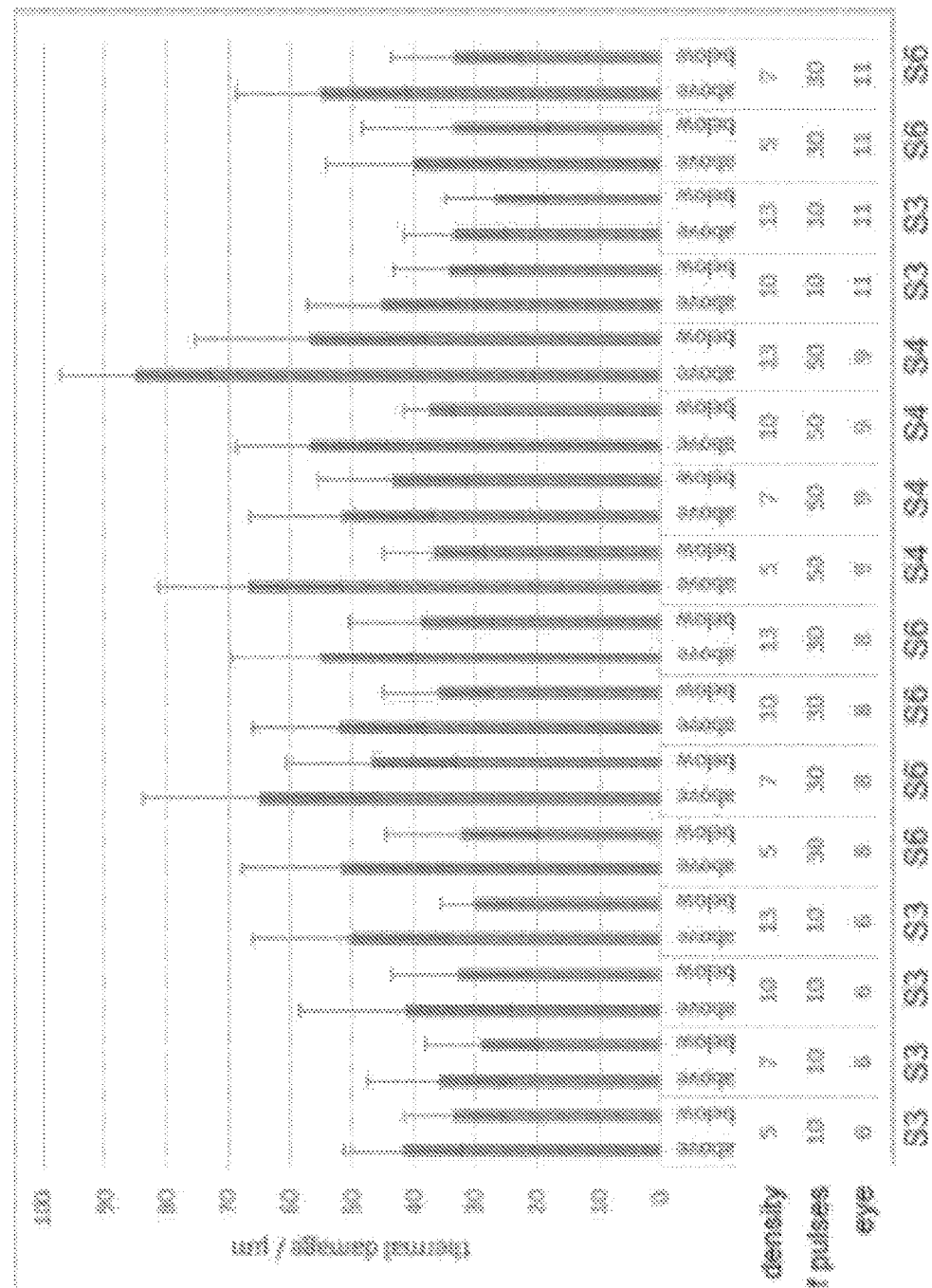

FIGS. 1F(a) to 1F(c) illustrate exemplary schematic projections of a basal plane of the hcp unit cell on close packed layers, according to an embodiment of the disclosure.

FIGS. 1G-1 to 1G-3 illustrate exemplary laser profiles, according to an embodiment of the disclosure.

FIG. 1G-4 illustrates exemplary chart of thermal damage zone (TDZ), according to an embodiment of the disclosure.

Figure 1H:
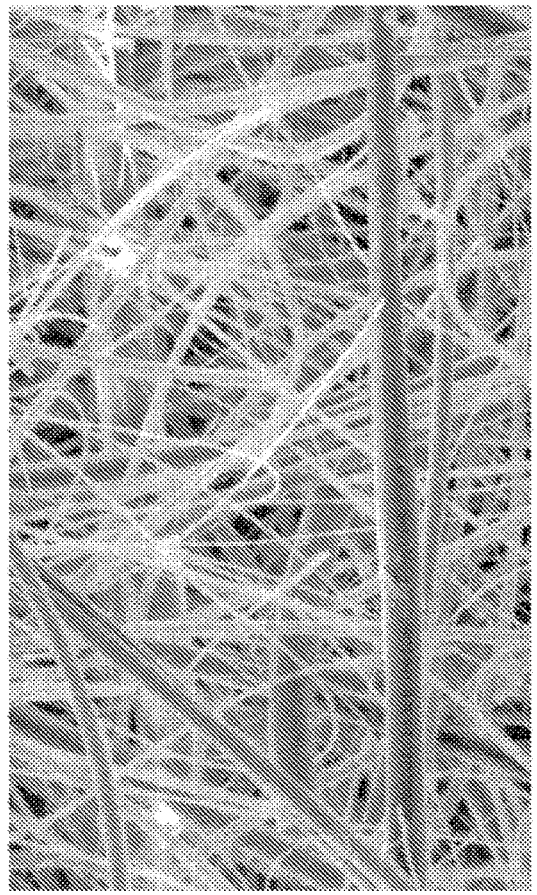

FIG. 1H illustrates exemplary pore structure characteristics, according to an embodiment of the disclosure.

Figures 1, 2A:
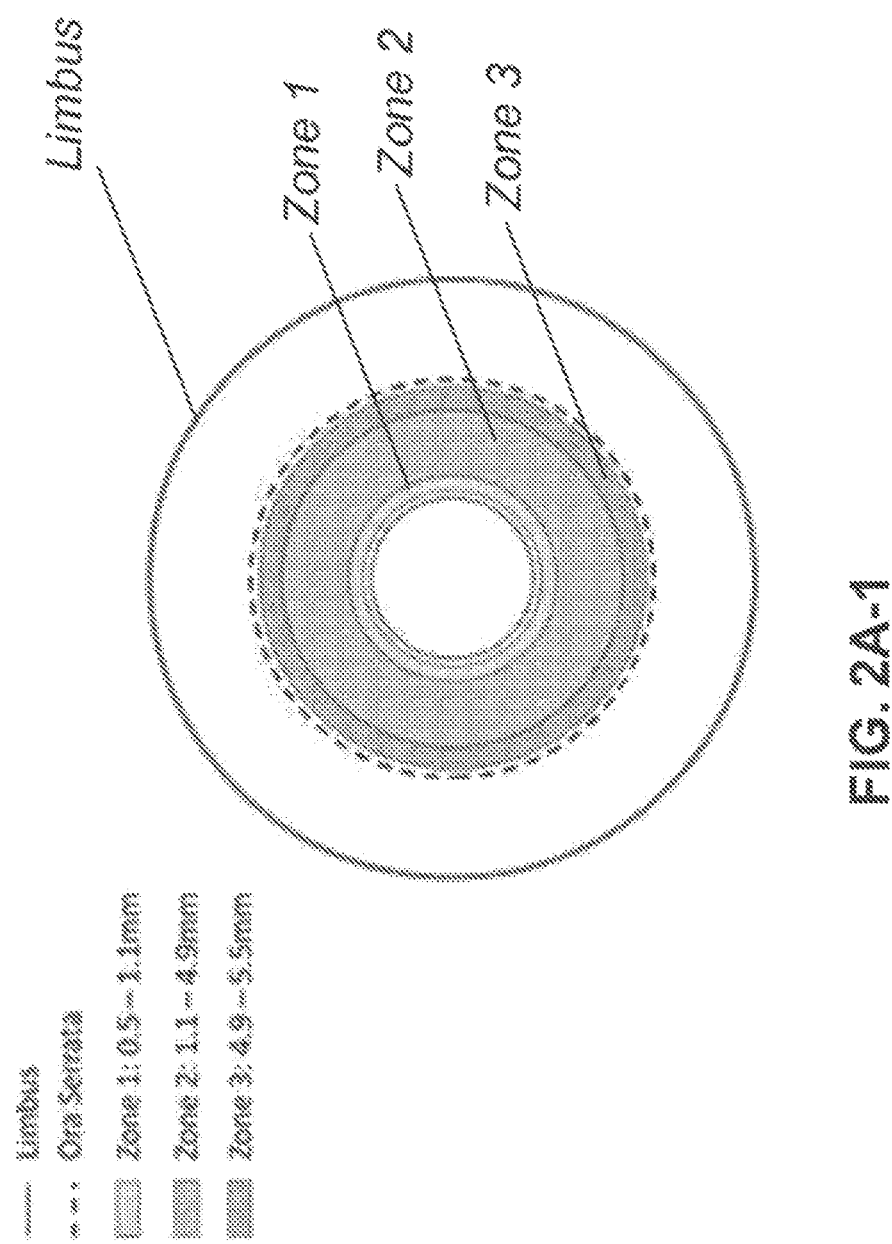
Figures 2, 2A:
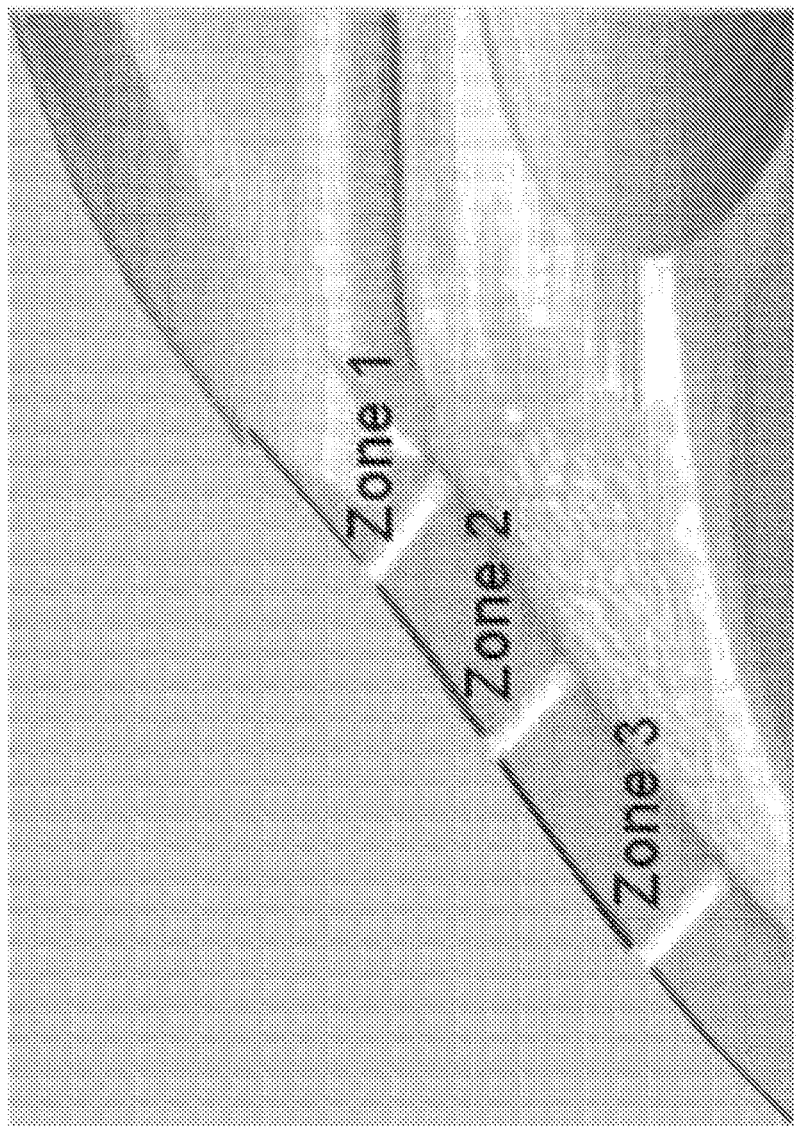
Figures 1, 2B:
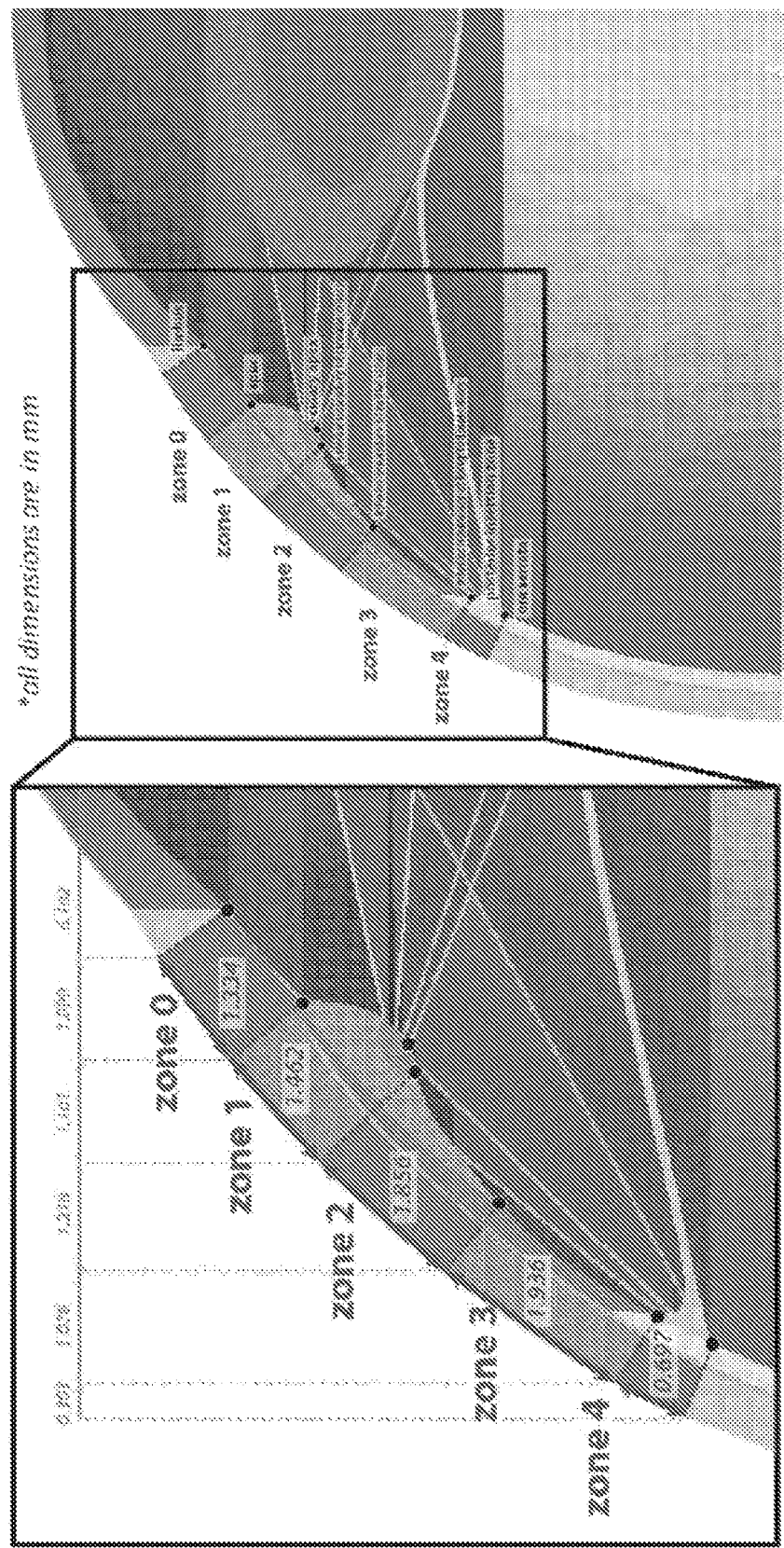
Figures 2, 2B:
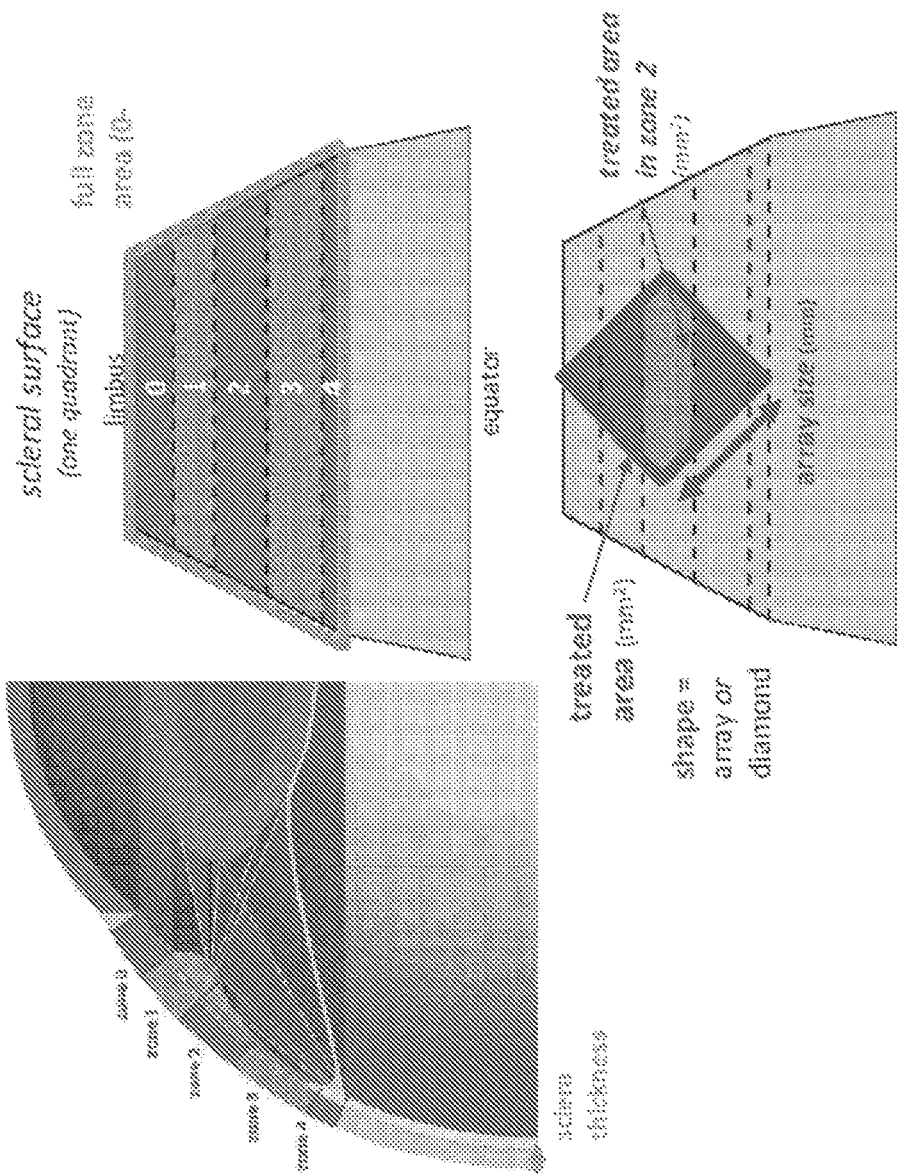
Figures 2, 2B, 3:
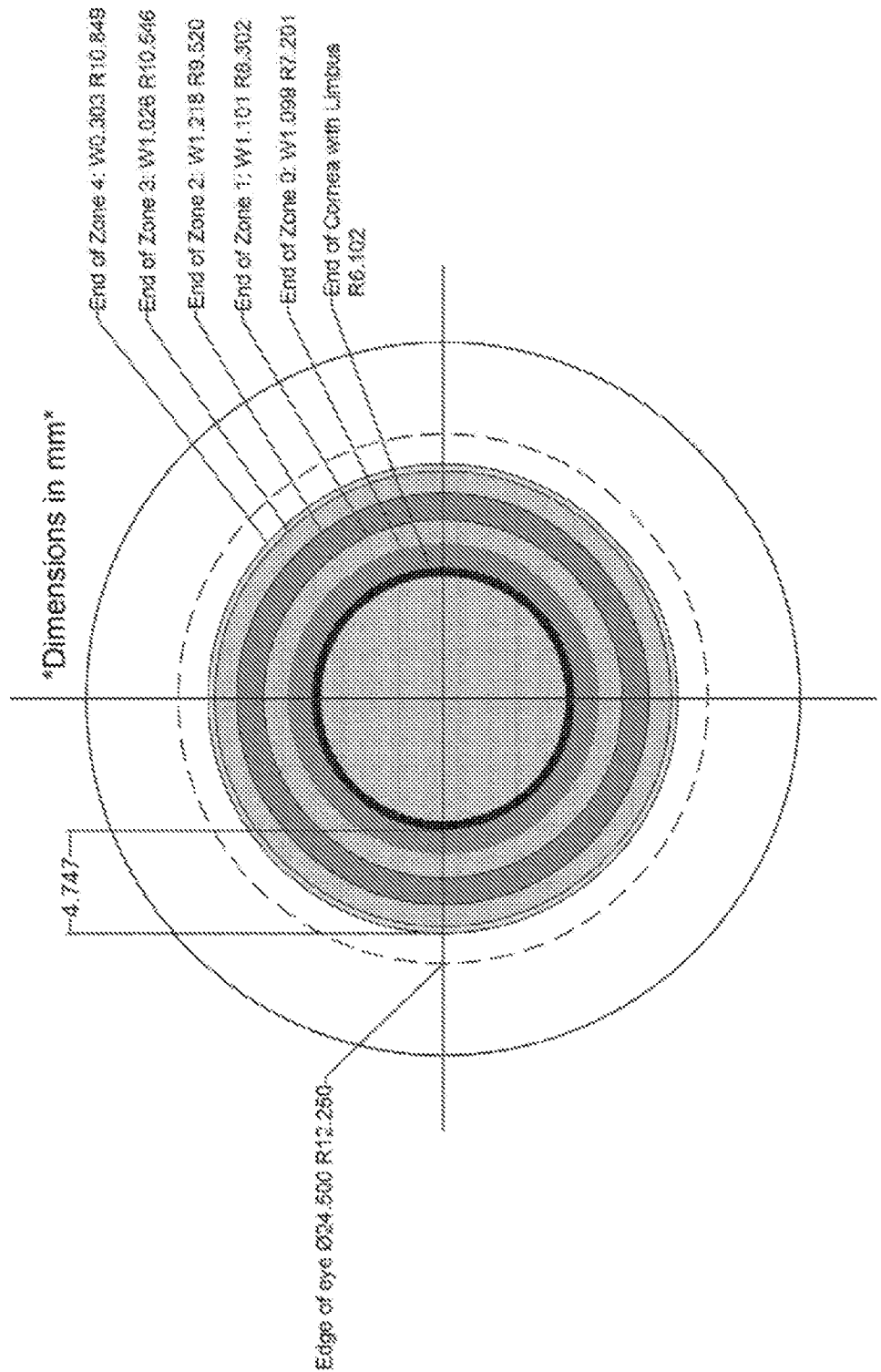
Figures 2, 2C, 3, 4:
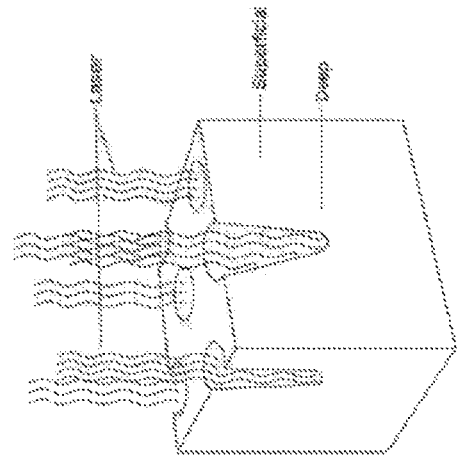
Figures 2, 2C, 3:
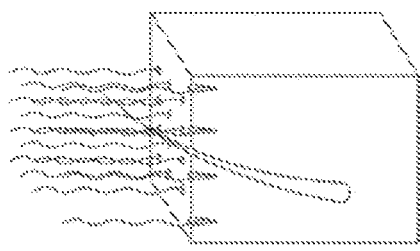
Figures 2, 2C:
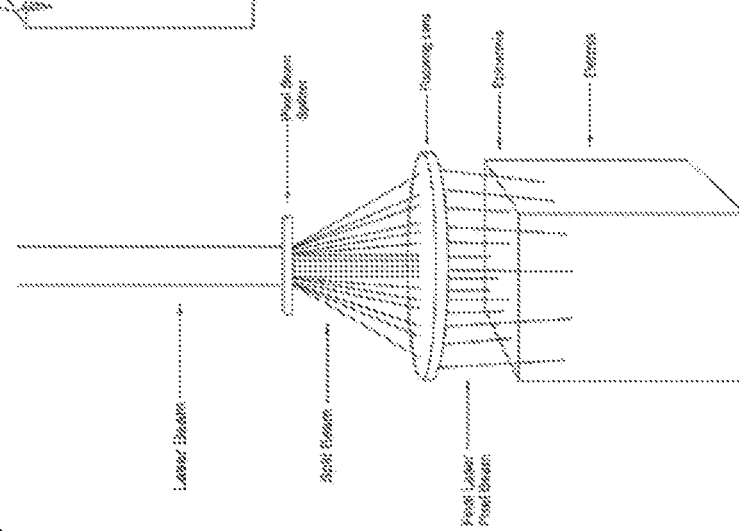
Figures 1, 2C:
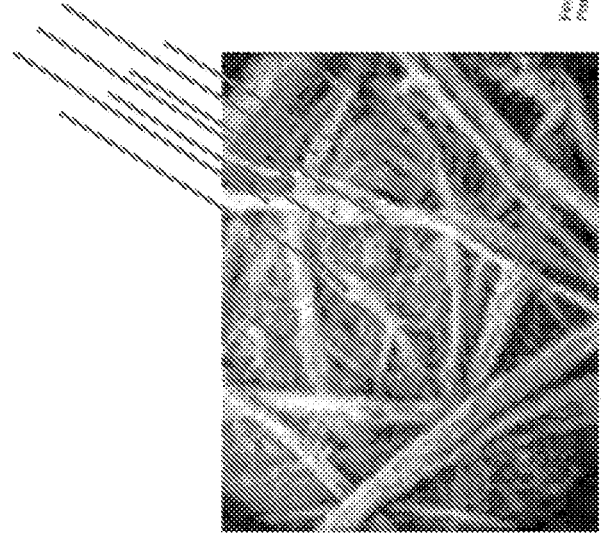
Figures 1, 2D:
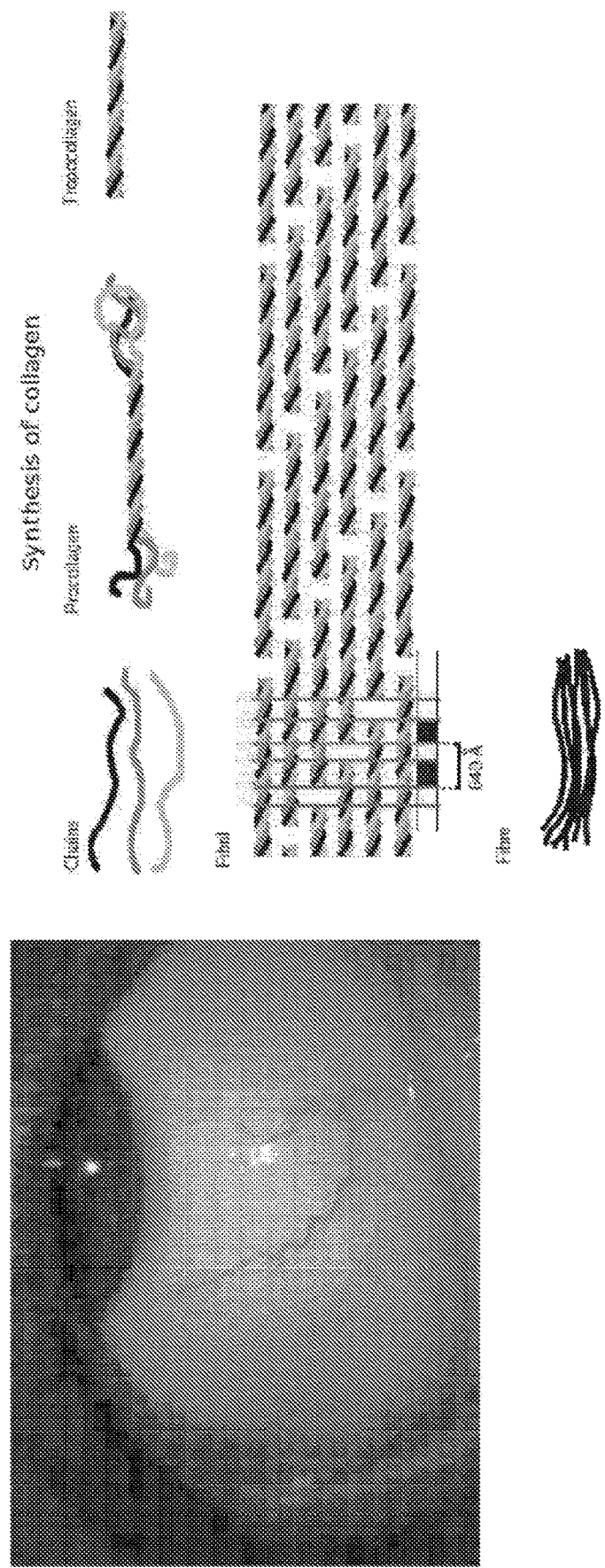
Figures 2, 2D, 3:
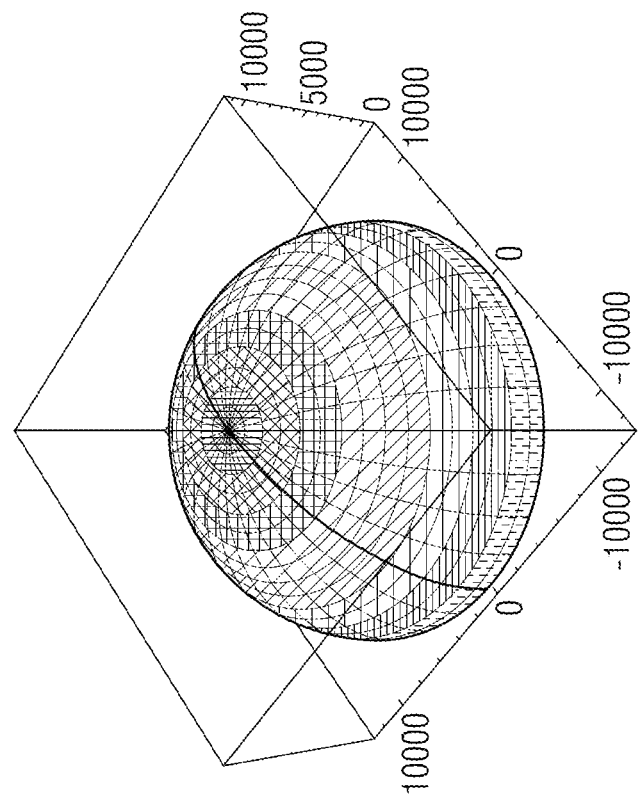
Figures 2, 2D:
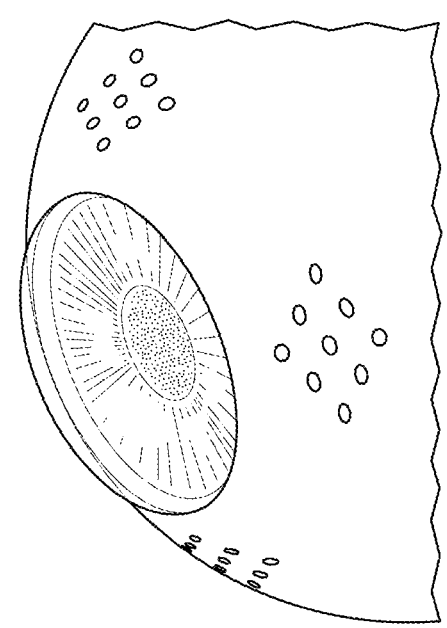
Figures 2, 2D, 3, 4:
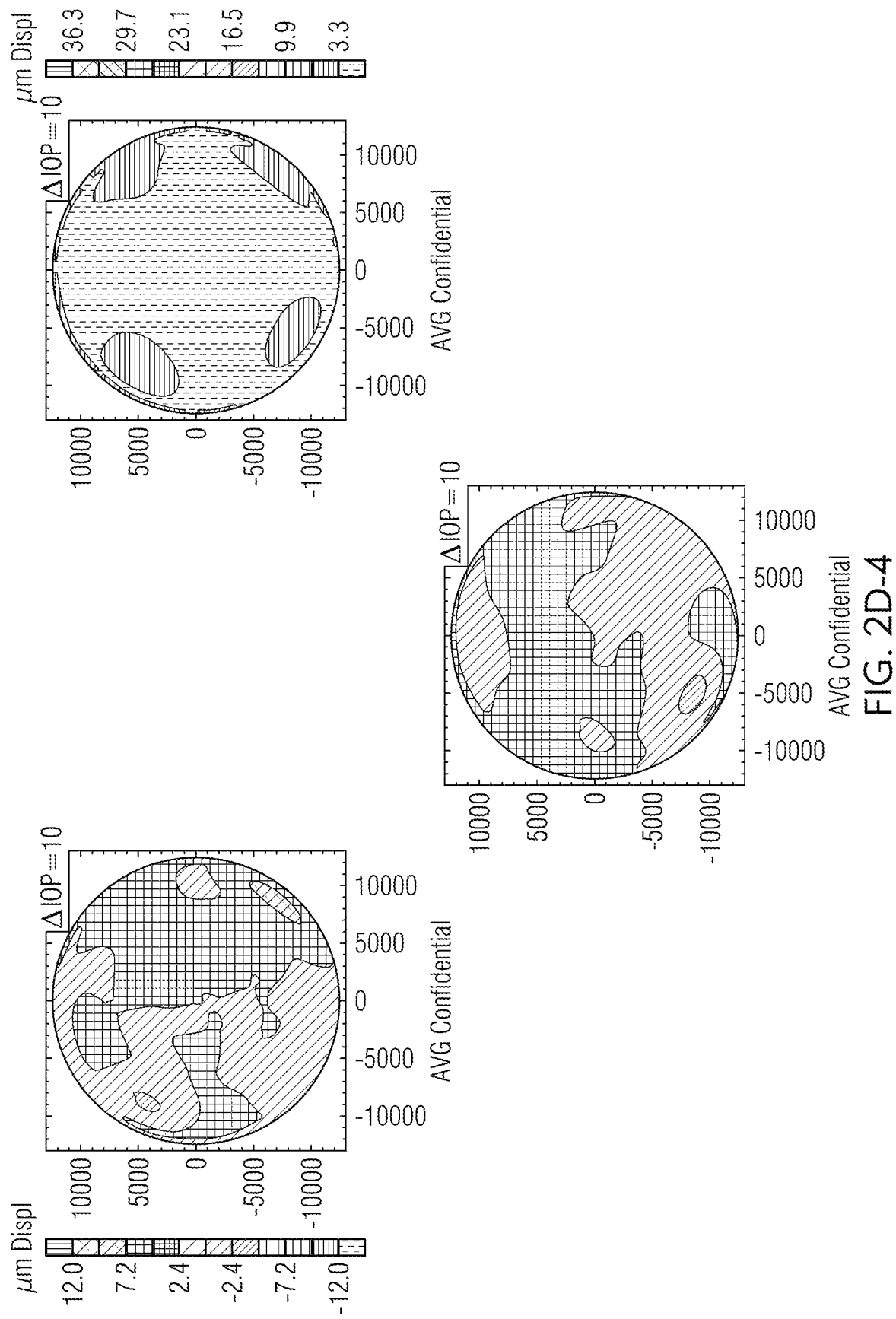

FIGS. 2A-1 to 2A-2 illustrate an exemplary treatment pattern with three critical zones, according to an embodiment of the disclosure.

FIGS. 2B-1 to 2B-3 illustrate an exemplary treatment pattern with five critical zones, according to an embodiment of the disclosure.

FIGS. 2C-1 to 2C-4 illustrate exemplary laser scleral uncrosslinking of scleral fibrils and microfibrils, according to an embodiment of the disclosure.

FIGS. 2D-1 to 2D-4 illustrate exemplary effect of treatment on ocular rigidity, according to an embodiment of the disclosure.

Figure 2E:
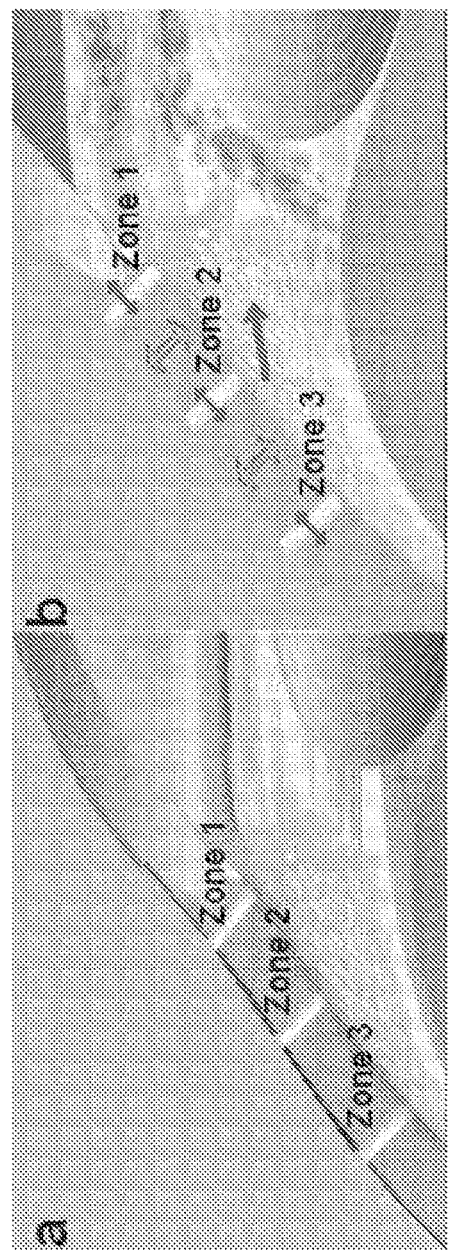

FIGS. 2E(a) and 2E(b) illustrate another exemplary three critical zones of significance, according to an embodiment of the disclosure.

Figure 2F:
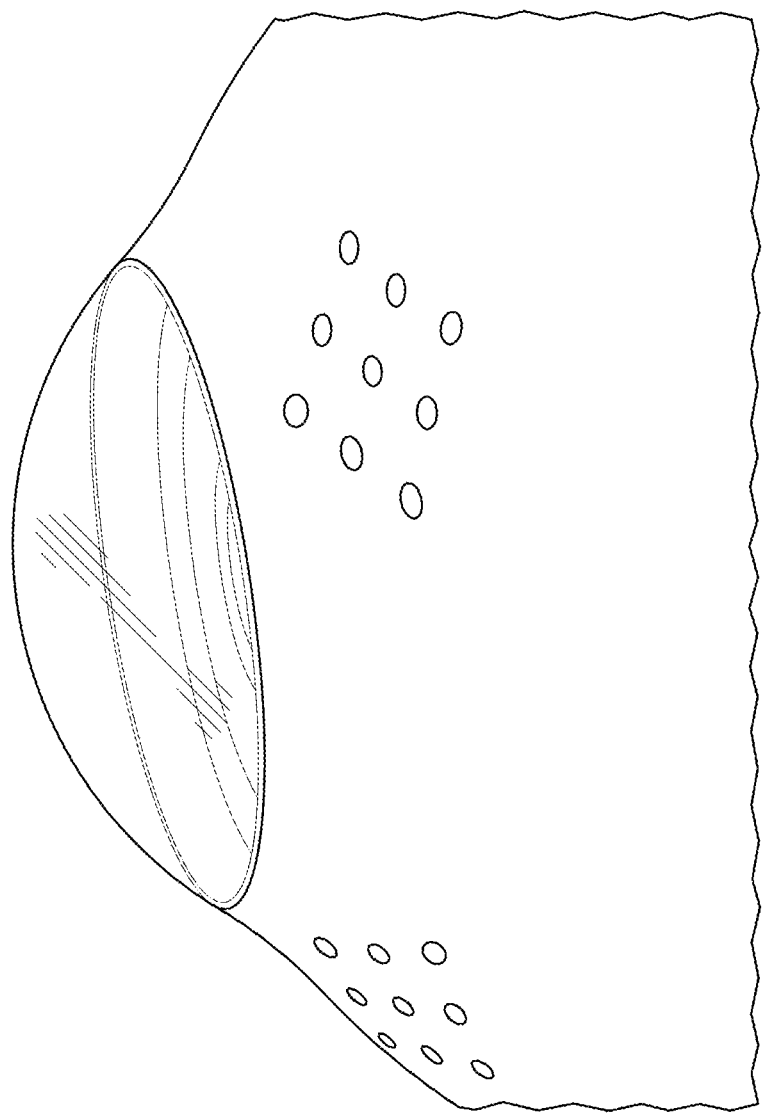

FIG. 2F illustrates an exemplary matrix array of microexcisions in four oblique quadrants, according to an embodiment of the disclosure.

Figure 2G:
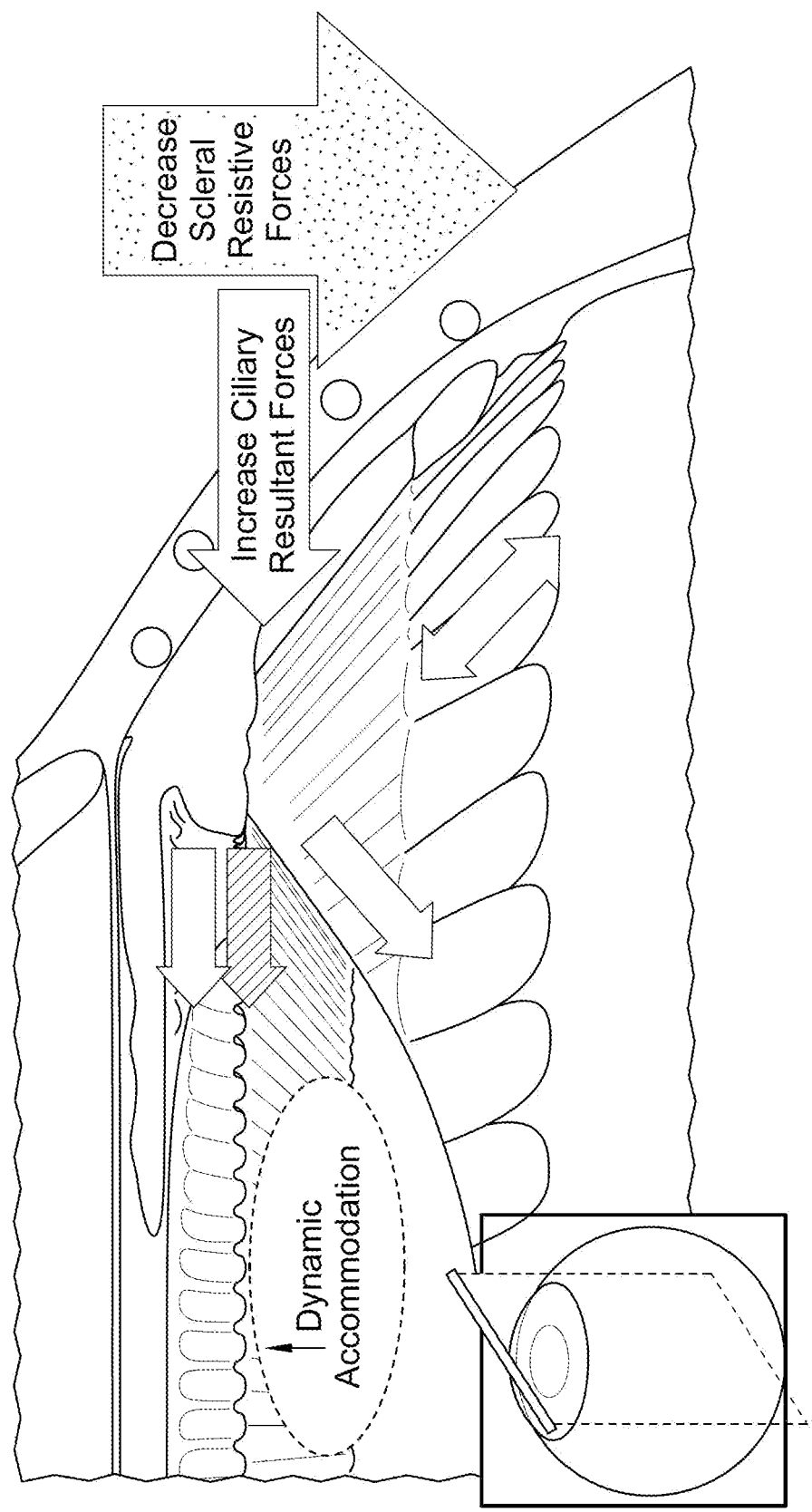

FIG. 2G illustrates an exemplary graphical representation of treatment results, according to an embodiment of the disclosure.

Figure 2H:
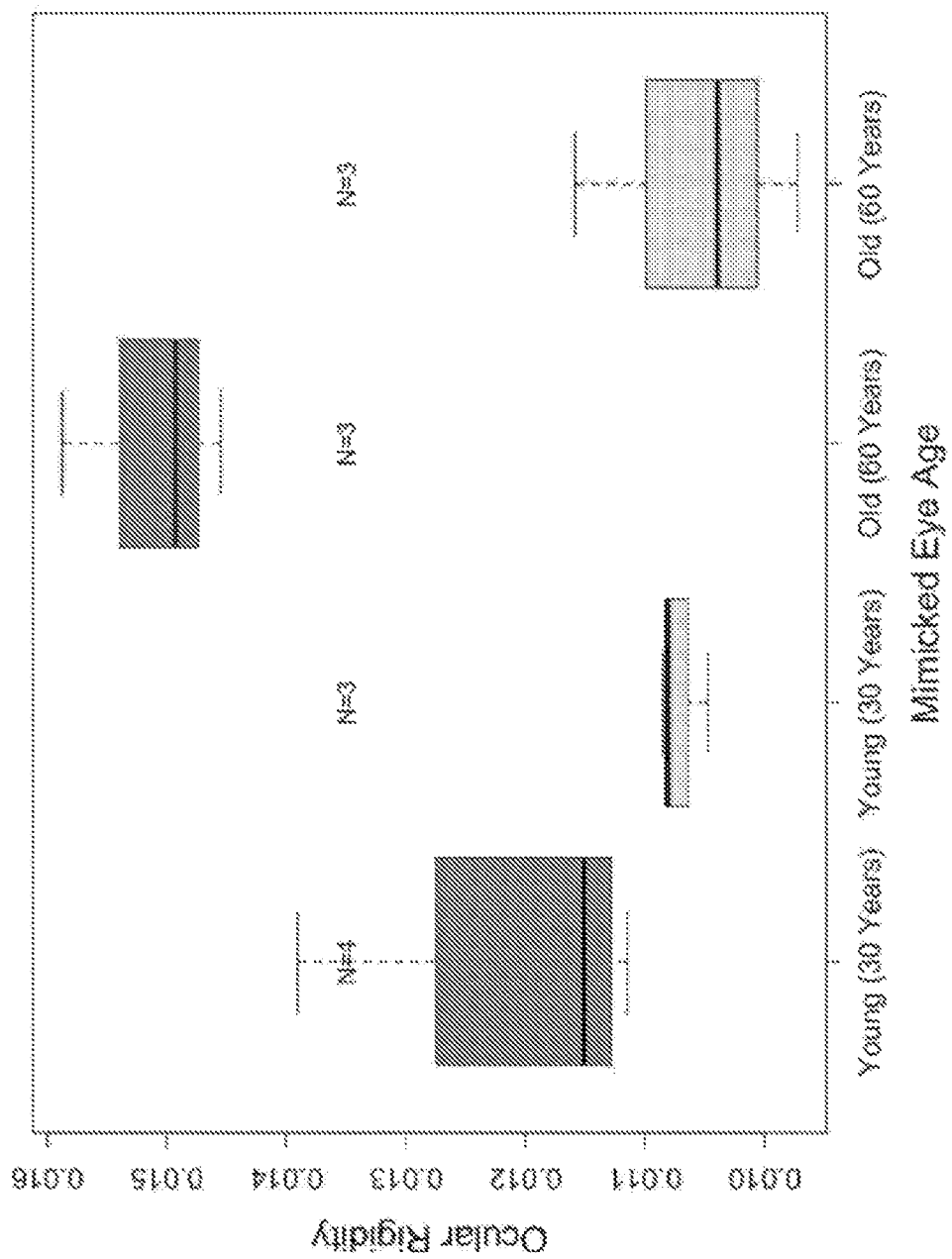
Figure 21:
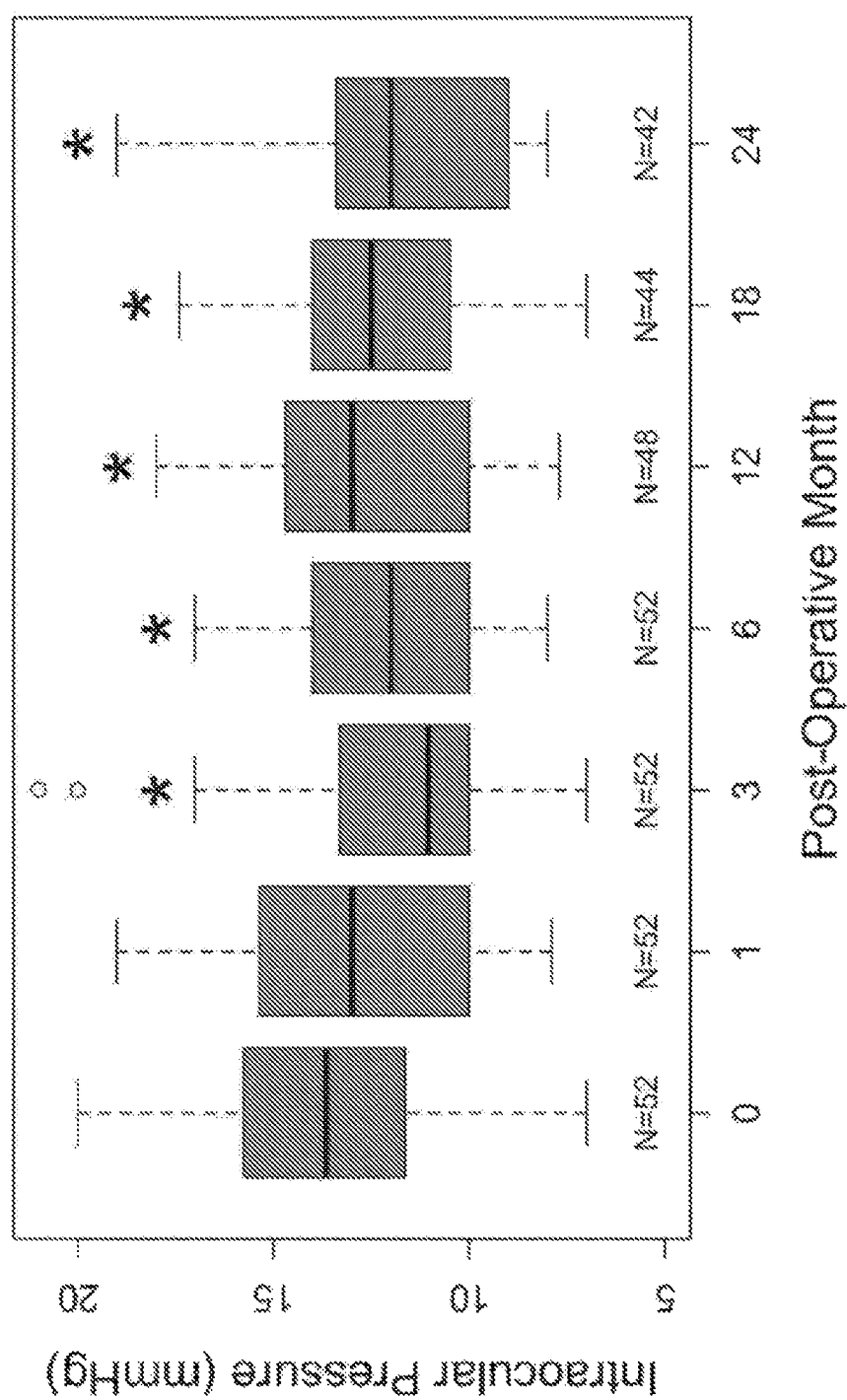

FIG. 2H illustrates an exemplary box-and-whiskers plot of the ocular rigidity, according to an embodiment of the disclosure.

FIG. 2I illustrates an exemplary box-and-whiskers plot of pre- and post-operative intraocular pressure, according to an embodiment of the disclosure.

Figure 2J:
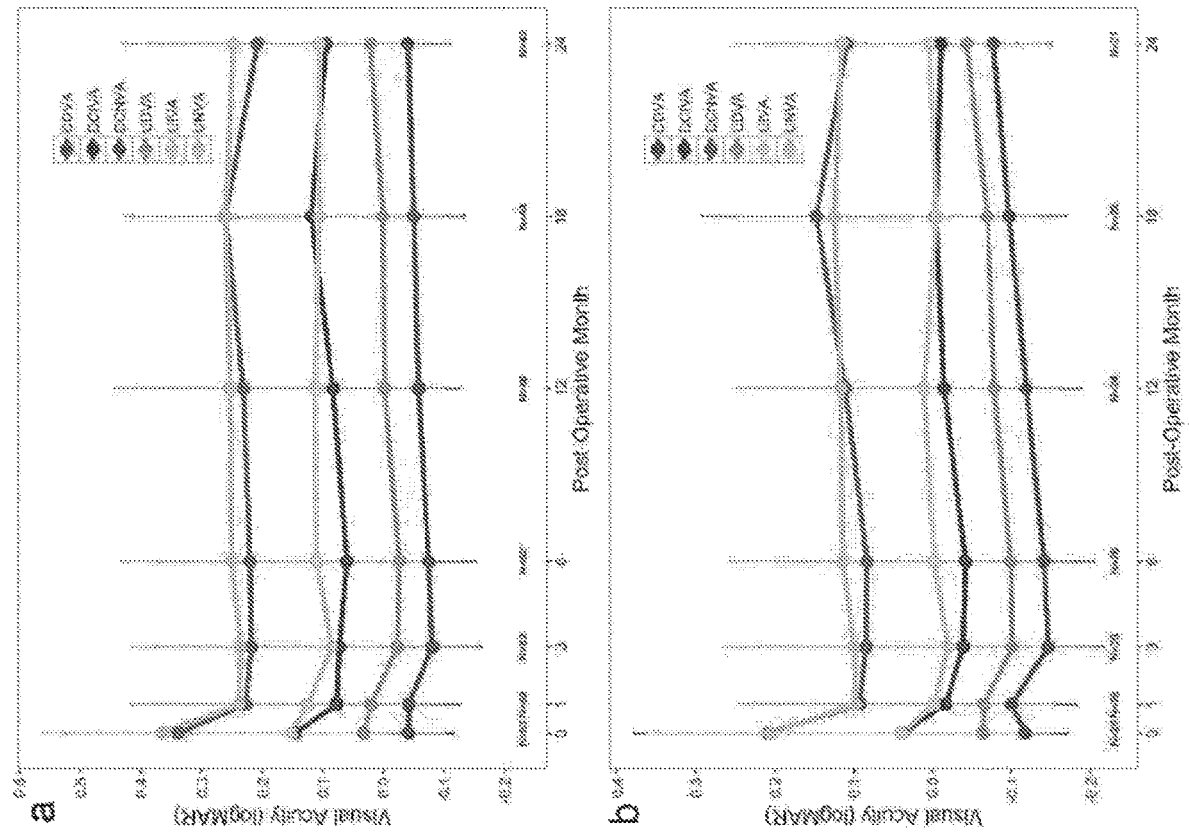

FIG. 2J illustrates exemplary charts showing uncorrected and distance-corrected visual acuity, according to an embodiment of the disclosure.

Figures 1, 2K:
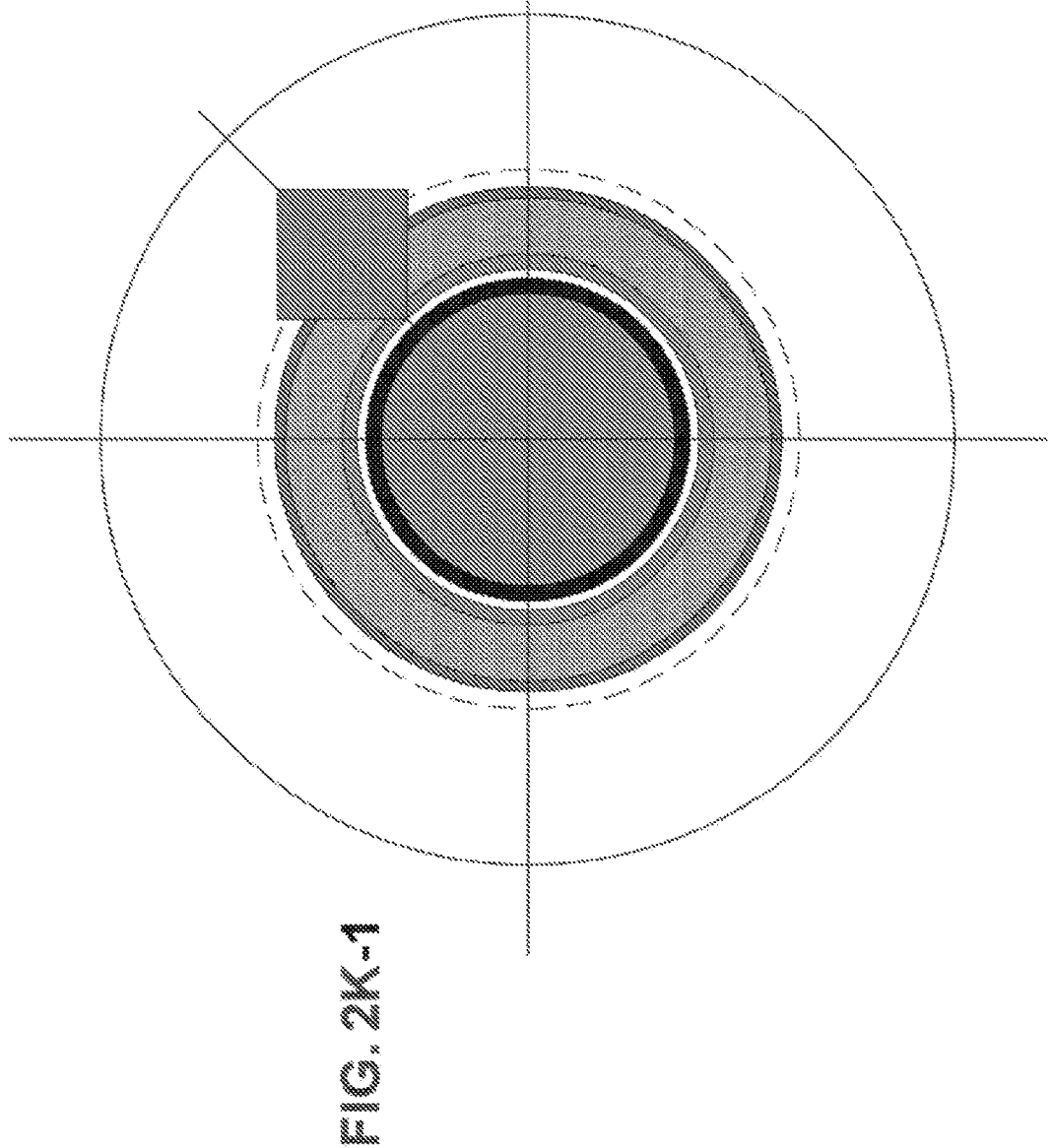
Figures 2, 2K:
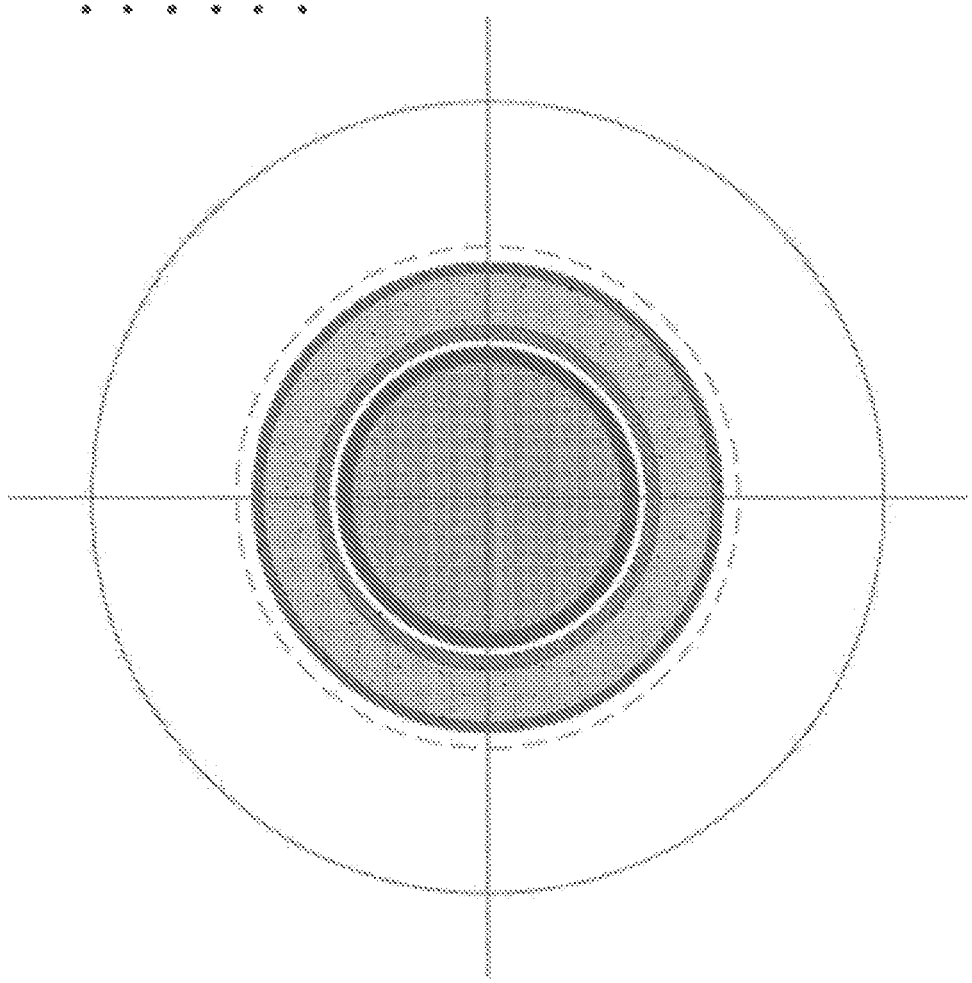
Figures 2, 2K, 3:
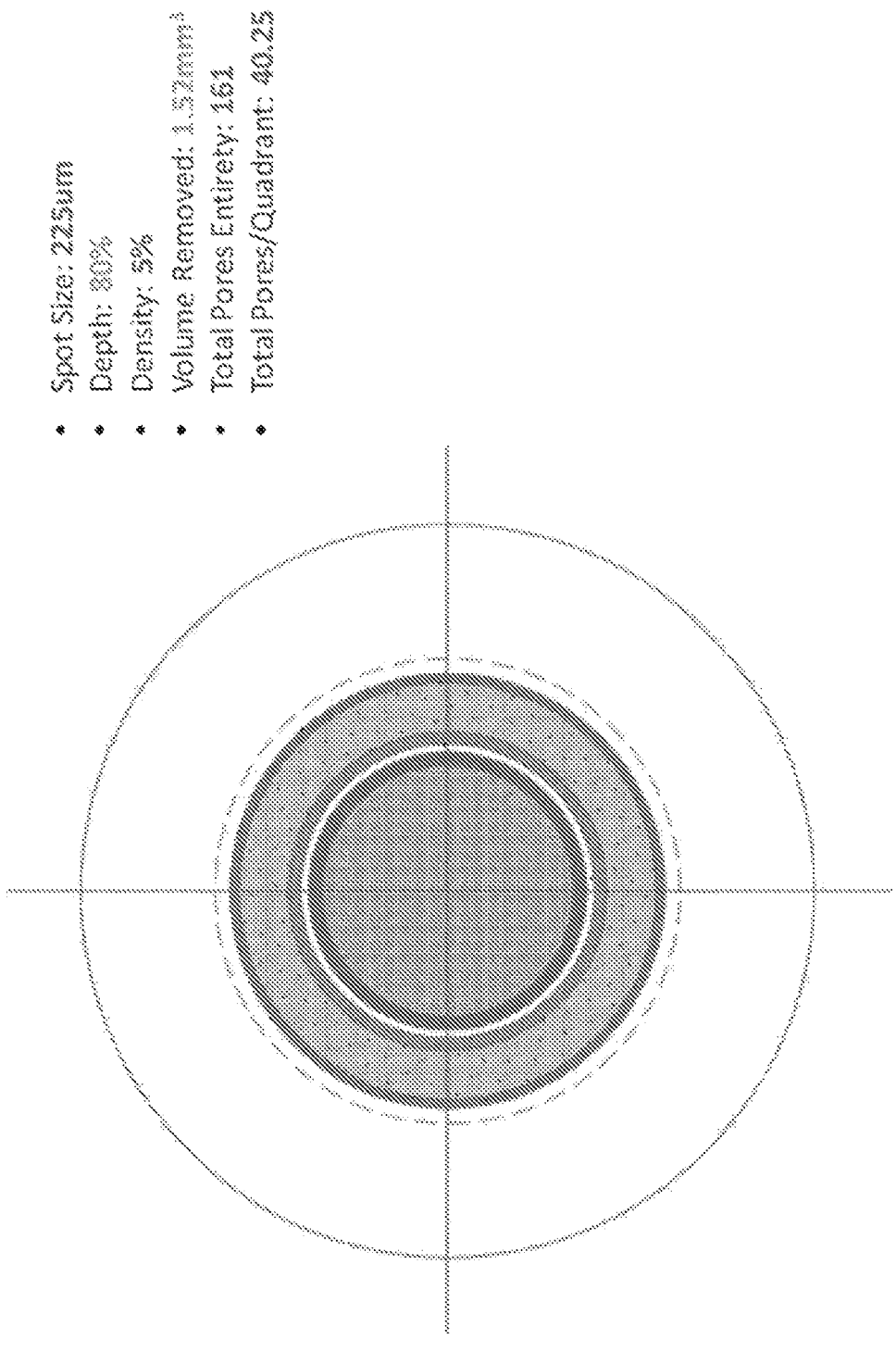
Figures 2, 2K, 3, 4:
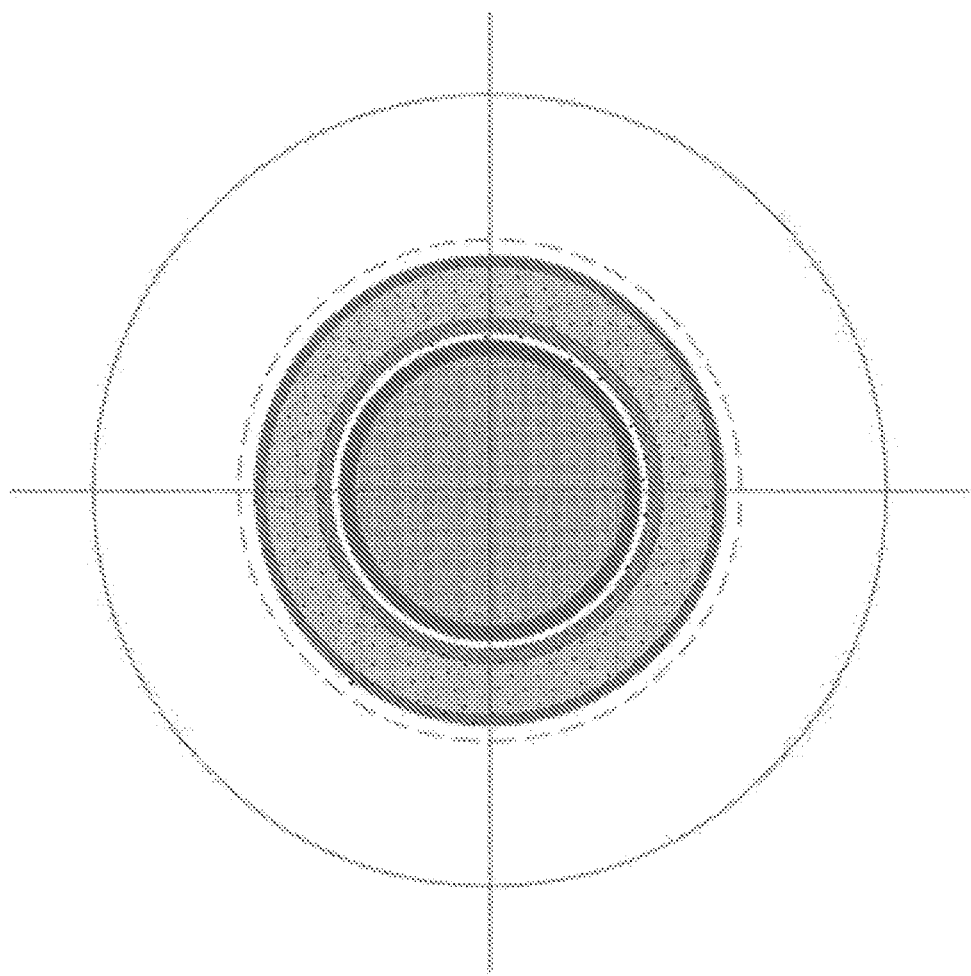
Figures 2, 2K, 3, 4, 5:
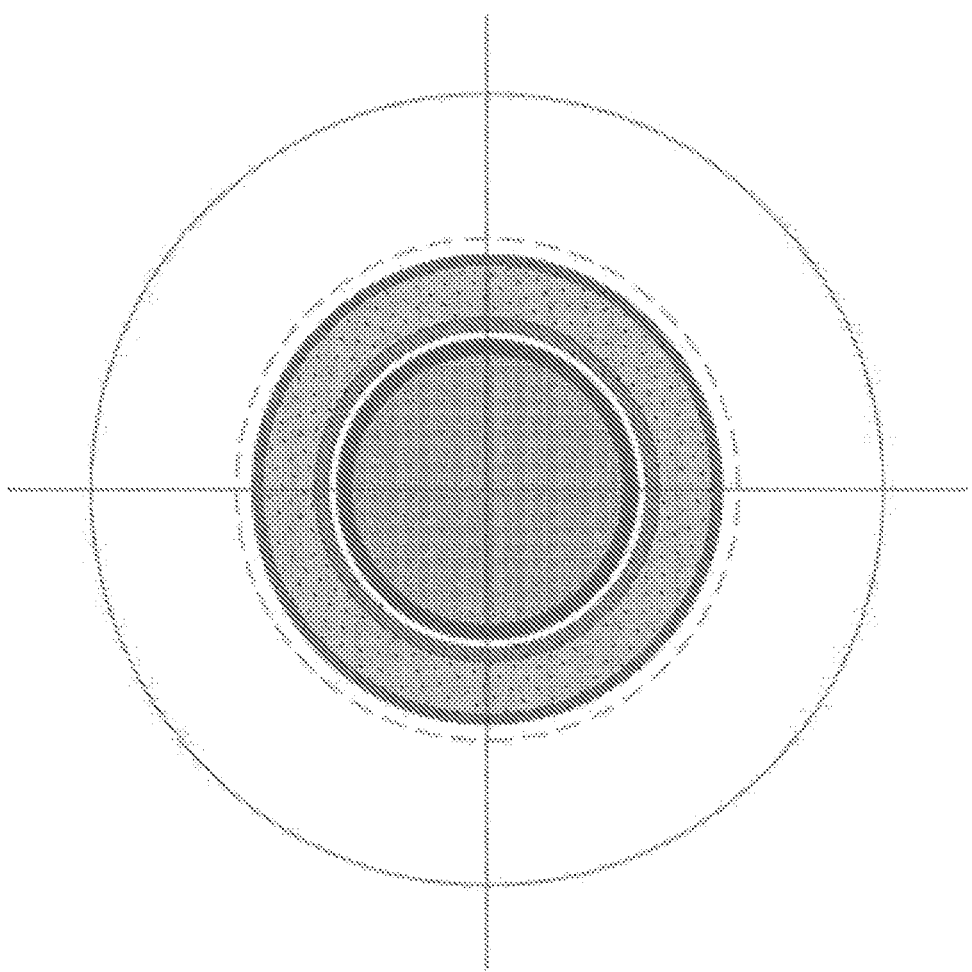

FIG. 2K-1 illustrates an exemplary protocol execution, according to an embodiment of the disclosure.

FIGS. 2K-1-A to 2K-1-C illustrate exemplary protocol parameters for three critical zones, according to an embodiment of the disclosure.

FIGS. 2K-2 to 2K-17 illustrate exemplary views of various protocols and their results, according to an embodiment of the disclosure.

FIGS. 2K-18 to 2K-19 illustrate other exemplary microporation patterns, according to an embodiment of the disclosure.

FIG. 2K-20 illustrates another exemplary pattern, according to an embodiment of the disclosure.

Figure 3A:
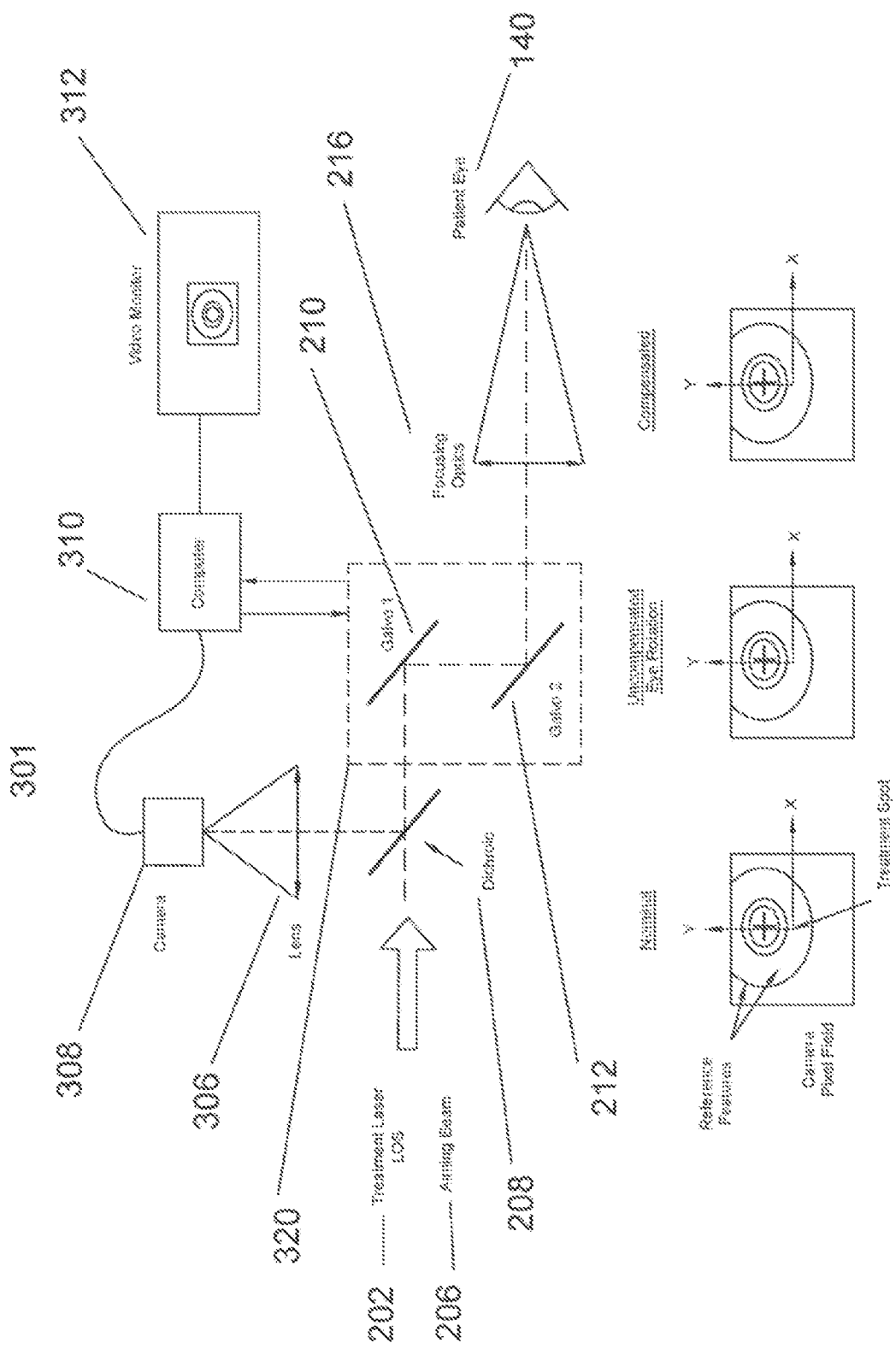

FIG. 3A illustrates an exemplary laser treatment system, according to an embodiment of the disclosure.

Figure 3B:
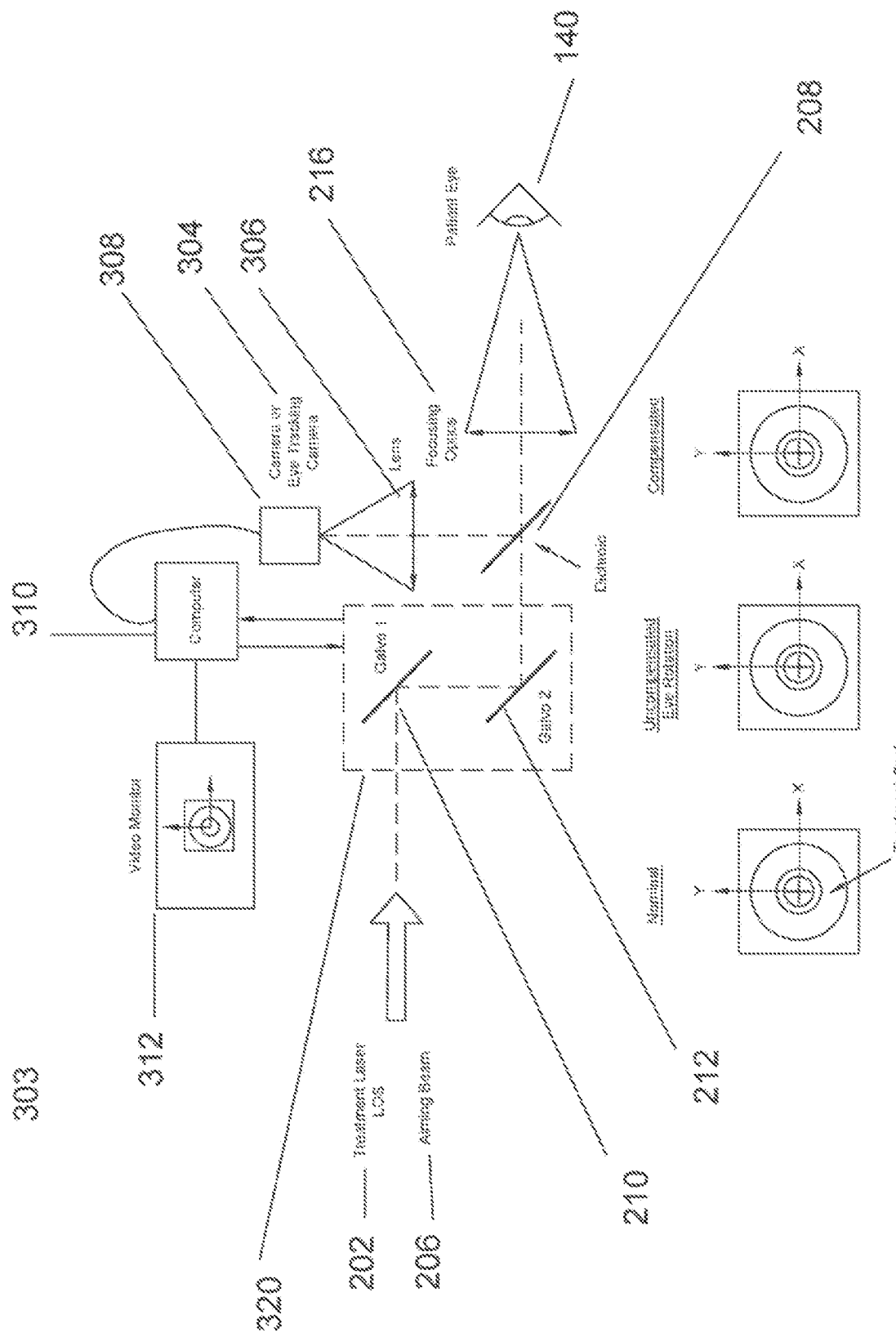

FIG. 3B illustrates another exemplary laser treatment system, according to an embodiment of the disclosure.

Figure 3C:
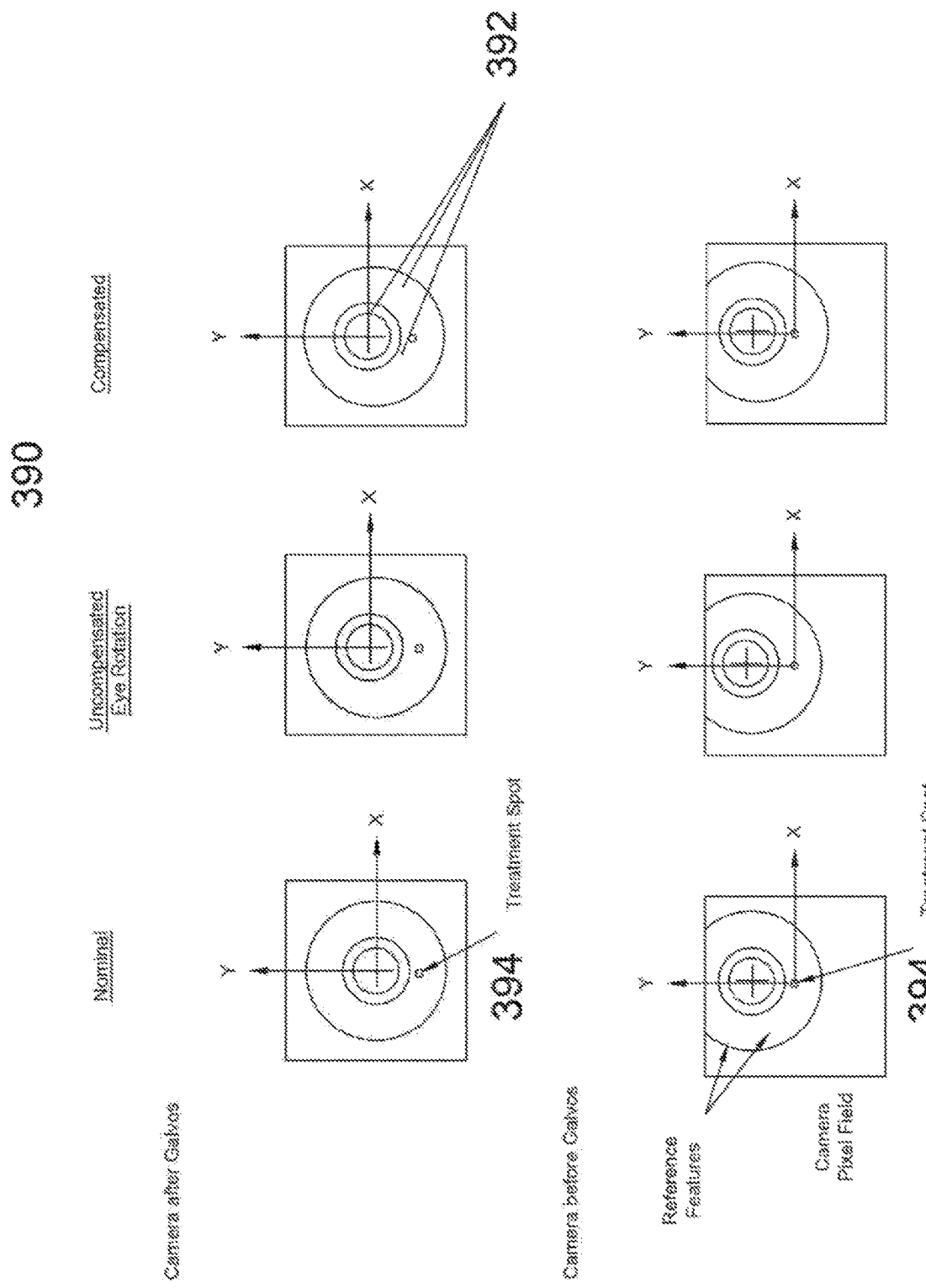

FIG. 3C illustrates an exemplary camera correction system, according to an embodiment of the disclosure.

Figure 3D:
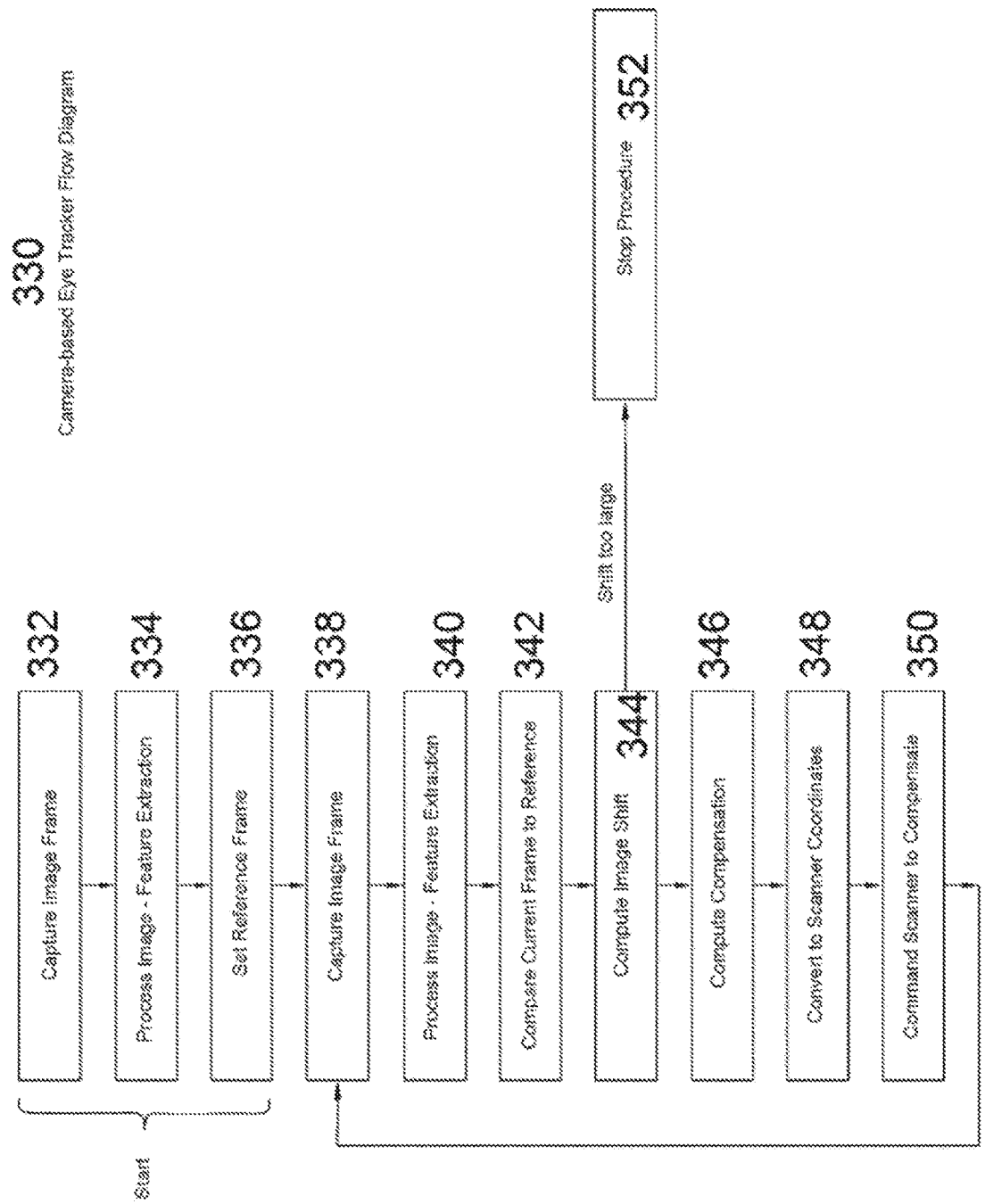

FIG. 3D illustrates an exemplary flow diagram of a camera-based eye tracker process, according to an embodiment of the disclosure.

Figure 4A:
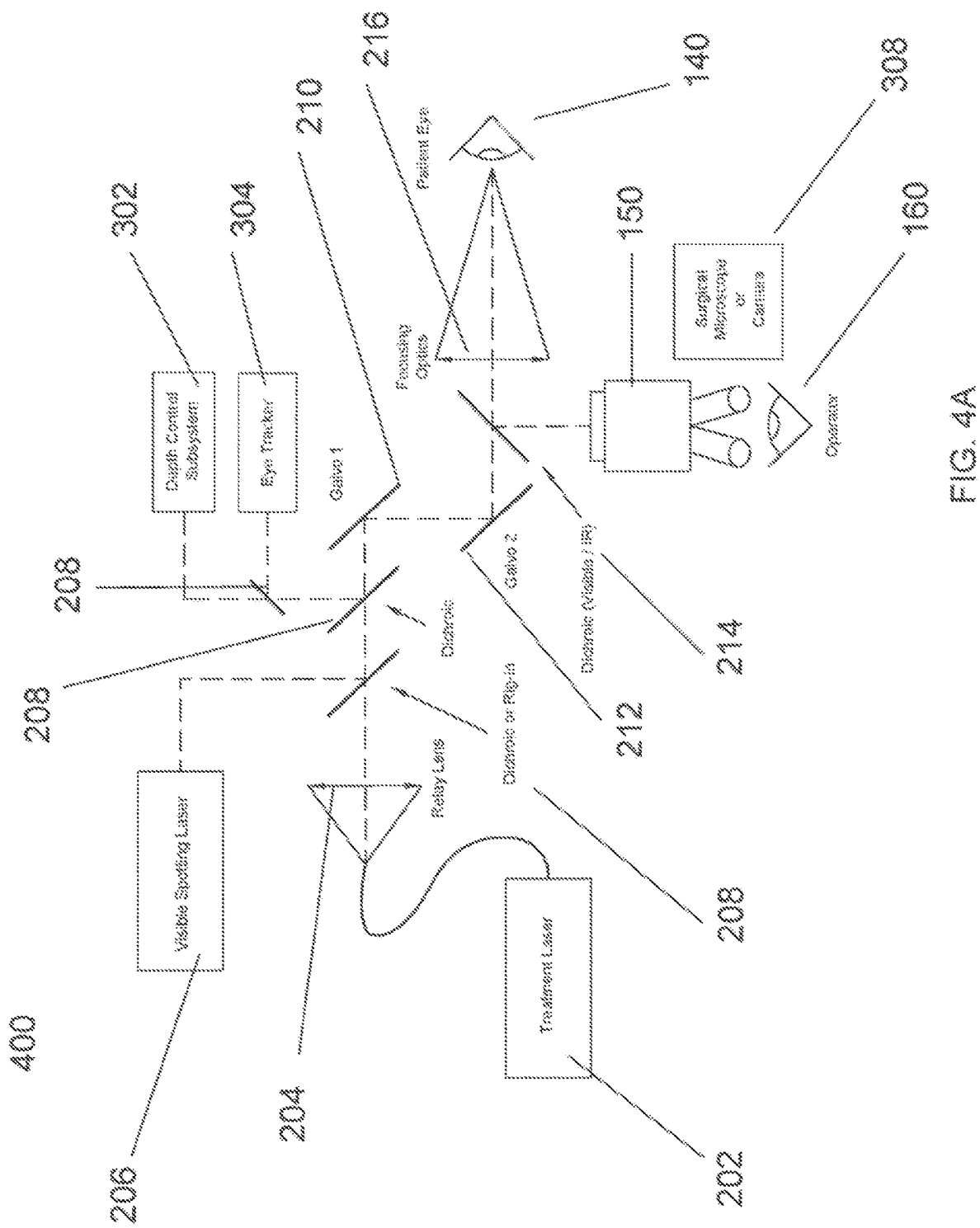
Figures 1, 4A:
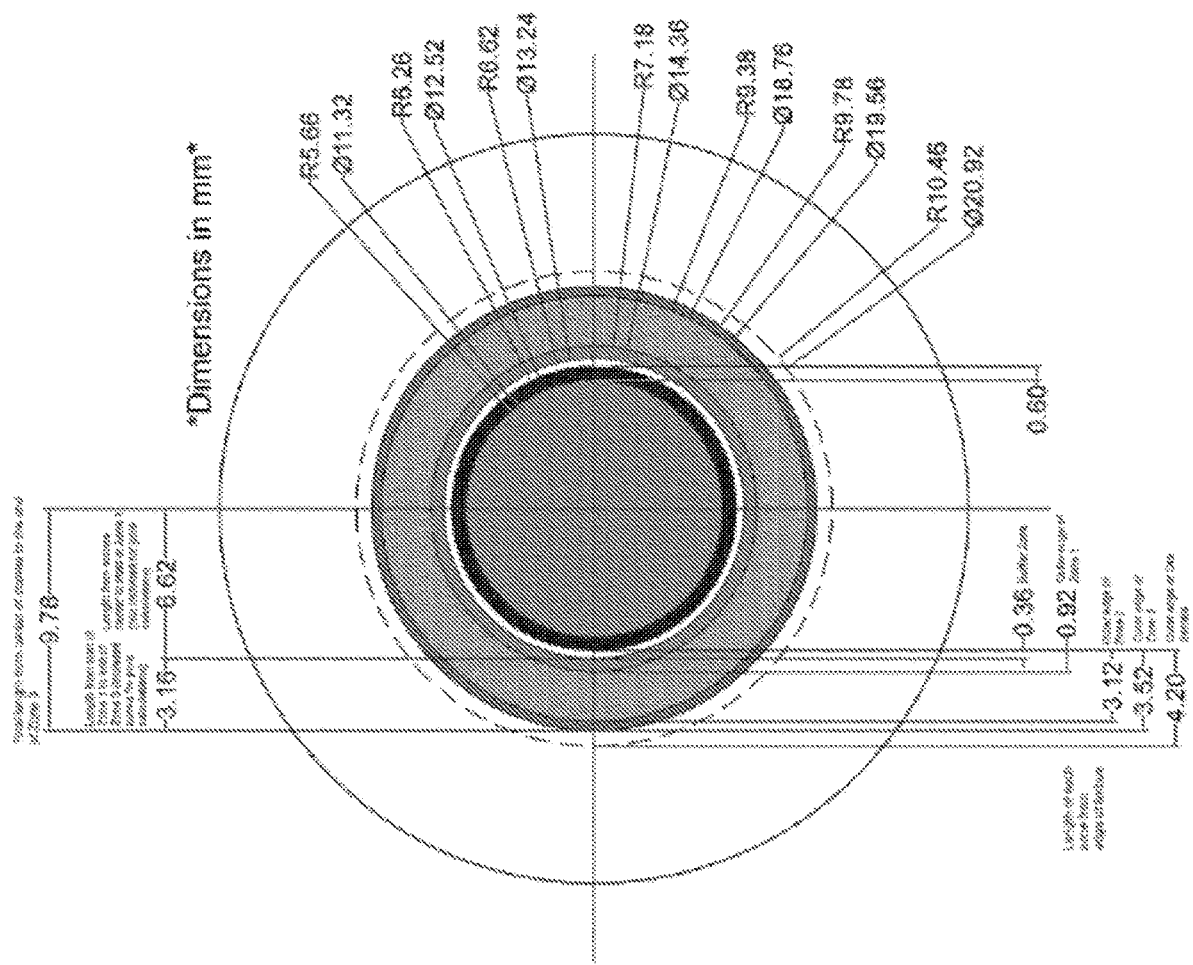
Figures 2, 4A:
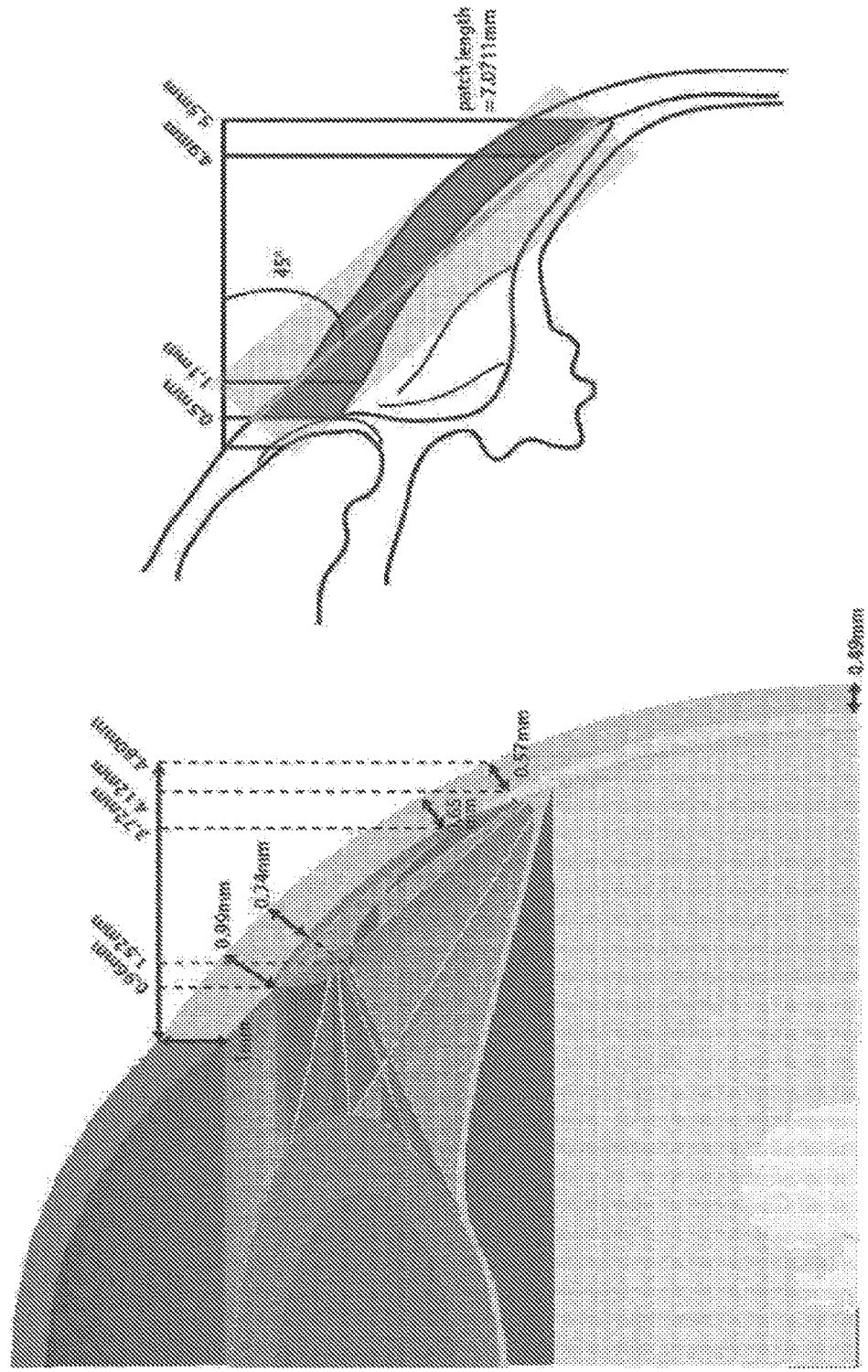
Figures 3, 4, 4A:
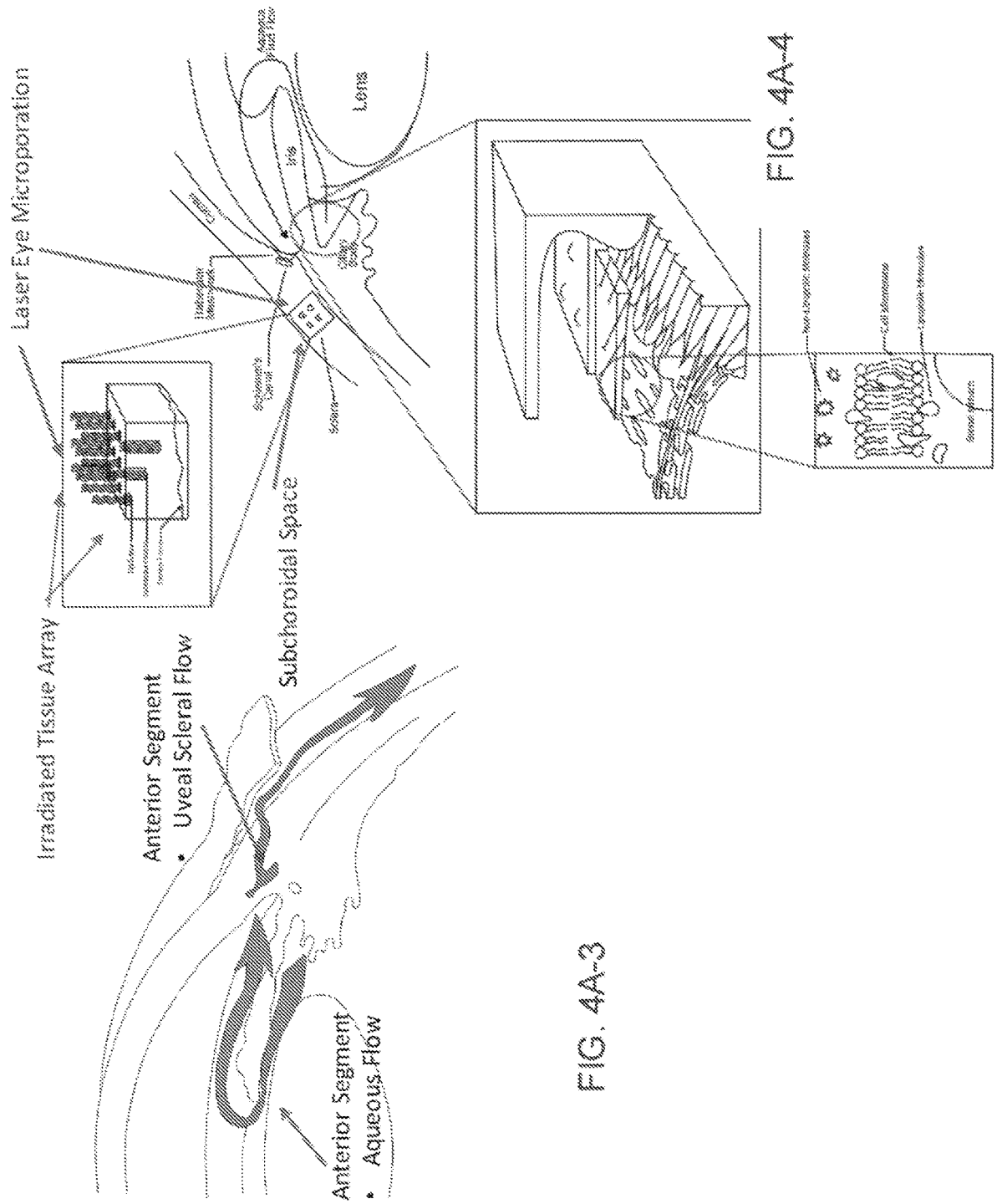
Figures 4, 4A, 5:
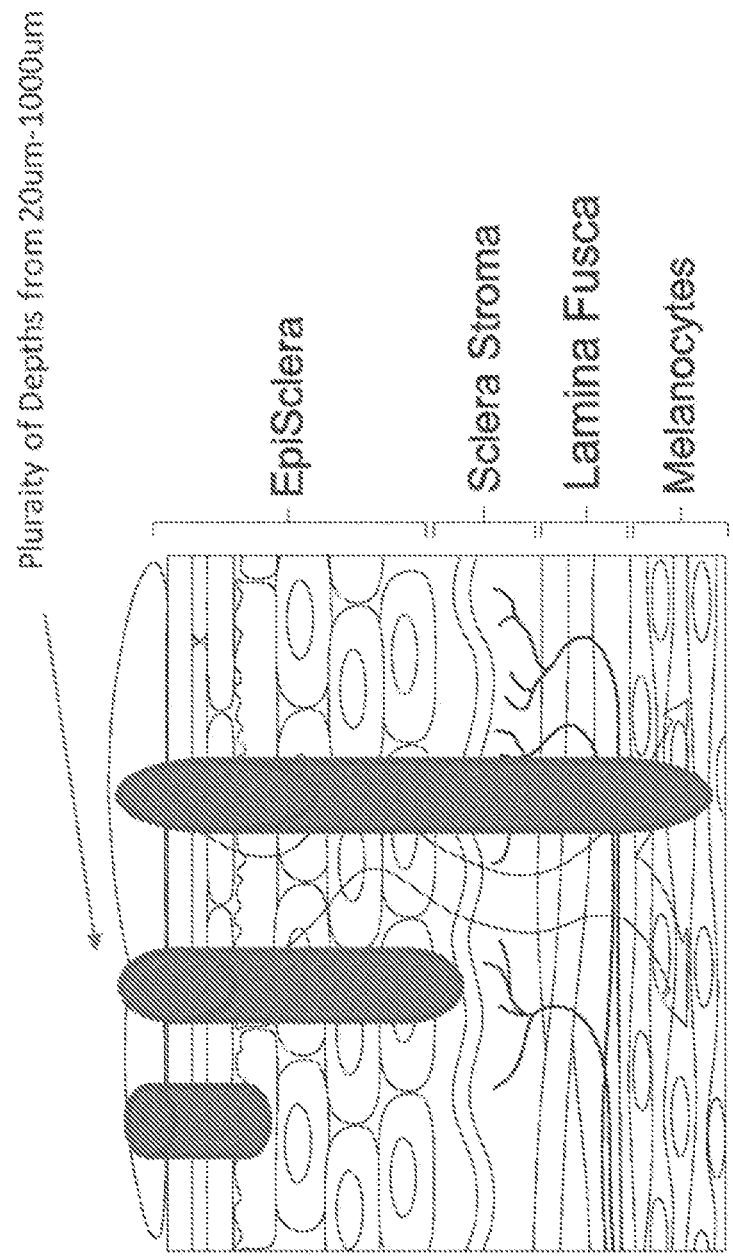
Figures 4, 4A, 5, 6, 7:
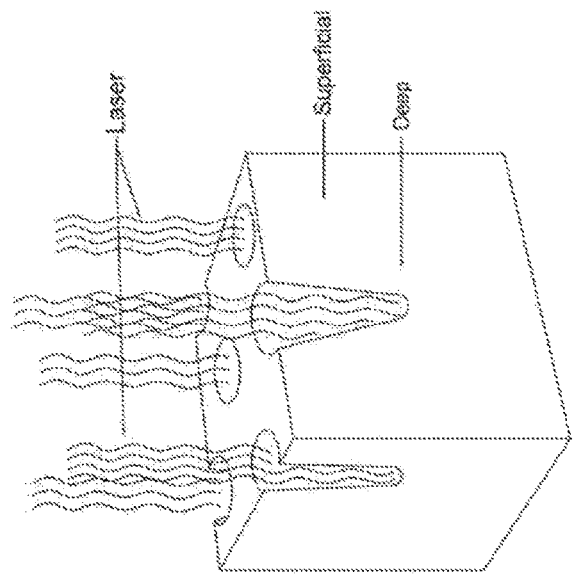
Figures 4, 4A, 5, 6, 7, 8:
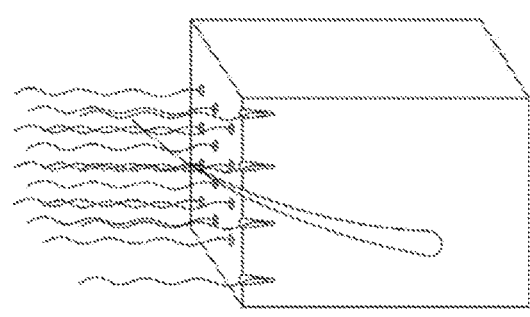
Figures 4, 4A, 5, 6:
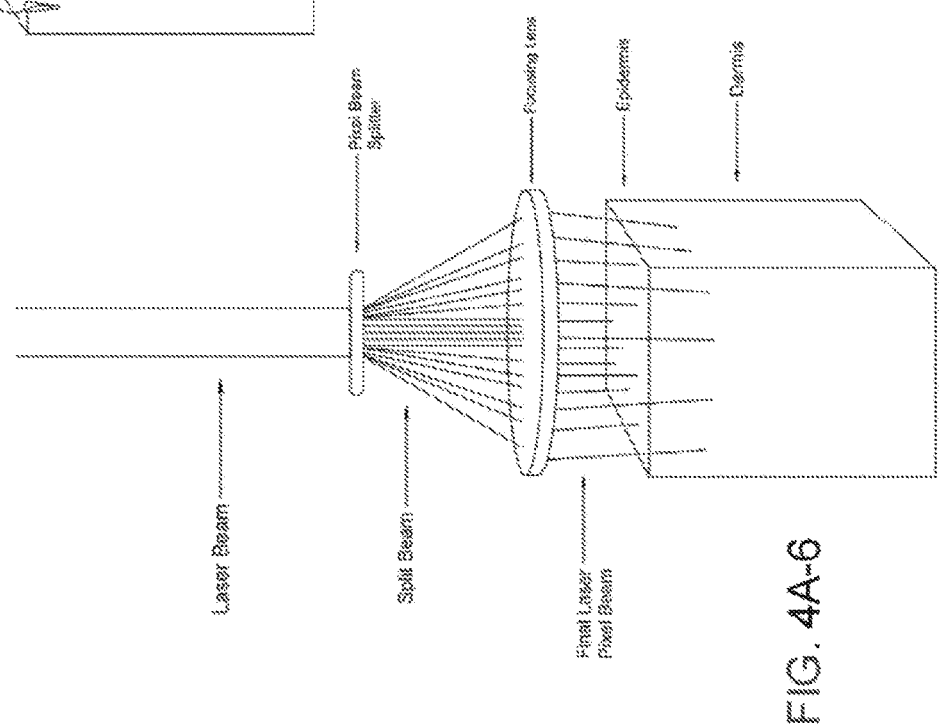
Figures 4, 4A, 5, 6, 7, 8, 9:
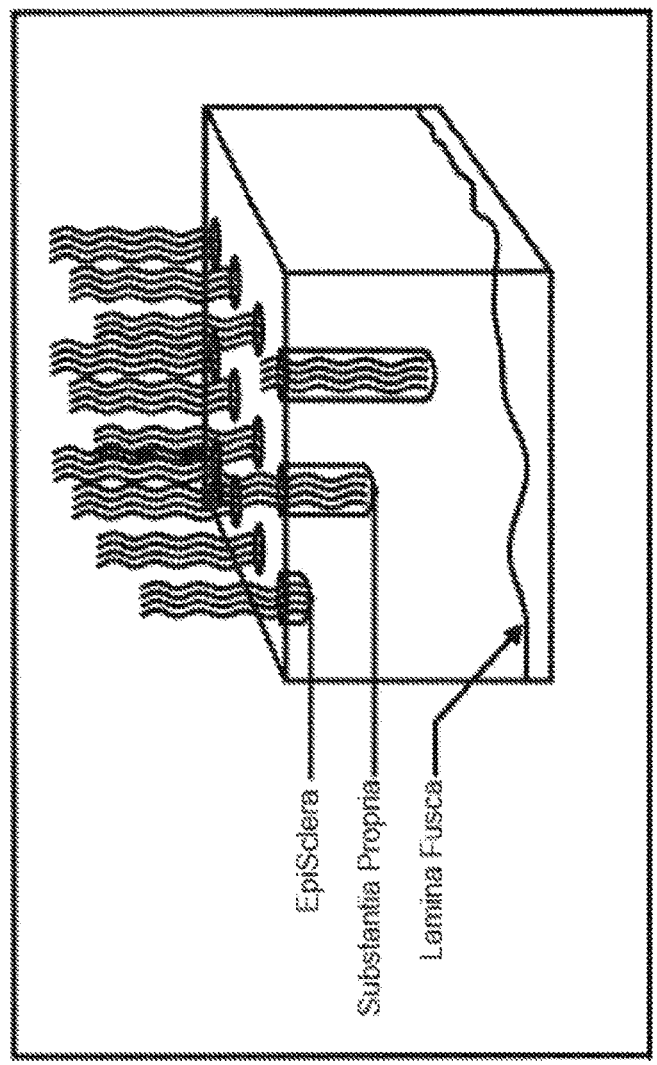
Figures 4, 4A, 5, 6, 7, 8, 9, 10:
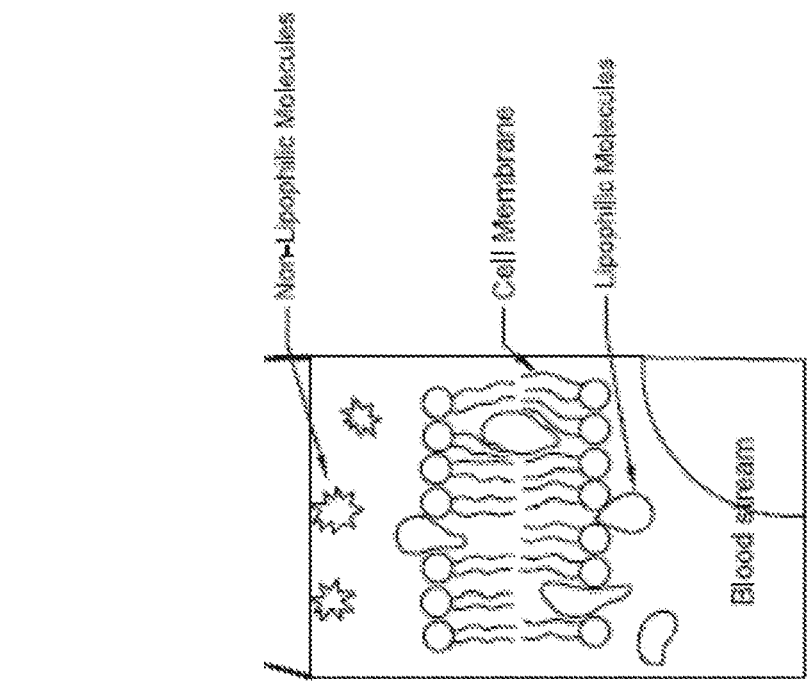
Figure 5:
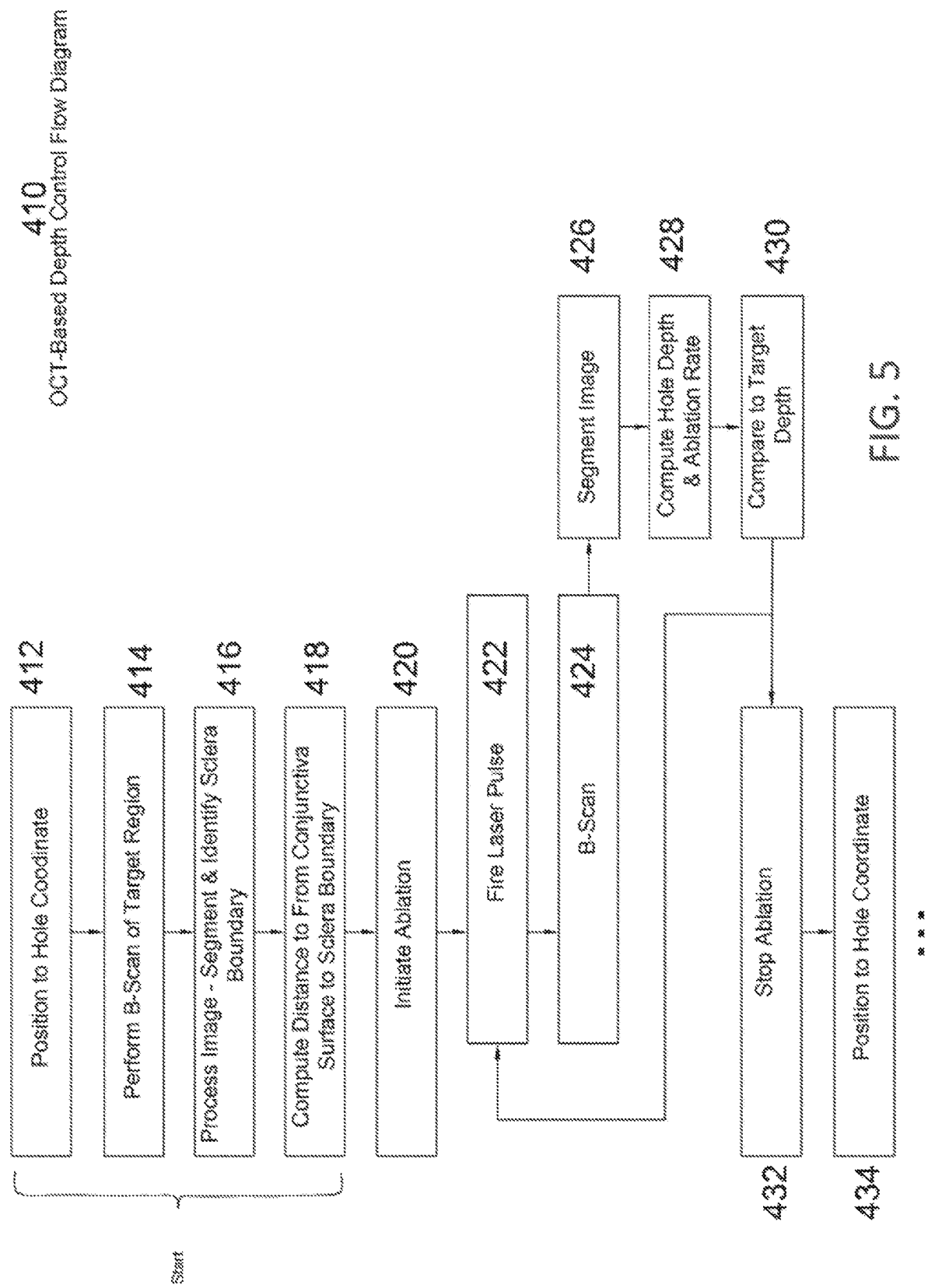
Figure 6:
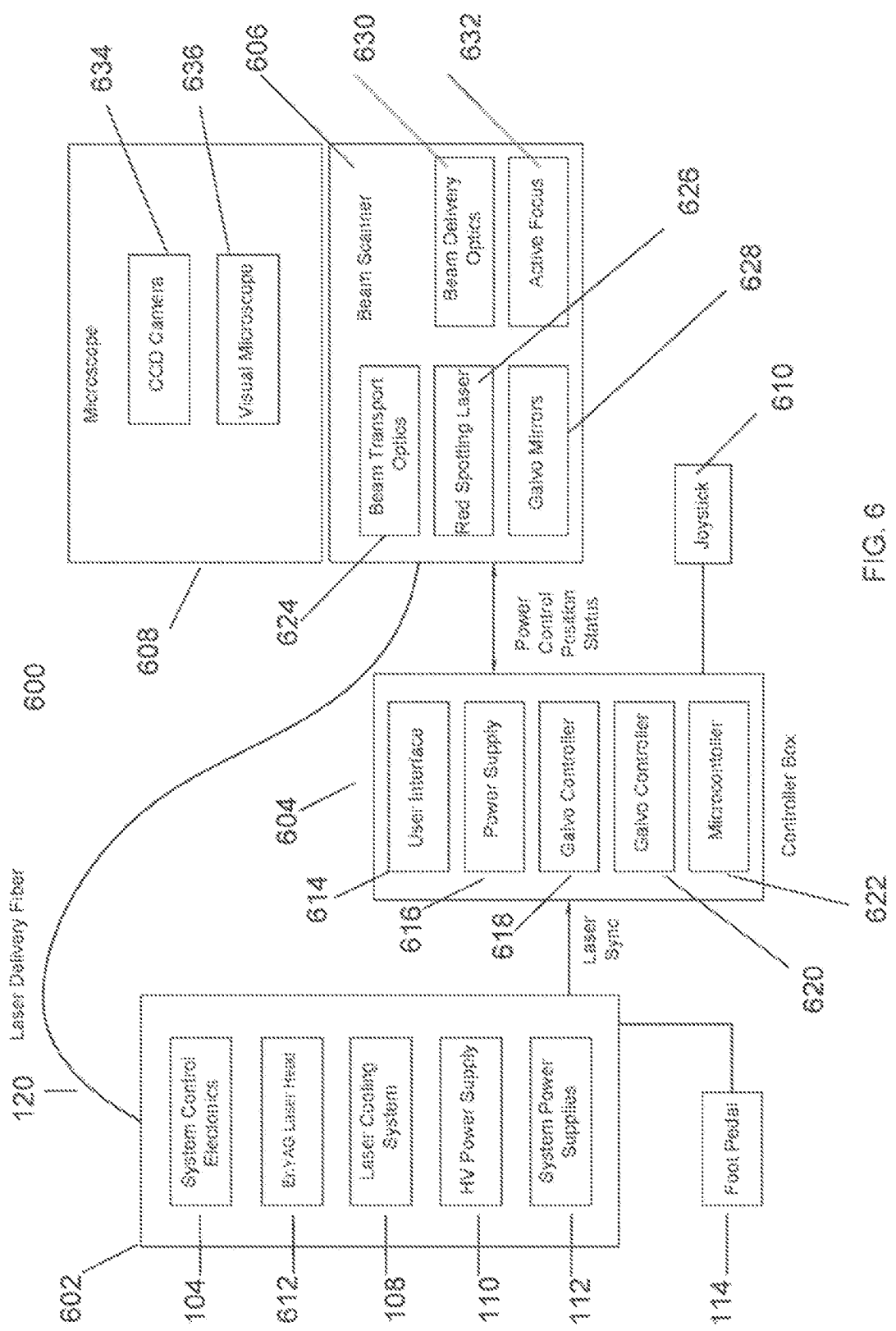
Figure 7:
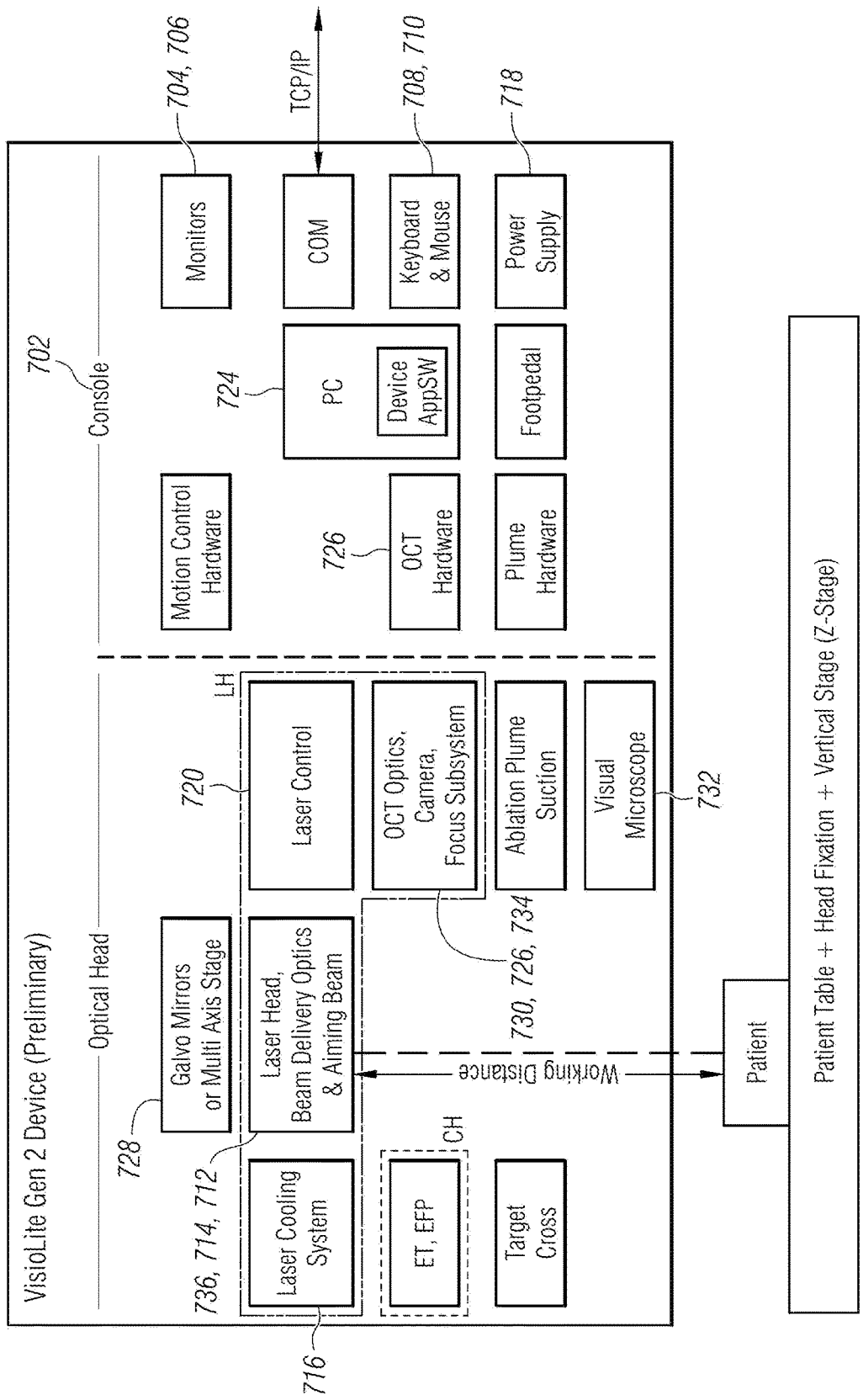
Figures 1, 7:
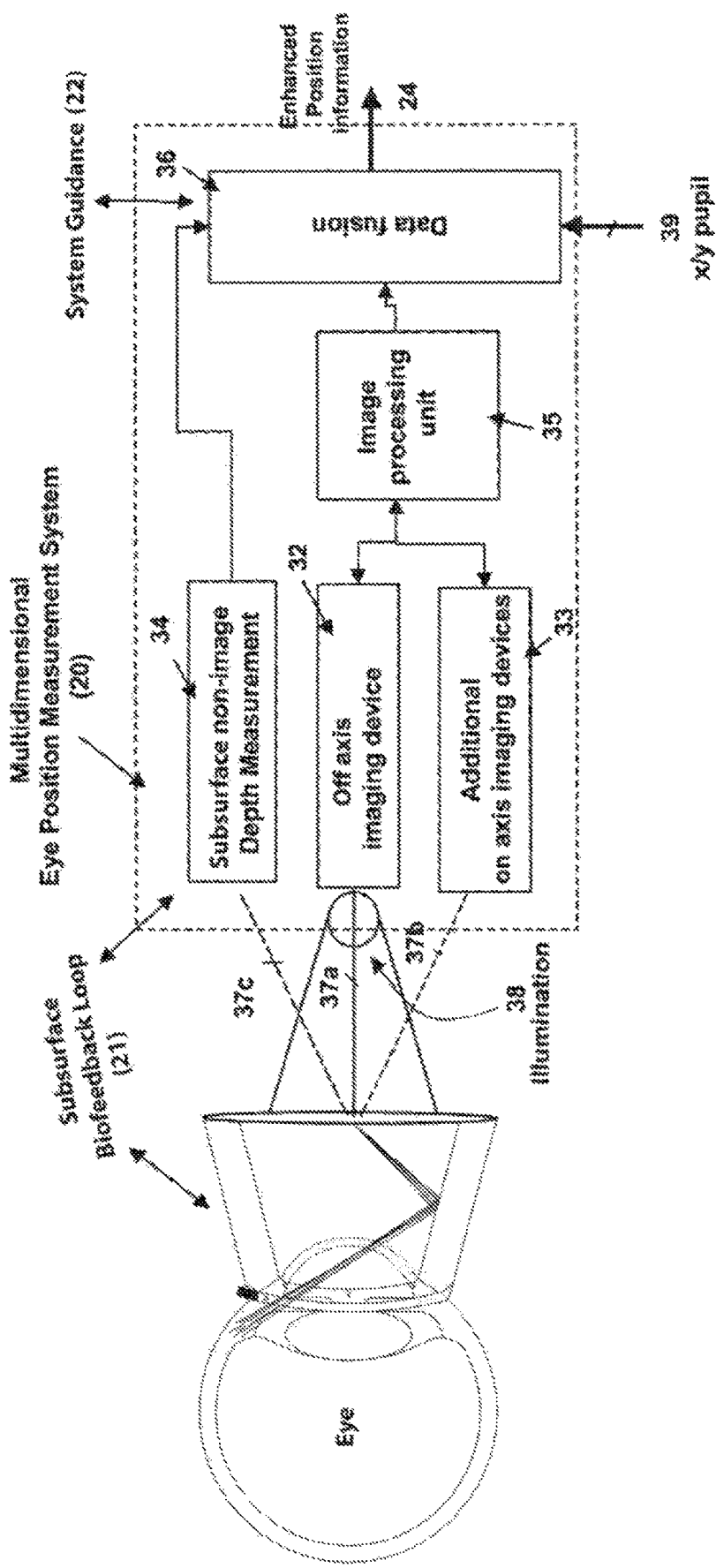
Figure 8:
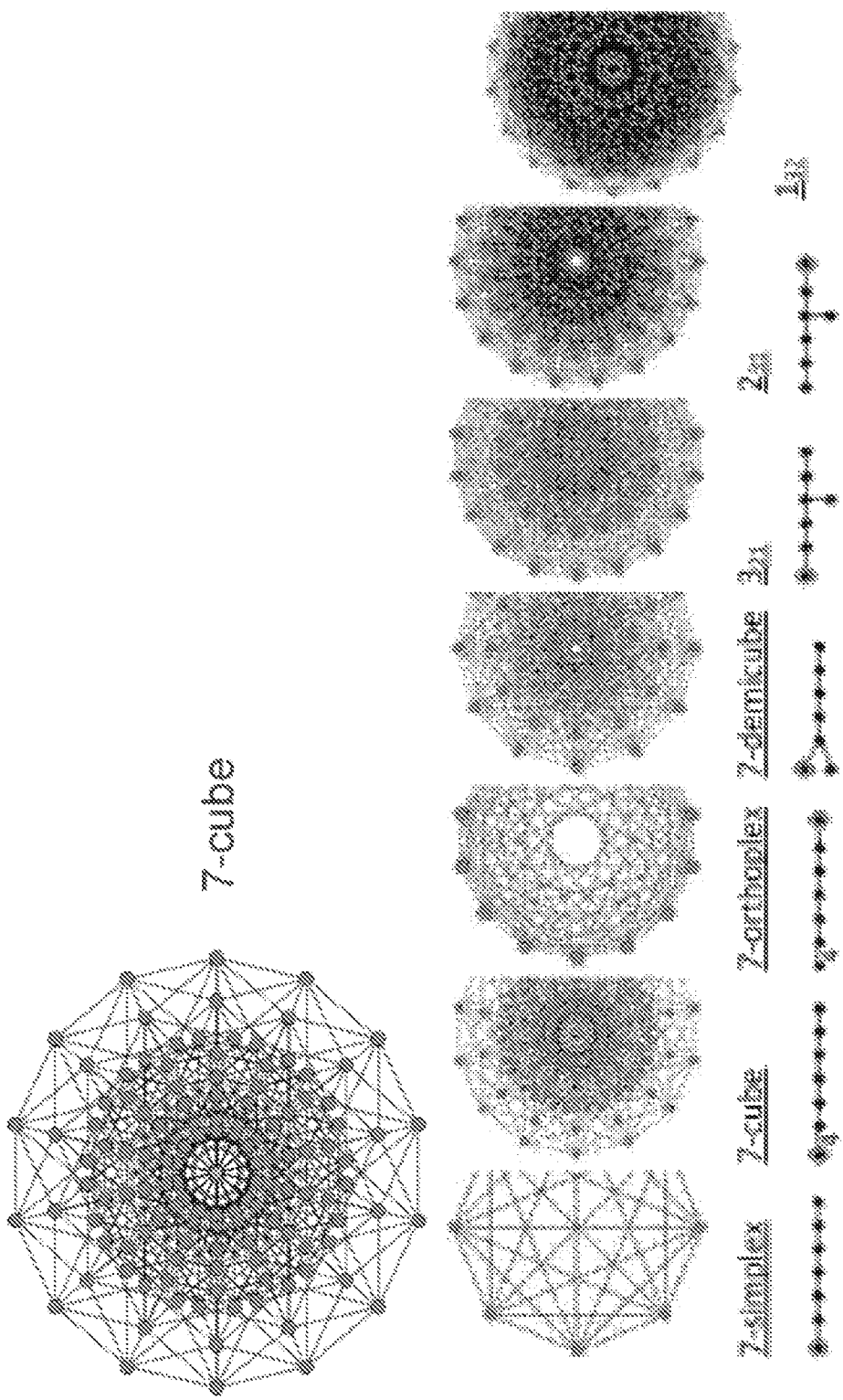
Figure 9:
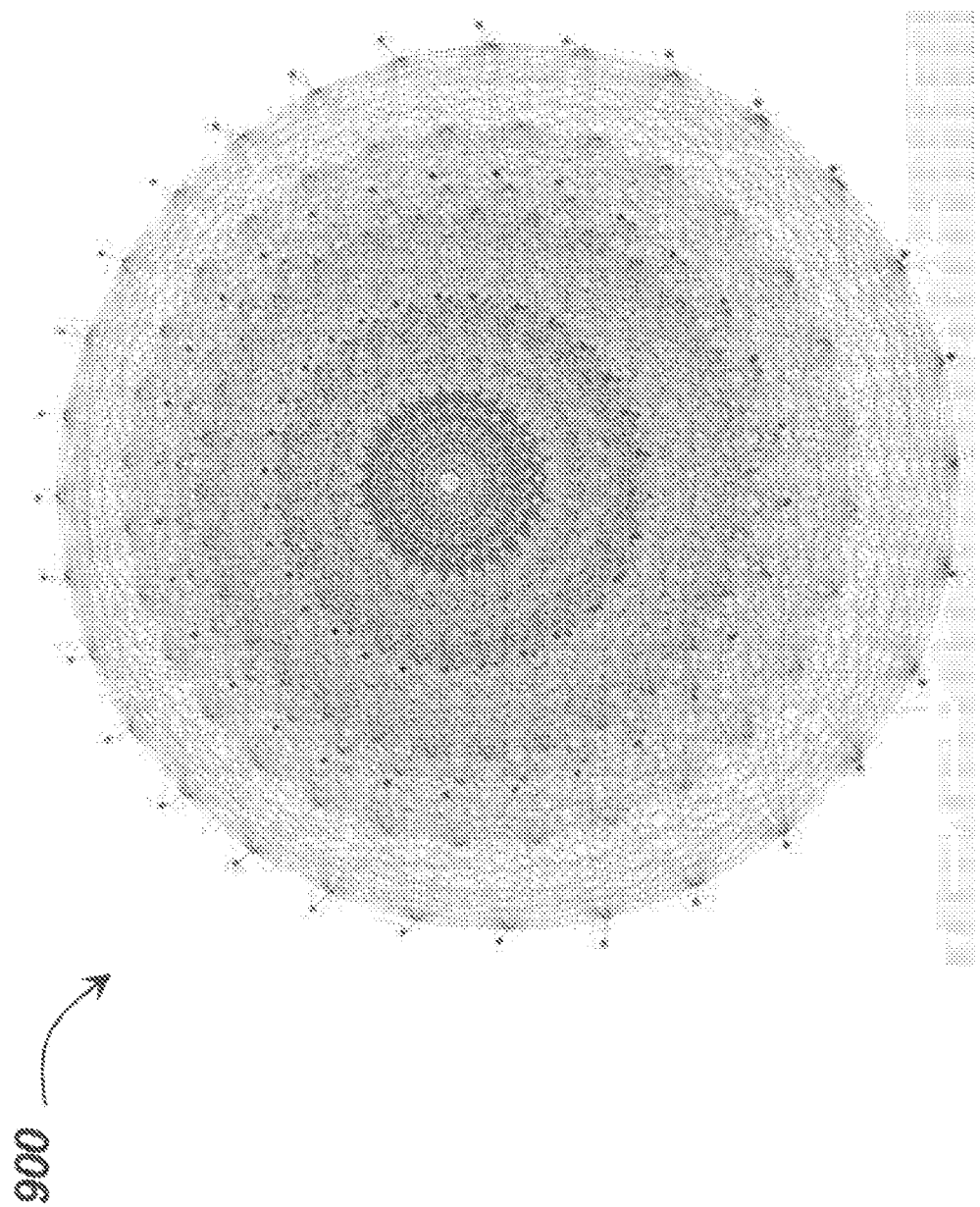
Figure 10:
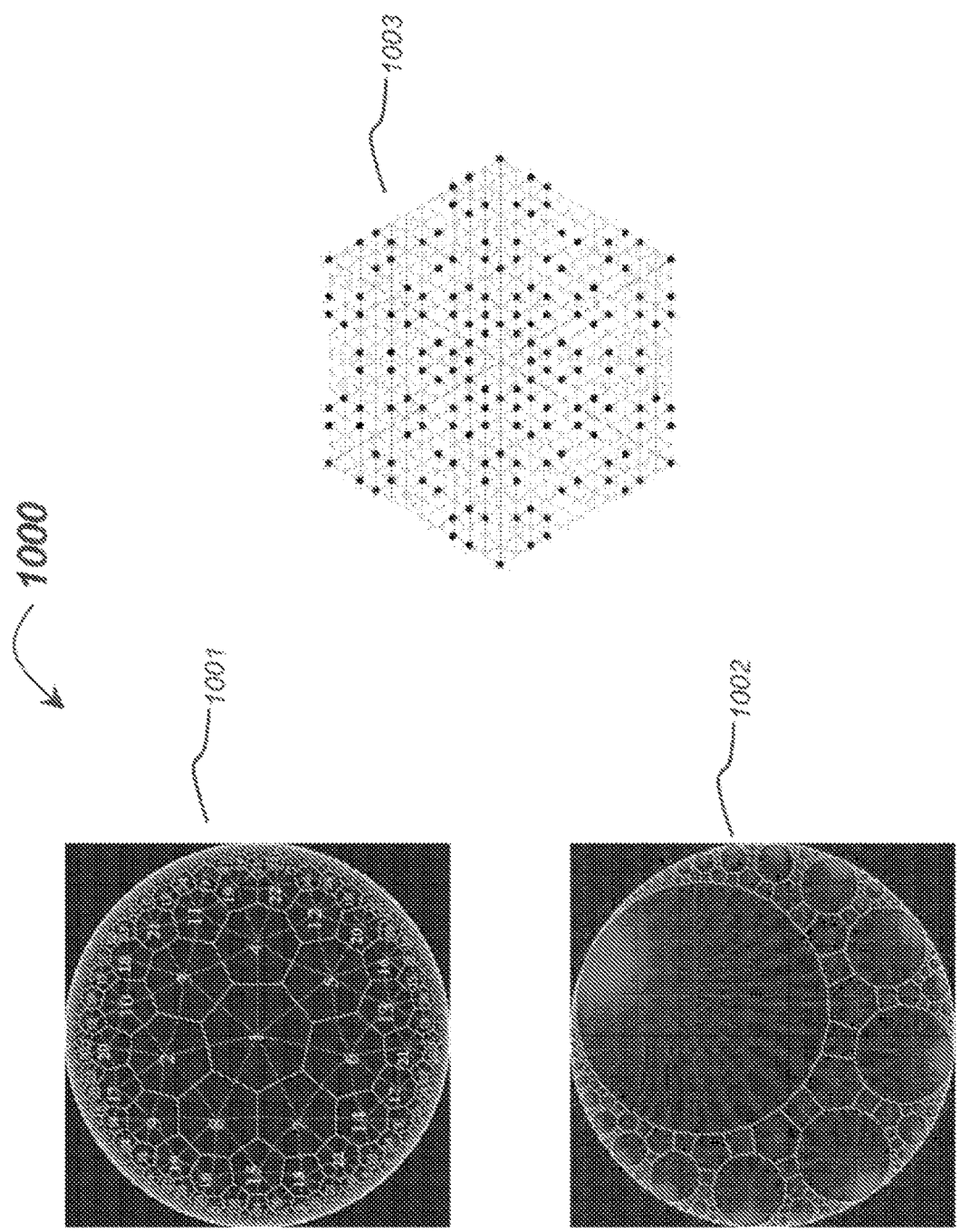
Figure 11:
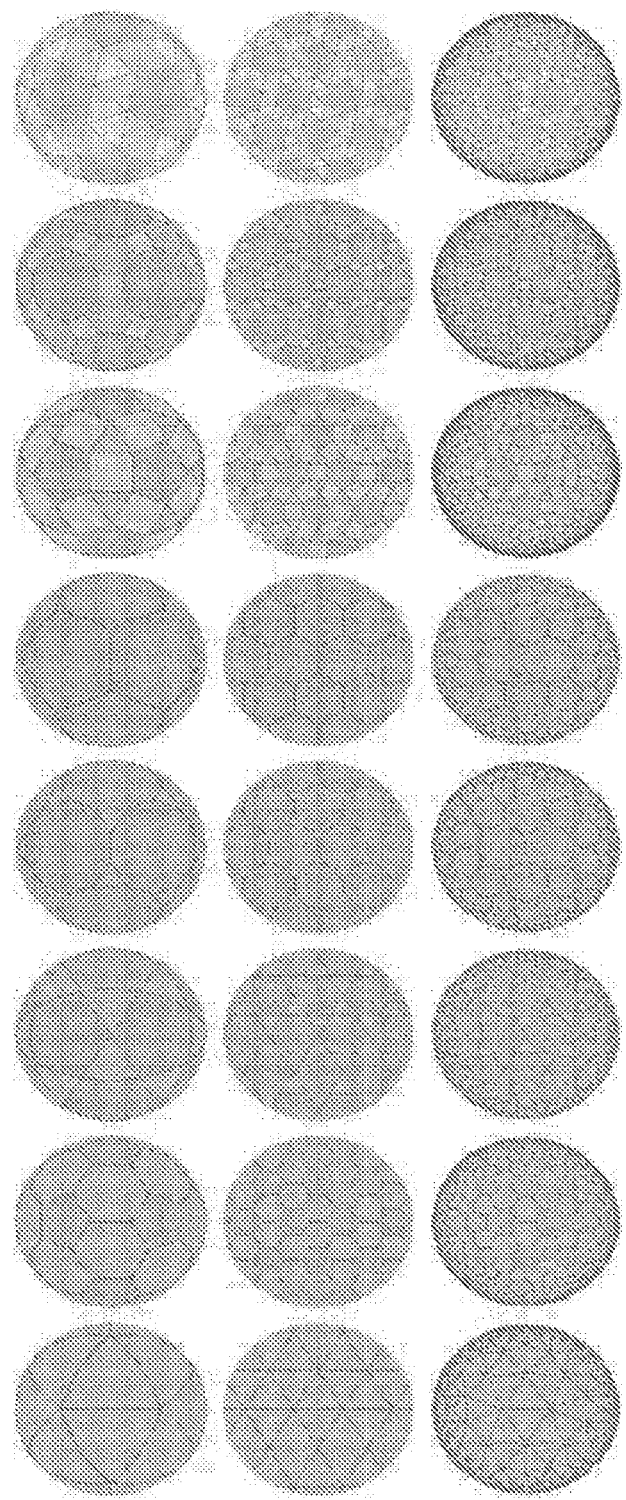
Figure 12:
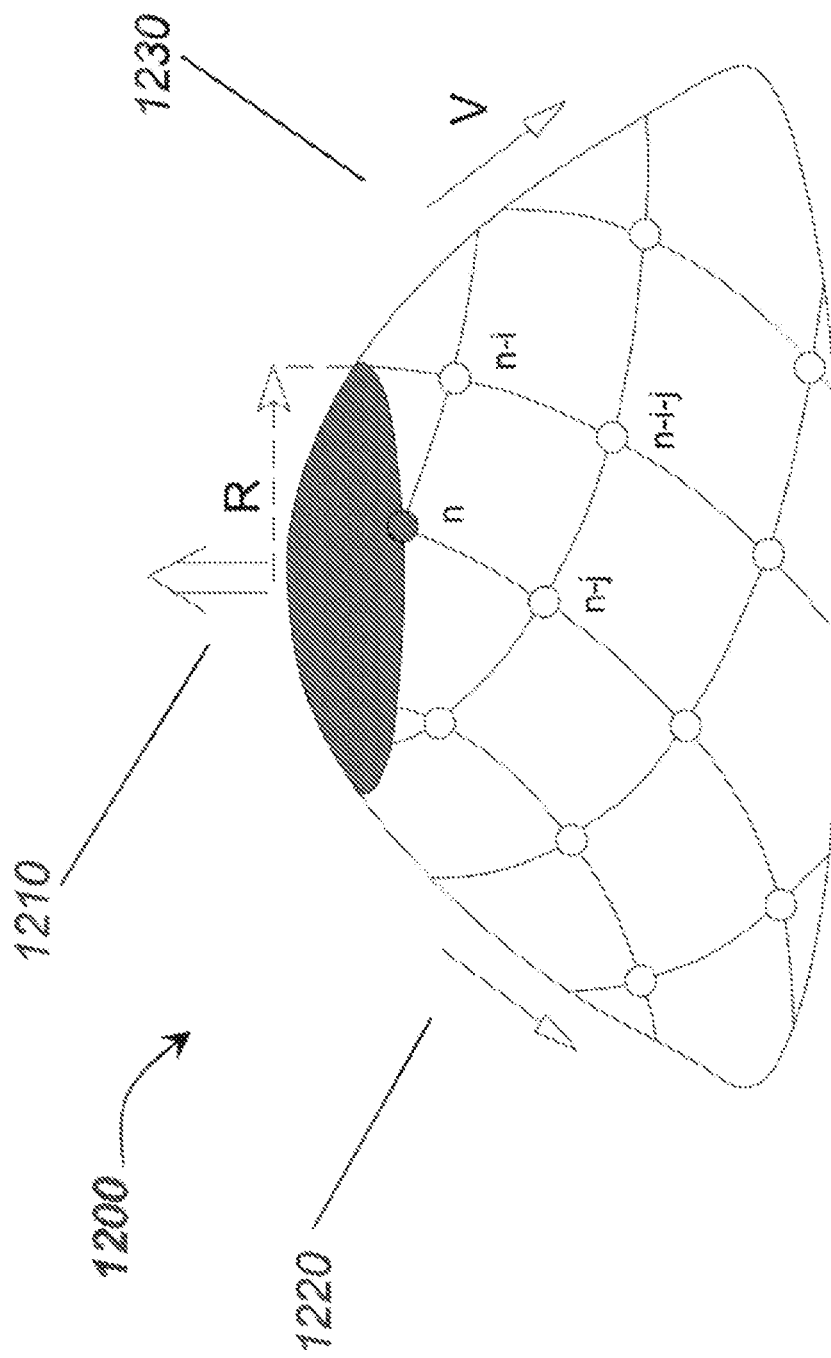
Figure 13:
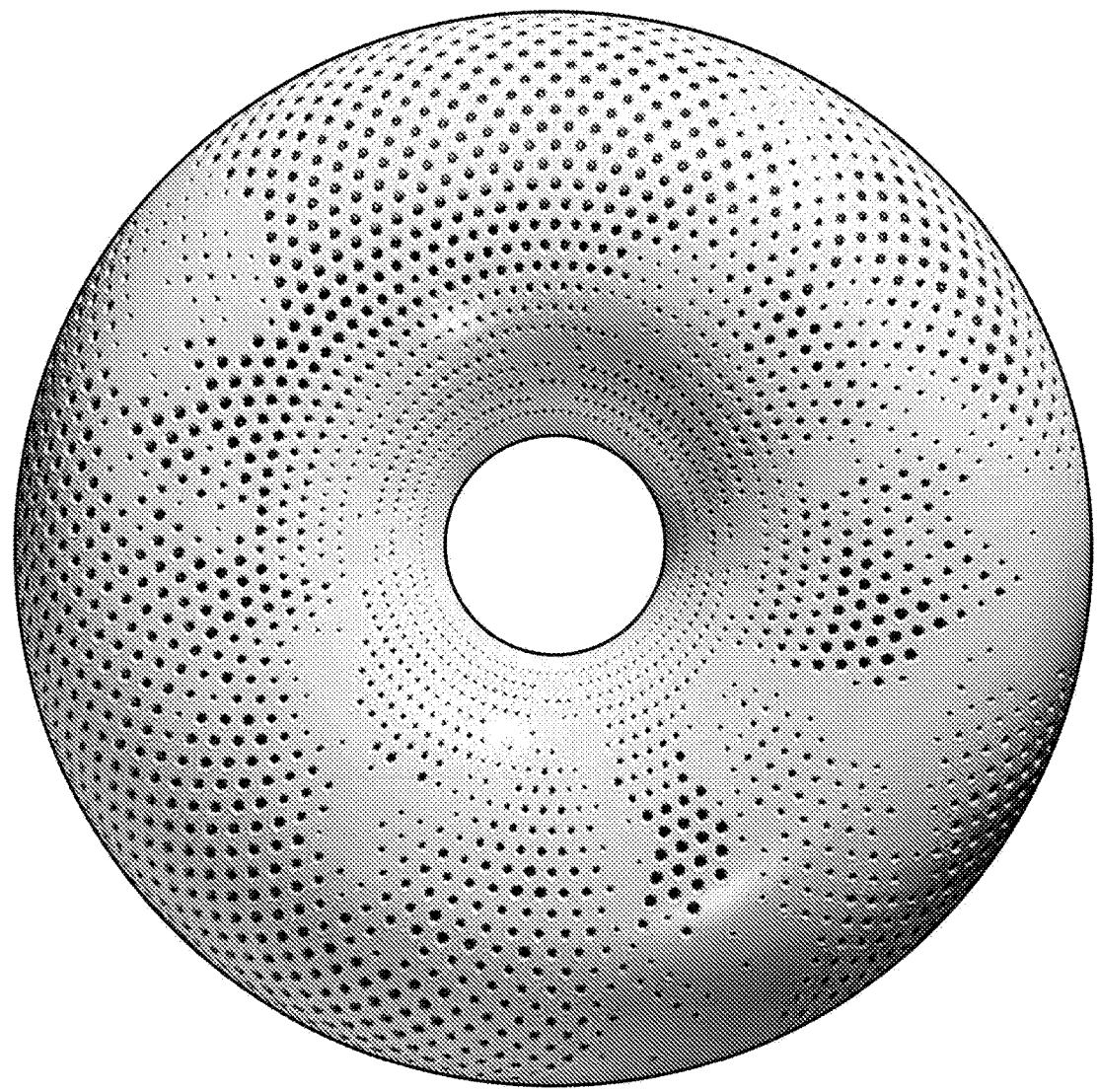

FIG. 4A illustrates another exemplary laser treatment system, according to an embodiment of the disclosure.

FIGS. 4A-(1-10) illustrate how microporation/nanoporation may be used, according to an embodiment of the disclosure.

FIG. 4B-1 illustrates another exemplary laser treatment system, according to an embodiment of the disclosure.

FIG. 4B-2 illustrates an exemplary diagram of an ablation pore in the sclera showing an example of the depth of an ablation, according to an embodiment of the disclosure.

FIG. 5 illustrates an exemplary flow diagram of OCT-based depth control, according to an embodiment of the disclosure.

Figures 2, 2K, 3, 4, 5, 6:
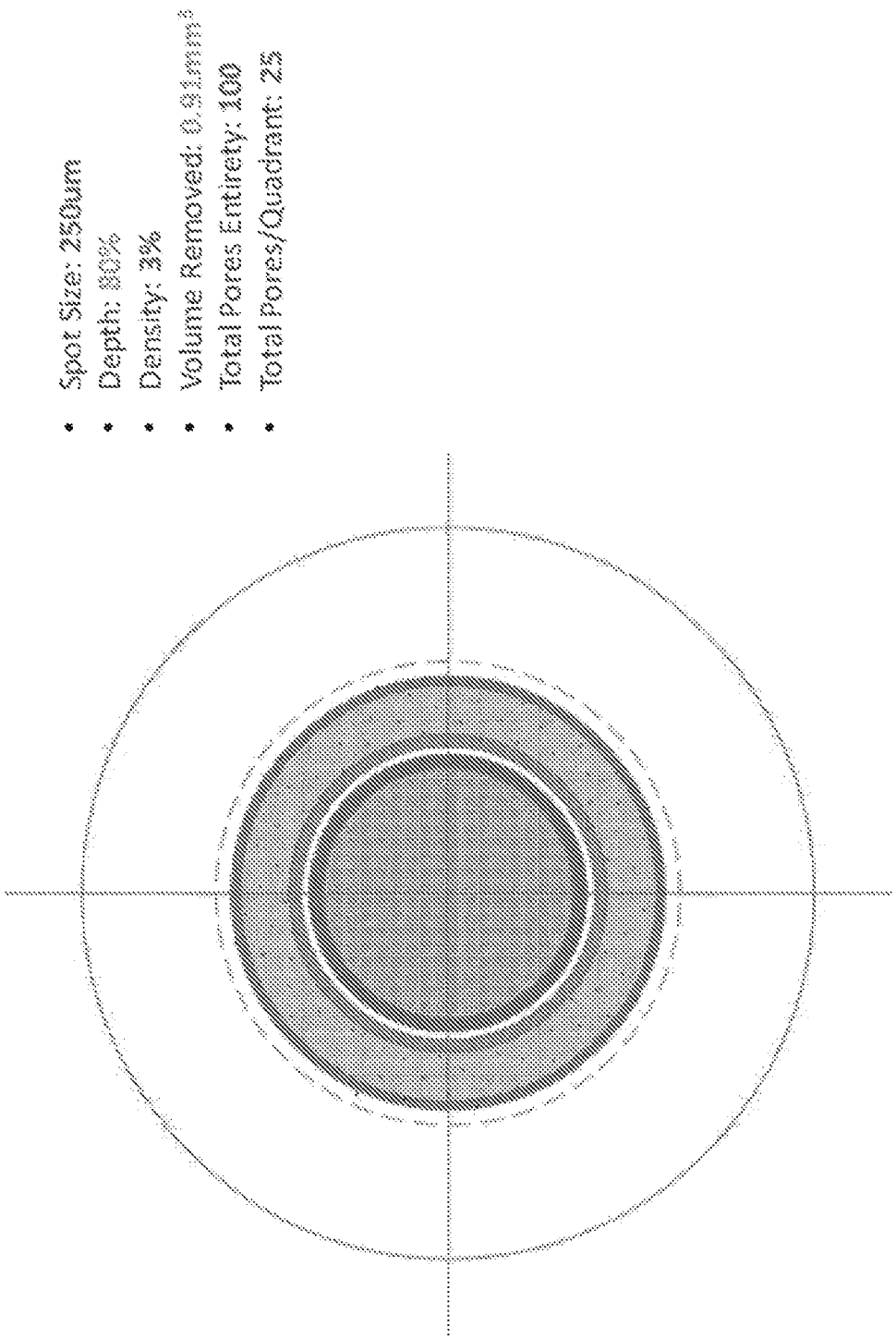

FIG. 6 illustrates an exemplary laser treatment system component map, according to an embodiment of the disclosure.

Figures 2, 2K, 3, 4, 5, 6, 7, 8:
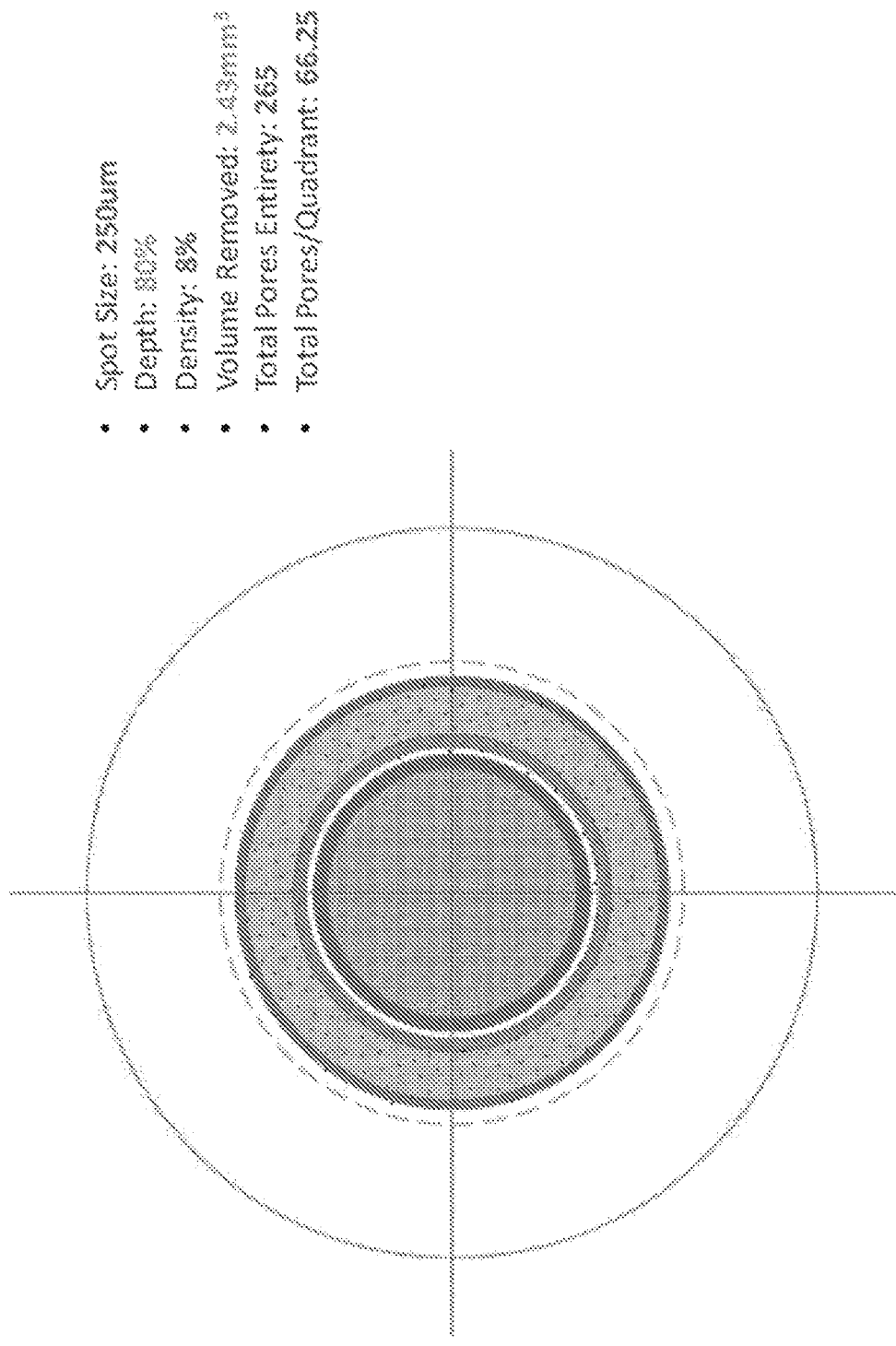

FIG. 7 illustrates another exemplary laser treatment system, according to an embodiment of the disclosure.

FIG. 7-1 illustrates another exemplary laser treatment system, according to an embodiment of the disclosure.

FIG. 8 illustrates exemplary orthogonal projections, according to an embodiment of the disclosure.

Figures 2, 2K, 3, 4, 5, 6, 7, 8, 9:
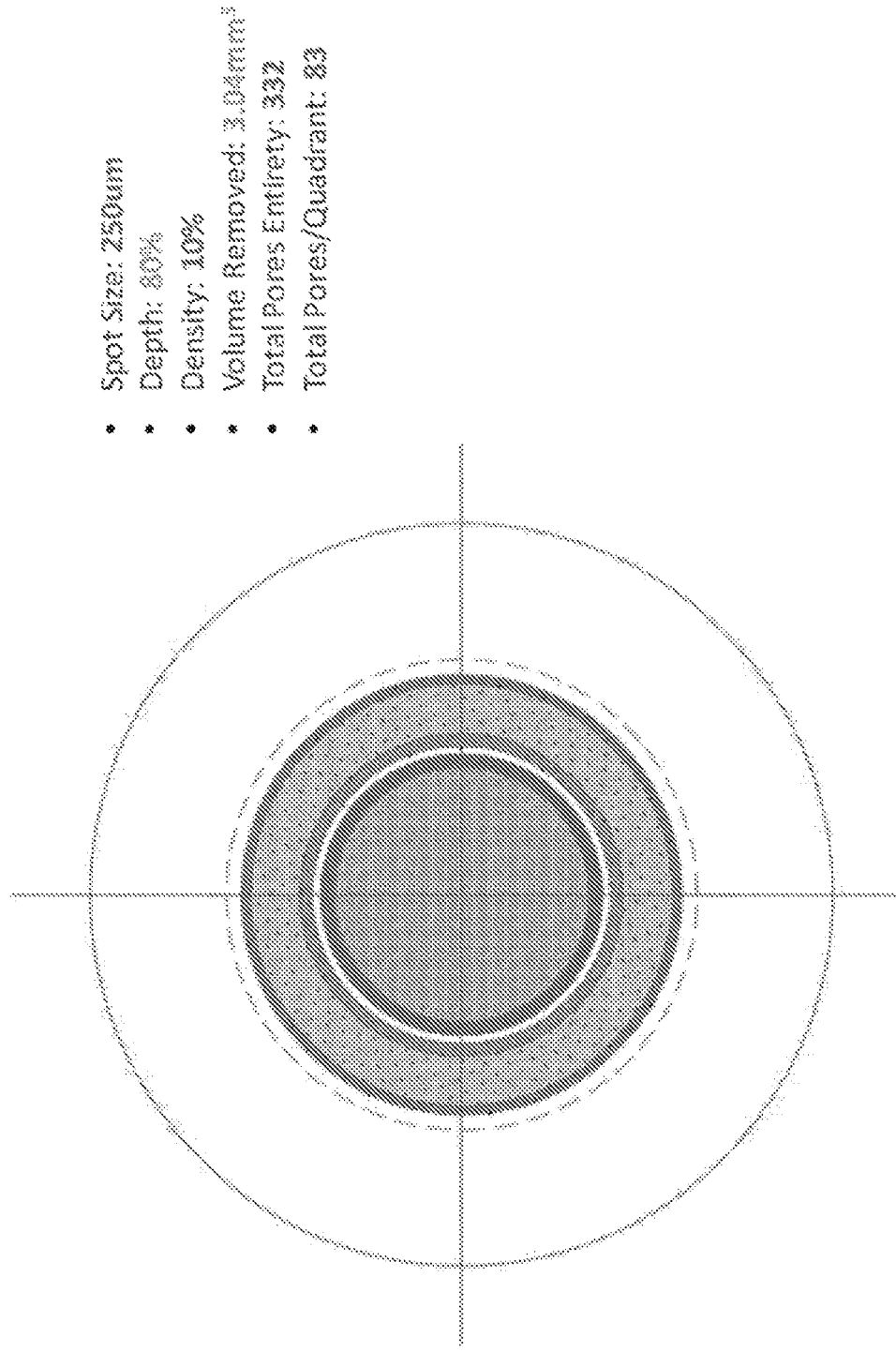

FIG. 9 illustrates exemplary 3D mapping, according to an embodiment of the disclosure.

Figures 2, 2K, 3, 4, 5, 6, 7, 8, 9, 10:
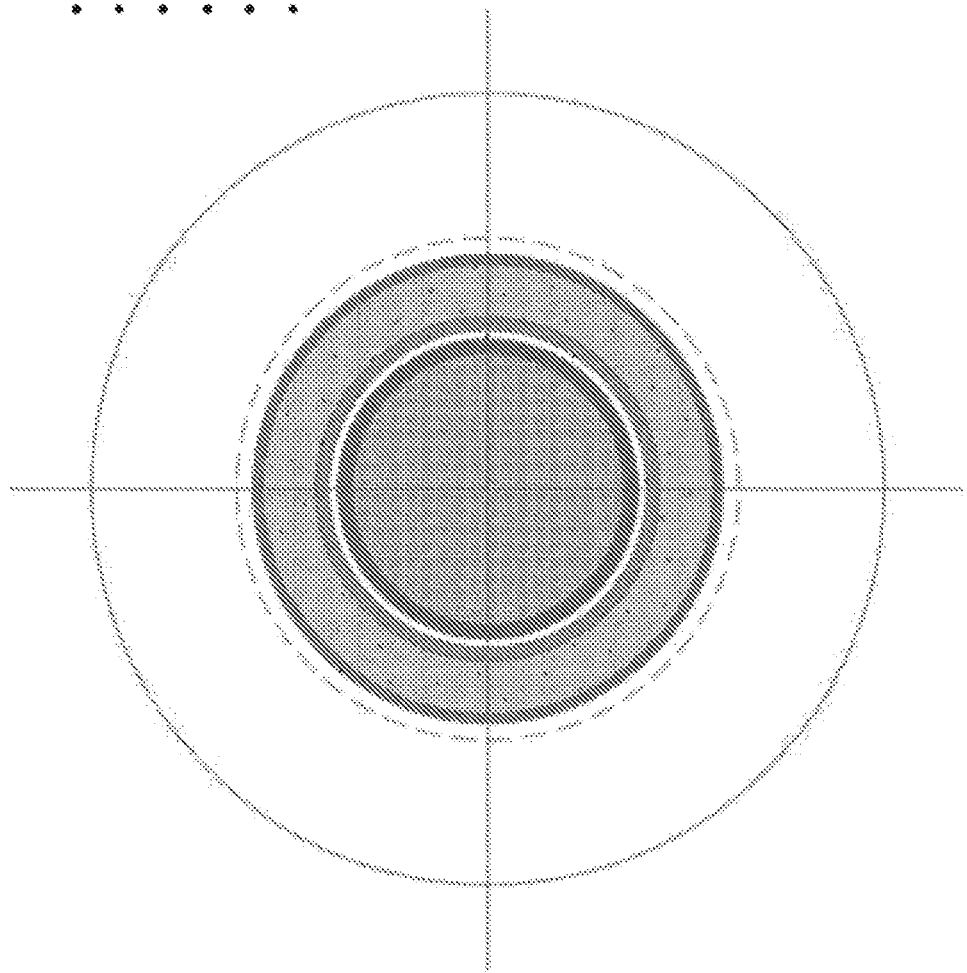

FIG. 10 illustrates exemplary design patterns, according to an embodiment of the disclosure.

Figures 2, 2K, 3, 4, 5, 6, 7, 8, 9, 10, 11:
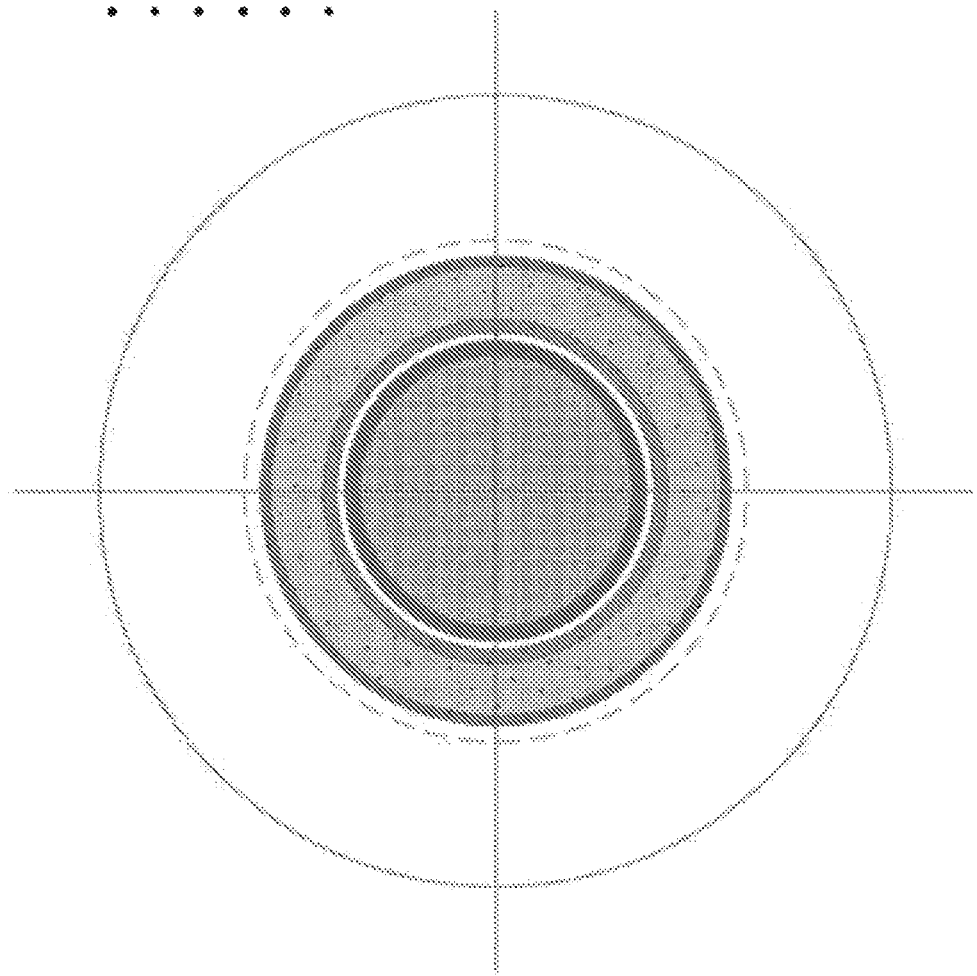

FIG. 11 illustrates exemplary models, according to an embodiment of the disclosure.

Figures 2, 2K, 3, 4, 5, 6, 7, 8, 9, 10, 11, 12:
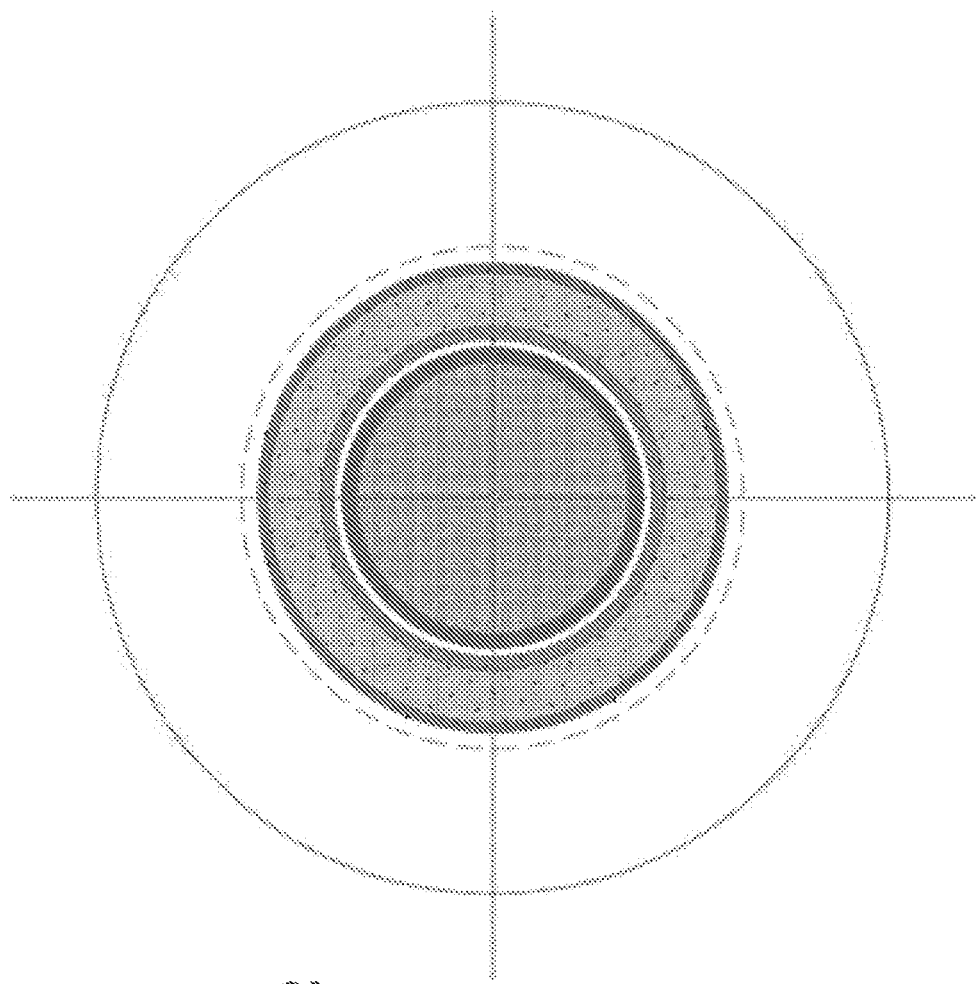

FIG. 12 illustrates an exemplary schematized representation of microporation, according to an embodiment of the disclosure.

Figures 2, 2K, 3, 4, 5, 6, 7, 8, 9, 10, 11, 12, 13, 14:
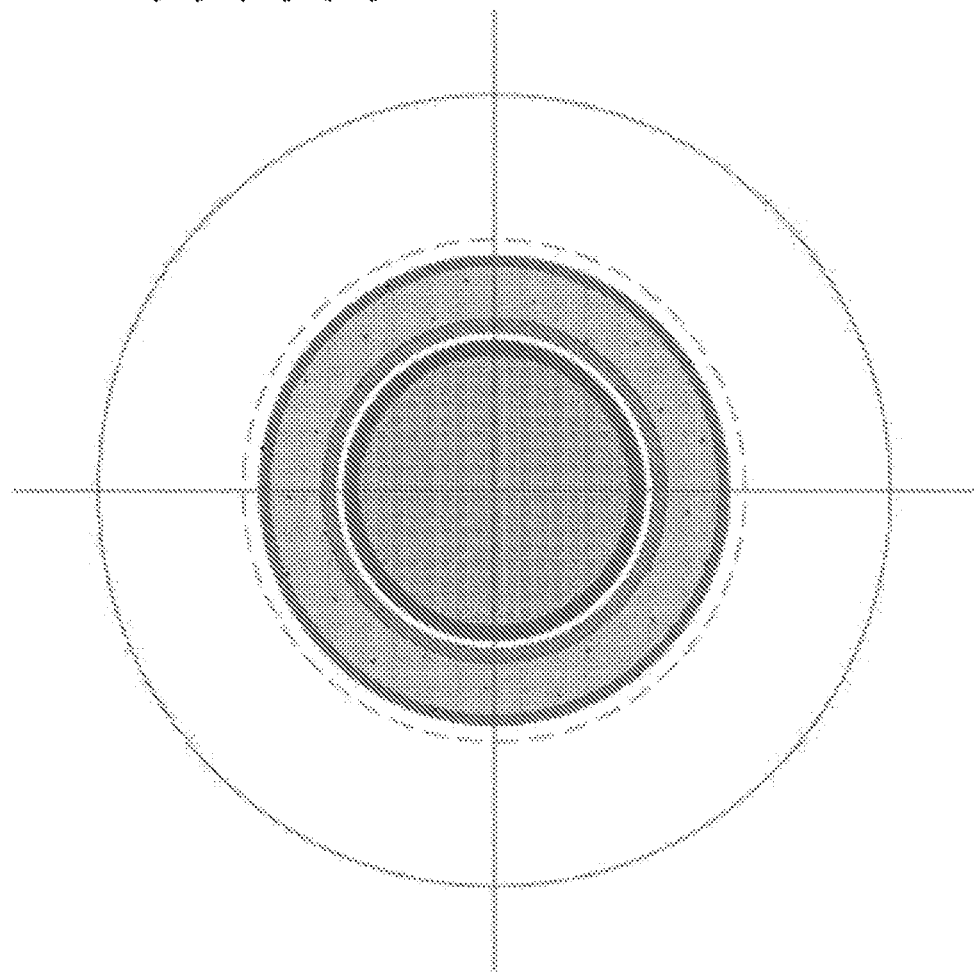
Figures 2, 2K, 3, 4, 5, 6, 7, 8, 9, 10, 11, 12, 13, 14, 15:
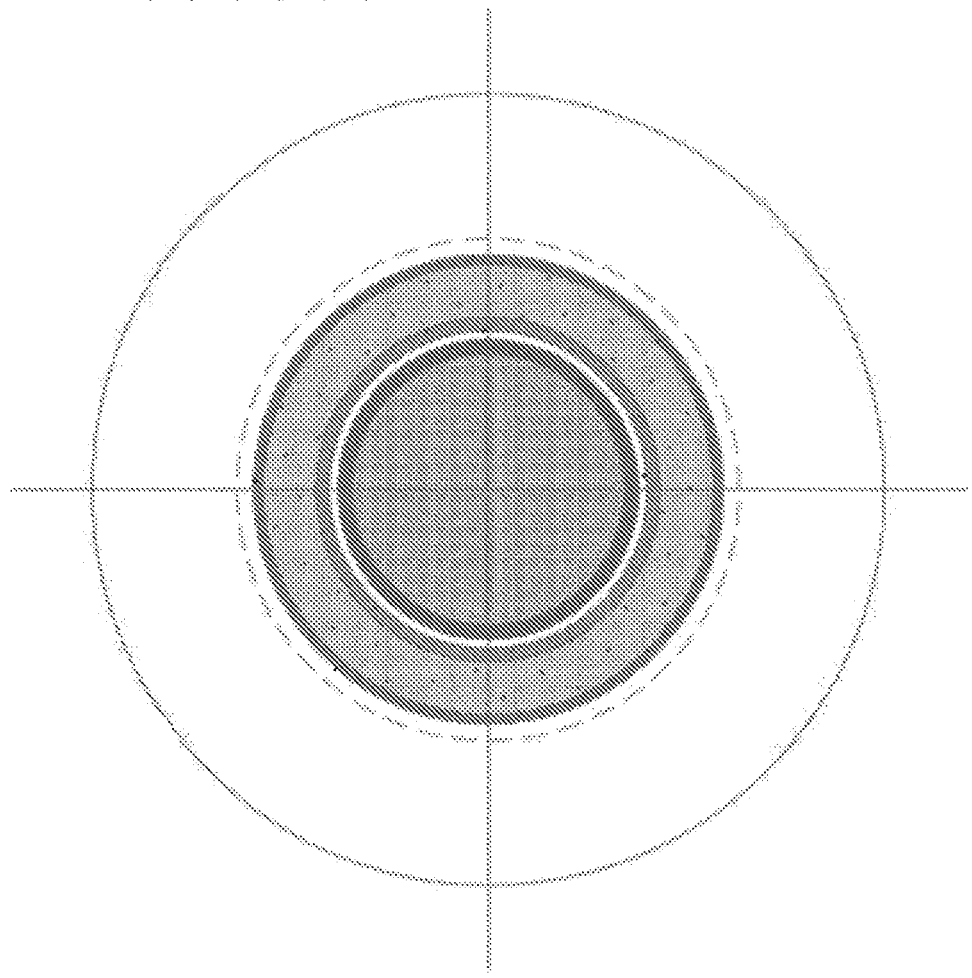

FIG. 13 illustrates an exemplary graphical image of microporation, according to an embodiment of the disclosure.

Figure 14C:
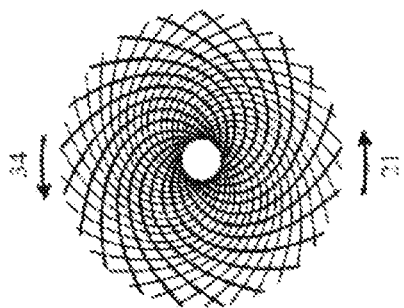
Figure 14B:
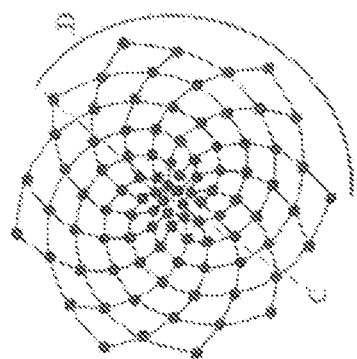
Figure 14A:
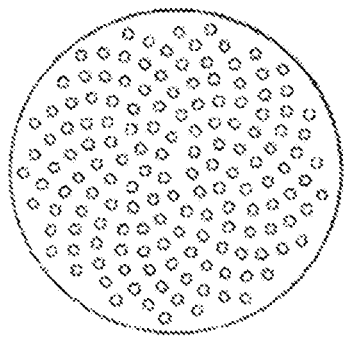

FIG. 14A illustrates an exemplary microporation pattern, according to an embodiment of the disclosure.

FIG. 14B is an exemplary illustration of a phyllotactic spiral pattern, according to an embodiment of the disclosure.

FIG. 14C is another exemplary illustration of another phyllotactic spiral pattern, according to an embodiment of the disclosure.

Figure 14D:
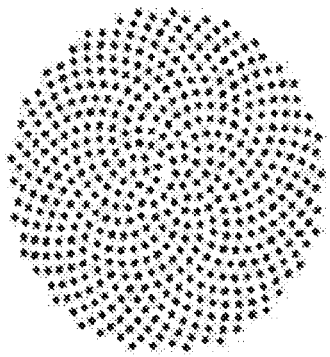
Figure 15A:
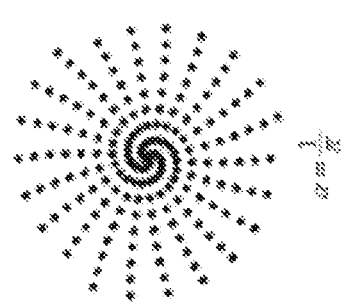
Figure 15B:
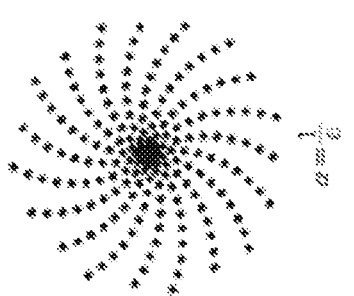
Figure 15C:
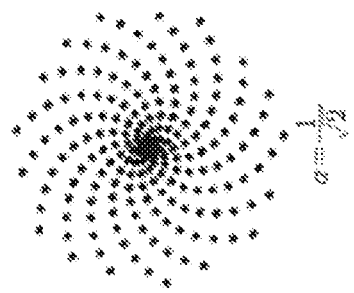
Figure 15D:
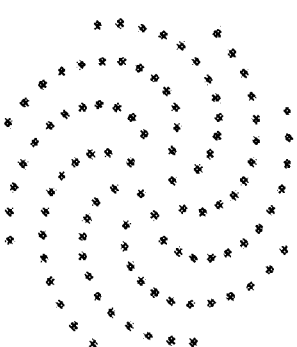
Figure 15E:
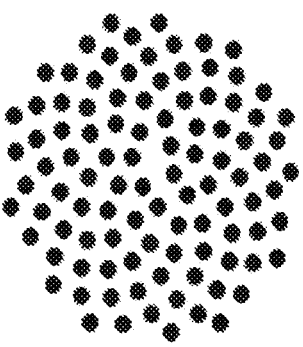
Figure 15F:
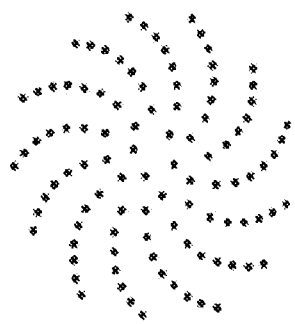

FIGS. 14D and 14E are exemplary illustrations of the Vogel model, according to an embodiment of the disclosure.

FIGS. 15A-15F are exemplary illustrations of other phyllotactic spiral patterns, according to an embodiment of the disclosure.

FIGS. 16A-16N are exemplary illustrations of exemplary microporation patterns derived from icosahedron pattern shapes, according to an embodiment of the disclosure.

Figure 17B:
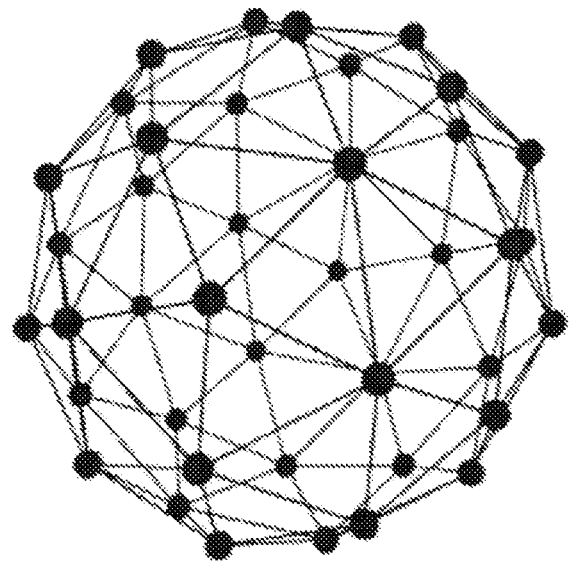
Figure 17A:
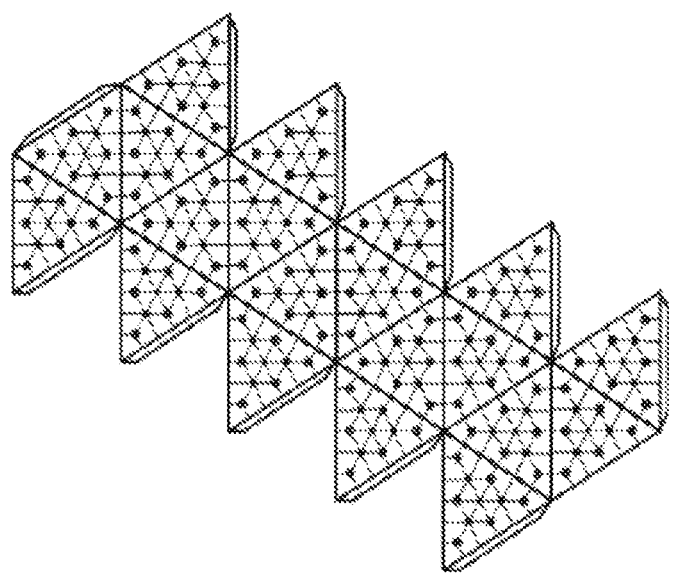
Figure 18:
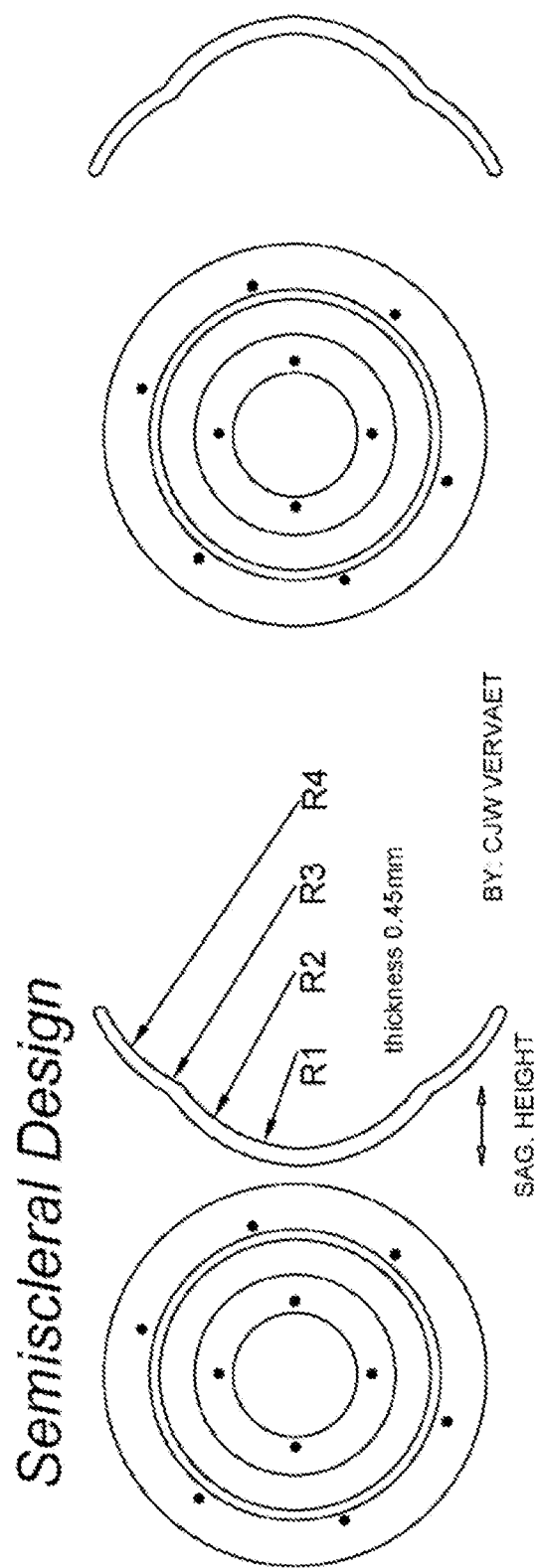
Figure 19:
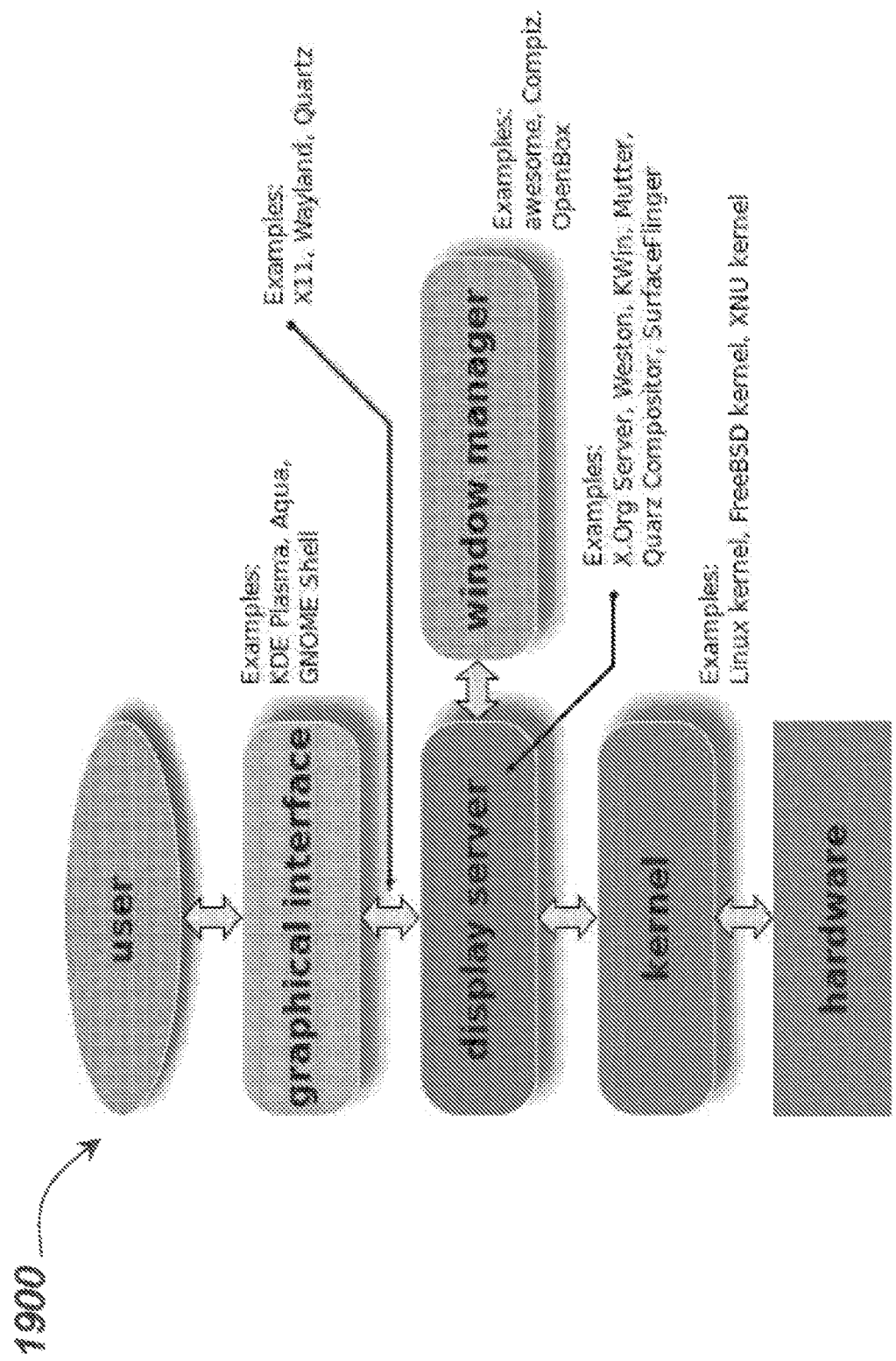

FIGS. 17A-17B are exemplary illustrations of other microporation patterns derived from icosahedron pattern shapes, according to an embodiment of the disclosure.

Figures 2, 2K, 3, 4, 5, 6, 7, 8, 9, 10, 11, 12, 13, 14, 15, 16:
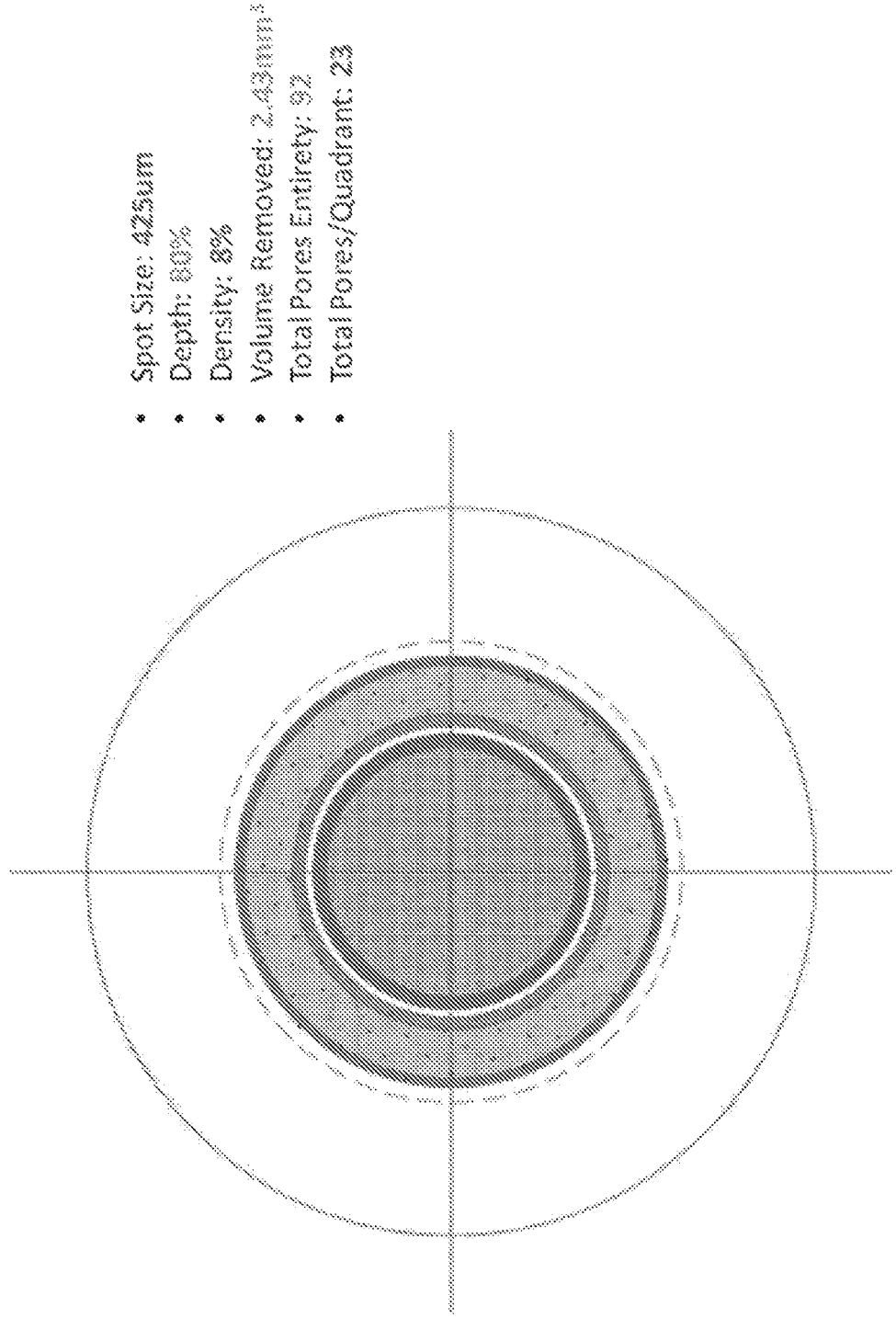
Figures 2, 2K, 3, 4, 5, 6, 7, 8, 9, 10, 11, 12, 13, 14, 15, 16, 17:
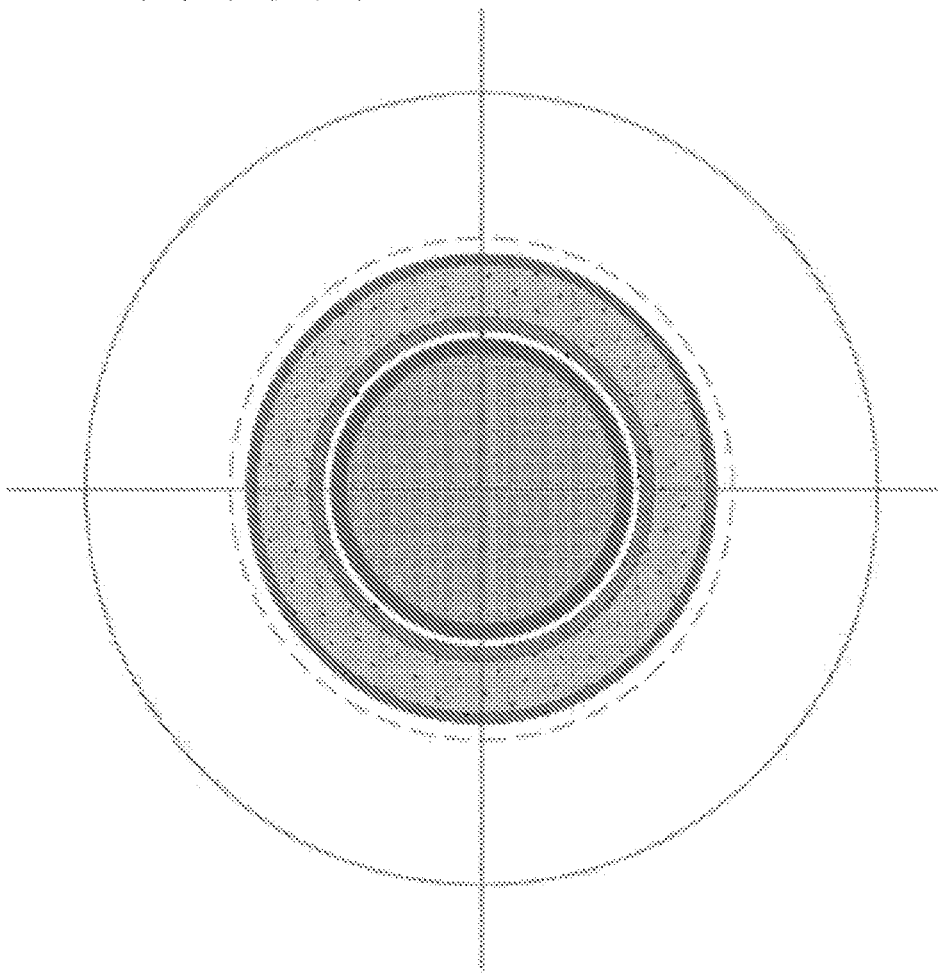
Figures 2, 2K, 3, 4, 5, 6, 7, 8, 9, 10, 11, 12, 13, 14, 15, 16, 17, 18:
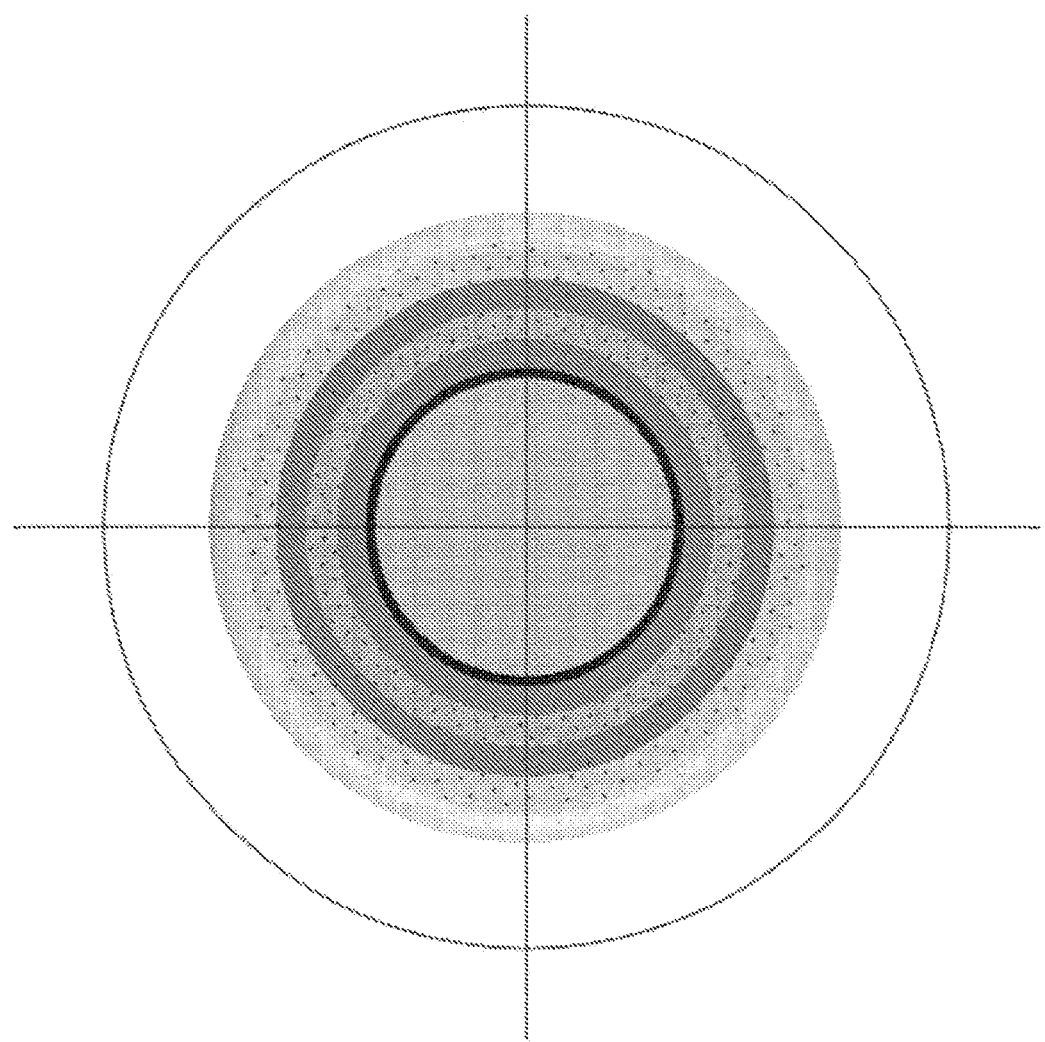

FIG. 18 is an exemplary lens design, according to an embodiment of the disclosure.

Figures 2, 2K, 3, 4, 5, 6, 7, 8, 9, 10, 11, 12, 13, 14, 15, 16, 17, 18, 19:
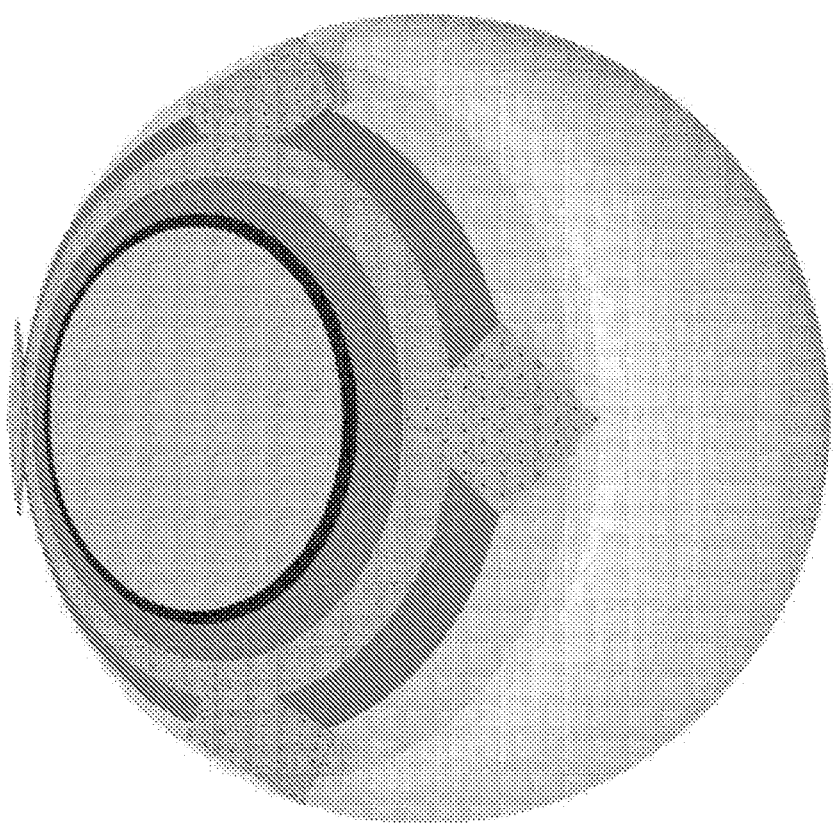

FIG. 19 illustrates another exemplary microporation system, according to an embodiment of the disclosure.

FIGS. 20 and 20A to 20C illustrate exemplary views of a docking station, according to an embodiment of the disclosure.

Figure 20:
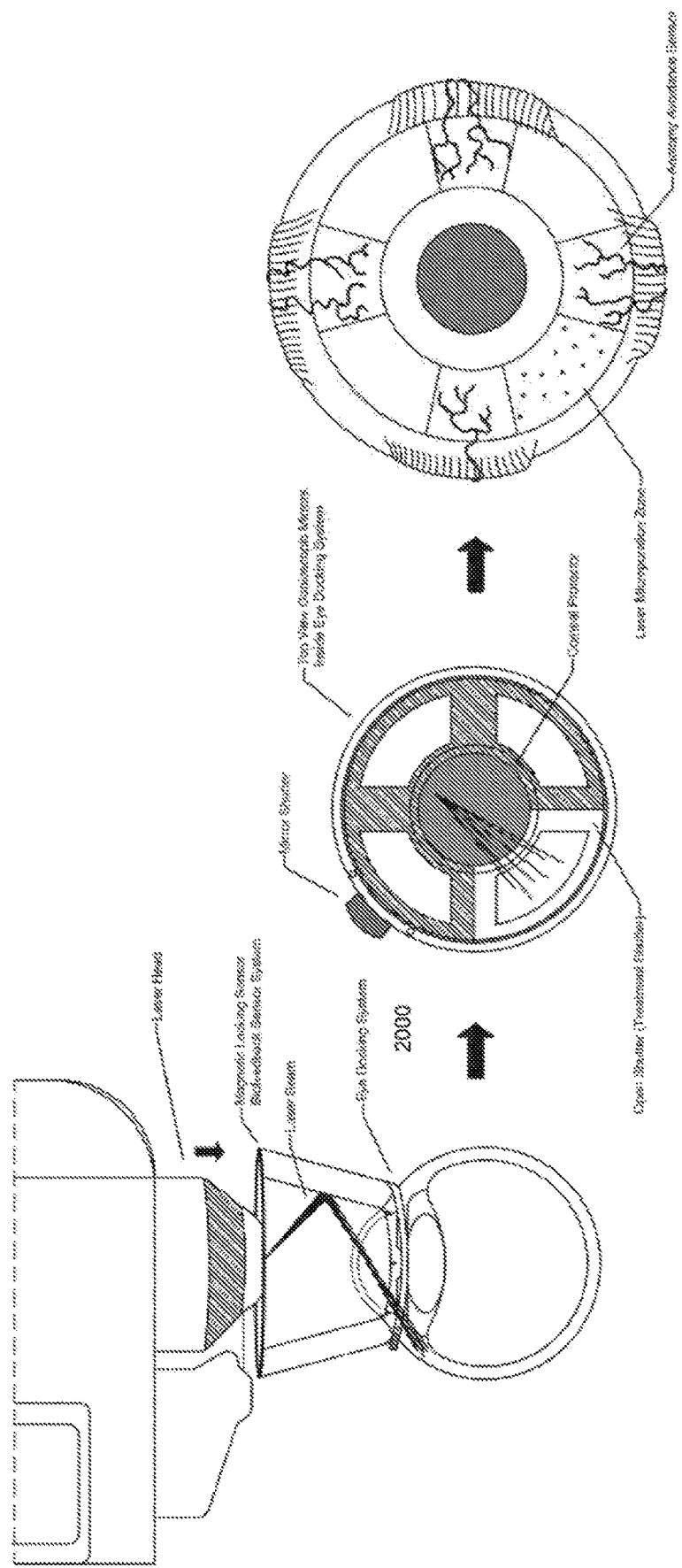
Figure 20B:
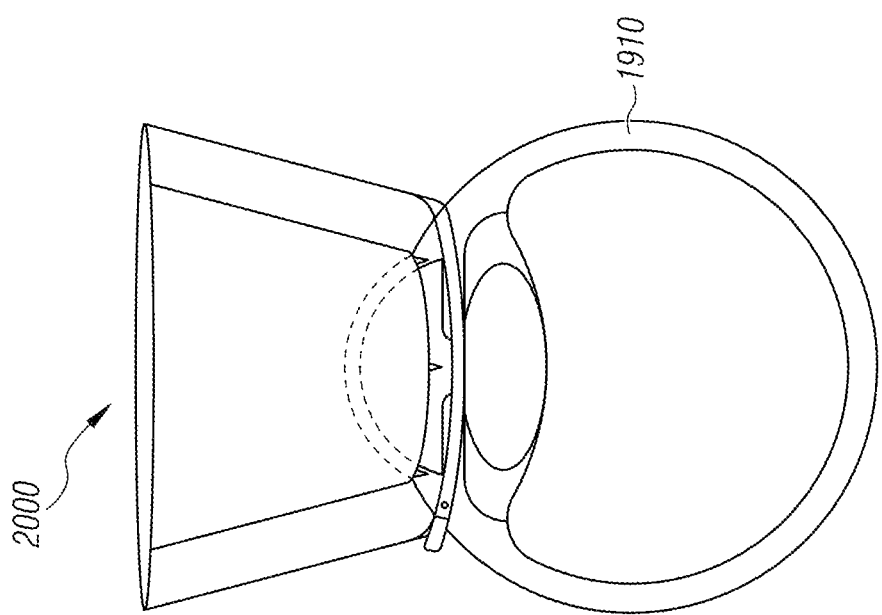
Figure 20A:
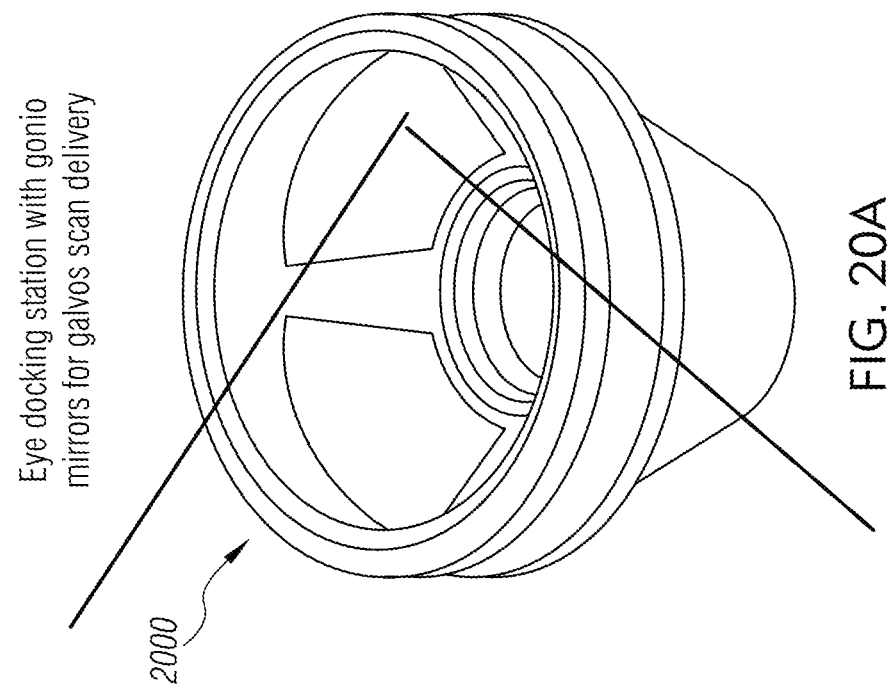
Figure 20C:
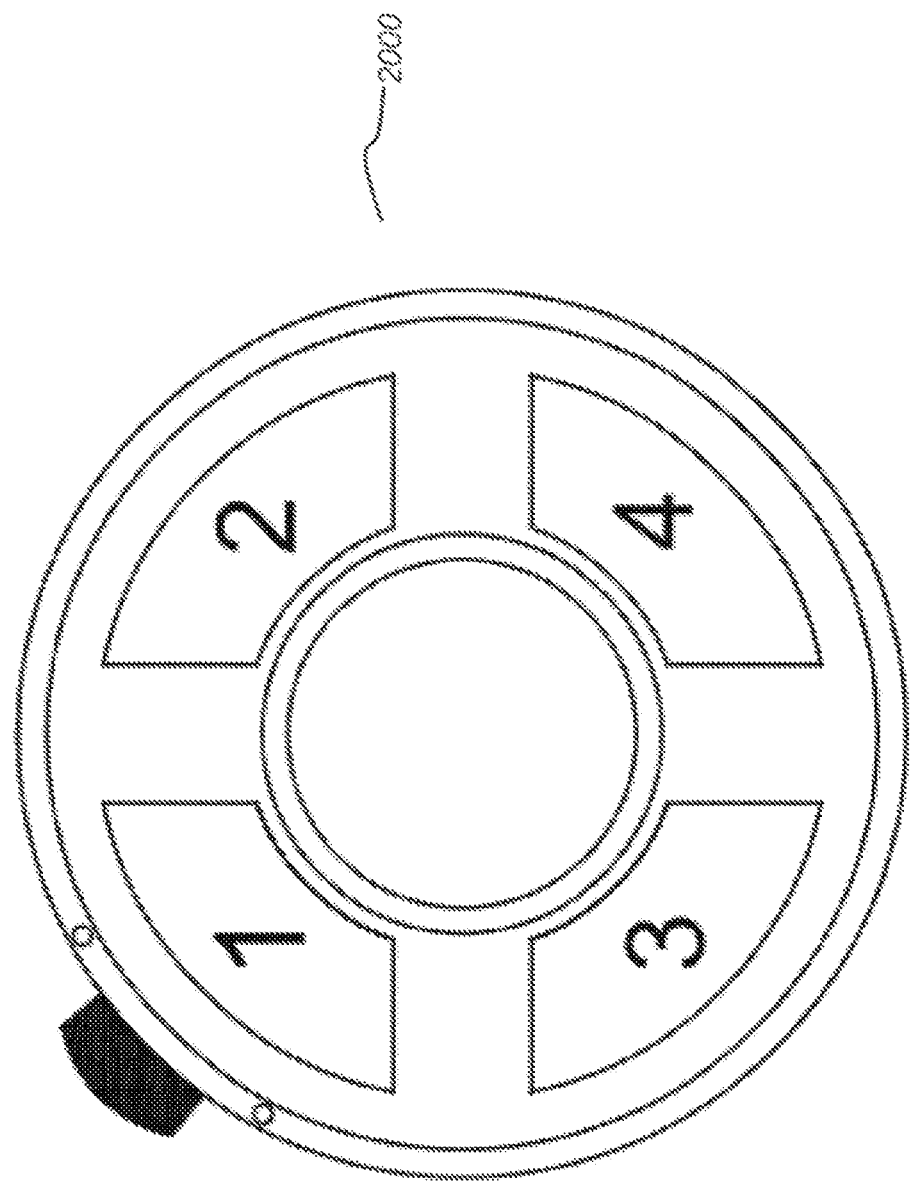
Figure 20D:
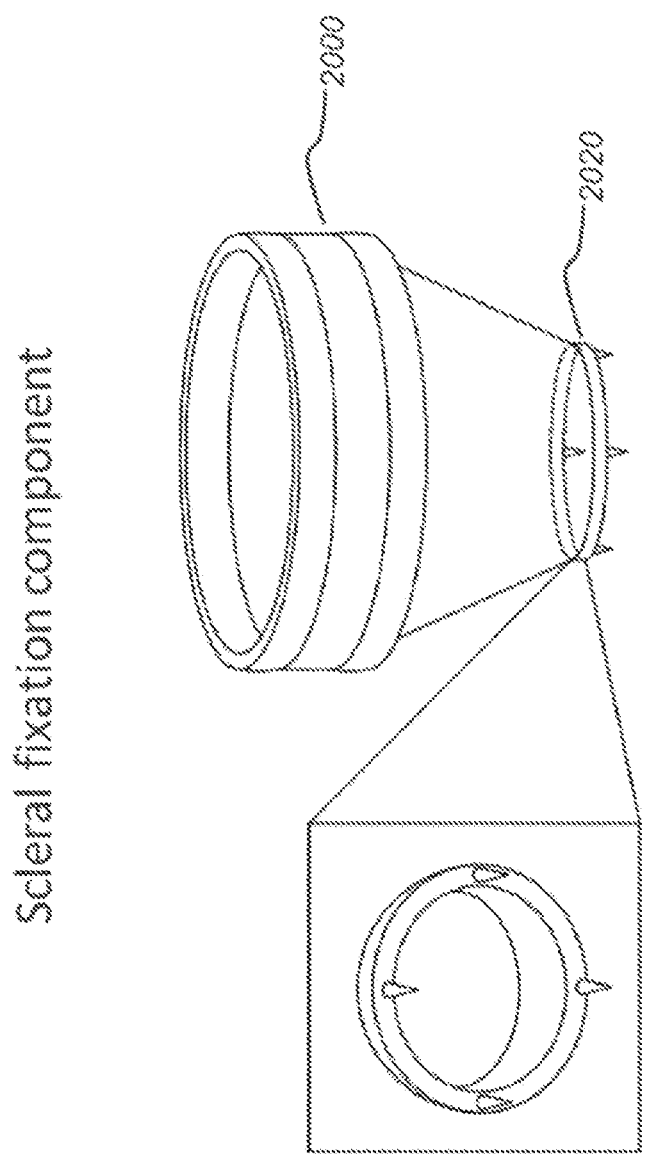
Figure 20E:
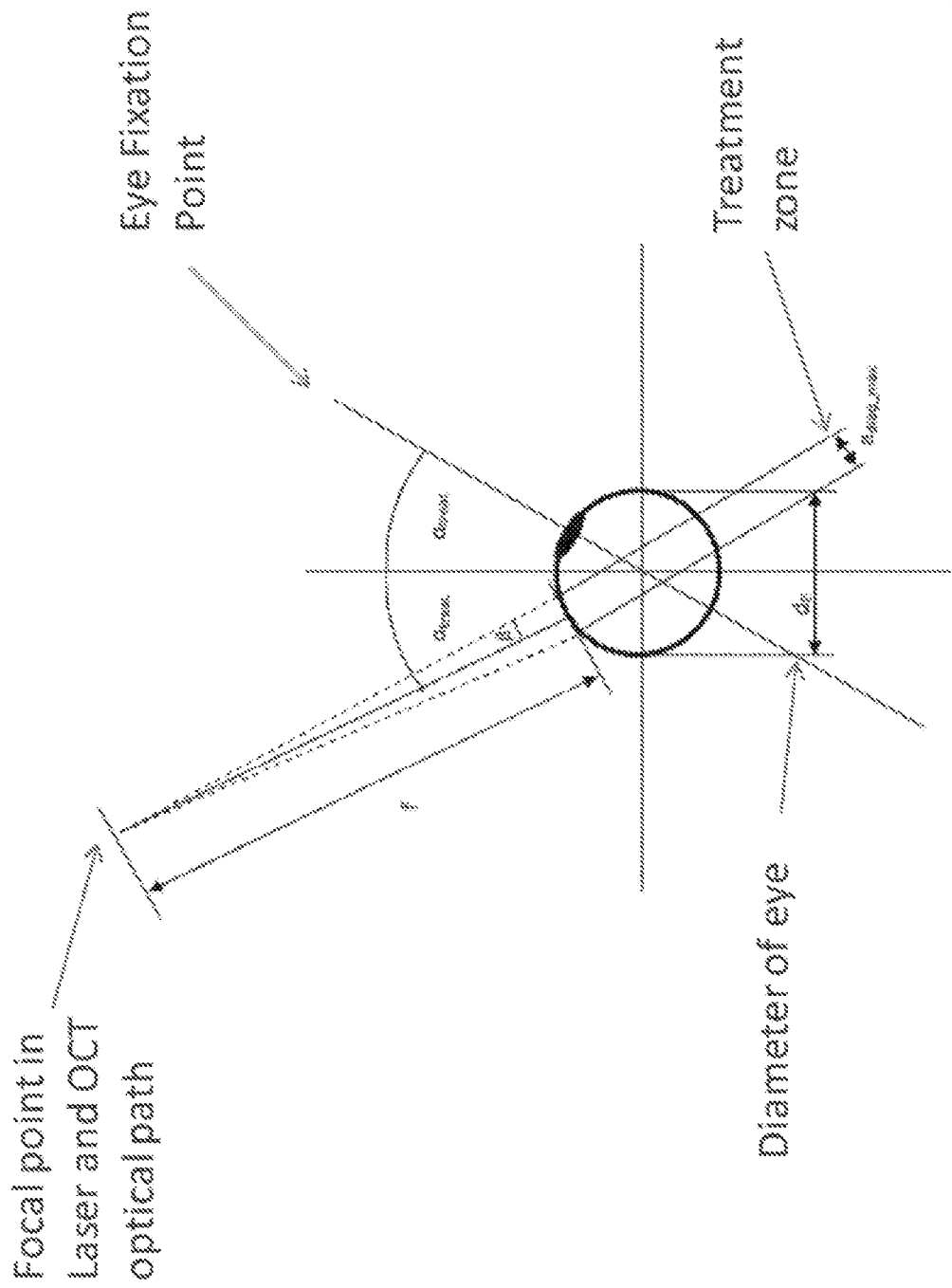

FIG. 20D illustrates an exemplary scleral fixation component, according to an embodiment of the disclosure.

FIGS. 20E to 20H illustrate different exemplary views of off axis scanning, according to an embodiment of the disclosure.

Figure 20G:
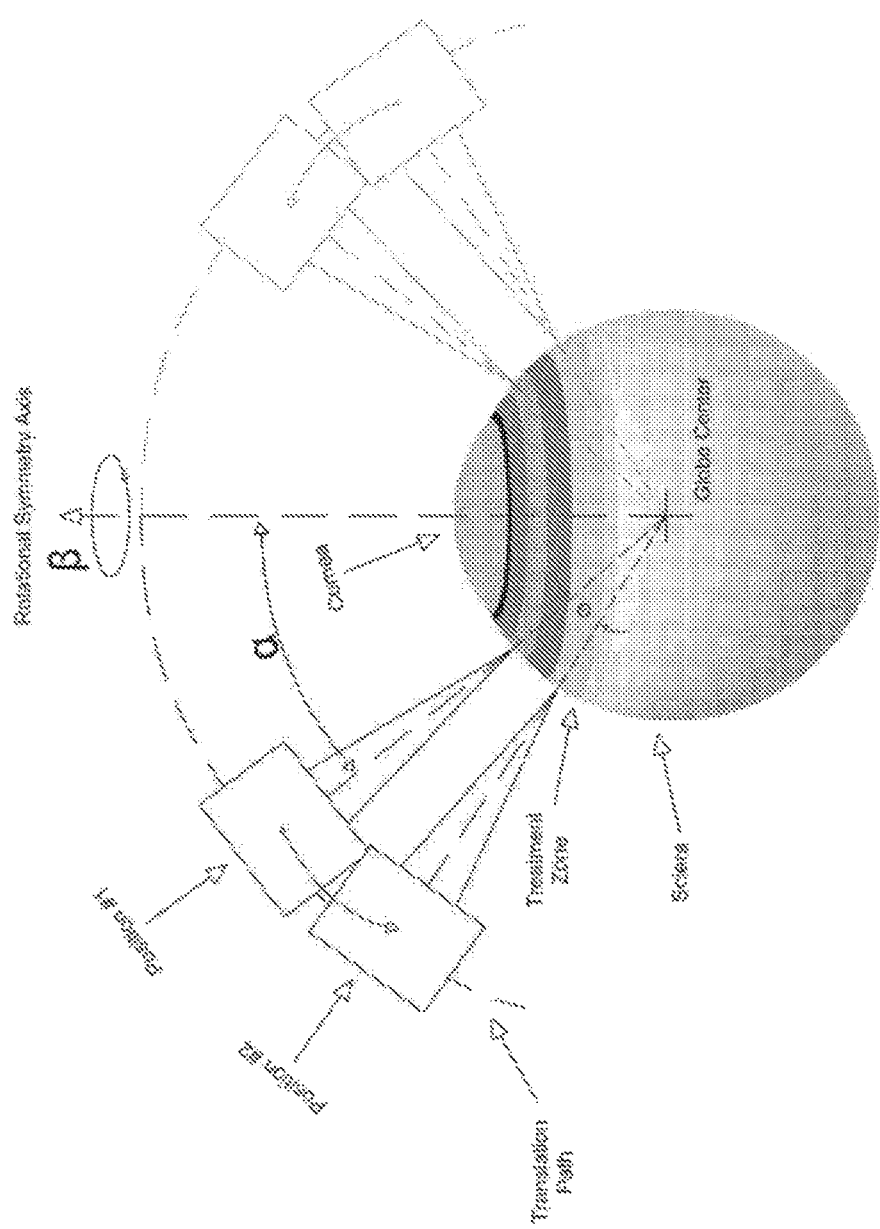
Figure 20H:
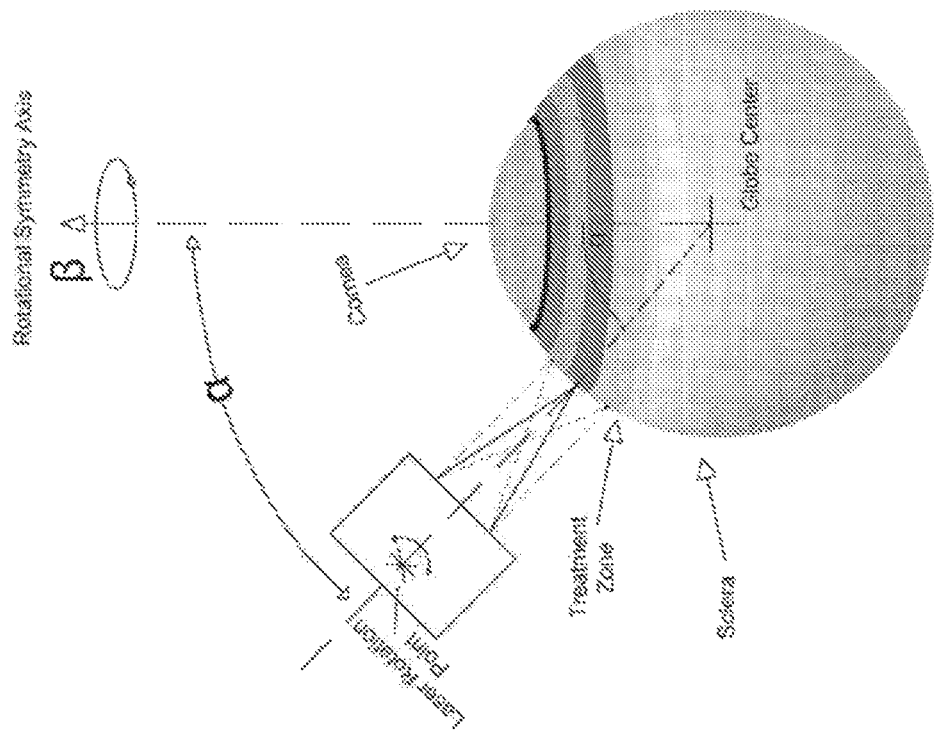
Figure 20I:
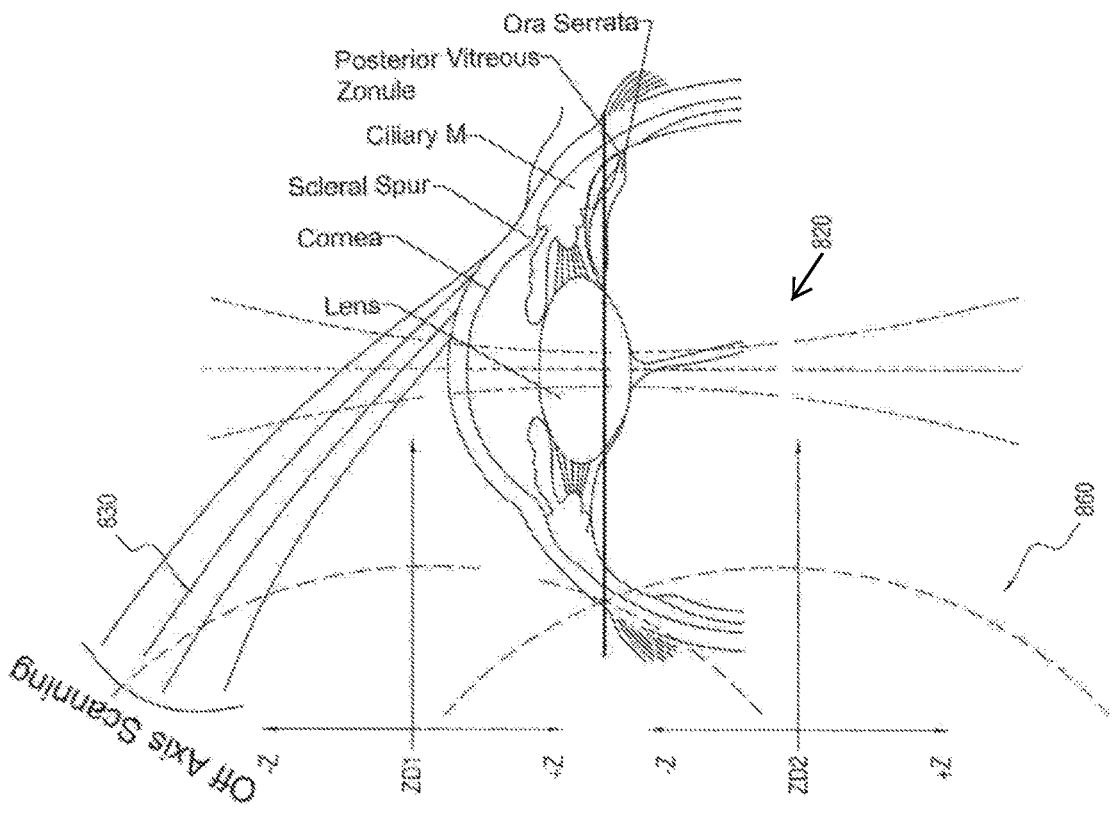

FIG. 20I illustrates exemplary off axis scanning with treatment being angular, according to an embodiment of the disclosure.

Figure 20J:
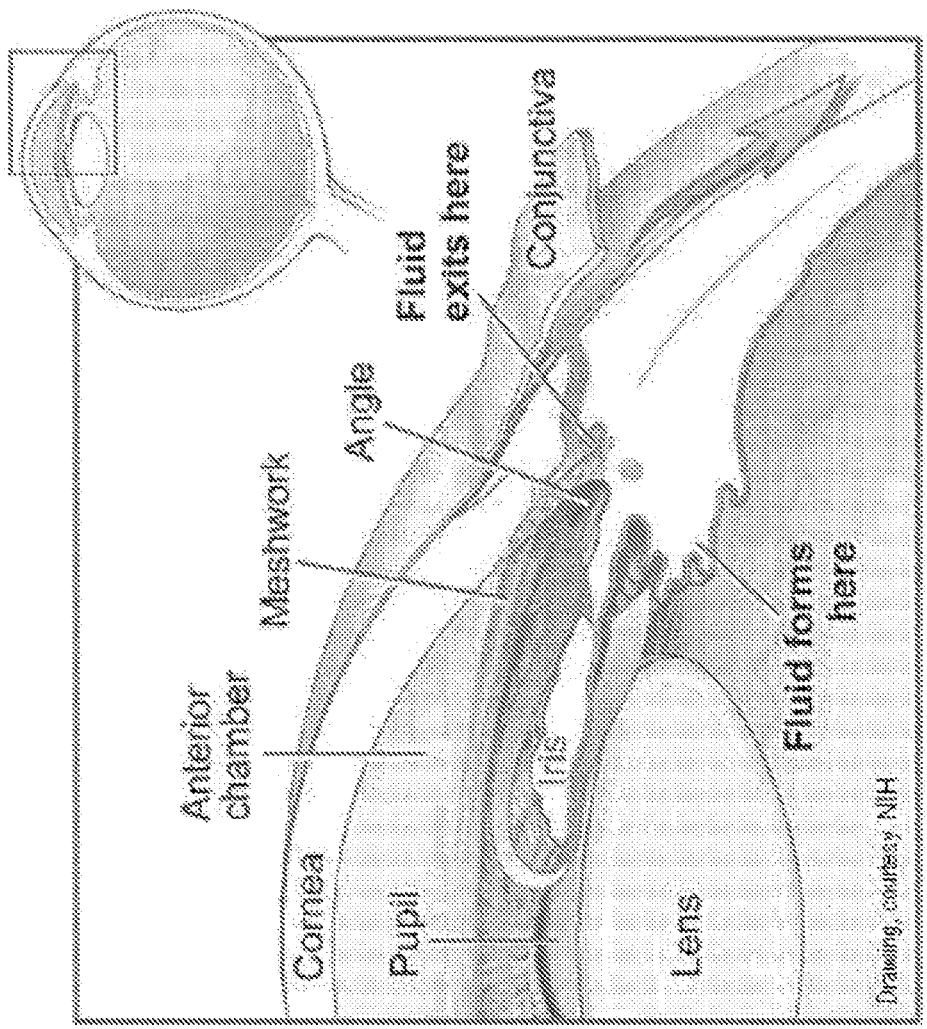

FIG. 20J illustrates the aqueous flow within the eye.

Figure 20K:
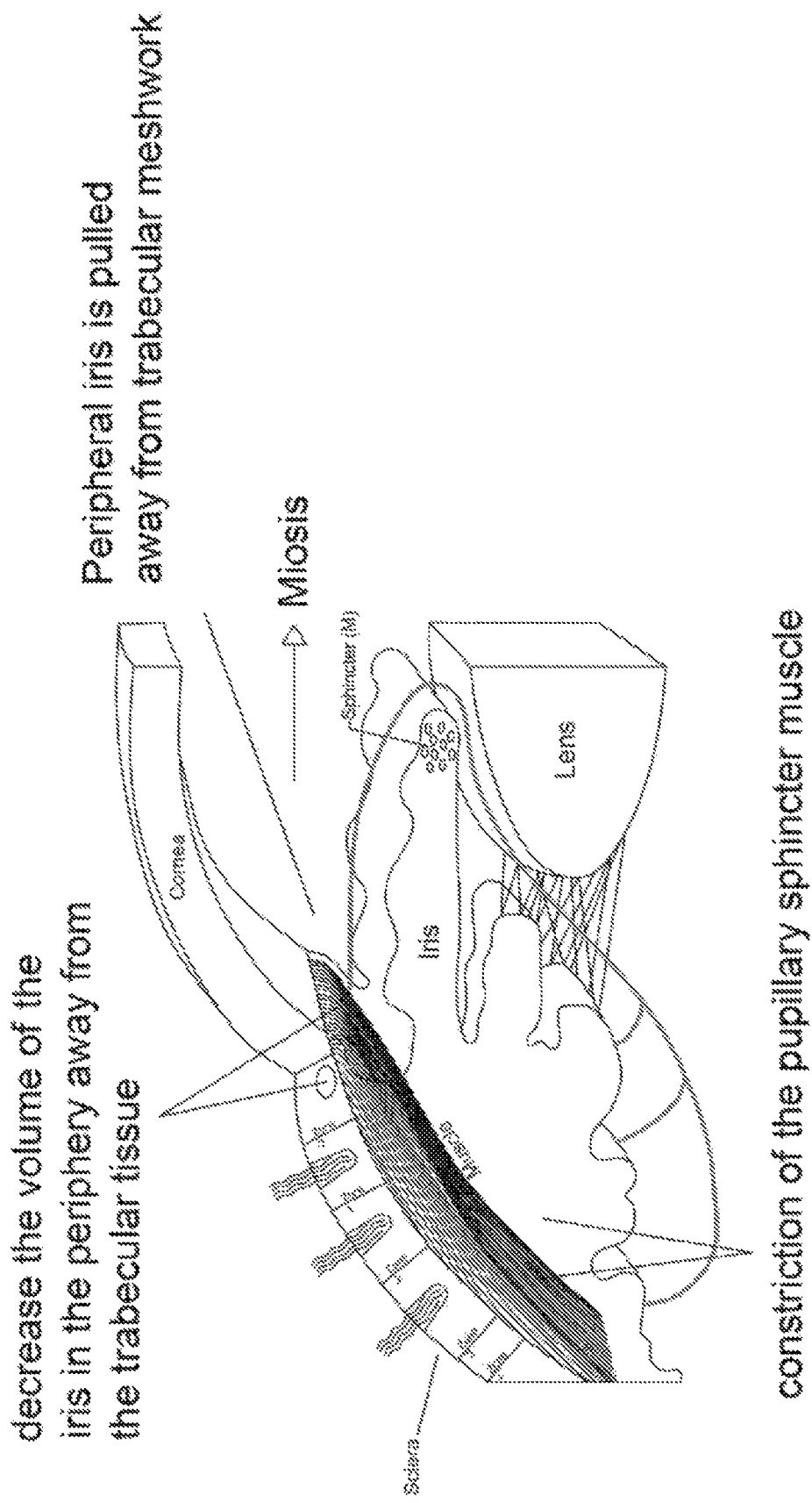
Figure 20L:
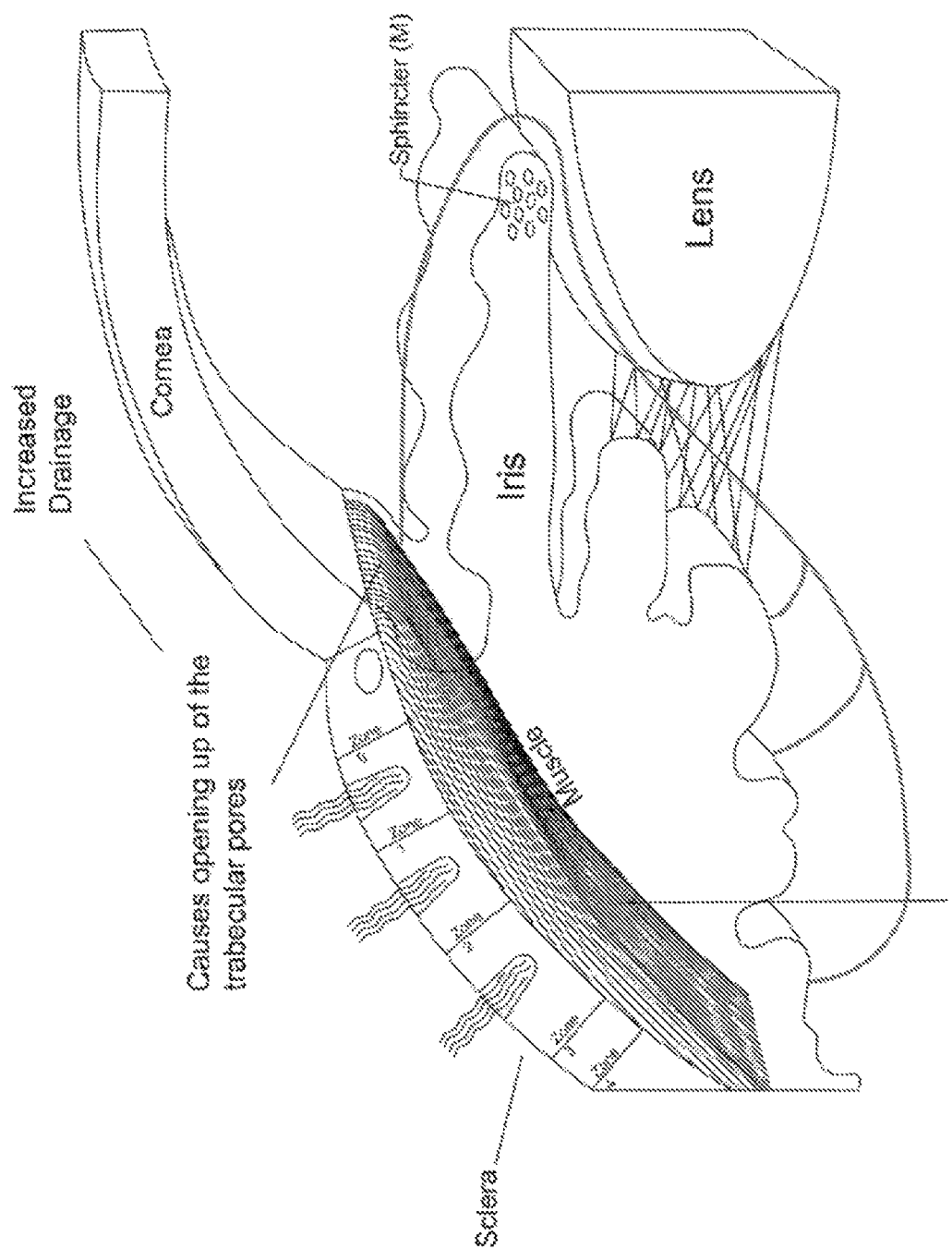

FIGS. 20K to 20L illustrate exemplary increase in uveal outflow, according to an embodiment of the disclosure.

Figure 20M:
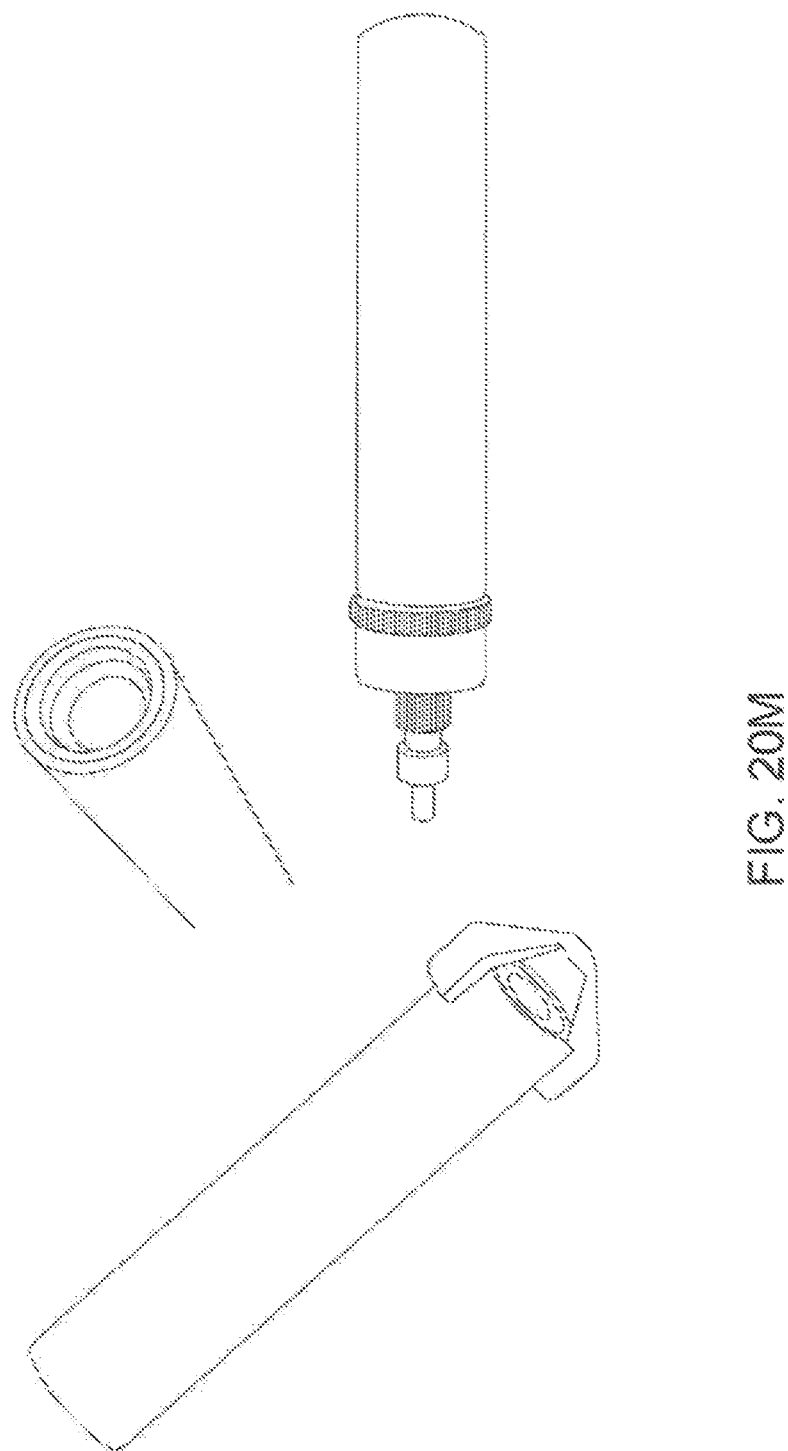

FIG. 20M illustrates an exemplary hand piece delivery system, according to an embodiment of the disclosure.

Figure 20N:
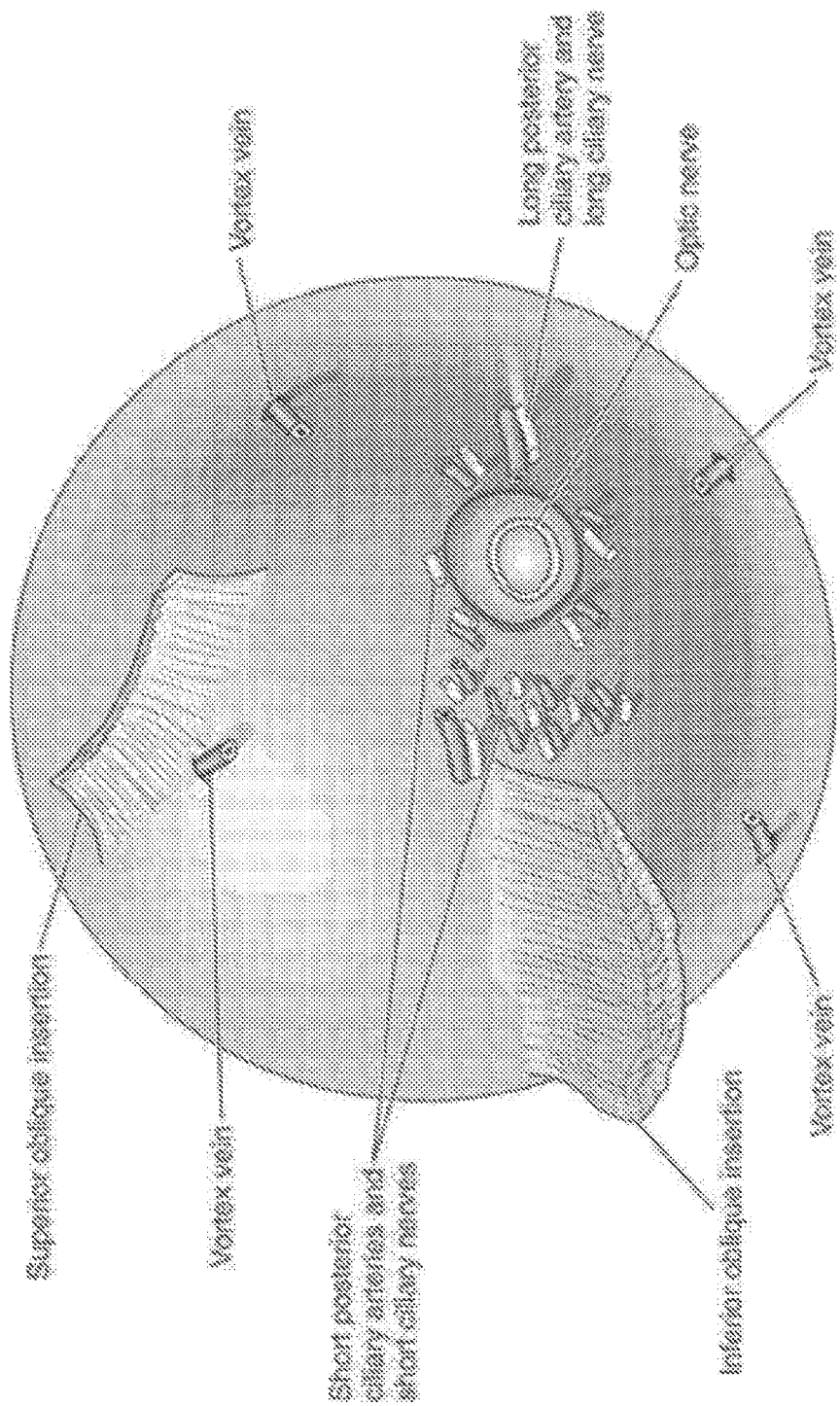

FIGS. 20N to 20O illustrate exemplary treatment zones in the anterior and posterior globe, according to an embodiment of the disclosure.

Figures 3, 20P:
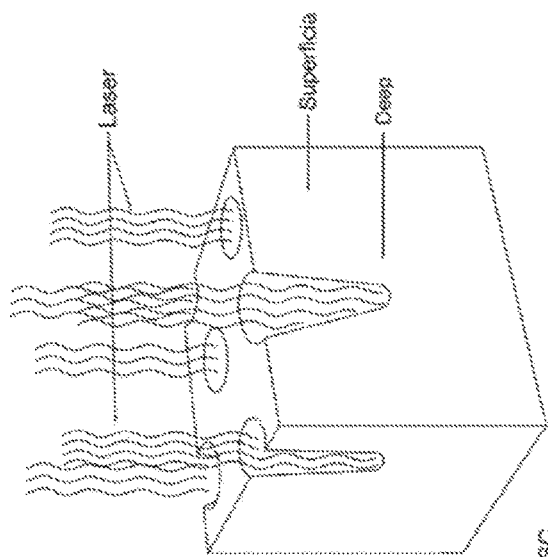
Figures 2, 20P:
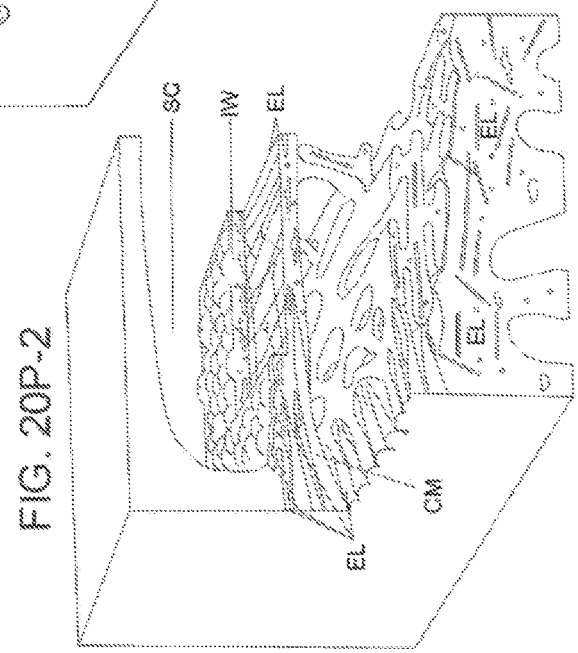
Figures 1, 20P:
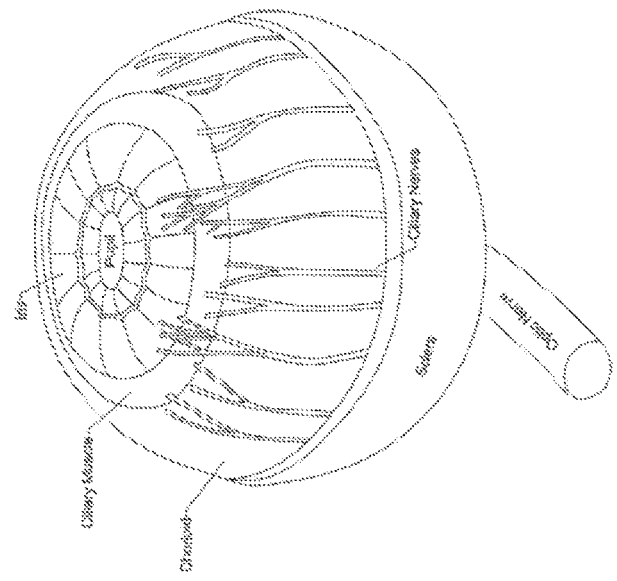

FIGS. 20P-1 to 20P-3 illustrate exemplary targets for drug delivery, according to an embodiment of the disclosure.

Figures 2, 20Q:
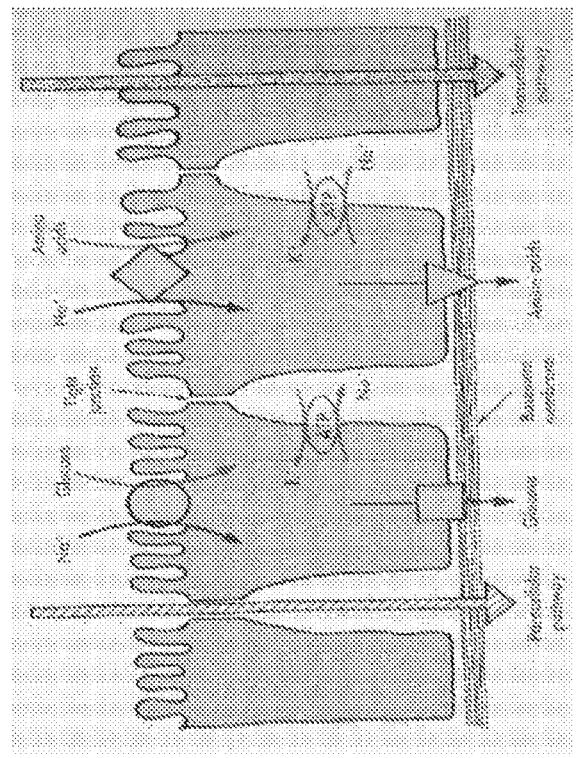
Figures 1, 20Q:
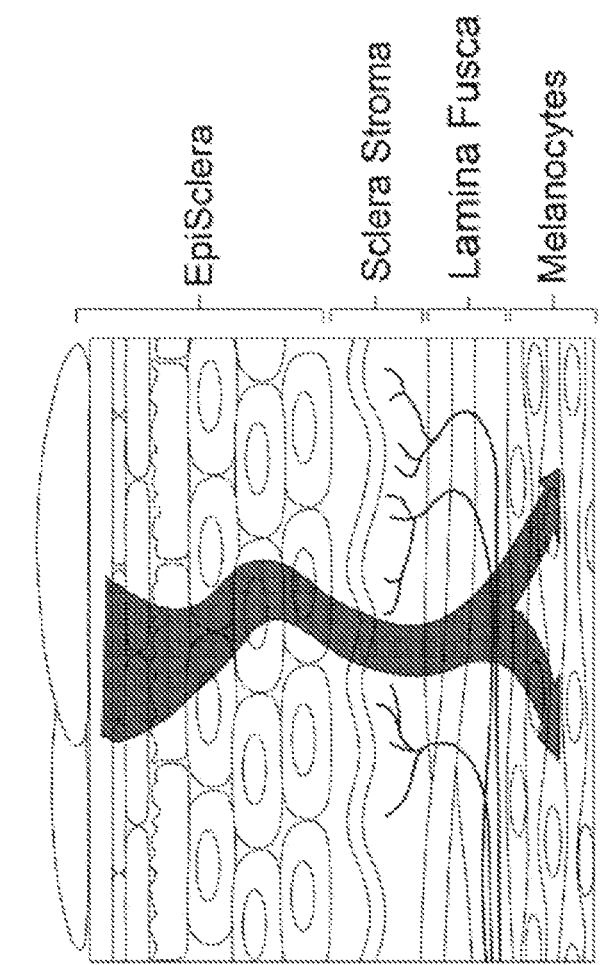
Figures 3, 20Q:
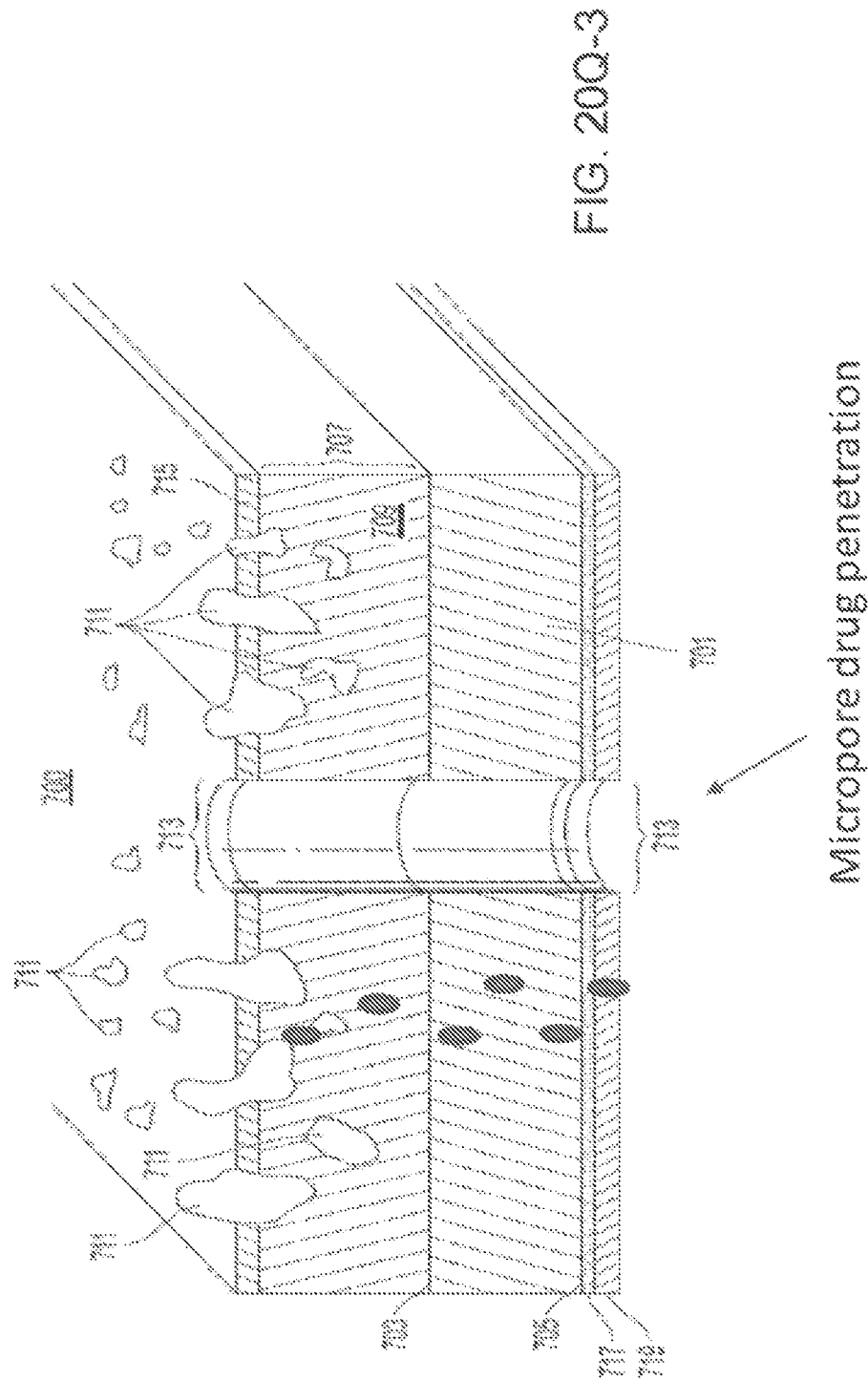

FIGS. 20Q-1 to 20Q-3 illustrate an exemplary drug delivery, according to an embodiment of the disclosure.

Figure 20R:
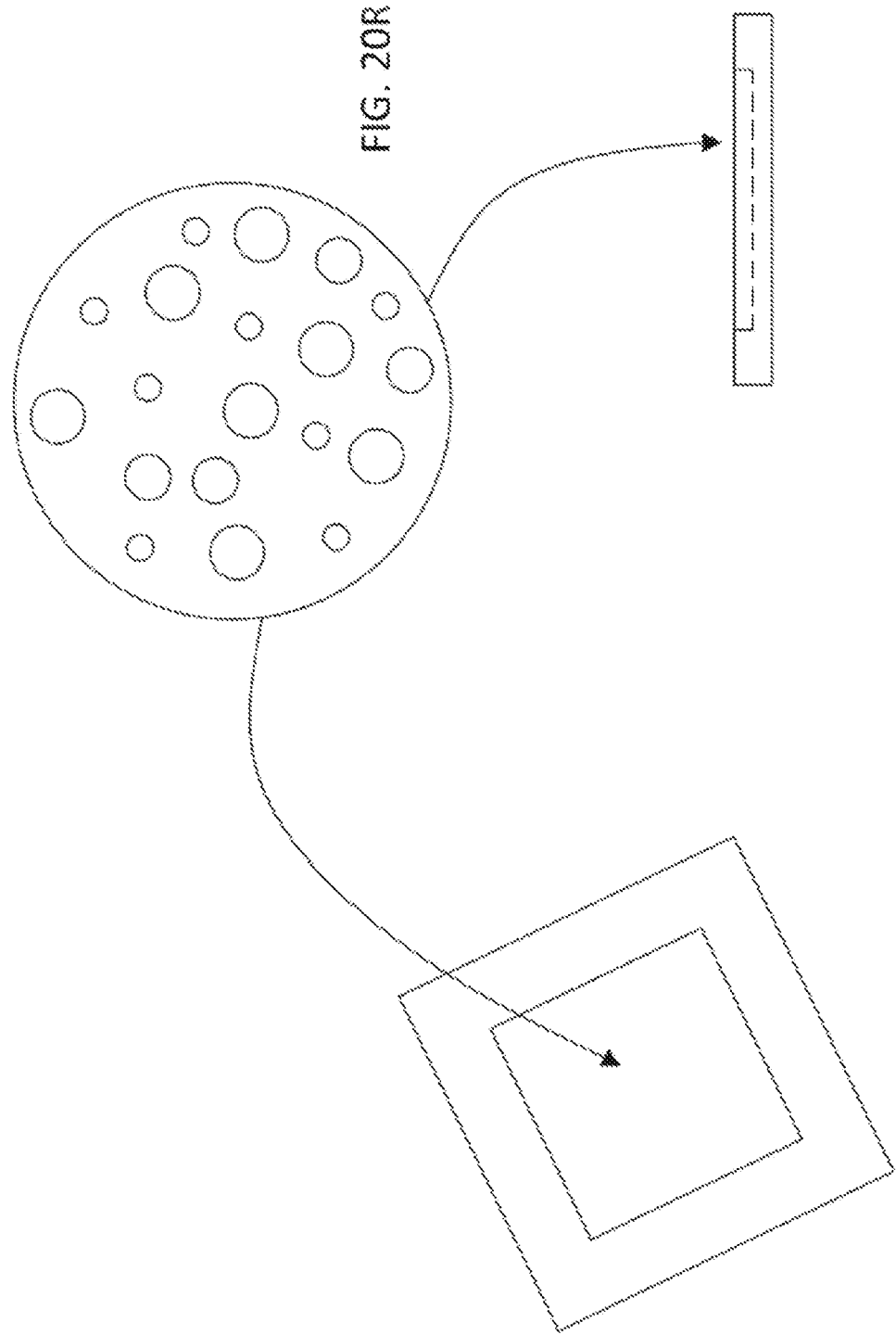

FIG. 20R illustrates an exemplary opthacoil, according to an embodiment of the disclosure.

Figure 20S:
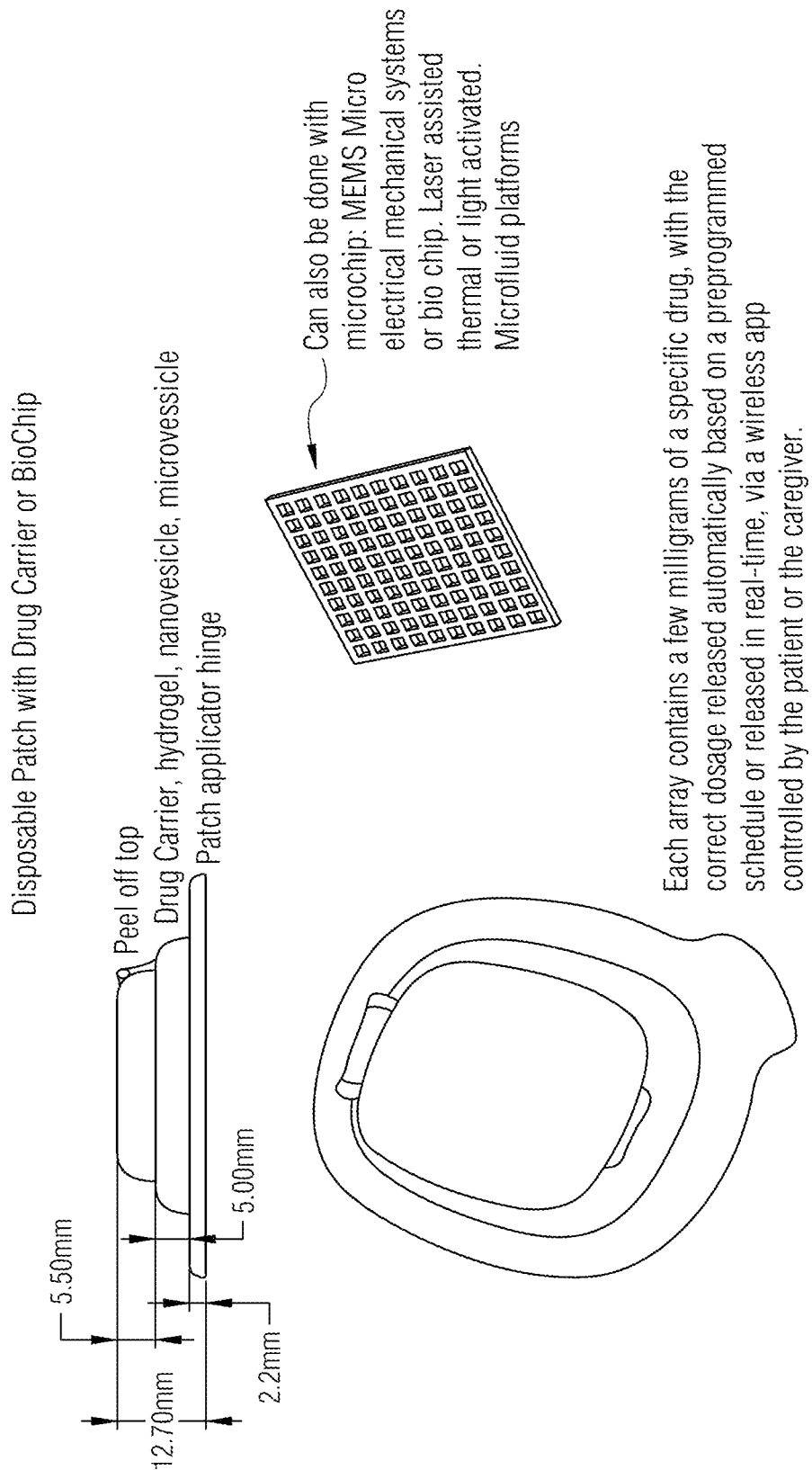

FIG. 20S illustrate exemplary drug delivery carriers, according to an embodiment of the disclosure.

FIGS. 20T-1 to 20T-3 illustrate an exemplary scleral wafer, according to an embodiment of the disclosure.

Figure 21B:
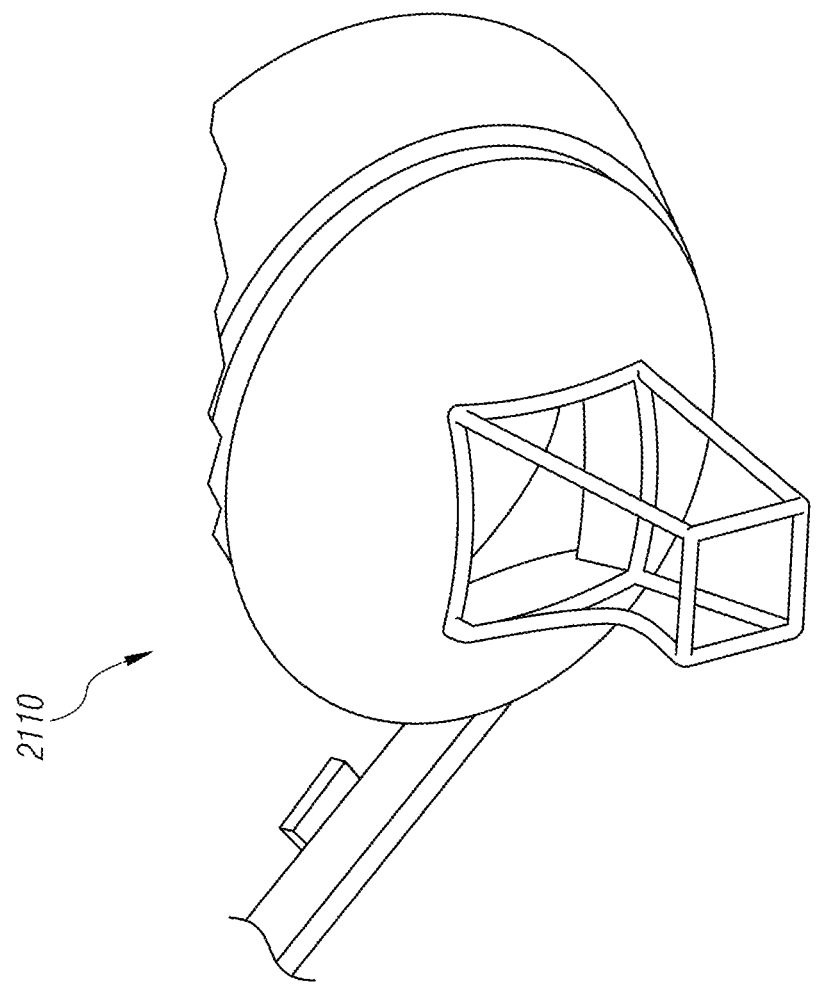
Figure 21A:
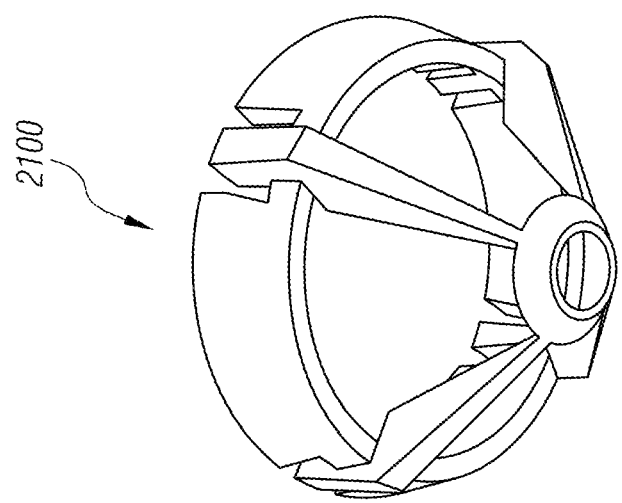

FIGS. 21A and 21B illustrate an exemplary a nozzle guard, according to an embodiment of the disclosure.

FIG. 22 illustrates an exemplary nozzle guard being attached to a nozzle, according to an embodiment of the disclosure.

FIG. 23 illustrates the nozzle being fitted with disposable insert and filter, according to an embodiment of the disclosure.

Figure 24:
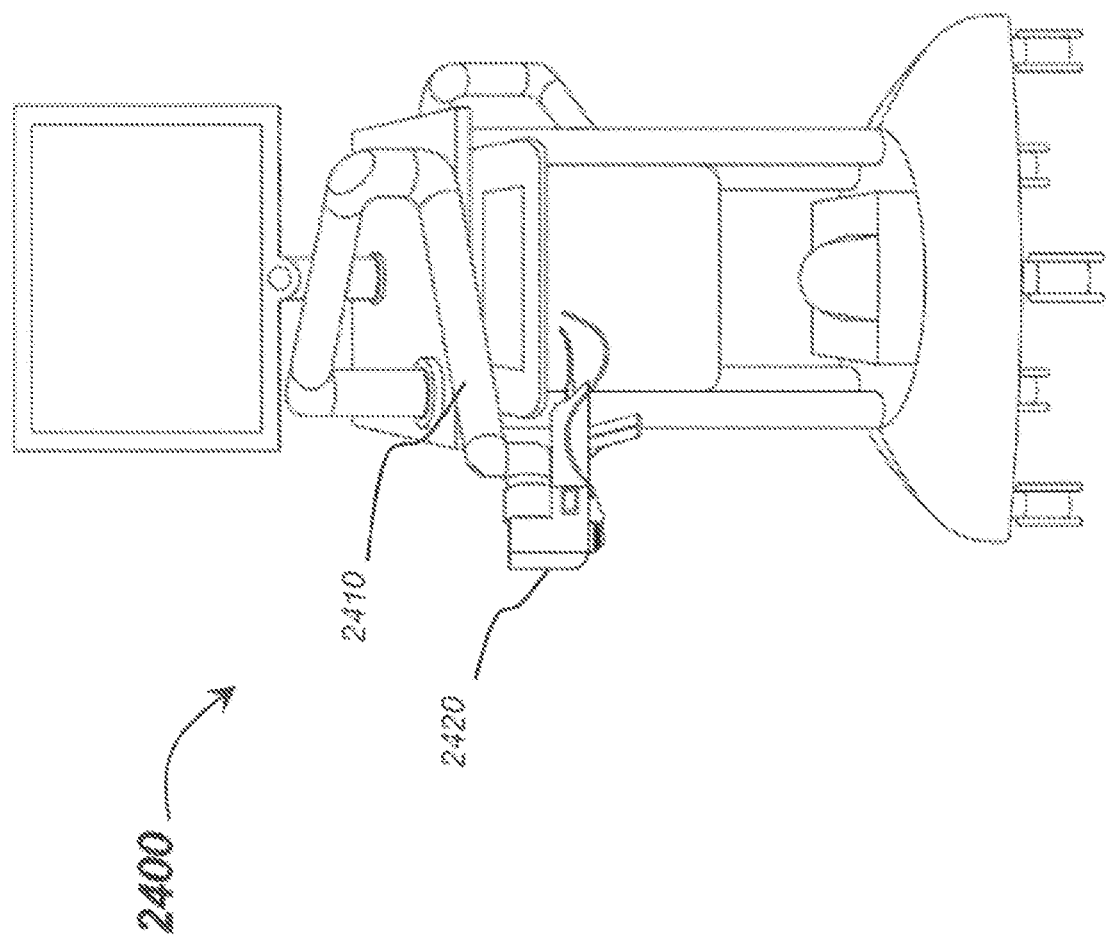

FIG. 24 illustrates an exemplary workstation, according to an embodiment of the disclosure.

FIGS. 25A and 25B illustrate the housing unit which is rotatable 360 degrees, according to an embodiment of the disclosure.

Figures 1, 26:
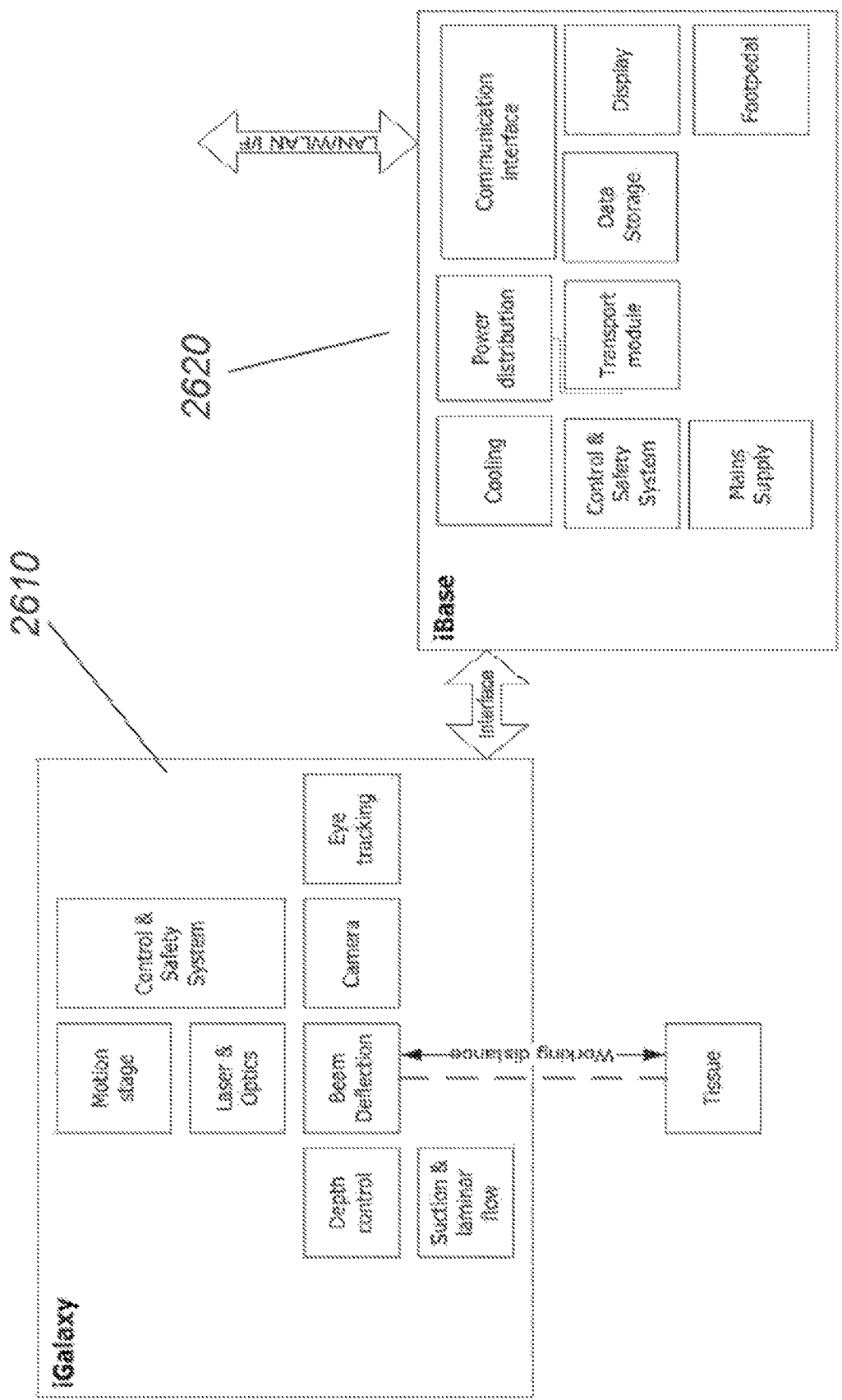
Figures 3A, 26:
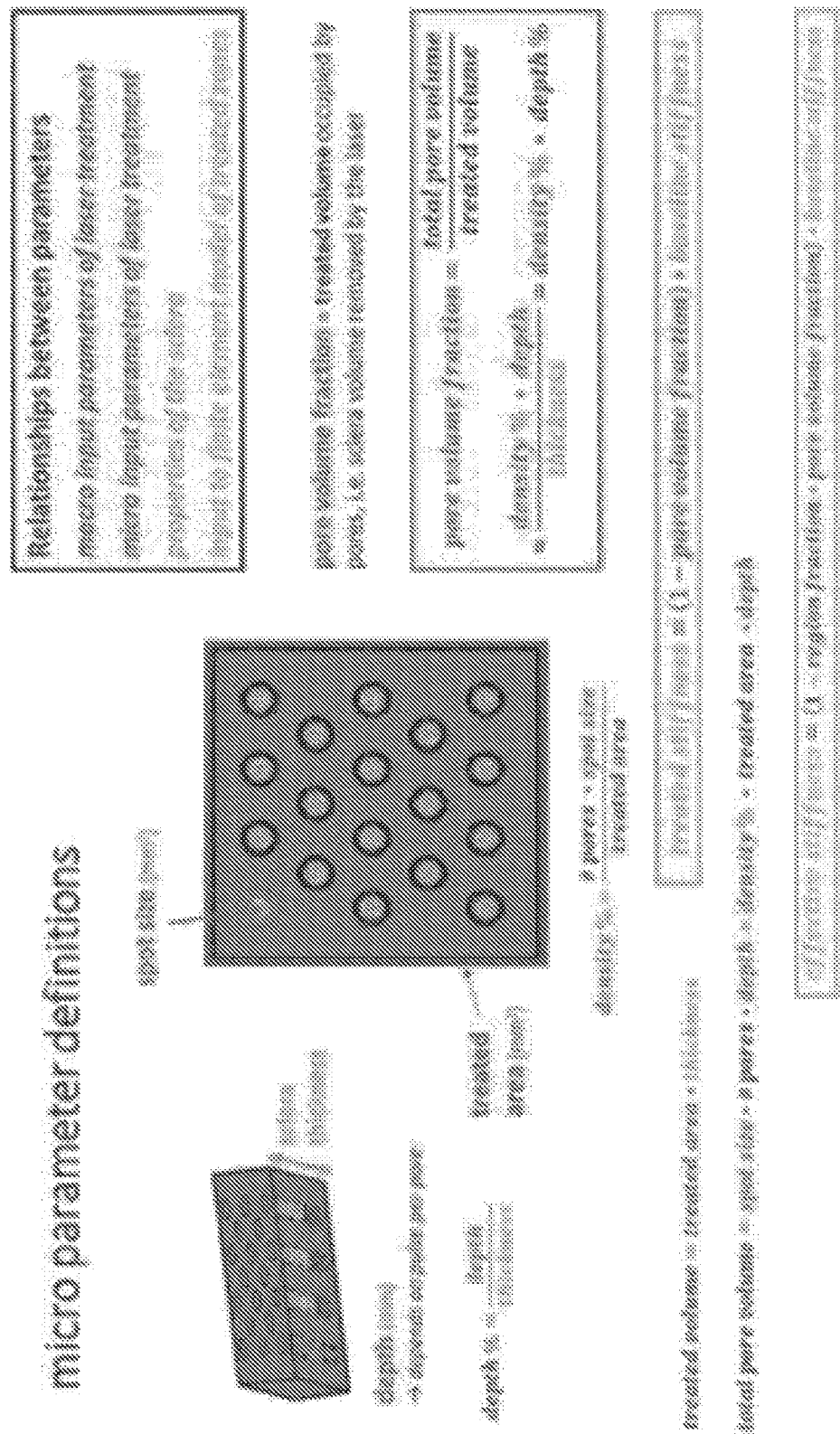
Figure 26:
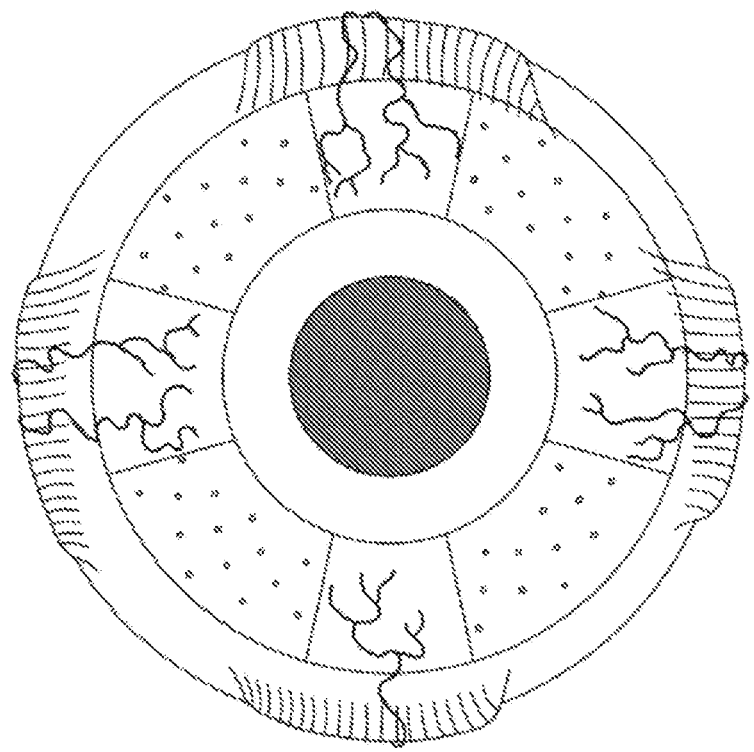
Figure 4:
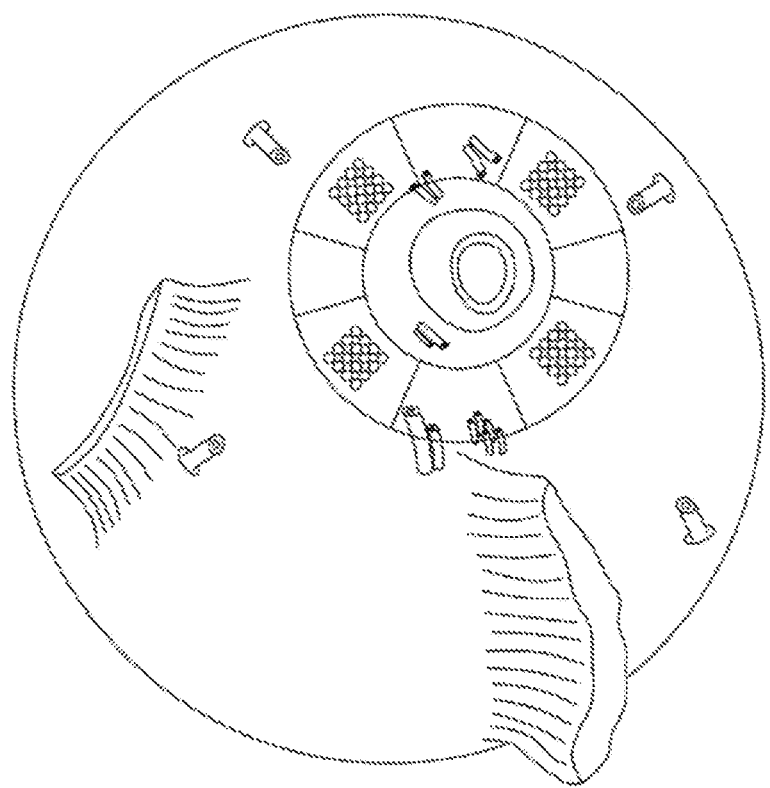
Figures 1, 4, 26:
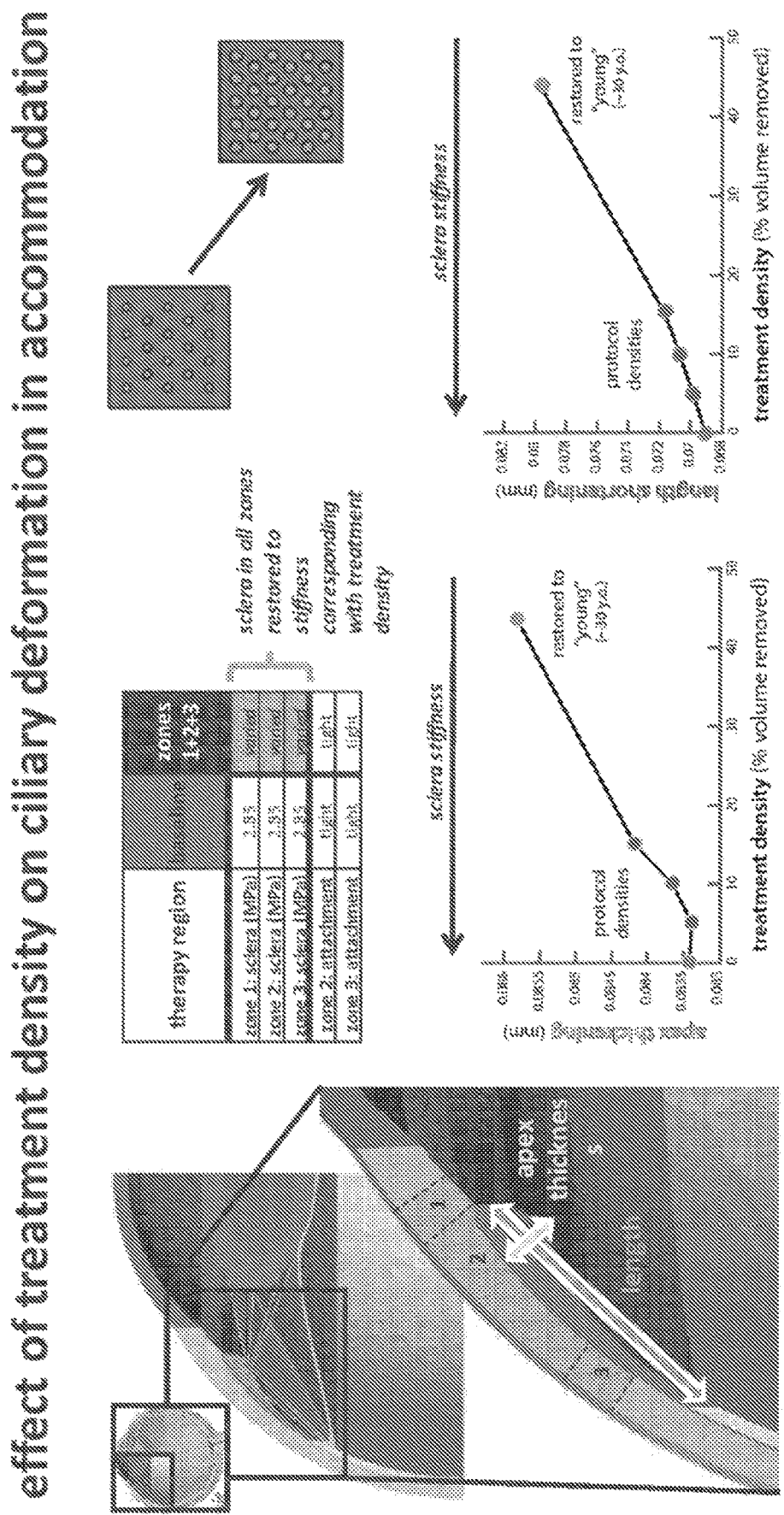
Figures 5, 26:
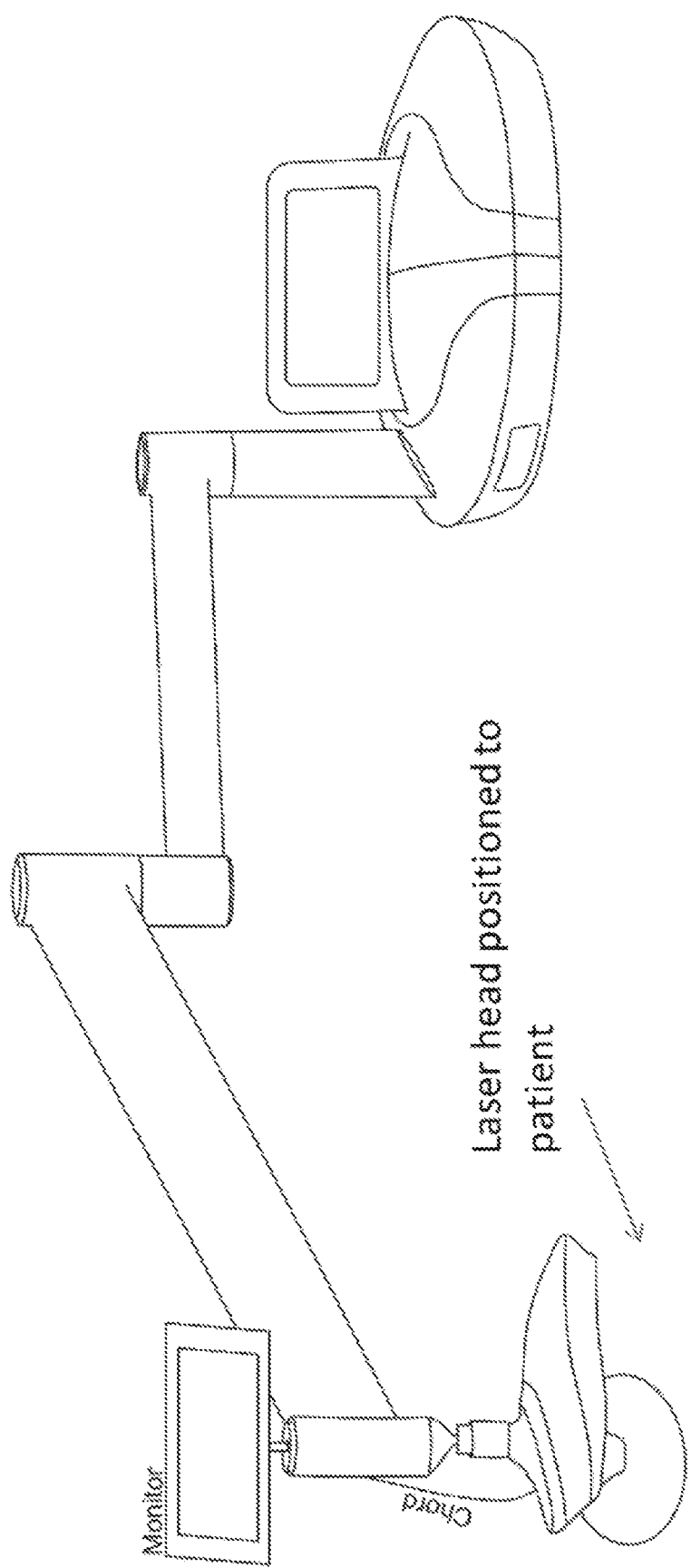

FIG. 26-A illustrates an exemplary multilayer imaging platform, according to an embodiment of the disclosure.

FIGS. 26-B and 26-C illustrate an exemplary CCD camera, according to an embodiment of the disclosure.

FIG. 26-D illustrates an exemplary camera view using a CCD camera, according to an embodiment of the disclosure.

FIG. 26-1 illustrates another exemplary laser system, according to an embodiment of the disclosure.

FIG. 26-2 illustrates exemplary chart for wavelengths with high water absorption, according to an embodiment of the disclosure.

FIGS. 26-3A, 26-3A1 and 26-3A2 illustrate exemplary treatment parameters, according to an embodiment of the disclosure.

FIG. 26-4 illustrates anatomy recognition, according to an embodiment of the disclosure.

FIG. 26-4-1 illustrates an exemplary effect of treatment density, according to an embodiment of the disclosure FIG. 26-5 illustrates another exemplary workstation, according to an embodiment of the disclosure.

Figure 27A:
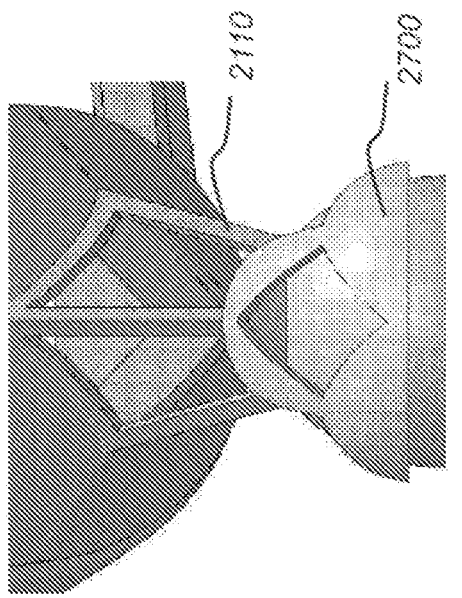
Figure 27B:
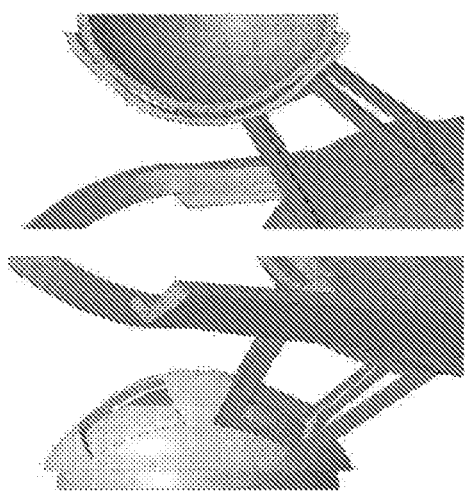
Figure 27C:
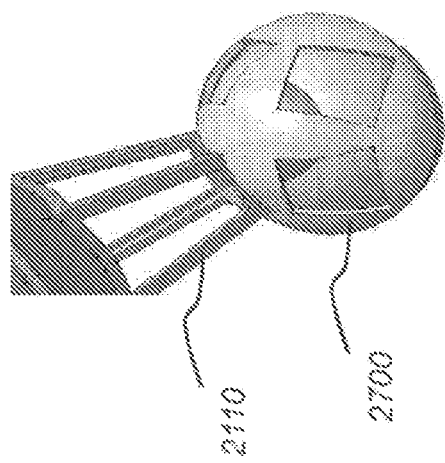

FIGS. 27A to 27C illustrate exemplary lens/mask, according to an embodiment of the disclosure.

FIGS. 28A to 28C and FIGS. 29A to 29B illustrate an exemplary speculum and exemplary operation using the speculum, according to an embodiment of the disclosure.

Figure 30:
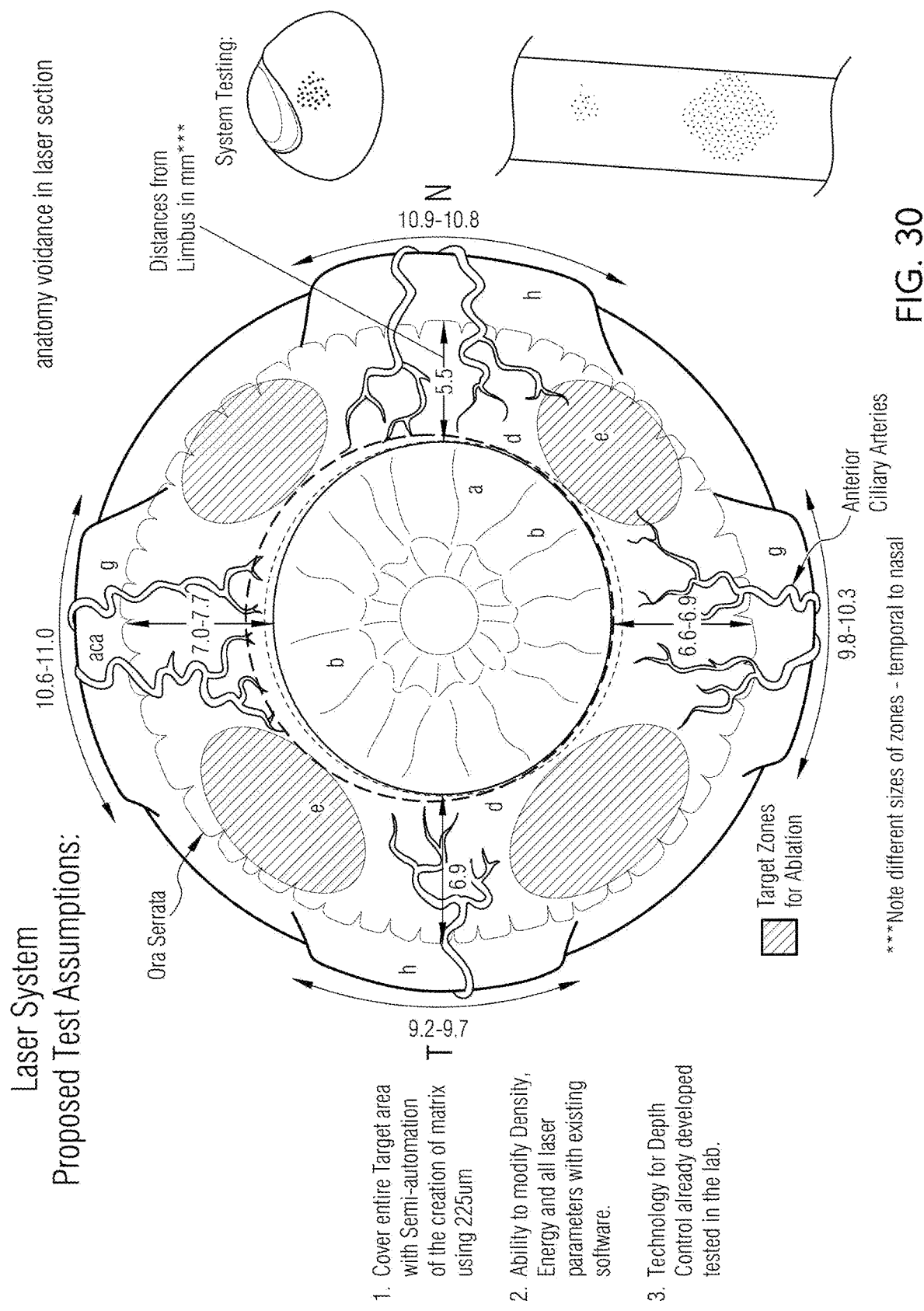

FIG. 30 illustrates an exemplary test and anatomy avoidance in a laser system, according to an embodiment of the disclosure.

Figure 31:
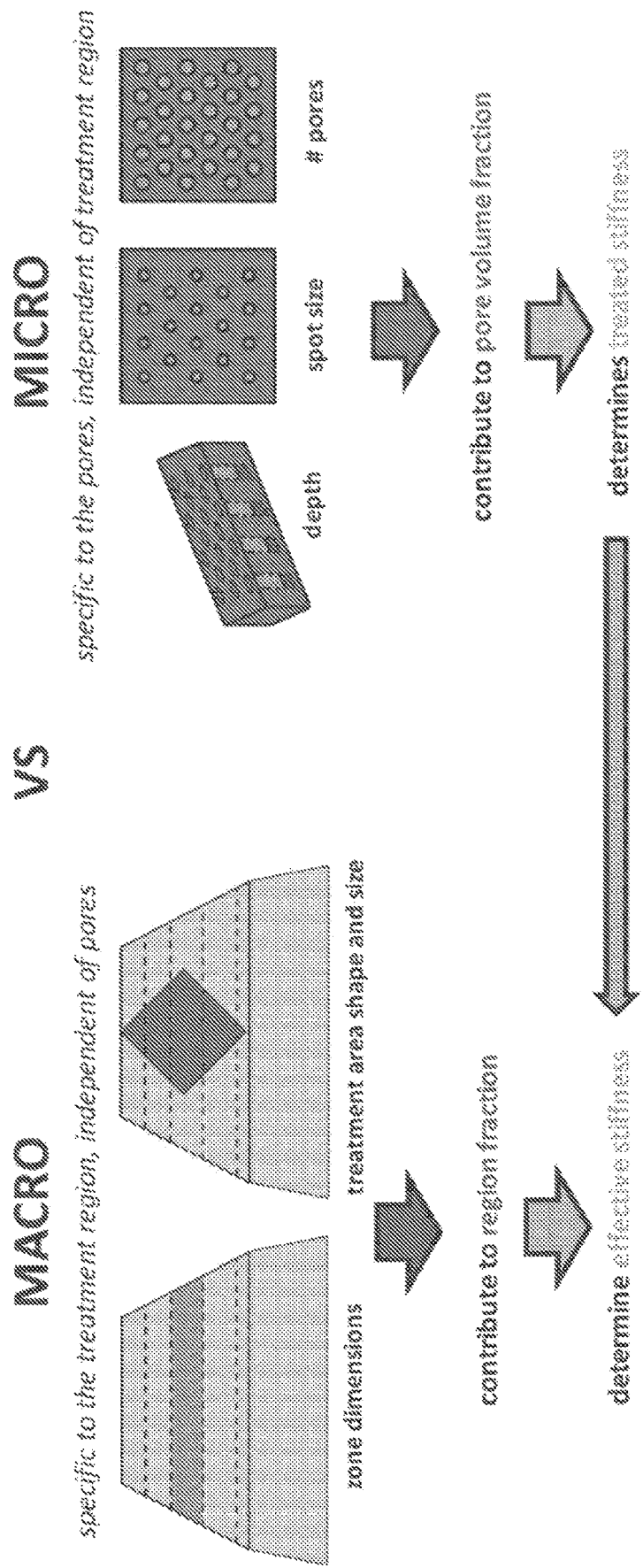
Figure 32:
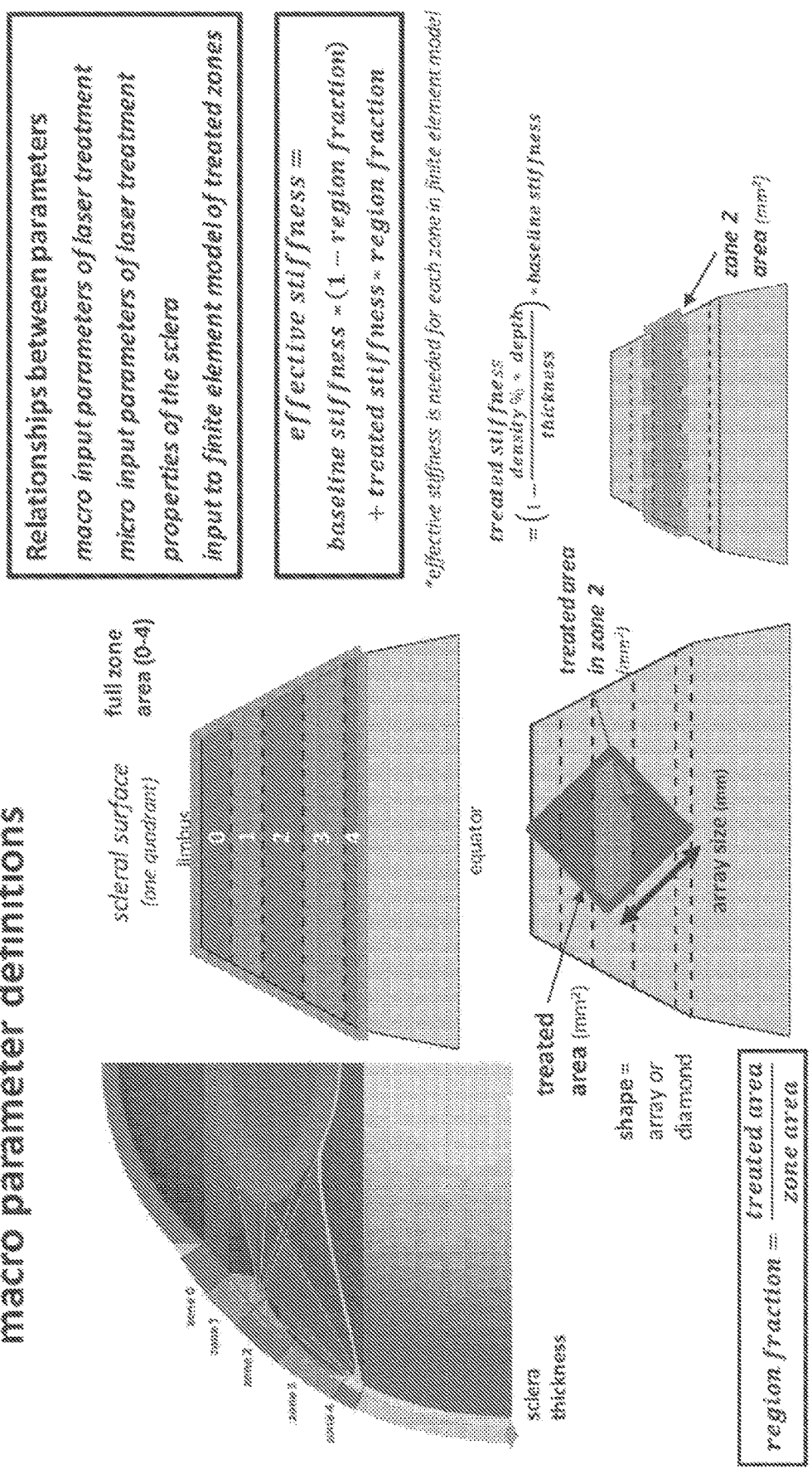

FIG. 31 and FIG. 32 illustrate further exemplary treatment parameters, according to an embodiment of the disclosure.

Figure 33:
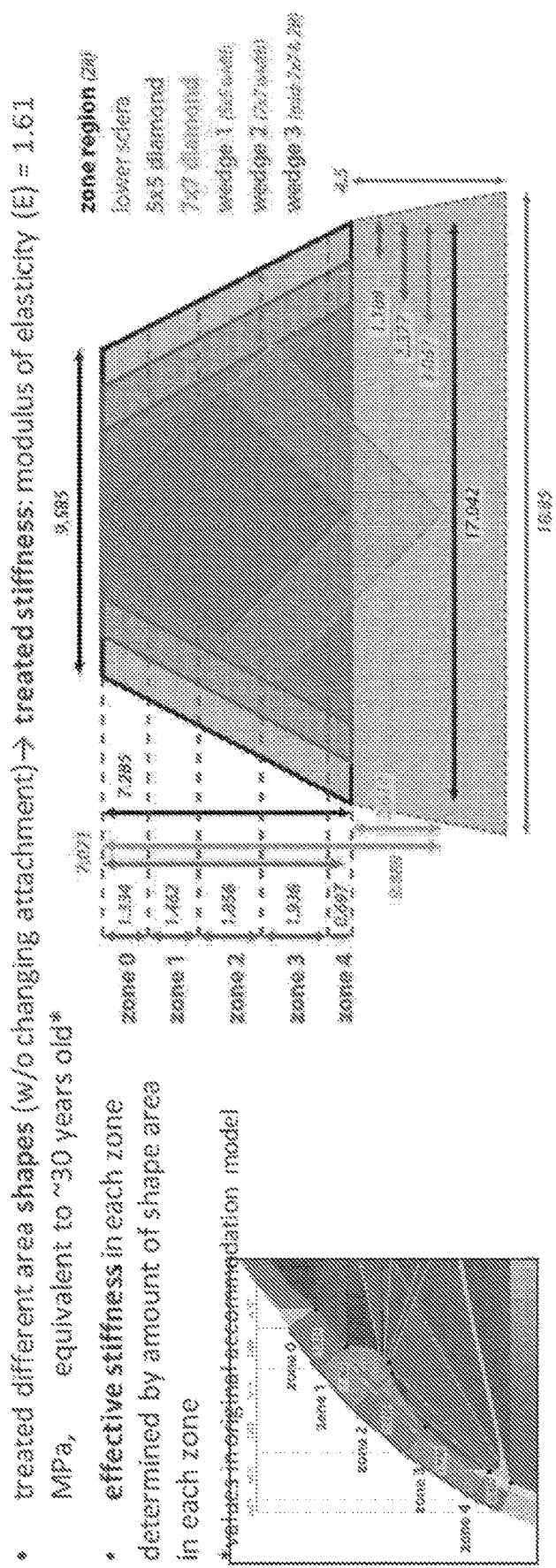

FIG. 33 illustrates exemplary treatment region shapes, according to an embodiment of the disclosure.

Figure 34:
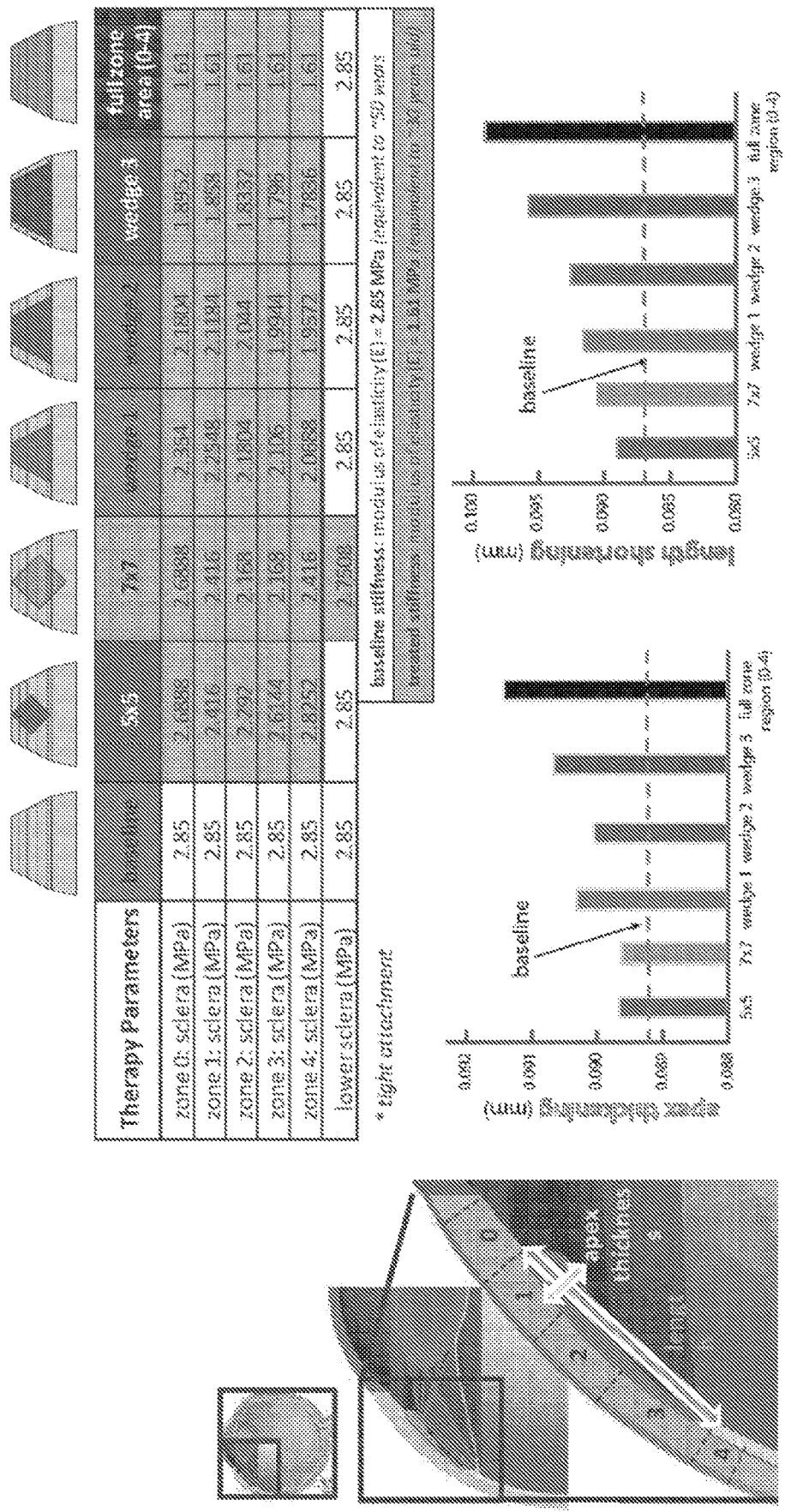

FIG. 34 illustrates exemplary effect of shape treatment, according to an embodiment of the disclosure.

FIG. 35 and FIG. 36 illustrate exemplary therapy simulation methods, according to an embodiment of the disclosure.

Figure 37:
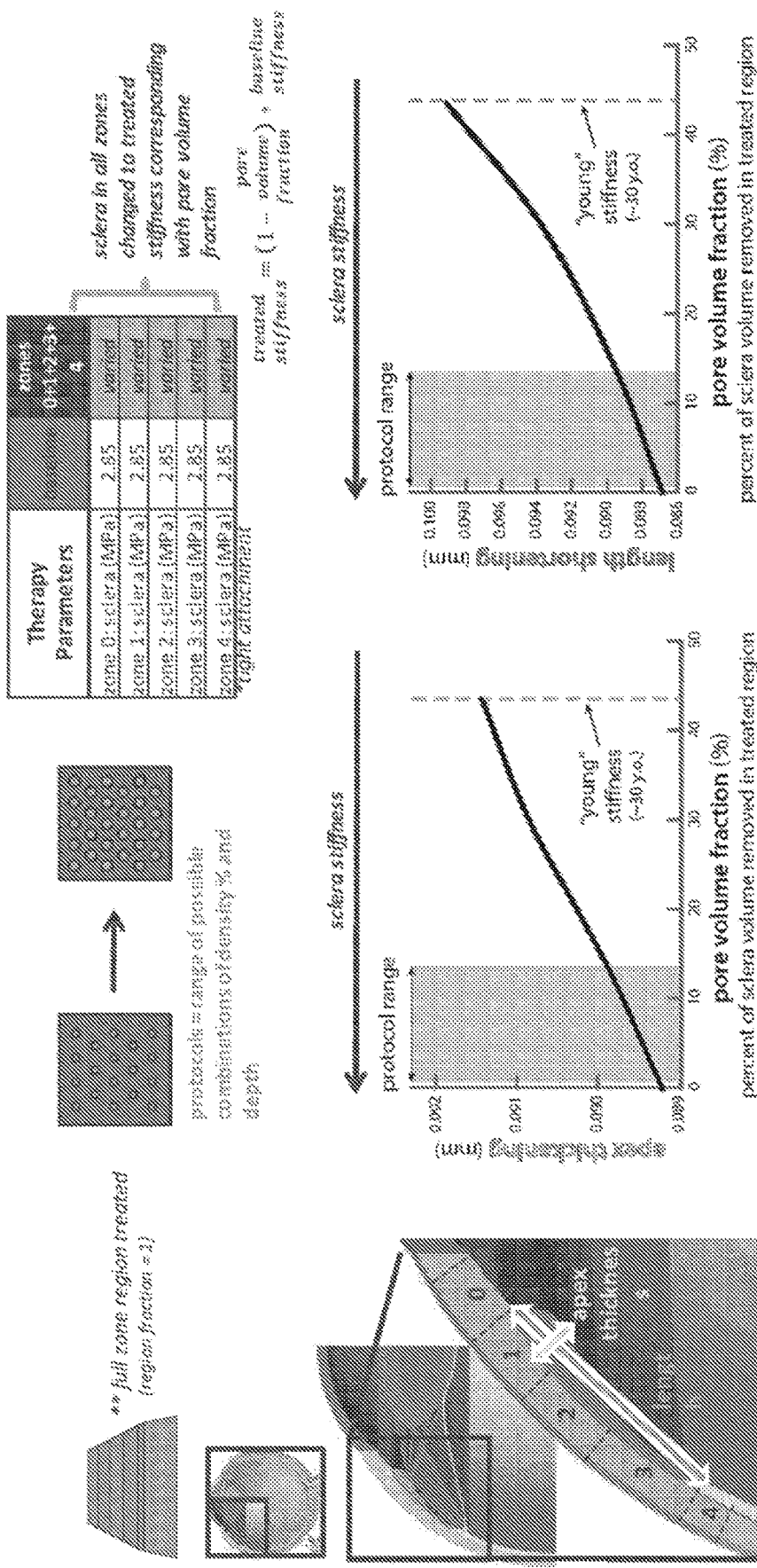
Figure 38:
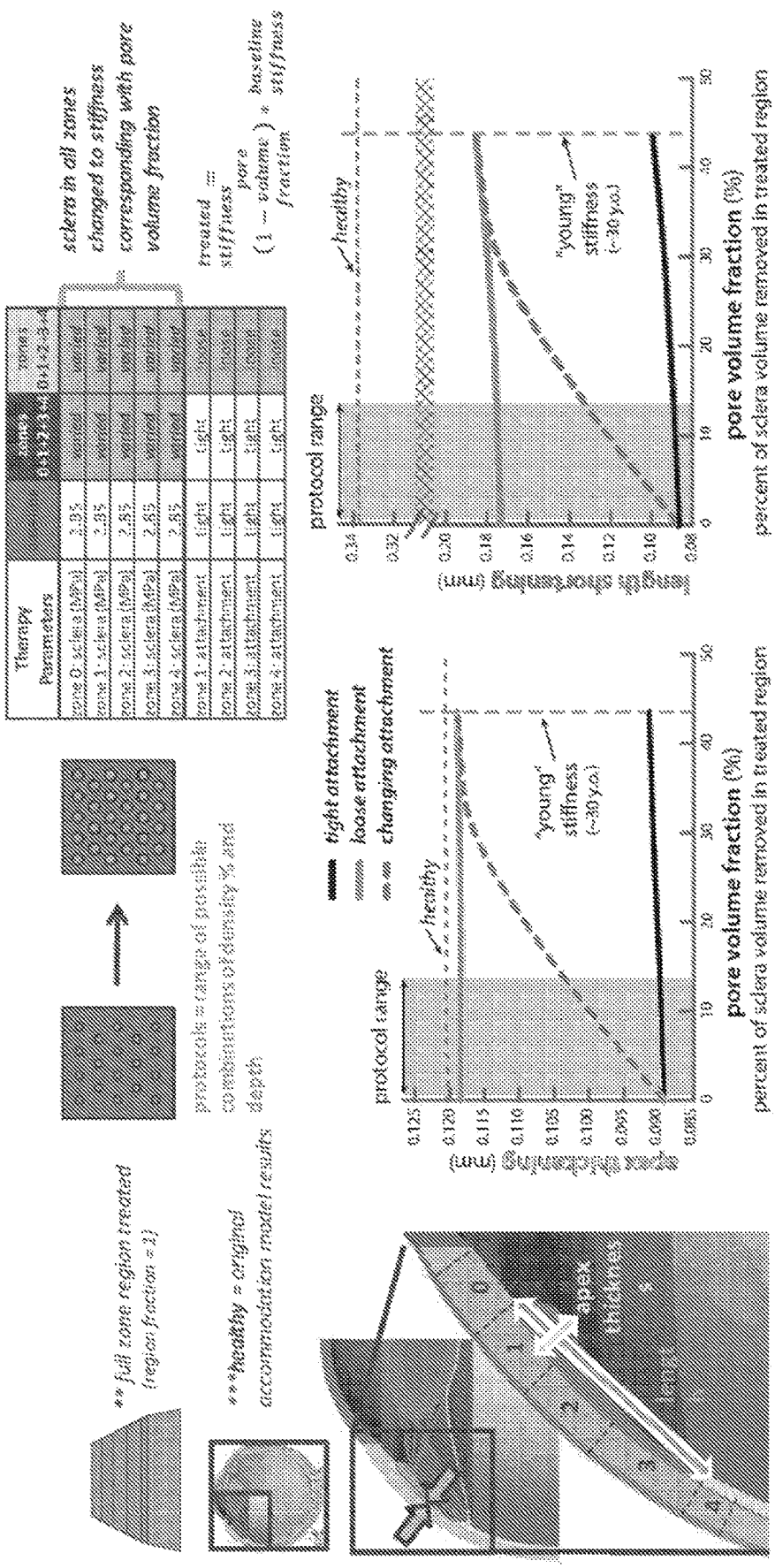
Figure 39:
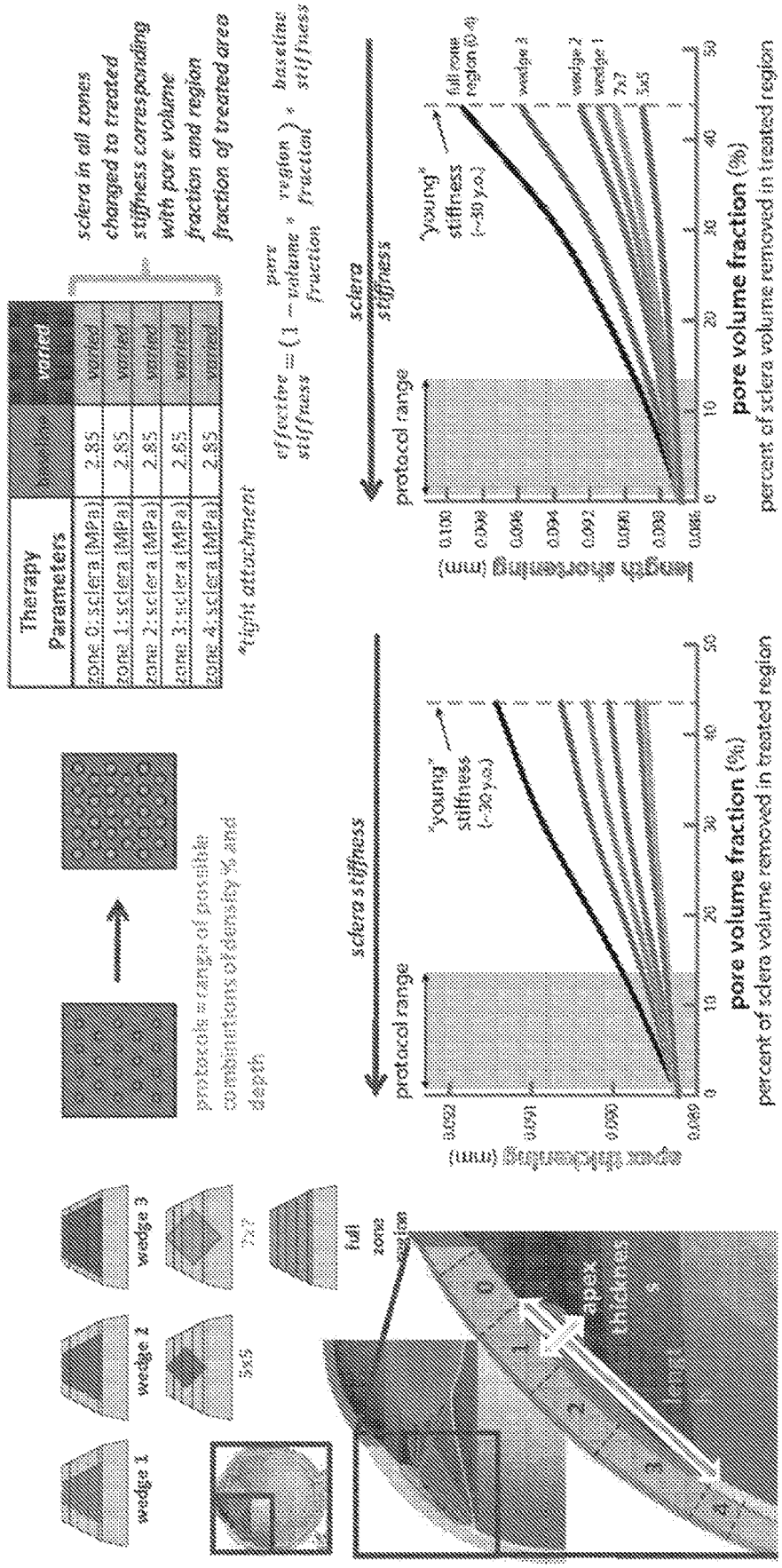

FIGS. 37-39 illustrate exemplary effects of volume fraction, according to an embodiment of the disclosure.

Figure 40:
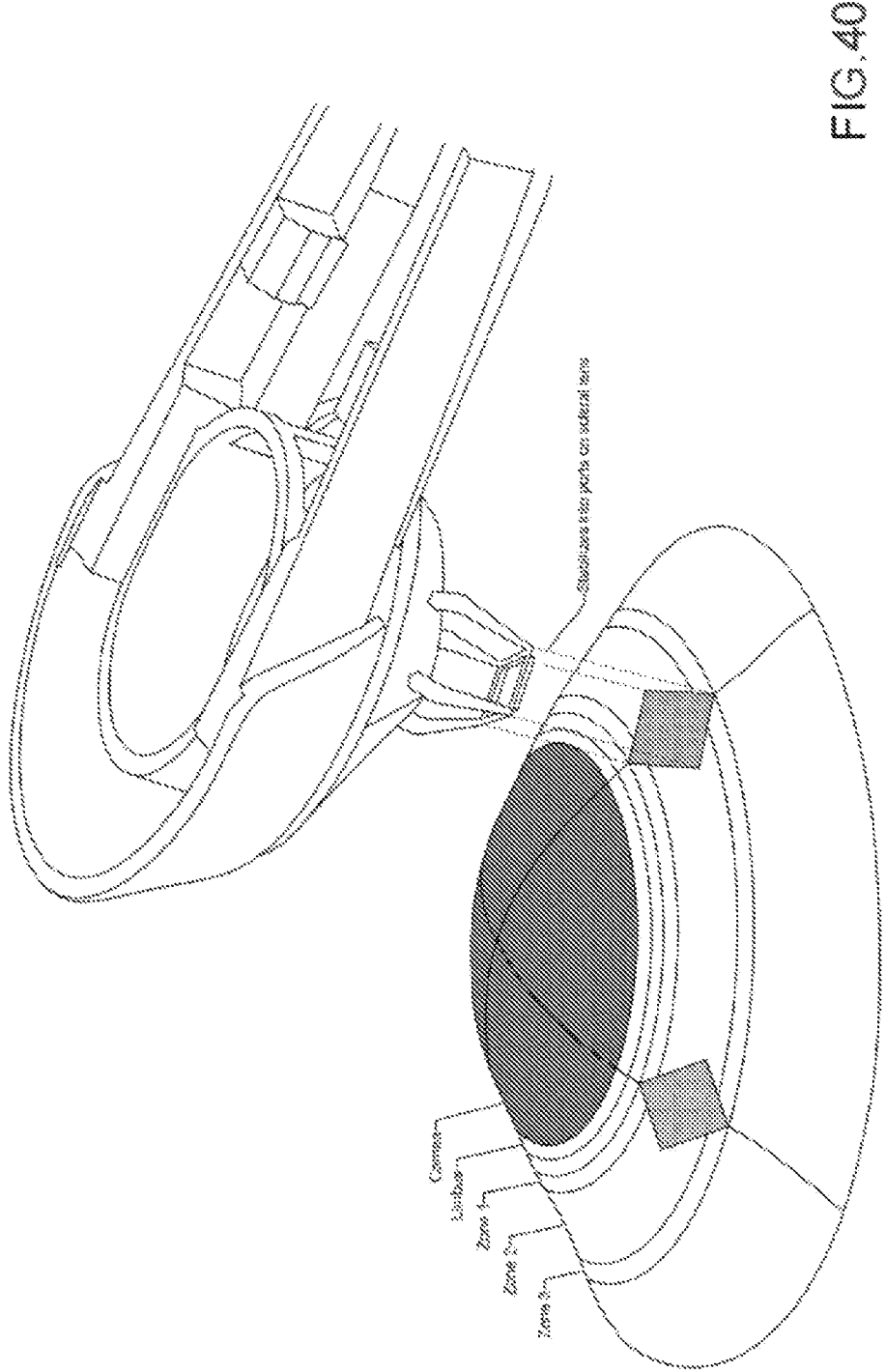

FIG. 40 illustrates another exemplary nozzle, according to an embodiment of the disclosure.

FIG. 41 illustrates exemplary model outcomes, according to an embodiment of the disclosure.

DETAILED DESCRIPTION

The below described figures illustrate the described invention and method of use in at least one of its preferred, best mode embodiment, which is further defined in detail in the following description. Those having ordinary skill in the art may be able to make alterations and modifications to what is described herein without departing from its spirit and scope. While this invention is susceptible of embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. All features, elements, components, functions, and steps described with respect to any embodiment provided herein are intended to be freely combinable and substitutable with those from any other embodiment unless otherwise stated. Therefore, it should be understood that what is illustrated is set forth only for the purposes of example and should not be taken as a limitation on the scope of the present invention.

FIGS. 1 to 41 illustrate exemplary embodiments of systems and methods for laser scleral microporation for rejuvenation of tissue of the eye, specifically regarding aging of connective tissue, rejuvenation of connective tissue by scleral rejuvenation.

Generally, the systems and methods of the present disclosure take into consideration combination of pores filling technique and creating matrices of pores in three dimensions (3D). Pores with a particular depth, size and arrangement in a matrix 3D scaffold of tissue produce plastic behavior within the tissue matrix. This affects the biomechanical properties of the scleral tissue allowing it to be more pliable. It is known that connective tissues that contain elastin are 'pliable' and meant to have elasticity. The sclera in fact has natural viscoelasticity.

Influence of ocular rigidity and ocular biomechanics on the pathogenesis of age-related presbyopia is an important aspect herein. Descriptions herein are made to modifying the structural stiffness of the ocular connective tissues, namely the sclera of the eye using the systems and methods of the present disclosure.

In order to better appreciate the present disclosure, ocular accommodation, ocular rigidity, ocular biomechanics, and presbyopia will be briefly described. In general, the loss of accommodative ability in presbyopes has many contributing lenticular, as well as extralenticular and physiological factors that are affected by increasing age. Increasing ocular rigidity with age produces stress and strain on these ocular structures and can affect accommodative ability. Overall, understanding the impact of ocular biomechanics, ocular rigidity, and loss of accommodation could produce new ophthalmic treatment paradigms. Scleral therapies may have an important role for treating biomechanical deficiencies in presbyopes by providing at least one means of addressing the true etiology of the clinical manifestation of the loss of accommodation seen with age. The effects of the loss of accommodation has impact on the physiological functions of the eye to include but not limited to visual accommodation, aqueous hydrodynamics, vitreous hydrodynamics, and ocular pulsatile blood flow. Using the systems and methods of the present disclosure to restore more pliable biomechanical properties of ocular connective tissue is a safe procedure and can restore accommodative ability in aging adults.

Accommodation has traditionally been described as the ability of the crystalline lens of the eye to change dioptric power dynamically to adjust to various distances. More recently, accommodation has been better described as a complex biomechanical system having both lenticular and extralenticular components. These components act synchronously with many anatomical and physiological structures in the eye organ to orchestrate not only the visual manifestations that occur with accommodation, but also the physiological functions integral to the eye organ, such as aqueous hydrodynamics and ocular biotransport.

Biomechanics is the study of the origin and effects of forces in biological systems. Biomechanics has remained underutilized in ophthalmology. This biomechanical paradigm deserves to be extended to the anatomical connective tissues of the intricate eye organ. Understanding ocular biomechanics as it relates to accommodation can allow for a more complete picture of the role this primary moving system has on overall eye organ function, while maintaining optical quality for visual tasks.

The eye is a biomechanical structure, a complex sense organ that contains complex muscular, drainage, and fluid mechanisms responsible for visual function and ocular biotransport. The accommodative system is the primary moving system in the eye organ, facilitating many physiological and visual functions in the eye. The physiological role of the accommodation system is to move aqueous, blood, nutrients, oxygen, carbon dioxide, and other cells, around the eye organ. In addition, it acts as a neuroreflexive loop, responding to optical information received through the cornea and lens to fine tune focusing power throughout a range of vision, and is essentially the "heart" of the eye organ.

Biomechanics is particularly important to the complexity of accommodative function and dysfunction which occurs with age-related eye diseases (e.g., presbyopia, glaucoma, age-related macular degeneration (AMD) and myopia. Age-related changes in the crystalline lens have long been understood and reported. Recent endeavors have demonstrated how stiffening ocular tissues manifest as presbyopia. Ocular rigidity has been correlated with a clinically significant loss of accommodation with age, age-related macular degeneration, increased intraocular pressure (TOP), decreased ocular pulsatile blood, and certain forms of glaucoma and cataracts. Stiffening of the zonular apparatus and loss of elasticity of the choroid may also contribute to accommodation.

Biomechanics plays a critical role in the pathophysiology of the eye organ. In healthy young eyes, this mechanism is biomechanically efficient and precisely achieves the focusing of objects at a particular distance. As we age, however, this biomechanical mechanism is affected by changes in material properties, anatomical relationships, and degradation of healthy connective tissue infrastructural relationships due to the aging process. These biomechanical dysfunctions result in a disruption of the functions of not only the accommodative mechanism, which affect the ability to dynamically focus the lens for ideal optical image quality, but also the functions of other physiologic mechanisms critical to the eye organ such as ocular biofluidics, ocular blood flow, and metabolic homeostasis. Thus, biomechanics plays a key role in the pathophysiology that occurs with aging, including glaucoma and AMD.

Presbyopia is a condition of sight traditionally defined as the progressive loss of accommodative ability with age. The loss of the ability to adjust the dioptric power of the lens for various distances, however, is only one consequence of this complex condition. As the eye ages, there are connective tissues changes in the eye organ or "oculus" that produce significant but reversible impacts on the biomechanical efficiencies of ocular function. Studies using ultrasound biomicroscopy (UBM) and endoscopy, optical coherence tomography (OCT), and magnetic resonance imaging (MM) have shown age-related changes in the vitreous membrane, peripheral choroid, ciliary muscle, and zonules. Age-related changes create biomechanical alterations that also manifest in the sclera, which bows inward with increasing age.

According to one model, during accommodation the ciliary muscle contracts, releasing tension on the zonules, which reduces tension on the lens and allows it to curve and increase its refractive power. The decrease in lens elasticity with age impedes the deformation of the lens and the lens refractive power will not increase enough to see objects at near. Current approaches to resolve the loss of near vision symptoms of presbyopia typically included spectacles, multifocal or monovision contact lenses, corneal procedures to induce monovision or multifocality, lens implants using multifocal lenses, corneal inlays, onlays, and accommodating intraocular lenses. However, none of these procedures restore true accommodation. Instead, these procedures attempt to improve near and intermediate vision by manipulating optics either in the cornea or in the lens.

For true physiological accommodation to occur, the eye must modify its focal length to see objects clearly when changing focus from far to near or from near too far. Generally, this is thought to be caused primarily by the ciliary muscles, which contract and force the lens into a more convex shape. However, the accommodation process is far more complex. Accommodation is also influenced by corneal aberrations, and thus to see clearly, the lens must be molded and undulated to corneal aberrations, creating a balance of the optics between the lens and the cornea before exerting a focal response to accommodative stimulus. In addition, the zonular tensions on the lens and the elastic choroid contribute to the accommodative range and biomechanical functionality of the entire accommodation complex. The malfunction of these complex components creates a biomechanical relationship dysfunction, which can affect the accommodative amplitude, lens deformation, and the central optical power generated from dynamic accommodative forces.

Scleral surgery, e.g., as a treatment for presbyopia has used corneal incisions to treat myopia, a treatment known as radial keratotomy (RK). Anterior ciliary sclerotomy (ACS) procedure was developed, which utilized radial incisions in the sections of the sclera overlaying the ciliary muscle. The incisions were thought to increase the space between the ciliary muscle and the lens, allowing for increased 'working distance' for the muscles and tightening of the zonules to restore the accommodative ability in presbyopes. The long-term results of ACS suggest that the procedure was largely unsuccessful at restoring accommodation and the effects were eliminated completely as the scleral wounds healed very quickly. Laser presbyopia reversal (LAPR) followed from ACS, using lasers to perform radial sclerectomy. The results of LAPR, however, were mixed. Scleral implants attempt to lift the ciliary muscle and the sclera, tightening the zonules holding the lens, and restore accommodative ability. Their effectiveness remains controversial.

Accommodation loss and presbyopia have been used interchangeably. However, it should be emphasized that accommodation loss is just one clinical manifestation of the consequences of an aging (or presbyopic) eye. With increasing age, there are numerous changes to the lens and surrounding tissues, which may contribute to accommodation loss. Research has shown that the lens substance stiffens with age, decreasing its ability to change shape (and refractive power) during accommodation, and decreasing accommodative ability. The softening of the lens capsule, flattening of the lens, and lens movement anteriorly with age may also contribute to the loss of accommodative ability, however, accommodation is a complex mechanism. Many lenticular-based models fail to incorporate effects from the extralenticular structures. To understand accommodation fully, both lenticular and extralenticular components need to be considered together.

The amount of accommodation lost with age, which is related to extralenticular factors (primarily the zonules, choroid, and sclera) has only been relatively recently investigated. The circumlental space decreases with age. The ciliary body has been shown to contract during accommodation, and there is a decrease in the distance from scleral spur to the ora serrata. Using UBM, an attachment zone of the posterior zonules adjacent to the ora serrata has been identified, and contraction of these zonules is thought to be the etiology of the decrease in distance found with accommodation. This complex action of the zonules is suspected to be reciprocal. While the anterior zonules relax, reducing their tension on the lens such that the lens changes shape anteriorly, the posterior zonules contract, moving the posterior capsule backward. This vitreal-zonular complex stiffens with age, losing its elasticity. It is also now known that the sclera becomes less deformable during accommodation in the nasal area with age. The vitreous has also been suggested as an important factor to lens shape changes during accommodation and may have a role in presbyopia. New models suggest up to 3 diopters that might be contributed by extralenticular structures. The age-related changes in these structures and their biomechanical interactions with the ciliary-lens complex may contribute to presbyopia.

The ciliary muscle plays a critical role in many functions of the eye organ including accommodation and aqueous hydrodynamics (outflow/inflow, pH regulation, and TOP). An optically significant role of the ciliary muscles is to adjust the lens dynamically to focus at various distances (near, intermediate, and far). During accommodation, the ciliary muscle contracts to change the shape of the lens and, in basic terms, moves the lens forward and inwards. This shape deformation is caused by the release of tension on the anterior zonules and by the aqueous fluid moving in the posterior chamber. This allows the lens to change from a relatively aspherical shape to a more spherical shape, thereby increasing its refractive power for near vision. Contraction of the ciliary muscle is also important for spreading the trabecular meshwork and aqueous drainage. Inadequate drainage or a cause of perturbance to the normal flow of aqueous drainage either by uveal outflow pathway or Schlemm's canal can increase TOP and contribute to the development of certain types of ocular hypertension or glaucoma. Ciliary muscle contraction during accommodation lowers intraocular pressure (TOP). This is likely due to a decrease in aqueous outflow resistance during accommodation, caused by the ciliary muscle moving inward and anteriorly, which dilates Schlemm's canal and opens the trabecular meshwork.

FIGS. 1A-1 to 1A-3 illustrate, in some embodiments, exemplary scleral laser rejuvenation of viscoelasticity allowing compliance for the ciliary muscle to exert force on the lens. The ciliary muscle and its components include the meridional or longitudinal (1), radial or oblique (2), and circular or sphincteric (3) layers of muscle fibres, as displayed by successive removal towards the ocular interior. The cornea and sclera have been removed, leaving the canal of Schlemm (a), collecting venules (b) and scleral spur (c). The meridional fibres (1) often display acutely angled junctions (d) and terminate in epichoroidal stars (e). The radial fibres meet at obtuse angles (f) and similar junctions, at even wider angles (g), occur in the circular ciliary muscle.

The rigidity of a structure describes its resistance to deformation and, in the case of a confined structure with incompressible contents, rigidity is related to the structure's volume and the pressure of the contents. Ocular rigidity refers to the resistance of the eyeball to stresses. Increases in ocular rigidity have been correlated with increasing age, lending support to the idea that presbyopia and ocular rigidity share a common biomechanical factor. In addition to affecting accommodation, ocular rigidity may also hinder the accommodation apparatus to return to a disaccommodated state, following an accommodated state, by dampening the elastic recoil of the choroid posteriorly.

Ocular rigidity has been correlated with decreased ocular pulsatile blood flow. The blood vessels that support the health of the entire eye pass through the sclera. An increase in ocular rigidity could increase scleral resistance to venous outflow and decrease the flow through choroidal vessels.

Ocular rigidity has been correlated to the pathogenesis of macular degeneration. An increase in ocular rigidity could increase scleral resistance to venous outflow and decrease the flow through choroidal vessels. This may compromise Bruch's membrane and lead to choroidal neovascularization. Decrease flow through the choroidal vessels may also decrease perfusion, which could lead to induced hypoxia and choroidal neovascularization.

Ocular rigidity has been correlated with certain forms of glaucoma. Recent models suggest that ocular rigidity affects the scleral response to increased intraocular pressure. Reducing ocular rigidity may decrease the mechanical strain that is transferred to the optic nerve head with elevated intraocular pressure due to age-related changes and ocular rigidity in both the anterior and posterior globe. During normal accommodation the retina and choroid are pulled forward near the optic nerve head when the ciliary muscle contracts. The ciliary muscle retains its contractile force with age, however increased rigidity of the sclera may affect ciliary muscle motility, which could increase the tensional forces on the optic nerve head during ciliary muscle contraction.

FIGS. 1A-4-1A-7 illustrate in some embodiments posterior scleral rejuvenation and ocular nerve head decompression.

Ocular rigidity or "stiffness" of the outer ocular structures of the eye including the sclera and the cornea, which occurs in the oculus with age, effects the biomechanical functions of all the internal anatomical structures, such as the extralenticular and lenticular anatomy of the accommodation complex as well as the trabecular meshwork, the choroid and the retina. In addition, ocular rigidity has a significant impact on the physiological functions of the eye organ, such as a change in the efficiency of aqueous dynamics and ocular pulsatile blood flow. Increased ocular rigidity affects other tissues as well, including ocular blood flow through the sclera and optic nerve. Ocular rigidity has been correlated to the pathogenesis many age-related eye diseases. Therefore, ocular rigidity may not only impact the loss of visual accommodation but also have more extensive clinical significance.

Ocular biomechanics is the study of the origin and effects of forces in the eye. All ocular tissues contain collagen, which provides them with viscoelastic properties. Viscoelastic substances contain the properties of both fluids and elastic materials. Fluids tend to take the shape of their container, while elastic materials can deform under a stress and return to their original form. When a stress is applied to viscoelastic materials, the molecules will rearrange to accommodate the stress, which is termed creep. This rearrangement also generates back stresses in the material that allow the material to return to its original form when the stress is removed. Thus, viscoelasticity is an important property that allows tissues to respond to stresses.

Chronic stress that exceeds the healing ability of tissues can lead to chronic inflammation and eventual cell death, which technically describes the pathophysiology of aging. Ocular connective tissues are impacted, like all other connective tissues, by age. The sclera constitutes ⅚ of the oculus and is made up of dense irregular connective tissue. It is comprised primarily of collagen (50-75%), elastin (2-5%), and proteoglycans. The connective tissues of the eye stiffen with increasing age, losing their elasticity, largely due to the crosslinking that occurs with age. Crosslinks are bonds between polymer chains, such as those in synthetic biomaterials or the proteins in connective tissues. Crosslinking can be caused by free radicals, ultraviolet light exposure, and aging. In connective tissues, collagen and elastin can crosslink to continuously form fibrils and microfibrils over time. With increasing amounts of fibrils and microfibrils, the sclera stiffens, undergoing a 'sclerosclerosis', as well as a concomitant increase in metabolic physiological stress. As mentioned previously, age- and race-related increases in collagen crosslinks, along with loss of elastin-driven recoil, and/or collagen microarchitectural changes, may underlie the change in scleral material properties leading to loss of compliance of scleral tissue when stress is applied. As this pathophysiology progresses, the sclera exerts compression and loading stresses on underlying structures, creating biomechanical dysfunction, specifically those related to accommodation.

Age-related increased ocular rigidity also has an impact on the ciliary muscle and the biomechanics of the accommodation mechanism. For example, it is known that the contractile power of the ciliary muscle does not decrease with age, however, it may have a decreased capability to contract or exert substantial forces on the lens to create the same dioptric changes as those in a youthful system. A further explanation may be that ocular rigidity affects the biomechanical contributions of the ciliary muscle by relaxing zonular tension and decreasing accommodative ability.

Age-related material property changes within the sclera affects the mobility of connective tissues of the scleral fibers, directly leading to the loss of compliance. This causes a decrease in the normal maintenance and turnover of proteoglycans (PG) in the sclera, leading to the loss of PG and eventual tissue atrophy. However, if the compliance and mobility of scleral connective tissues are restored, this PG loss can be reversed.

As mentioned above, the systems and methods of the present disclosure take into consideration combination of pores filling technique and creating matrices of pores in three dimensions. Pores with a specific depth, size and arrangement in a matrix 3D scaffold of tissue produce plastic behavior within the tissue matrix. This affects the biomechanical properties of the scleral tissue allowing it to be more pliable. The plurality of pores may be created in a matrix 3D scaffold, in an array pattern or a lattice(s). Various microporation characteristics may be supported. These may include volume, depth, density, and so on.

It is advantageous to create a tetrahedral or central hexagon shape. In order to create a central hexagon within a matrix there must be a series of 'pores' with specific composition, depth, and relationship to the other 'pores' in the matrix and spatial tissue between the pores in the matrix. A substantial amount of depth (e.g., at least 85%) of the tissue is also needed to gain the full effect of the entire matrix throughout the dimensions of the polygon. The matrix within the tissue contains a polygon. The central angle of a polygon stays the same regardless of the plurality of spots within the matrix. This is an essential component of the systems and methods of the present disclosure since they take advantage of a matrix with a polygon which includes the unique relationship and properties of the pore pattern in the matrix or lattice.

The central angle of a polygon is the angle subtended at the center of the polygon by one of its sides. Despite the number of sides of the polygon, the central angle of the polygon remains the same.

Current implanting devices in the sclera obtain the mechanical effect upon accommodation. No current devices or methods take into account the effects of 'pores' or creating a matrix array of pores with a central hexagon or polygon in 3D tissue. The systems and methods of the current disclosure may create a pore matrix array in biological tissue to allow the change in the biomechanical properties of the tissue itself to create the mechanical effect upon biological functions of the eye. A primary requirement of the 'pores' in the matrix is the polygon.

A polygon by definition can have any number of sides and the area, perimeter, and dimensions of the polygon in 3D can be mathematically measured. In a regular polygon case the central angle is the angle made at the center of the polygon by any two adjacent vertices of the polygon. If one were to draw a line from any two adjacent vertices to the center, they would make the central angle. Because the polygon is regular, all central angles are equal. It does not matter which side one chooses. All central angles would add up to 360° (a full circle), so the measure of the central angle is 360 divided by the number of sides. Or, as a formula:

$$\text{Central Angle} = 360/n \text{ degrees, where } n \text{ is the number of sides.}$$

The measure of the central angle thus depends only on the number of sides, not the size of the polygon.

As used herein, polygons are not limited to "regular" or "irregular." Polygons are one of the most all-encompassing shapes in geometry. From the simple triangle, up through squares, rectangles, trapezoids, to dodecagons and beyond.

Types of polygons include regular and irregular, convex and concave, self-intersecting and crossed. Regular polygons have all sides and interior angles the same. Regular polygons are always convex. Irregular polygons include those where each side may have a different length, each angle may be a different measure and are the opposite of regular polygons. Convex is understood to mean all interior angles less than 180°, and all vertices 'point outwards' away from the interior. The opposite of which is concave. Regular polygons are convex. Concave is understood to mean one or more interior angles greater than 180°. Some vertices push 'inwards' towards the interior of the polygon. A polygon may have one or more sides cross back over another side, creating multiple smaller polygons. It is best considered as several separate polygons. A polygon that in not self-intersecting in this way is called a simple polygon.

Properties of all polygons (regular and irregular) include the interior angles at each vertex on the inside of the polygon and the angle on the outside of a polygon between a side and the extended adjacent side. The diagonals of a polygon are lines linking any two non-adjacent vertices. For regular polygons, there are various ways to calculate the area. For irregular polygons there are no general formulae. Perimeter is the distance around a polygon or the sum of its side lengths.

Properties of regular polygons include the apothem (inradius) which is a line from the center of the polygon to the midpoint of a side. This is also the inradius—the radius of the incircle. The radius (circumradius) of a regular polygon is a line from the center to any vertex. It is also the radius of the circumcircle of the polygon. The incircle is the largest circle that will fit inside a regular polygon. Circumcircle is the circle that passes through all the vertices of a regular polygon. Its radius is the radius of the polygon.

Some embodiments herein illustrate a plurality of polygons within the matrix array. Each can impact the CT (coherence tomography). They contain enough pores to allow for a 'central hexagon'. A square/diamond shape may be apparent. As a formula:

$$\text{diagonal} = \sqrt{s^2 + s^2}$$

where:
s is the length of any side
which simplifies to:

$$\text{diagonal} = s\sqrt{2}$$

where:
s is the length of any side

A 'pore' described herein may have a specific form, shape, composition and depth. The creating of pores within a matrix array changing biomechanical properties of connective tissue is a unique feature of the current disclosure.

The 'pore matrix' used herein may be used to control wound healing. In some embodiments, it may include the filling of pores to inhibit scar tissue.

In some embodiments, pores may have at least 5%-95% depth through the connective tissue, and help create the intended biomechanical property change. They may have a specific composition, arrangement in the matrix and desirably have the mathematical qualities of a polygon. In three-dimensional (3D) space the intended change in the relationship between the pores in the matrix or lattice is the unique characteristic of the current disclosure (see FIGS. 1F(a) to 1F(c)). The matrix or array can comprise of a 2D Bravais lattice, a 3D Bravais Lattice or a Non-Bravais lattice.

Referring to FIGS. 1B-1E, exemplary pore matrix arrays are illustrated. The pore matrix arrays herein are the basic building block from which all continuous arrays can be constructed. There may be a plurality of different ways to arrange the pores on the CT in space where each point would have an identical "atmosphere". That is each point would be surrounded by an identical set of points as any other point, so that all points would be indistinguishable from each other. The "pore matrix array" may be differentiated by the relationship between the angles between the sides of the "unit pore" and the distance between pores and the "unit pore". The "unit pore" is the first "pore created" and when repeated at regular intervals in three dimensions will produce the lattice of the matrix array seen on the surface throughout the depth of the tissue. The "lattice parameter" is the length between two points on the corners of a pore. Each of the various lattice parameters is designated by the letters a, b, and c. If two sides are equal, such as in a tetragonal lattice, then the lengths of the two lattice parameters are designated a and c, with b omitted. The angles are designated by the Greek letters $\alpha$, $\beta$, and $\gamma$, such that an angle with a specific Greek letter is not subtended by the axis with its Roman equivalent. For example, $\alpha$ is the included angle between the b and c axis.

A hexagonal lattice structure may have two angles equal to 90°, with the other angle ($\gamma$) equal to 120°. For this to happen, the two sides surrounding the 120° angle must be equal (a=b), while the third side (c) is at 90° to the other sides and can be of any length.

Referring to FIGS. 1F(a) to 1F(c), an exemplary schematic projection of the basal plane of the hcp unit cell on the close packed layers is illustrated. Matrix array is defined as the particular, repeating arrangement of pores throughout a target connective tissue, e.g., the sclera. Structure refers to the internal arrangement of pores and not the external appearance or surface of the matrix. However, these may not be entirely independent since the external appearance of a matrix of pores is often related to the internal arrangement. There may be a specific distance between each of the pores in the designated matrix to fulfill the mathematical characteristics and properties of the polygon. The pores created may also have a relationship with the remaining tissue within the matrix thus changing the biomechanical properties of the matrix.

Spatial relationships of the pores within the matrix may have geometric and mathematical implications.

In some embodiments, the laser microporation system (see, e.g., FIGS. 3A, 3B, and 4A below) of the present disclosure generally includes at least these parameters: 1) a laser radiation having a fluence between about 1-3 μJoules/cm2 and about 2 Joules/cm2; ≥15.0 J/cm$^2$ on the tissue; ≥25.0 J/cm$^2$ on the tissue; to widen treatment possibilities 2900 nm+/−200 nm; around the mid IR absorption maximum of water; Laser repetition rate and pulse duration may be adjustable by using pre-defined combinations in the range of 100-500 Hz and 50-225 μs. This range may be seen as a minimum range ≥15.0 J/cm$^2$ on the tissue; ≥25.0 J/cm$^2$ on the tissue; to widen treatment possibilities; 2) irradiated using one or more laser pulses or a series of pulses having a duration of between about 1 ns and about 20 μs. Some embodiments can potentially have a up to 50 W version; 3) The range of Thermal Damage Zone (TDZ) can be less than 20 μm in some embodiments or between 20-50 μm in some embodiments; 4) Parameters of pulse width from 10 μm-600 μm can also be included. (See FIG. 1E-1)

The energy per pulses 1-3 microJoules may link to femtolasers and pico lasers with high rep rates, e.g., 500 Hz (Zeiss) up to several kilohertz (Optimedica). The benefit of the femto-lasers and pico-lasers are the small spot sizes (for example, 20 microns and up to 50 microns) and the energy densities are high for minimal thermal problems to surrounding tissues. All this can lead to an effective scleral rejuvenation. In some embodiments, the lasers may produce substantially round and conically shaped holes in sclera with a depth up to perforation of sclera and thermal damage from about 25 μm up to about 90 μm. The hole depth can be controlled by the pulse energy and the number of pulses. The hole diameter may vary by motion artifacts and/or defocusing. The thermal damage may correlate with the number of pulses. The pulse energy may be increased, which may lead to a decrease of number of pulses and with this to a further decrease of thermal damage. The increase of pulse energy may also reduce the irradiation time. An exemplary design of the laser system described may allow for laser profiles optimized for lower thermal damage zone while preserving irradiation time thus maintaining a fast speed for optimal treatment time, and chart showing the correlation between thermal damage zone and pulse (see FIG. 1E-2 and FIGS. 1G-1 to 1G-4).

The nanosecond lasers for micro poring or micro tunneling, in some embodiments, may include the following specifications: wavelengths UV-Visible-Short infrared 350-355 nm; 520-532 nm; 1030-1064 nm typical; -pulse lengths 0.1-500 nanoseconds, passive (or active Q-switching); pulse rep. rate 10 Hz-100 kHz; peak energies 0.01-10 milliJoules; peak powers max. over 10 Megawatts; free beam or fiber delivered.

Scleral rejuvenation can be performed with femto- or pico second lasers and Er:YAG laser. Other preferred embodiments may include laser energy parameters ideal for 2.94 Er:YAG laser or other laser possibilities with Er:YAG preferred laser energy or other lasers of different wavelengths with high water absorption.

MilliJoules and energy densities for different spot sizes/shapes/pores can include:

Spot size 50 microns: a) 0.5 mJoules pp is equal to 25 Joules/cm2; b) 1.0 mJoule pp is equal to 50 Joules/cm2 (possible with Er:YAG); 3) 2.0 mJoules pp is equal to 100 Joules/cm2.

Spot size 100 microns (all these possible with Er:YAG): a) 2.0 mJoules pp is equal to 25 Joules/cm2; b) 5.0 mJoules pp is equal to 62.5 Joules/cn2; c) 9.0 mJoules pp is equal to 112.5 Joules/cm2.

Spot size 200 microns: a) 2.0 mJoules pp is equal to 6.8 Joules/cm2; b) 9.0 mJoules pp is equal to 28.6 Joules/cm2; c) 20.0 mJoules pp is equal to 63.7 Joules/cm2.

Spot size 300 microns: a) 9.0 mJoules pp is equal to 12.8 Joules/cm2—possible with Er:YAG; b) 20.0 mJoules pp is equal to 28 Joules/cm2—possible with DPM-25/30/40/X; c) 30.0 mJoules pp is equal to 42.8 Joules/cm2 d) 40.0 mJoules pp is equal to 57 Joules/cm2 e) 50.0 mJoules pp is equal to 71 Joules/cm2.

Spot size 400 microns: a) 20 mJoules pp is equal to 16 Joules/cm2-D PM-25/30/40/50/X; b) 30 mJoules pp is equal to 24 Joules/cm2; c) 40 mJoules pp is equal to 32 Joules/cm2; d) 50 mJoules pp is equal to 40 Joules/cm2

It is noted that round or square pores or spots are possible as well.

Regarding femto & picosecond lasers, some available wave lengths include IR 1030 nm; Green 512 nm and UV 343 nm. The peak energies can vary from nanoJoules (at MHz rep rate) via 5-50 microJoules up to several hundred microJoules in picosecond region. Femtosecond lasers having pulse length 100-900 femtosec; peak energies from a nanoJoules to several hundred microJoules, pulse rep. rates from 500 Hz to several Megahertz (Ziemer LOV Z; Ziemer AG, Switzerland: nanoJoules peak energies at over 5 MHz rep. rate, beam quality/density very good-focuses in a small spot—50 micron and under is possible).

The beam quality being so precise in the best femtolasers that, in some embodiments, femtolaser Micro Tunneling of sclera as micro pores using Erbium lasers can be accomplished.

As used herein, nuclear pores can be defined as openings in the nuclear envelope, diameter about 10 nm, through which molecules (such as nuclear proteins synthesize in the cytoplasm) and ma must pass (see FIG. 1H). Pores are generated by a large protein assembly. Perforations in the nuclear membrane may allow select materials to flow in and out.

Formula for porosity in biological tissue may be defined as: $X(Xa,t)=qT''(X'', t)=x^*+u''(X'', t)$, where qT'' is a continuously differentiable, invertible mapping from 0 to a, and u'' is the cY-constituent displacement. The invertible deformation gradient for the a-constituent (F''), and its Jacobian (J'') may be defined as J''=det F'', where J'' must be strictly positive to prohibit self-interpenetration of each continuum. The right Cauchy-Green tensor % and its inverse, the Piola deformation tensor B for the solid-constituent may be defined as $V=F^{s^t}F^s$, $B=F^{s^{-1}}F^{s^{-1}}$, where the superscript t indicates transposition.

Current theoretical and experimental evidence suggests that creating or maintaining pores in connective tissue accomplishes three important tasks. First, it transports nutrients to the cells in the connective tissue matrix. Second, it carries away the cell waste. Third, the tissue fluid exerts a force on the wall of the sclera or outer ocular coat, a force that is large enough for the cells to sense. This is thought to be the basic mechanotransduction mechanism in the connective tissue, the way in which the ocular coat senses the mechanical load to which it is subjected and the response to the increase in intraocular pressure. Understanding ocular mechanotransduction is fundamental to the understanding of how to treat ocular hypertension, glaucoma and myopia, Deriving the physical properties of a porous medium (e.g., hydraulic conductivity, thermal conductivity, water retention curve) from parameters describing the structure of the medium (e.g., porosity, pore size distribution, specific surface area) is an ongoing challenge for scientists, whether in soft tissues or for porosities of bone tissue and their permeabilities. To verify the assumption of a porous medium having a self-similar scaling behavior, fractal dimensions of various features have been determined experimentally.

System Procedure and Mechanism of Action

While some current accommodative theory states that the lens is primarily responsible for the refractive change allowing us to read, all elements of the zonular apparatus have been found to be involved. Illumination of the role that extralenticular processes play in accommodation support the theory that scleral therapies, which modify biomechanical properties by restoring compliance to an otherwise rigid tissue, may influence accommodative ability in presbyopes.

Recent studies have found that presbyopia may not be a refractive error or simply the loss in the ability to focus on near objects. Instead, it is the age-related consequences on connective tissues of the eye organ or oculus, just as they occur throughout the body. This produces a significant but reversible impact on the biomechanical efficiencies of ocular functions, specifically accommodation, which potentially improves not only dynamic visual focusing capability but also ocular biotransport, and ocular metabolic efficiency. These studies are based on the fundamental and natural biological occurrences that occur with age, and specifically resonates on the effects of ocular rigidity to the accommodative structures beneath the major outer coat of the eye or sclera. The sclera undergoes a gradual "sclerosclerosis" with age, which represents the normal and gradual irreversible changes which occur in all connective tissues. This sclerotic process increases scleral compression, which imposes staggeringly significant load, stress, and strain upon underlying and related ocular and intraocular structures. This ocular rigidity or stress and strain upon the ciliary body and related structures which control dynamic accommodation, impact the biomechanics of the eye and compromises the eye's ability to perform its core organ functions.

In some embodiments, an ocular laser surgery and therapeutic treatments system may provide an eye laser therapy procedure designed to alleviate the stresses and strain that occur with an increasingly rigid sclera with age by creating compliance in the scleral tissue using a laser generated matrix of micropores in the scleral tissue. The system may facilitate biomechanical property changes in the sclera, alleviate compression of the subliminal connective tissue, facial tissue, and biophysiological structures of the eye, and restore accommodative ability. The system may alleviate stress and increase biomechanical compliance over the ciliary muscle, the accommodation complex, and key physiological anatomy that lies directly beneath the aging scleral tissue.

In some embodiments, the laser therapy procedure of the present disclosure may target specific treatment areas which are in distinct physiological zones covering critical anatomy inside the eye relative to eye function. Although examples of 3 or 5 physiological zones are described herein, other number of physiological zones may also be considered for treatments.

In some embodiments, a treatment pattern may be described as 3 critical zones in 3 distinct distances from the outer edge of the anatomical limbus (AL), not touching any components or relative tissues of the cornea. These zones are illustrated in FIGS. 2A-1 to 2A-2. In some embodiments, a treatment pattern may be described as 5 critical zones in 5 distinct distances from the outer edge of the anatomical limbus (AL), not touching any components or relative tissues of the cornea, as illustrated in FIGS. 2B-1 to 2B-3.

The laser therapy procedure may use an erbium: yttrium-aluminum-garnet (Er:YAG) laser to create microspores in the sclera. These micropores may be created at a plurality of depths with preferred depth range, e.g., from 5%-95% of the sclera, up to the point where the blue hue of the choroid is just visible. The micropores may be created in a plurality of arrays including a matrix array, e.g., 5 mm×5 mm, 7 mm×7 mm, or 14 mm×14 mm matrix array. These microporation matrices break bonds in the scleral fibrils and microfibrils having an 'uncrosslinking' effect in the scleral tissue. A direct consequence of this matrix pattern may be the creation of areas of both positive stiffness (remaining interstitial tissue) and negative stiffness (removed tissue or micropores) in the rigid sclera. These areas of differential stiffness allow the viscoelastic modulus of the treated sclera to be more compliant over the critical zones when subjected to force or stress, such as contraction of the ciliary muscles. Additionally, the treated regions of the sclera may produce a dampening effect in rigid scleral tissue when the ciliary muscles contract, due to increased plasticity. This enhances accommodative effort by directing unresisted forces inward and centripetally toward the lens or facilitating inward upward movement of the accommodative mechanism. This is an advantage over models that postulate a net outward-directed force at the lens equator. For example, techniques which are directed at scleral expansion such as scleral implants or surgical laser radial ablations such as LAPR are all directed at increasing 'space' or circumlental space to allow the sclera to expand for the intention of giving the ciliary muscle room. These techniques are based on the 'lens crowding' theory and aim to induce the outward movement rather than the upward and inward movement of the sclera and ciliary mechanism. Overall, the creation of the micropore matrices in the scleral tissue may induce an 'uncrosslinking effect', severing the fibrils and microfibrils of the layers of the sclera allowing a more compliant response to applied stress. Thus, the proposed mechanism of action for the system of the present disclosure is to increase plasticity and compliance of scleral tissue over critical zones of anatomical significance by creating these regions of differential stiffness over the ciliary complex, and thereby improve biomechanical function and efficiency of the accommodation apparatus. FIGS. 2C-1 to 2C-4 illustrate in some embodiments laser scleral uncrosslinking of scleral fibrils and microfibrils.

Referring to FIGS. 2D-1 to 2D-4, using a novel model, the effect of the procedure on ocular rigidity has been investigated. Ocular connective tissues are impacted, like all other connective tissues, by age. The sclera constitutes ⅚ of the oculus and is made up of dense irregular connective tissue. It is comprised primarily of collagen (50-75%), elastin (2-5%), and proteoglycans. The connective tissues of the eye stiffen with increasing age losing their elasticity largely due to the crosslinking that occurs with age. Crosslinking creates an "increase in biomechanical stiffness" in connective tissues such as those in the eye. Crosslinks are bonds between polymer chains, such as those in synthetic biomaterials or the proteins in connective tissues. Crosslinking can be caused by free radicals, ultraviolet light exposure, and aging.

In connective tissues, collagen and elastin can crosslink to continuously form fibrils and microfibrils over time. With increasing amounts of fibrils and microfibrils, the sclera stiffens, undergoing a 'sclerosclerosis', as well as a concomitant increase in metabolic physiological stress. As this pathophysiology progresses, the sclera exerts compression and loading stresses on underlying structures, creating biomechanical dysfunction, specifically those related to accommodation. Laser scleral microporation breaks scleral fibrils and microfibrils effectively "uncrosslinking" bonds thereby increasing scleral compliance and "decreasing biomechanical stiffness".

In some exemplary operations, six freshly harvested porcine eyes were modified by crosslinking (0.8 ml of 2% glutaraldehyde for 10 minutes) to mimic the ocular rigidity of an older human eye (e.g., 60 years), based on the ocular rigidity coefficient model of Pallikaris et al. Seven freshly harvested porcine eyes were left unmodified to mimic the ocular rigidity of a young human eye (e.g., 30 years). Three of the eyes in each group received the treatment, while the remaining eyes were used as controls. In brief, the investigation used a pressure transducer (up to 5 psi), a dosage injector controller, a data computerized reader, and tissue holding frame to which each porcine eye was fixed, to generate an intraocular pressure (IOP) versus injected volume curve for each eye. The ocular rigidity coefficient ($K=d \ln(P)/dV$ [in mmHg/μl]) was then calculated as the slope of $\ln(IOP)$ (from IOP between 30-50 mmHg) versus injected volume. In the young eye, the treatment resulted in a 10.8% decrease in rigidity. In the older eye, the treatment resulted in a 30.1% decrease in rigidity. Using an analysis of variance (e.g., ANOVA) and Tukey honestly significant difference (TukeyHSD) test, the investigation found that the system of the present disclosure significantly reduced ocular rigidity in the old eyes and overall ($p=0.0009$; $p=0.0004$). This decrease in ocular rigidity may be caused by 'uncrosslinking' aging tissue.

In some exemplary operations, twenty-six subjects underwent the treatment, and 21 completed 24 months of post-operative care. Five patients withdrew, due to occupational travel conflicts. The pre-operative (month 0) and post-operative IOP (determined by pneumatic tonometry) data were kept. There is an immediate 5% drop in IOP for the patient eyes compared to pre-operative IOP. Over the two years following the treatment, patient IOP remains approximately 15% lower than pre-operative IOP. The immediate and sustained reduction in IOP could be demonstrative of an improvement in aqueous outflow following the treatment. Using an ANOVA and TukeyHSD test, these differences were statistically significant beginning at post-operative month 3 and continued through all subsequent months ($p=0.000063$ at 24 months postoperatively). This reduction in IOP may be indicative of enhanced ocular mobility and a decrease in ocular rigidity following the treatment.

The biomechanical improvements with the treatment may prove to increase the biomechanical efficiency of the accommodative apparatus. In some embodiments, by creating micropores in a matrix over four oblique quadrants, the treatment may restore functional extralenticular forces, and restore a minimum of 1-3 diopters of accommodation. Treatments using the system and methods of the present disclosure may show an average of 1.5 diopters of accommodation post-operatively. This significantly improved the visual acuity of our patients. Visual acuity was measured using standard Early Treatment Diabetic Retinopathy Study (ETDRS) charts, and statistical analysis was done using an ANOVA and TukeyHSD test. The uncorrected monocular near visual acuity of the patients was 0.25±0.18 log MAR (mean±standard deviation) at 24 months post-operatively, compared to 0.36±0.20 log MAR (mean±standard deviation) pre-operatively ($p<0.00005$).

Utilizing innovative biometry and imaging technologies that were not previously available has illuminated that the loss of accommodative ability in presbyopes has many contributing lenticular, as well as extralenticular and physiological factors. The lens, lens capsule, choroid, vitreous, sclera, ciliary muscles, and zonules all play a critical role in accommodation, and are affected by increasing age. Increasing ocular rigidity with age produces stress and strain on these ocular structures and can affect accommodative ability.

Scleral therapies may have an important role in treating biomechanical deficiencies in presbyopes, by providing at least one means to address the true etiology of the clinical manifestation of the loss of accommodation seen with age. The treatment, utilizing laser microporation of the sclera to restore more pliable biomechanical properties, is a safe procedure, and can restore accommodative ability in aging adults. As a result, the treatment may improve dynamic accommodative range as well as aqueous outflow. With the advent of improved biometry, imaging, and research focus, information about how the accommodation complex works and how it impacts the entire eye organ can be achieved.

Referring to FIG. 2(a), exemplary three critical zones of significance as measured from the anatomical limbus (AL)) are shown. Zone 1) 0.5-1.1 mm from the AL, over the scleral spur at the origin of the ciliary muscle; Zone 2) 1.1-4.9 mm from the AL, over the mid ciliary muscle body; Zone 3) 4.9-5.5 mm from the AL, over the insertion of the longitudinal muscle fibers of the ciliary, just anterior to the ora serrata at the insertion of the posterior vitreous zonules. FIG. 2E(b) illustrates exemplary restored mechanical efficiency and improved biomechanical mobility.

In some embodiments, the laser scleral microporation procedure may involve using the laser described above to perform partial-thickness micro-ablations in the sclera in a matrix in five critical anatomic zones, for example, 0-7.2 mm from the anatomical limbus (AL). In some embodiments, the five zones may include: Zone 0) 0.0-1.3 mm from AL; distance from the AL to the superior boundary of ciliary muscle/scleral spur; Zone 1) 1.3-2.8 mm from AL; distance from the sclera spur to the inferior boundary of the circular muscle; Zone 2) 2.8-4.6 mm from AL; distance from the inferior boundary of the circular muscle to the inferior boundary of the radial muscle; Zone 3) 4.6-6.5 mm from AL; inferior boundary of the radial muscle to the superior boundary of the posterior vitreous zonule zone; and Zone 4) 6.5-7.2 mm from AL; superior boundary of the posterior vitreous zonule zone to the superior boundary of the ora serrata.

FIG. 2F illustrates an exemplary matrix array of micro-excisions, using the systems and methods of the present disclosure, in four oblique quadrants.

FIG. 2G illustrates an exemplary graphical representation of restored ocular compliance, decreased scleral resistive forces, increased ciliary resultant forces, and restored dynamic accommodation following the treatment.

FIG. 2H illustrates an exemplary box-and-whiskers plot of the ocular rigidity for control (black) and treated (grey) porcine eyes. The upper and lower extremities of the box represent the 75th and 25th percentiles, the bar within the box represents the median, and the whiskers represent the full extent of the data ranges.

FIG. 2I illustrates an exemplary box-and-whiskers plot of pre- and post-operative intraocular pressure (TOP) for the patient eyes. The stars indicate a significant difference from pre-operative TOP. The upper and lower extremities of the box represent the 75th and 25th percentiles, the bar within the box represents the median, the whiskers represent the full extent of the data ranges, and the white circles represent outliers.

FIG. 2J illustrates exemplary charts showing uncorrected and distance-corrected visual acuity at distance 4 m, intermediate (60 cm), and near (40 cm) for a) monocular and b) binocular patient eyes. Error bars represent mean±SD.

As described herein, accommodation of a human eye may occur through a change or deformation of the ocular lens when the eye transitions from distant focus to near focus. This lens change may be caused by contraction of intraocular ciliary muscles (ciliary body), which relieves tension on the lens through suspensory zonule fibers and allows the thickness and surface curvature of the lens to increase. The ciliary muscle can have a ring-shaped and can be composed of three uniquely oriented ciliary fiber groups that contract toward the center and anterior of the eye. These three ciliary fiber groups are known as longitudinal, radial and circular. Deformation of the ciliary muscle due to the contraction of the different muscle fibers translates into or otherwise causes a change in tension to the surface of the ocular lens through zonule fibers, whose complex patterns of attachment to the lens and ciliary muscle dictate the resultant changes in the lens during accommodation. Ciliary muscle contraction also applies biomechanical strain at the connection locations between the ciliary muscle and the ocular sclera, known as the white outer coat of the eye. Additionally, biomechanical compression, strain or stress can be caused during accommodation can occur at connection locations between the ciliary muscle and the choroid, known as the inner connective tissue layer between the sclera and ocular retina. Ciliary muscle contraction can also cause biomechanical forces on the trabecular meshwork, lamina cribrosa, retina, optic nerve and virtually every structure in the eye.

In some embodiments, applying the techniques and models described with respect to the various embodiments herein using simulations can lead to outputs and results that fall within known ranges of accommodation of a young adult human.

3D mathematical models can incorporate mathematics and non-linear Neohookean properties to recreate behavior of the structures of biomechanical, physiological, optical and clinical importance. Additionally, 3D (Finite Element Model) FEM models can incorporate data from imaging, literature and software relating to the human eye.

Visualization of accommodation structures during and after simulations may be included in addition to means for measuring, evaluating and predicting Central Optical Power (COP). These can be used to simulate and view age specific whole eye structures, optics, functions and biomechanics. Further, they can independently simulate properties of the ciliary muscle, extra-lenticular and lenticular movements of the ocular lens and functions on the ocular lens. Individual simulations of anatomical structures and fibers can reveal biomechanical relationships which would otherwise be unknown and undefined. Numerical simulation of the patient's eye can be created using 3D FEM meshing to accomplish these operations.

To elaborate, representative 3D geometry of resting ocular structures can be computationally defined based on extensive review of literature measurements and medical images of the anatomy of young adult eyes and through modeling. Specialized methods implemented in software, such as AMPS software (AMPS Technologies, Pittsburgh, Pa.), can be used to perform geometric meshing, material property and boundary conditions definitions, and finite element analysis during the modeling stage. Ciliary muscle and zonules can be represented as a transverse isotropic material with orientations specified to represent complex fiber directions. Additionally, computational fluid dynamic simulations can be performed in order to produce fiber trajectories, which can then be mapped to the geometric model.

Initially, a lens modeling can include a lens in a relaxed configuration, before being stretched by pre-tensioning zonule fibers to an unaccommodated position and shape. Unaccommodated lens position can be reached when zonules are shortened, e.g., to between 75% and 80% of their starting length, and more particularly to about 77% of their starting length. Then accommodative motion can be simulated by performing active contraction of the various fibers of the ciliary muscle. In some embodiments, this can be accomplished using previous models of skeletal muscle that are modified to represent dynamics particular or otherwise specific or unique to the ciliary muscle. Model results representing lens and ciliary anterior movement and deformed ocular lens thickness at a midline and apex can be validated or otherwise verified by comparing them to existing medical literature measurements for accommodation. In order to investigate contributions of the various ciliary fiber groups to the overall action of the ciliary muscle, simulations can be performed for each fiber group by activating each in isolation while others remain passive or otherwise unchanged.

Various beneficial aspects of the embodiments described below are described with respect to simulations applying pre-tensioning zonules models and contracting ciliary muscle models.

With respect to the pre-tensioning zonules, modeling can include: 1) Creation of 3D material sheets oriented between measured zonular attachment points of insertion on the lens and origination on the ciliary/choroid; 2) specified fiber direction in the plane of the sheet (e.g., fibers directed from origin to insertion); and 3) Transversely isotropic constitutive material with tension development in the preferred direction. Further, with particular respect to 3), advantages have been achieved, including: a) Time-varying tension parameter input regulates the stress developed in the material; b) Time-varying tension input may be tuned to produce required strain in the lens to match measurements of the unaccommodated configuration; c) Age variation in material properties and geometries to produce age-related impact; and d) others.

With respect to the contracting ciliary muscle models, modeling can include: 1) Modified constitutive model to represent smooth and skeletal aspects of ciliary mechanical response; 2) a plurality of, e.g., 3, sets of specified fiber directions to represent physiological orientation of muscle cells and lines of action of force production; and 3) Transversely isotropic constitutive material with active force development in the preferred direction. Further, with particular respect to 3) advantages have been achieved, including: a) Activation parameter input regulates the active stress developed in the material; b) Activation input may be tuned to produce appropriate accommodative response to match literature measurements; c) Activation of individual muscle fiber groups can be varied in isolation to assess contributions to lens strain/stress; d) Activation of individual muscle fiber groups can be varied in isolation to assess contributions to ocular scleral strain/stress; e) Activation of individual muscle fiber groups can be varied in isolation to asses contributions to choroidal strain/stress; and f) others.

In various embodiments, simulation results can be governed by modification of tensioning and activation inputs to the zonule and ciliary materials, as opposed to performing an applied displacement to external node(s) of a mesh.

Thereafter, systems, methods and devices for providing a predictive outcome in the form of a 3D Computer Model with integrated Artificial Intelligence (AI) can be used to find predictive best instructions for a therapeutic ophthalmic correction, manipulation, or rehabilitation of a patient's vision defects, eye disease, or age-related dysfunction are disclosed. The predictive best instruction can be derived from physical structural inputs, neural network simulations, and prospective therapeutic-outcome-influencing. New information can be analyzed in conjunction with optimized, historical therapeutic-outcome information in order to provide various benefits. The concepts herein can be used to perform a multitude of simulations and include a knowledge-based platform so that the system may be able to improve its instruction response as the database is expanded.

In some embodiments, the stored instructions contemplated can preferably be an optimized, custom, photoablative algorithm for driving a photoablative, photothermal laser. The instructions can be provided along with an AI processor via direct integration, stand-alone importation or remotely, e.g., via a Bluetooth or other wireless enabled application or connection. These instructions can be performed a priori or intraoperatively.

In some embodiments, the stored instructions contemplated can preferably be an optimized custom ocular lens simulation algorithm used for simulating manipulation of an implantable intraocular lens in order to improve medical procedures and understanding.

The instructions can also be set up as a 'stand-alone' system, whereby the instructions can be provided with independent research design inputs and outputs to test various conditions and responses of the eye to surgical manipulations, implantation devices, or other therapeutic manipulations of the eye, in order to optimize design and outcome response.

Additionally, these instructions can also include one or more of: an algorithm for image processing interpretation, expansion of ophthalmic imaging data platforms and a companion diagnostic to an imaging device.

As described herein, methods for improving ophthalmic treatments, surgeries, or pharmacological interventions can include obtaining topological, topographical, structural, physiological, morphological, biomechanical, material property, and optical data for a human eye along with applied physics and analyzing through mathematical simulations using artificial intelligence networks.

In some embodiments, applications using simulation can include techniques executed via devices, systems and methods for automated design of an ophthalmic surgical procedure including physical measurements and applied physics of a patient's whole eye are obtained. Techniques known in the art can be used to obtain these measurements. The information measured can be interpolated and extrapolated to fit nodes of a finite element model (FEM) of a human eye for analysis, which can then be analyzed to predict an initial state of stress of the eye and obtain pre-operative conditions of the cornea, lens and other structures. Incision data constituting an "initial" surgical plan can be incorporated into the finite element analysis model. A new analysis can then be performed to simulate resulting deformations, biomechanical effects, stresses, strains, curvatures of the eye as well as dynamic movements of the eye, more specifically the ciliary muscles, lens and accommodative structures. These can be compared to original values thereof and to a vision objective. If necessary, a surgical plan can be modified and resulting new ablation data can be entered into the FEM and the analysis is repeated. This procedure can be repeated as desired or necessary until the vision objectives are met.

In some embodiments, Artificial Intelligence (AI) software can use a learning machine, e.g., an artificial neural network, to conduct machine learning, whereby the system can learn from the data, and therefore has a learning component based on the ongoing database expansion. It can be operative to improve reliability as the database is formulated and updated, heretofore unknown in the prior art of 3D predictive modeling systems, methods and devices.

Simulation can include Age Progression simulation of a patient's eye, having a predictive capacity to simulate ophthalmic surgical outcomes, determine rates of regression of treatments, as well as execute predictive algorithms for future surgical or therapeutic enhancement, heretofore unknown in the prior art of 3D predictive modeling systems, methods and devices.

In some embodiments, the systems of the present disclosure may include a virtual eye simulation analyzer that can include integration of information related to all structures of an eye into a computer program for the purpose of simulating biomechanical and optical functioning of the eye, as well as age related simulations for clinical application purposes.

The virtual eye simulation analyzer systems, devices and methods can include an output display that can be viewed by users as a standalone or integrated display system, along with other equipment.

Information used as inputs for the simulator can include imaging information for Biometry (UBM, OCT and others). Dynamic Imaging can be performed using UBM, OCT and others. Anatomy information can include geometry, histology and others. Physiological function information can include dynamic accommodation, aqueous flow, intraocular pressures, pulsatile ocular blood flow, retinal performance or compromise and others. Material Properties of tissues of the eye, physics and biomechanical information related to relative biomechanics can also be used.

The simulator can incorporate mathematics and non-linear Neohookean properties in order to recreate behavior of the structures of biomechanical, physiological, optical and others that may be valuable or otherwise of clinical importance. The simulator can use methods known in the art to input data incorporated into a 3D FEM with a patient's unique data based on analysis of their own individual eye or eyes. Further, the simulator can use methods known in the art to input data and create a numerical simulation of the patient's eye using a 3D FEM meshing—essentially creating a custom dynamic real-time "Virtual Eye," heretofore unknown in the prior art of 3D predictive modeling systems, methods and devices.

In some embodiments, the AI may be capable of learning via predictive simulation and can be operative to improve simulative predictions for surgical or therapeutic manipulations of the eye through learning machine, such as artificial neural networks, e.g., in an "ABACUS" program. Such program can also be capable of providing instructions directly to a communicatively coupled processor or processing system to create and apply algorithms, mathematical sequencing, formula generation, data profiling, surgical selection and others. It can also be capable of providing instructions directly to a workstation, an image processing system, a robotic controller or other device for implementation. Further, it can be capable of providing instructions indirectly through a Bluetooth or other remote connection to a robotic controller, an image system or other workstation.

The models herein can have various applications for clinical, research and surgical use, including: 1) use of prior evaluation and simulation of accommodation functions of the eye (examples including Presbyopia indication-IOL design and use, extra-lenticular therapeutics and their uses); 2) use of prior evaluation and simulation of aqueous flow of the eye, such as for glaucoma indications; 3) virtual simulations and real time simulations of efficacy of IOL's, therapeutic treatments and various biomechanical implications; 4) virtual simulations using the AI and CI to reproduce customized aging effects on an individual's biomechanical and physiological functions of their eye which have clinical importance; 5) Surgical Planning; 6) design model (such as FEM) importation and simulation, such as for IOL's and others; 7) Virtual clinical trials and analysis; 8) real-time intraoperative surgical analysis, planning and execution; 9) Performance of a crystalline lens of the eye as it relates to optical and biomechanical dysfunction, cataract formation and the like; and 10) others.

Additional components of simulators may include: 1) Eye Scanning; 2) Optical inputs such as a) Cornea optics, wavefronts, elastography, hysteresis, visual acuity topography, connective tissue macro and micro structure and b) lens optics such as wavefront, visual acuity, topography, lens opacity, light scatter, central optical power (COP) during accommodation and disaccommodation, elastography, viscoelastic properties and others; 3) Scleral biomechanics, viscoelastic, material properties, stress, strain mapping, connective tissue macro/micro structure; 4) Trabecular meshwork material, viscoelastic, connective tissue macro and micro structure; 5) Lamina cribrosa material properties, stress, strain viscoelastic, connective tissue macro and microstructure; 6) Physiological Inputs including a) Aqueous outflow and inflow, b) Intra Ocular Pressure (IOP), c) Ocular pulsatile blood flow, d) Retinal activity and others; 7) Surface Spectroscopy; 8) Collagen Fibril characterization of the cornea, sclera, lens, and others; and 9) others.

Benefits of simulators in an accommodation embodiment may include: 1) Measuring, analyzing and simulating accommodation of an eye in real-time; 2) Demonstrating accommodation biomechanics in real-time; 3) Evaluating accommodation biomechanics; 4) Visualization of accommodation structures; 5) Measuring, evaluating and predicting Central Optical Power; 6) Simulating age progression of whole eye structures, functions and biomechanics; and 7) others.

Major structural component inputs can be based on the sclera, cornea, lens, trabecular meshwork, lamina cribrosa, retina and others. For the sclera, these can include: Scleral rigidity, viscoelasticity, Scleral thickness, Scleral depth, 3D surface topology, top surface spectral dimensions, 3D spectroscopy and others. For the cornea, these can include: Corneal Wavefront, viscoelasticity, Topography, Keratotomy, Corneal thickness, 3D topology, K readings, Corneal stiffness, 3D spectroscopy and others. For the lens, these can include: Lenticular Wavefront, Central optical power, Accommodative amplitude, Light scattering, Opacity and others. For the trabecular meshwork, these can include: elasticity, outflow, inflow and others. For the lamina cribrosa this can include: porosity, mechanical dependence, perfusion, poroelasticity, cup floor depth, and others.

Some of the various major optical profiles, properties, information and visual acuity information outputs for a cornea can include: Total aberrations, Visual Strehl Ratio, Depth of focus, MRSE, Visual acuity, lens scatter and others. Some of the various major optical profiles, properties, information and visual acuity information outputs for a lens can include: Total aberrations, VSOF, Depth of focus and others.

Described herein are example embodiments of a creation of a 3D Microporation Model on a spherical surface, and example embodiments of Pantec Protocols Revised Fibonacci MatLab Pore Calculation for Whole Eye Patterns.

Referring to FIG. 2K-1, an example of Protocol Execution is now described: Protocol 1.1: 225 µm (169 Total Pores @ 3%=42.25 Pores/Quadrant). An example of Matlab code used for Protocol 1.1 may include: >>fibonacci_spiral_connected ('r',0.225,3,6.62,9.78). Matlab code parameter breakdown may include: Parameter 1, 'r'=pore shape: type in 'r' for rectangular or 'c' for circular pore shape. [[.]] Use 'r' for 'please' and 'c' for 'DPM25'*; Parameter 2, 225 µm (0.225)=r_shape: length of the rectangular pore shape or the radius of the circular pore shape in [mm]; Parameter 3, 3%=D: pore density in [percent]; Parameter 4, 6.62 mm (Radius of the zone taken away from the pore calculation). This is so there is no pore calculated in the corneal/limbus area (6.62 mm)=r_b: radius for the beginning of the circle in [mm]; Parameter 5, 9.78 mm (Radius to the end of the zone for pore calculation). The 6.62 mm radius will be subtracted from the process of the pore calculation, thus allowing 6.62 mm to 9.78 mm radius being the only calculated area with pores=r_e: radius for the ending of the circle in [mm]. Once the code (('r',0.225,3,6.62,9.78)) is entered in Matlab, it will output the figure generated specifically for this pore protocol. It is how the exemplary title got its total pore number.

Therapy Manipulation protocols: The following are exemplary protocols for Therapy Manipulation, which may be 2 Manipulations per Protocol: a) First Manipulation of entire quadrant area; b) Second Manipulation of "Patch" area 5×5 mm diamond, i) A diamond having a length of its diagonal=5*√(2)=7.07 mm, ii) A 5×5 matrix to place on the sphere we have updated so the Fibonacci spirals can meet models.

Sphere comparison: the "Patch" is 5×5 in some embodiments Er:YAG laser with fiber optic probe; 600 µm spot size; Nine micro-excisions in the 4 oblique quadrants; 10 min/eye treatment time; Micropores in the critical zones (e.g., 3 or 5 zones) over the ciliary complex; Creation of pliable matrix zones in the sclera.

Procedure Objectives can include: 1) Improve compliance of sclera over ciliary muscle complex critical anatomy; 2) Restore mechanical efficiency of the natural accommodative mechanism; 3) Improve biomechanical mobility to achieve accommodative power; and others.

In some exemplary operations, an exemplary Fibonacci treatment pattern was generated through Matlab or other programs in two dimensions. When having correctly sized patches, such as 5×5 mm, it may make an actual treatment that may not fit in the critical zones (e.g., zones 1-3, or 1-5). There is a way to get an actual estimate from a 3D model to a 2D model. As illustrated in FIG. 2K-1, exemplary parameters can include:

Baseline: 600 µm (92 Total Pores @ 16%=23 Pores/Quadrant).

Spot Size: 600 µm; Depth: 80%; Density: 16%; Volume Removed: 1.16 mm³; Total Pores Entirety: 92; Total Pores/Quadrant: 23.

Protocol 1.1: 225 µm (169 Total Pores @ 3%=42.25 Pores/5.5 mm Patch: Validated) Total Pores/5.5 mm patch.

FIGS. 2K-1-A to 2K-1-C illustrate exemplary protocol parameters producing a diamond pattern for 3 critical zones.

In some embodiments, it can be important to know what is in each protocol how many pores are in the 5×5 patch on the 3D model pursuant to the changing density and the changing spot size. Once known, patch manipulations can be performed.

FIGS. 2K-2 to 2K-17 illustrate exemplary embodiments of microporation patterns of a plurality of micropores with a plurality of densities and a plurality of spot sizes, with their various exemplary protocols used. These protocols include:

Protocol 1.1: 225 µm (96 Total Pores @ 3%=24 Pores/Quadrant: Validated)
Spot Size: 225 µm; Depth: 80%; Density: 3%; Volume Removed: 0.91 mm$^3$; Total Pores Entirety: 96; Total Pores/Quadrant: 24

Protocol 1.2: 225 µm (161 Total Pores @ 5%=40.25 Pores/Quadrant: Validated)
Spot Size: 225 µm; Depth: 80%; Density: 5%; Volume Removed: 1.52 mm$^3$; Total Pores Entirety: 161; Total Pores/Quadrant: 40.25

Protocol 1.3: 225 µm (257 Total Pores @ 8%=64.25 Pores/Quadrant: Validated)
Spot Size: 225 µm; Depth: 80%; Density: 8%; Volume Removed: 2.43 mm$^3$; Total Pores Entirety: 257; Total Pores/Quadrant: 64.25

Protocol 1.4: 250 µm (565 Total Pores @ 10%=141.25 Pores/Quadrant: Validated)
Spot Size: 250 µm; Depth: 80%; Density: 10%; Volume Removed: 3.04 mm$^3$; Total Pores Entirety: 565; Total Pores/Quadrant: 141.25

Protocol 2.1: 250 µm (100 Total Pores @ 3%=25 Pores/Quadrant: Validated)
Spot Size: 250 µm; Depth: 80%; Density: 3%; Volume Removed: 0.91 mm$^3$; Total Pores Entirety: 100; Total Pores/Quadrant: 25

Protocol 2.2: 250 µm (166 Total Pores @ 5%=41.5 Pores/Quadrant: Validated)
Spot Size: 250 µm; Depth: 80% Density: 5%; Volume Removed: 1.52 mm$^3$; Total Pores Entirety: 166; Total Pores/Quadrant: 41.5

Protocol 2.3: 250 µm (265 Total Pores @ 8%=66.25 Pores/Quadrant: Validated)
Spot Size: 250 µm; Depth: 80%; Density: 8%; Volume Removed: 2.43 mm$^3$; Total Pores Entirety: 265; Total Pores/Quadrant: 66.25

Protocol 2.4: 250 µm (332 Total Pores @ 10%=83 Pores/Quadrant: Validated)
Spot Size: 250 µm; Depth: 80%; Density: 10%; Volume Removed: 3.04 mm$^3$; Total Pores Entirety: 332; Total Pores/Quadrant: 83

Protocol 3.1: 325 µm (59 Total Pores @ 3%=14.75 Pores/Quadrant: Validated)
Spot Size: 325 µm; Depth: 80%; Density: 3%; Volume Removed: 0.91 mm$^3$; Total Pores Entirety: 59; Total Pores/Quadrant: 14.75

Protocol 3.2: 325 µm (98 Total Pores @ 5%=24.5 Pores/Quadrant: Validated)
Spot Size: 325 µm; Depth: 80%; Density: 5%; Volume Removed: 1.52 mm$^3$; Total Pores Entirety: 98; Total Pores/Quadrant: 24.5

Protocol 3.3: 325 µm (157 Total Pores @ 8%=39.25 Pores/Quadrant: Validated)
Spot Size: 325 µm; Depth: 80%; Density: 8%; Volume Removed: 2.43 mm$^3$; Total Pores Entirety: 157; Total Pores/Quadrant: 39.25

Protocol 3.4: 325 µm (196 Total Pores @ 10%=49 Pores/Quadrant: Validated)
Spot Size: 325 µm; Depth: 80%; Density: 10%; Volume Removed: 3.04 mm$^3$; Total Pores Entirety: 196; Total Pores/Quadrant: 49

Protocol 4.1: 425 µm (34 Total Pores @ 3%=8.5 Pores/Quadrant: Validated)
Spot Size: 425 µm; Depth: 80%; Density: 3%; Volume Removed: 0.91 mm$^3$; Total Pores Entirety: 34; Total Pores/Quadrant: 8.5;

Protocol 4.2: 425 µm (57 Total Pores @ 5%=14.25 Pores/Quadrant: Validated)
Spot Size: 425 µm; Depth: 80%; Density: 5%; Volume Removed: 1.52 mm$^3$; Total Pores Entirety: 57; Total Pores/Quadrant: 14.25

Protocol 4.3: 425 µm (92 Total Pores @ 8%=23 Pores/Quadrant: Validated)
Spot Size: 425 µm; Depth: 80%; Density: 8%; Volume Removed: 2.43 mm$^3$; Total Pores Entirety: 92; Total Pores/Quadrant: 23

Protocol 4.4: 425 µm (115 Total Pores @ 10%=28.75 Pores/Quadrant: Validated)
Spot Size: 425 µm; Depth: 80%; Density: 10%; Volume Removed: 3.04 mm$^3$; Total Pores Entirety: 115; Total Pores/Quadrant: 28.75

Below are exemplary code references for the protocols:
```
fibonacci_spiral_connected ('r',0.225,3,6.62,9.78)>>1.1
fibonacci_spiral_connected ('r',0.225,5,6.62,9.78)>>1.2
fibonacci_spiral_connected ('r',0.225,8,6.62,9.78)>>1.3
fibonacci_spiral_connected ('r',0.225,10,6.62,9.78)>>1.4
fibonacci_spiral_connected ('c',0.125,3,6.62,9.78)>>2.1
fibonacci_spiral_connected ('c',0.125,5,6.62,9.78)>>2.2
fibonacci_spiral_connected ('c',0.125,8,6.62,9.78)>>2.3
fibonacci_spiral_connected ('c',0.125,10,6.62,9.78)>>2.4
fibonacci_spiral_connected ('c',0.1625,3,6.62,9.78)>>3.1
fibonacci_spiral_connected ('c',0.1625,5,6.62,9.78)>>3.2
fibonacci_spiral_connected ('c',0.1625,8,6.62,9.78)>>3.3
fibonacci_spiral_connected ('c',0.1625,10,6.62,9.78)>>3.4
fibonacci_spiral_connected ('c',0.2125,3,6.62,9.78)>>4.1
fibonacci_spiral_connected ('c',0.2125,5,6.62,9.78)>>4.2
fibonacci_spiral_connected ('c',0.2125,8,6.62,9.78)>>4.3
fibonacci_spiral_connected ('c',0.2125,10,6.62,9.78)>>4.4
```

As noted, the inputs may include: Pore Diameter (µm); Pore Depth (µm); # of Pores; Density of Pores; Angle of the Zones of the pores; Position of the laser beam from the surface and others if desired or required.

Various inputs may be used for adequate and accurate modeling. These can include, for example, pore size in µm, since pore size actually changes parameters and not just the proportions of # spots and pattern. Density may also be factored in, as well as surface area formula, number of pores as related to Pore Size as per the Power Calculations, angle and long arc in each zone of the eye sphere where each spot or row of spots will be placed are needed, angles that will the laser spots be in for each zone are using eye parameter inputs, and others.

In some embodiments, depth is fixed and at least two tests can be simulated, such as depth at 50%=454 µm or Depth at 80%=700 µm.

FIGS. 2K-18 and 2K-19 illustrate other exemplary microporation patterns, according to an embodiment of the disclosure.

FIG. 2K-20 is an exemplary graphical image of an exemplary embodiment of a microporation with a pattern having 41 number of micropores, according to some embodiments of the present disclosure.

In some embodiments, protocol requirements for each treatment pattern can include: Spot size; Depth; Number Pores Whole Globe in All Quadrants; Number Pores/Quadrant; Number Pores/5.5 mm patch; Volume removed; Density ------ (How many spots). Performing therapy manipulations can include: whole quadrant vs. patch (surface area), where specific corneal diameter of the shape change eye can be important.

An example embodiment of applications of Artificial Intelligence, simulations and field applications may include: 1) use for R&D of the eye for various modeling implementations; 2) Virtual clinical trials; 3) Laser integration as a diagnostic companion or robotics controller; 4) Performing virtual surgery on the eye for a "Smart Surgery" plan; 5) Integration to imaging devices to improve image interpretation; 6) Integration to surgical microscope for "real time" modification of surgery/therapy (e.g., IOL surgery); and 7) others.

Exemplary functions of simulations can include: 1) Simulations of ideal biomechanics for optimizing total visual function and best central optical power for accommodation; 2) Simulations of ideal biomechanics for optimizing total visual function and best optical power of the cornea; 3) Simulations of ideal biomechanics for optimizing decreased outflow of aqueous from the trabecular meshwork; 4) Simulations of ideal biomechanics for optimizing retinal decompression of lamina cribrosa and parapapillary sclera; 5) Simulations for optimizing scleral rejuvenation; 5) Simulations for optimizing surgical outcomes of intra ocular lens surgery; 6) Simulations for optimizing surgical or therapeutic outcomes for corneal surgery; 7) Age progression simulations to evaluate long term effects of aging on eye function; 8) Age progression simulations to evaluate long term stability and outcomes of various surgical procedures of the eye; 9) Simulations for analyzing testing of applications, therapies, surgical manipulation, implantation devices and pharmacological treatments of the eye via virtual clinical trials; and 10) others.

In various embodiments, algorithms and other software used to implement the systems and methods disclosed herein are generally stored in non-transitory computer readable memory and generally contain instructions that, when executed by one or more processors or processing systems coupled therewith, perform steps to carry out the subject matter described herein. Implementation of the imaging, machine-learning, prediction, automated correcting and other subject matter described herein can be used with current and future developed medical systems and devices to perform medical procedures that provide benefits that are, to date, unknown in the art.

In some embodiments, the described systems, methods and devices are performed prior to or contemporaneous with various medical procedures. In some embodiments, they may be implemented in their own systems, methods and devices, along with any required components to accomplish their respective goals, as would be understood by those in the art. It should be understood that medical procedures benefitting from the herein described material are not limited to implementation using the material described hereafter, but other previous, currently performed and future developed procedures can benefit as well.

Turning to FIG. 3A, an exemplary laser treatment system is illustrated, according to some embodiments of the present disclosure. In some embodiments, a treatment laser beam travels to dichroic 208. At dichroic 208 the laser beam travels to Galvo Setup 320 which consists of Galvo1 210 and Galvo2 212. The beam then passes from Galvo Setup 320 to focusing optics 216 and ultimately to patient eye 140.

Also provided for in this embodiment is a control and monitoring system which broadly consists of a computer 310, video monitor 312, and camera 308. Camera 308 provides monitoring of the laser beam at dichroic 208 via lens 306. Camera 308 transmits its feed to computer 310. Computer 310 is also operable monitor and control Galvo Setup 320. Computer 310 is also coupled to video monitor 312 to provide a user or operator a live feed from camera 308.

Although not shown, in some embodiments, the eye tracking system may have a camera near the fixation point, aimed at the treatment zone to provide a large area view and the image of features used for eye tracking as described. This may not go through the optical systems in FIG. 3A or 3B.

In some embodiments, the second user treatment area camera may not go through beam focusing optics and may provide a large area image with adequate resolution to be able to provide color information down in the pore and of the entire treatment area for the user, to be displayed on the monitor.

In some embodiments of the invention a dual axis closed loop galvanometer optics assembly may be used.

Since multiple lasers systems may be used for treatment in some embodiments, additional laser systems will now be described.

The laser system may include a cage mount galvanometer containing a servo controller, intelligent sensor, feedback system and mount assembly with an optical camera. Some embodiments may include use of a cage mount galvanometer optics assembly. Some embodiments may include ultra-high resolution nano-positioners to achieve sub-nanometer resolution.

To expand, FIG. 3A shows more exemplary detail of a CCD (or CMOS) camera-based eye tracker subsystem. Dichroic 208 beam splitter may be used to pick off visible light, while allowing the IR treatment beam to transmit. The beam splitter 208 is located in front of the steering elements, shown here as galvo mirrors 320. Lens 306 images the tissue plane (eye) onto the camera. Features in the image field (e.g. blood vessels, edge of the iris, etc.) are identified by image processing and their coordinates in the camera pixel field computed. If the eye moves within the pixel field frame-to-frame, the change in position of the reference features can be computed. An error function is computed from the change in reference feature position and commands issued to the galvo mirrors 320 to minimize the error function. In this configuration, the optical line of sight is always centered on the treatment spot, which is at a fixed coordinate in the camera pixel field. The apparent motion from repositioning the galvos 320 will be to move the eye image relative to the fixed treatment spot.

FIG. 3B illustrates an exemplary laser treatment system 303 according to some embodiments of the present disclosure. The laser treatment system 303 is similar to that of FIG. 3A, except that the eye tracking subsystem is located after galvo mirrors 320. FIG. 3B also shows an exemplary area camera image, not impacted by galvo beam steering. The camera may provide the eye tracking image and user visualization.

In this embodiment, a treatment laser beam travels to Galvo Setup 320 which consists of Galvo1 210 and Galvo2 212. The beam then passes from Galvo Setup 320 to dichroic 208. At dichroic 208 the laser beam travels to focusing optics 216 and ultimately to patient eye 140.

Also provided for in this embodiment is a control and monitoring system which broadly consists of a computer 310, video monitor 312, and camera 308. Camera 308 provides monitoring of the laser beam at dichroic 208 via lens 306. Camera 308 transmits its feed to computer 310. Computer 310 is also operable monitor and control Galvo Setup 320. Computer 310 is also coupled to video monitor 312 to provide a user or operator a live feed from camera 308.

Here, the eye image is shown centered in the pixel field. When eye motion is detected within the pixel field, the galvos 320 are repositioned to move the treatment spot to a new position within the pixel field corresponding to the movement of the eye, and to a desired fixed position relative to the eye reference features.

The system may include a biofeedback loop, where eye tracking, in some embodiments, may include use of light source producing an infrared illumination beam projected onto an artificial reference affixed to an eye. The infrared illumination beam may be projected near the visual axis of the eye and has a spot size on the eye greater than the reference and covering an area when the reference moves with the eye.

In some embodiments, the reference may have a retro-reflective surface that produces backward scattering orders of magnitude stronger than backward scattering from the eye would. An optical collector may be configured and positioned a distance from the eye to collect this backward scattered infrared light in order to form a bright image spot of the reference at a selected image location.

The bright image spot may appear over a dark background with a single element positioning detector positioned at the selected image location to receive the bright image spot and configured to measure a two-dimensional position of the bright image spot of the reference on the positioning detector. An electric circuit may be coupled to the positioning detector to produce positioning signals indicative of a position of the reference according to a centroid of the bright image spot based on the measured two-dimensional position of the bright image spot on the positioning detector.

FIG. 3C illustrates an exemplary camera correction system, according to an embodiment of the present disclosure. In the example embodiment, the top row illustrates the camera focus location after galvos have been used and the bottom row illustrates the camera focus location before galvos. Various landmarks 392 may be seen in the example embodiments including capillaries, iris, pupil, etc. Exemplary treatment spot 394 may also be seen in each embodiment.

As is shown in the example embodiment the top row of focus before the galvos each show the pupil of as the center pixel of each image. Compensation after galvos in the bottom row allows the treatment spot 394 to remain the focus of the camera's attention in each image and thereby allow the system to remain in position for the associated procedure.

In some embodiments, the camera may be positioned to support eye tracking system separate for the main laser optical system, near the fixation point. This may still allow the camera to center the pixel image on the treatment area and support the intended compensation. This may allow using a camera as part of the main laser optical system after the galvos to work as stated above.

FIG. 3D illustrates an exemplary flow diagram 330 of a camera-based eye tracker process, according to some embodiments of the present disclosure.

Broadly put, the diagram represents the use of a camera, for example, a CCD or CMOS camera to capture an image of eye. The image may be in color. Image data is transmitted to a computer, where key features are segmented/extracted (e.g. blood vessels, iris features, edge of pupil). The image is stored as a reference frame. Subsequent images are then compared to the reference frame. Any shift is computed after comparing reference features in pixel coordinates. Conversion of pixel coordinates to scanning system coordinates then occurs before commanding the scanning (or treatment laser beam pointing) system to deviate treatment beam line of site to restore relationship relative to reference features. If the shift is too large or out of range of the scanning system, the procedure may be halted and take steps may be taken to reacquire the target image field.

In some embodiments, the system may not utilize galvo scanning mirrors and utilize a multi-axis motion control system to position the laser for each pore (see, e.g., FIG. 20H). This may provide coordinate measuring.

In some embodiments, an initialization or starting sequence may require capturing image frame in step 332 before processing the captured image frame in order to extract features in step 334. This captured frame with extracted features is then used to set a reference frame in step 336.

After a reference frame is set, step 338 may consist of capturing an additional image frame, called a current frame, according to some embodiments. This image or current frame is processed in step 340 in order to extract features. Step 342 may include comparing the current frame to the reference frame which was set in step 336. Any image shift is computed between the current frame and the reference frame in order to determine the difference between the frames. A comparison to a pre-set threshold allows the system to determine if the image shift exceeds the pre-set threshold and stops the procedure at this point by going to step 352.

If an image shift does not exceed the pre-set threshold and therefore is not too large, the system may compute a compensation level in step 346 in order to compensate for the change or shift between the current frame and the reference frame. This compensation level is computed into physical coordinates used by a scanner in step 348. The scanner may then command to compensate using the coordinates in step 350. After this compensation step 338 occurs and another current image frame is captured, and the cycle may continue.

FIG. 4A illustrates an exemplary laser treatment system 400 according to some embodiments of the present disclosure. In the example embodiment, laser treatment system 400 may include a treatment laser 202 emitting a laser beam which travels through relay lens 204 to dichroic or flip-in 208. Visible spotting laser 206 emits a laser beam which also travels to dichroic or flip-in 208. In some embodiments, the beams from treatment laser 202 and visible spotting laser 206 may meet simultaneously at first dichroic or flip-in 208. In other embodiments, the beams may reach first dichroic or flip-in 208 at staggered times.

The beam or beams leave first dichroic or flip-in 208 and travels to a second dichroic 208. The beam or beams leave second dichroic 208 and travel to Galvo 210. Galvo1 210 may include a mirror which rotates through a galvanometer set-up in order to move a laser beam. The beam or beams leave Galvo 210 and travel to Galvo2 212 which may be a similar setup to Galvo1 210. The beam or beams leave Galvo2 212 and travel to dichroic (visible/IR) 214. In some embodiments, an operator 160 may monitor the beam or beams at dichroic (visible/IR) 214 by using a surgical microscope 150. The beam or beams travel from dichroic (visible/IR) 214 through focusing optics 216 to patient eye 140.

Still in FIG. 4A, additional monitoring elements may be provided for use by operator 160 to aid in medical procedures. Depth control subsystem 302 assists in controlling the depth of ablation procedures in accordance with some embodiments of the present disclosure, and receives input from second dichroic 208. FIGS. 4A-1 to 4A-10 illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

Similarly, eye tracker 304 may assist in tracking landmarks on patient eye 140 during medical procedures in accordance with some embodiments of the present disclosure, and receives input from second dichroic 208. Another dichroic 208 is shown in the example embodiment splitting the beam with outputs to eye tracker 304 and depth control subsystem 302.

FIG. 4B-1 illustrates an exemplary laser treatment system including ablation pore depth according to some embodiments of the present disclosure. FIG. 4B-1 generally shows a treatment laser beam traveling to dichroic 208 before travelling to Galvo 210, then to Galvo 212, through focusing optics 216, and to patient eye 140. As shown above, FIGS. 4A-1 to 4A-10 illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

In some embodiments, system 404, which may be an Optical Coherence Tomography (OCT) system, may be used to obtain subsurface images of the eye. As such, when coupled to computer 310 which is coupled to video monitor 312, system 404 provides a user or operator the ability to see subsurface images of the tissue ablation. As noted herein, pore ablation can be between 5% and 95% of the sclera thickness, with average sclera thickness as 700 μm a typical pore depth could be magnitudes of order larger than refractive surface ablation at around 200 μm-300 μm deep. This is significantly greater depth than other surface refractive ablative procedures that are typically between 10 μm-45 μm in depth on average and generally >120 μm.

In at least some embodiments, system 404 may provide a real-time, intraoperative view of depth levels in the tissue. System 404 may provide for image segmentation in order to identify sclera interior boundary to help better control depth. As shown and mentioned above, FIGS. 4A-1 to 4A-10 illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

In some embodiments, system 404 may use an OCT measurement beam, injected into the treatment beam line of sight via a dichroic beam splitter 208, located before the scanning system. In this way, the OCT system line of sight is always centered on the pore being ablated. System 404 may be connected to a computer 310 for processing the images and for control of the laser.

In some embodiments of the present disclosure, an anatomy avoidance subsystem is provided to identify critical biological obstacles or locations during procedures (e.g. blood vessels and others). As such, subsurface visualization may be provided to identify obstacles such as blood vessels or anatomy that is desired to be avoided intraoperatively.

FIG. 4A-5 and FIG. 4B-2 show exemplary simplified diagrams of an ablation pore in the sclera showing an example of the depth of an ablation in relation to the inner boundary of the sclera.

FIG. 5 illustrates an exemplary flow diagram of depth control process 410, according to some embodiments of the present disclosure.

In general, the depth-control system, e.g., an OCT system executes a repetitive B-scan, synchronized with the laser. The B-scan may show the top surface of the conjunctiva and/or sclera, the boundaries of the pore being ablated, and the bottom interface between the sclera and the choroid or ciliary body. Automatic image segmentation algorithms may be employed to identify the top and bottom surfaces of the sclera (for example, 400-1000 microns thick) and the boundaries of the ablated pore. The distance from the top surface of the sclera to the bottom surface of the pore may be automatically computed and compared to the local thickness of the sclera. In some embodiments, this occurs in real time. When the pore depth reaches a predefined number or a fraction of sclera thickness, ablation may be halted, and the scanning system indexed to the next target ablation location. In some embodiments, images may be segmented to identify interior sclera boundaries.

With reference to the steps in the figure, in the example embodiment a starting or initialization set of steps may occur first. This starting set of steps begins with positioning to a pore coordinate in step 412. A B-scan of the target region occurs in step 414. This scan creates an image which is processed in step 416 in order to segment and identify the sclera boundary. A distance is then computed in step 418 between the conjunctive surface and the sclera boundary.

After completion of this starting set of steps ablation may be initiated in step 420. A laser beam pulse is fired in step 422 followed by a B-scan in step 424. This B-scan creates an image that may then be segmented in step 426 and pore depth and ablation rate are computed from the image. This pore depth and ablation rate are compared to the target depth in step 430. If the target depth has not been reached, then the process loops back to step 422 and repeats. Upon reaching a target depth, step 432 stops the ablation process and the starting process begins again at step 434 with positioning to next pore coordinates. In some embodiments, the depth-control system can monitor ablation depth during a single pulse and can stop the ablation as a risk mitigation means, there may also be other internal processes running that can end the ablation if the process is out of range; eye tracking operational limits exceeded, max preset # of pulses exceeded, laser power monitoring is not in limits. All of these are risk mitigation measures.

FIG. 6 illustrates an exemplary laser treatment system component diagram 600 showing relation of related subsystems according to some embodiments of the present disclosure.

In general laser treatment system component 600 may include a laser 602, a laser delivery fiber 120, laser control system 604, monitoring system 608, and beam control system 606.

Laser 602 may generally be made up of several subsystems. In the example embodiment, these subsystems include system control electronics 104, Er:YAG laser head 612, laser cooling system 108, HV power supply 110, and system power supplies 112. Foot pedal 114 provides some control for the system user. Laser 602 transmits a laser beam via laser delivery fiber 120 to beam control system 606.

Beam control system 606 may generally be made up of beam transport optics 624, red spotting laser 626, galvo mirrors 628, beam delivery optics 630, and active focus 632.

Laser control system 604 maintains a link to laser 602 via a laser sync and to beam control system 606 via power control position status. Laser control system 604 may generally be made up of a user interface 614, power supply 616, galvo controller 618, galvo controller 620, and microcontroller 622. Laser control system 604 may also be manipulatable via joystick 610.

Monitoring system 608 may generally be made up of camera 634 (e.g., a CCD or suitable camera), and visual microscope 636.

In some embodiments, a fiber laser may be composed of an undoped cladding and a doped core of higher refraction. The laser beam travels through the fiber guided within the fiber core and experiences a high amplification due to the length of interaction. Fiber lasers are considered advantageous to other laser systems because, among other qualities, they have simple thermal management properties, high beam quality, high electrical efficiency, high optical efficiency, high peak energy, in addition to being low cost, requiring low maintenance, having superior reliability, a lack of mirror or beam path alignment, and they are lightweight and generally compact.

In some embodiments of the present disclosure, spot arrays may be used in order to ablate multiple pores at once. These spot arrays may, in some cases, be created using microlenses and also be affected by the properties of the laser. A larger wavelength may lead to a smaller number of spots with increased spot diameter.

Turning to FIG. 7, an exemplary laser treatment system 700 is shown according to some embodiments of the present disclosure. Laser treatment system 700 may generally be made up of control system 702, optics and beam controls.

Control system 702 may include monitor 704 and monitor 706, as well as keyboard 708 and mouse 710 to provide a user the ability to interact and control with a host computer 724 running computer programs. In many embodiments, the computer programs running on host computer 724 include control programs for controlling visible spotting laser 712, laser head 714, laser cooling system 716, system power supplies 718, laser power supply 720, and beam transport optics 722.

Also provided for in this embodiment are depth control subsystem 726, galvo mirrors 728, camera 730 (e.g., CCD camera, or suitable camera), visual microscope 732, focus subsystem 734, and beam delivery optics 736.

FIG. 7-1 illustrates another exemplary laser treatment system, according to some embodiments of the present disclosure.

Turning to some other aspects of the present disclosure, preoperative measurement of ocular properties and customization of treatment to an individual patient's needs is beneficial in many embodiments. Preoperative measurement of ocular properties may include measuring intraocular pressure (TOP), scleral thickness, scleral stress/strain, anterior vasculature, accommodative response, and refractive error. Measurement of scleral thickness may include use of optical coherence tomography (OCT). Measurement of scleral stress/strain may include using Brillouin scattering, OCT elastography, photoacoustics (light plus ultrasound). Measurement of anterior vasculature may include using OCT or Doppler OCT. Measurement of refractive error may include using the products such as the iTrace trademarked product from Tracey Technologies Corp. Those of ordinary skill in the art will recognize that other measurements, methods and systems may also be used.

Intraoperative biofeedback loops may be important during a treatment procedure in order to keep the physician informed on the progress of the procedure. Such feedback loops may include use of topographical measurements and monitoring "keep away" zones such as anterior ciliary arteries.

Biofeedback loops may include a closed-loop sensor to correct for nonlinearity in the piezo scanning mechanism. The sensor in some embodiments may offer real-time position feedback, e.g., in a few milliseconds and utilizing capacitive sensors for real-time position feedback. Real-time position feedback may be communicated to a controller, and, upon identification of specific biological features based on tissue characteristics, may cease laser operation intraoperatively.

Sensor/feedback apparatus may also perform biological or chemical "smart sensing" to allow ablation of target tissue and protect or avoid surrounding tissue. In some instances, this smart sensing may be accomplished by using a biochip incorporation in a mask which is activated by light irradiation and senses location, depth, size, shape, or other parameters of an ablation profile. Galvo-optic assemblies are also contemplated in some embodiments and may be used to gage numerous parameters of laser steering and special function.

Those of ordinary skill in the art will recognize that other feedback methods and systems may also be used.

In some embodiments, the systems, methods and devices of the present disclosure may include image display transfer and GUI interface features that can include each image frame taken and send information to a video display after each firing inside the 3-dimension-7-dimension micropore before and after the firing of the laser in dynamic real time and surface view. The GUI may have integrated multiview system in 7-directionality for image capture including: surface, internal pore, external pore, bottom of the micropore, whole globe eye view, target array area.

In some embodiments, 7-cube may be a preferred projection for the microprocessor but other examples exist in dimensional sphere shape, integrated into the GUI and microprocessor. Orthogonal projections can include examples as shown in FIG. 8.

In some embodiments, support vector machine (SVM) pattern recognition may be integrated into the AI (artificial intelligence) network directed to the microprocessor path. For the non-linear classification problem, the SVM may turn the input space into a high dimensional space by a nonlinear mapping K(X). Hence, the nonlinear problem will may turn into a linear problem and then the optimal separating hyperplane will be calculated in a new high dimensional space, e.g., using Matlab or Mathematica integrated programming. As the optimization functions and classification functions involve only the inner product between samples (xi–xe) the transformed higher dimensional space is also just the inner product (k(xi)–k(xe)). If the kernel function k(xi–k(xe)

satisfies with Mercer condition, it corresponds to a transform space of inner product K (xi, x=(k(xi)–k(x)). The common kernel functions include linear kernel polynomial kernel and radial bias kernel function. The use of appropriate kernel function can be an alternative to non-linear mapping of high dimensional space, which will achieve a linear classification after nonlinear transformation. The corresponding classification discriminant function can be obtained as follows:

$$g(x) = \text{sgn}\left(\sum_{i=1}^{n} a_i^* y_i(x_i \cdot x) + b^*\right)$$

$$= \text{sgn}\left(\sum_{x_i \in SV} \alpha_i^* y_i(x_i \cdot x) + b^*\right),$$

In some instances, mapping and optimization formulas for machine learning may include:

$$g(x) = \text{sgn}\sum_{i=1}^{n} a^* y_i(x_i \cdot x) + b^*)$$

$$g(x) = \text{sgn}\sum_{i=1}^{n} a^* y_i(x_i \cdot x) + b^*)$$

$$g(x) = \text{sgn}(\sum \alpha i^* yiK(xi \times x) + b^*)$$

Instrument of the GUI interface and code may include multi-dimensional scaling, linear discriminant analysis and linear dimensional reduction processing as well as locally linear embedding and isometric maps (ISOMAP) and non-linear dimensionality reduction methods may also be included.

In some embodiments, continuous mapping p: E→B satisfying the homotopy lifting property with respect to any space may be used. Fiber bundles (over paracompact bases) constitute important examples. In homotopy theory, any mapping may be 'as good as' a fibration—i.e. any map can be decomposed as a homotopy equivalence into a "mapping path space" followed by a fibration into homotopy fibers.

The fibers are by definition the subspaces of E that are the inverse images of points b of B. If the base space B is path connected, it is a consequence of the definition that the fibers of two different points $b_1$ and $b_2$ in B are homotopy equivalent. Therefore, one usually speaks of "the fiber" F.

Some embodiments can utilize a Serre fibration or Weak fibration. They are able to produce mapping of each cylinder micropore in the array and the total array across the 3D surface and interstitial mapping of pore arrays in cross section. An exemplary 3D mapping 900 is shown in FIG. 9.

FIG. 10 illustrates, according to some embodiments of the present disclosure, exemplary design patterns that can be performed as follows. Step 1001: Treatment design/planning may begin with tissue hierarchy which is established using the 7-Sphere mathematical projection over entire sphere to establish congruent treatment platform built on 7D shape and hyperbolic planar tessellation. Step 1002: Off Axis mathematical algorithm derived from tissue hierarchy and Fibonacci patterning is displayed as mathematical imagery. Step 1003: Algorithmic Code is then implemented to develop customized microporation patterns that are reflective of the tissue biorheology including all inputs of rigidity, viscoelastic modulus, topology, topography, biometry etc. Step 1004 (not shown): Anatomy avoidance software may be executed erasing or eliminating untargeted fields, arrays, regions. Step 1005 (not shown): Surgeon/user can also manipulate the targeted or untargeted areas via touch screen interface.

In some embodiments, the described systems, methods and devices of the present disclosure may include the following features of laser user interface system delivery of treatment algorithms. Real time mathematical imagery is incorporated and displayed both in 3D mathematical files which can also be run in a GIF animation format to display apriori information regarding the array effectiveness. The workstation/algorithms work together with the VESA system in order to produce the mathematical imagery to the user/surgeon for ideal configuration of the 3D array on the eye. The topological representation of the image is projected stereographically to the display. The array is prefixed formularies and in addition can be simulated in Fibonacci sequencing with a plurality of densities, spot sizes, micro and nano pore geometries and configurations. The benefit of the Fibonacci sequencing is to produce the most balanced array formulary which corresponds to the body's own natural tissue hierarchy both in macro and micro scales.

The array can also follow a hyperbolic geometry model or a uniform (regular, quasiregular, or semiregular) hyperbolic tiling which is an edge-to-edge filling of the hyperbolic plane which has regular polygons as faces and is vertex-transitive (transitive on its vertices, isogonal, i.e. there is an isometry mapping any vertex onto any other). Examples are shown in FIGS. 10 and 11. It follows that all vertices are congruent, and the tiling has a high degree of rotational and translational symmetry.

The uniform tilings can be identified by their vertex configuration, a sequence of numbers representing the number of sides of the polygons around each vertex. One example below represents the heptagonal tiling which has 3 heptagons around each vertex. It is also regular since all the polygons are the same size, so it can also be given the Schläfli symbol.

The uniform tilings may be regular (if also face- and edge-transitive), quasi-regular (if edge-transitive but not face-transitive) or semi-regular (if neither edge- nor face-transitive). For right triangles (p q 2), there are two regular tilings, represented by Schläfli symbol {p,q} and {q,p}.

Exemplary models are illustrated in FIG. 11.

In some embodiments, the described systems, methods and devices of the present disclosure may include mechanism of creating an array of micropores the micropore array pattern having a controlled non-uniform distribution, or a uniform distribution, or a random distribution, and may be at least one of a radial pattern, a spiral pattern, a phyllotactic pattern, an asymmetric pattern, or combinations thereof. The phyllotactic spiral pattern may have clockwise and counterclockwise parastichy according to the present disclosure.

FIG. 12 illustrates an exemplary schematized representation 1200 of creation of an asymmetrical controlled distribution of an array algorithm pattern on an eye with spiral phyllotaxis, where each array of micropore successively appear. Ro is the radius of the region that corresponds to the center of the meristem around which the micropores are generated. The big vertical arrow 1210 symbolizes vertical microporation expansion in the array, while the laterally depicted arrows 1220, 1230 indicate the spatial expansion of the system of new micropores. i and j are pairs of successive Fibonacci numbers, i.e. such a pair of successive Fibonacci numbers is indicated as (i, j). The symbols n, n–i, n–j, n–i–j stand for numbers indicating the order of appearance of micropores along the generative spiral during expansion of the array. However, they may better be symbolized by n, n+i, n+j, n+i+j. There are consecutive numbers in one and the same family of secondary spirals display a constant difference between them. So for the anticlockwise family: (n+i)−n=i, which is a Fibonacci number. (n+i+j)−(n+j)=i, which is the same Fibonacci number. For the clockwise family: (n+j)−n=j, which is the second Fibonacci number. (n+i+j)−(n+i)=j, which is the same Fibonacci number. So here we have a case of (i, j) phyllotaxis.

In some embodiments, the micropore array pattern may be one of an Archimedean spiral, a Euler spiral, a Fermat's spiral, a hyperbolic spiral, a lituus, a logarithmic spiral, a Fibonacci spiral, a golden spiral, or combinations thereof.

In some embodiments, the described systems, methods and devices of the present disclosure may include creation of a 3D microporation model on a spherical surface. FIG. 13 illustrates an exemplary graphical image 1300 created on CAD program of an exemplary embodiment of a microporation with a pattern having a mechanism of creating the micropore array and expanding the microporation array in radial and lateral directions utilizing phyllactic spiral to expand the array face to face and edge to edge while mainlining a non-uniform distribution through divergence angels consistent with the Vogel Model and Fibonacci sequence wherein X number of micropores at a plurality of densities, sizes and geometric shapes are created according to the present invention. Although this example embodiment is the anterior or posterior sclera of the eye, it could also be the cornea.

In some embodiments, the described systems, methods and devices of the present disclosure may include utilization of Fibonacci and mathematical parameters to optimize surgical execution, outcomes and safety in a laser assisted microporation treatment array having a pattern of micropores/nanopores, wherein the pattern is a non-uniform distribution pattern that is delivered in cross sectional tissue in alignment with the existing tissue hierarchy on a macro scale and microscale so that there is a congruent rejuvenation effect of the treatment. A treatment array or lattice having a plurality of micropores/nanopores/ablations/incisions/targets may be arranged in a non-uniform distribution pattern, wherein the pattern is spiral or phyllotactic. The patterns may be described by the Vogel equation. Also, included is a plurality of other geometries/densities/depths and shapes having a spiral or phyllotactic patterns of flow paths, such as in the form of open channels or pores. The micropores/nanopores can be specifically adapted to correspond with any given contact lens, mask or other template material or design having a non-uniform distribution pattern. Alternatively, the microporation can be used in conjunction with conventional perforated coated or non-coated polymers such as hydrophilic or hydrophobic types. The array pattern having a non-uniform distribution pattern of micropores and the lens or mask can be used together as a treatment system As shown above, FIGS. 4A-1 to 4A-10 and also FIG. 26-3A illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue. Additionally, the present disclosure may include various types of automated processing systems to process the delivery of microporations of various compositions and configurations.

Tissue characteristics effected include, among others, porosity, texture, viscoelasticity, surface roughness, and uniformity. Surface characteristics, such as roughness and gloss, are measured to determine quality. Such microporation can also affect tissue deformation, pliability and flexibility and have an "orange peel" texture. Hence, the properties of the tissue treated with microporation/nanoporation will generally influence and/or enhance the tissue quality by means of restoring or rejuvenating the biomechanical pliability of the tissue when at rest and under stress/strain.

In some embodiments, microporation can include a plurality of micropore paths disposed in a pattern. The pattern of micropore paths can comprise regular polygons, irregular polygons, ellipsoids, arcs, spirals, phyllotactic patterns, or combinations thereof. The pattern of micropore paths can comprise radiating arcuate paths, radiating spiral paths, or combinations thereof. The pattern of micropore paths can comprise a combination of inner radiating spiral paths and outer radiating spiral paths. The pattern of air flow paths can comprise a combination of clock-wise radiating spiral paths and counter clock-wise radiating spiral paths. The micropore paths can be discrete, or discontinuous, from each other. Alternatively, one or more of the micropore paths can be fluidly connected. The number of radiating arcuate paths ("arcs"), radiating spiral paths, or combinations thereof can vary.

In some embodiments, microporation can comprise a pattern that is a controlled nonlinear distribution pattern, a controlled linear distribution pattern or a random pattern. In some embodiments, eye contact lens/eye mask can comprise a pattern of micropore paths wherein the pattern of micropore paths is generated from x and y co-ordinates of a controlled non-uniform distribution pattern. The controlled non-uniform distribution pattern used to generate the eye lens/eye mask micropore path can be the same or different than the array pattern of the laser microporation algorithm being used with the eye lens/eye mask. In an embodiment, the controlled non-uniform distribution pattern is the same as the array pattern of the laser microporation algorithm being used with the eye lens/eye mask. In some embodiments, the controlled non-uniform distribution pattern is different than the array pattern of the laser microporation algorithm being used.

In some embodiments, the laser microporation system may have phyllotactic patterns according to the laser microporation algorithm embodiments described herein. An eye lens/eye mask is co-operative with a laser microporation system having phyllotactic patterns when the laser microporation system includes a plurality of micropores, a plurality of openings, a plurality of cavities, a plurality of channels, plurality of passages, or combinations thereof, that are configured in a pattern designed to promote improvement of natural biological functions such as fluid flow, blood flow, muscular movement, as well as static and dynamic biological function through the eye lens/eye mask and tissue having a phyllotactic pattern. The micropores, openings, cavities, channels, passages, or combinations thereof can define biological flow paths that are located along, within, or though the back-up pad, or combinations thereof. In an embodiment, the pattern of micropores, openings, cavities, channels, passages or combinations thereof can be in the form of a regular polygons, irregular polygons, ellipsoids, arcs, spirals, phyllotactic patterns, or combinations thereof. In another embodiment, the air-flow paths can be in the form of a regular polygons, irregular polygons, ellipsoids, arcs, spirals, phyllotactic patterns, or combinations thereof.

In some embodiments, a suitable spiral or phyllotactic pattern can be generated from the x and y co-ordinates of any phyllotactic array pattern of the microporation system embodiments described above. In an embodiment, the x and y co-ordinates of a spiral or phyllotactic pattern are transposed and rotated to determine the x' and y' co-ordinates of the spiral or phyllotactic back-up air flow pattern, wherein θ is equal to it/n in radians and n is any integer. The (x' and y') can be plotted, such as by the use of computer aided drafting (CAD) software, to generate a suitable pattern such as a spiral or phyllotactic pattern.

The patterns can then be used to define radiating accurate and spiral channels, as well as, annular channels that can intersect the arcuate and spiral channels, or combinations thereof. The annular, arcuate, spiral, or combination channels can produce shape deformation, such as in the form of grooves, cavities, orifices, passages, or other pathways to form. Exemplary embodiments of channel patterns that are based on transposed phyllotactic patterns are also shown in FIGS. 10, 13, and 16. Additional exemplary embodiments based on transposed phyllotactic patterns are shown in FIGS. 14A-14D, 15A-15F, and 41.

As shown below, microporation pattern may have a number of clockwise spirals and a number of counter-clockwise spirals, wherein the number of clockwise spirals and the number of counterclockwise spirals are Fibonacci numbers or multiples of Fibonacci numbers.

FIG. 14A illustrates an exemplary embodiment of a microporation pattern which can be implemented directly on the target tissue or alternatively on a contact lens, mask, or other such template having an micropore pattern with a controlled non-uniform distribution of the micropores in the distribution of the Fibonacci sequence, according to some embodiments of the present disclosure.

FIG. 14B is an exemplary illustration of a phyllotactic spiral pattern having clockwise and counterclockwise parastichy, according to some embodiments of the present disclosure.

FIG. 14C is another exemplary illustration of a phyllotactic spiral pattern having clockwise and counterclockwise parastichy, according to some embodiments of the present disclosure.

FIGS. 14D and 14E are exemplary illustrations of the Vogel model, in accordance with some embodiments of the present disclosure. The Vogel model includes the pattern of florets. Briefly, each floret is oriented towards the next at about 137.5°. The number of left spirals and the number of right spirals are Fibonacci numbers. The sunflower pattern has been described by Vogel's model, which is a type of "Fibonacci spiral", or a spiral in which the divergence angle between successive points is a fixed Fibonacci angle that approaches the golden angle, which is equal to 137.508°. In an exemplary sunflower pattern, there are 34 in one direction and 55 in the other.

FIGS. 15A-15F are exemplary illustrations of phyllotactic spiral patterns conforming to the Vogel model that have differing divergence angles, according to some embodiments of the present disclosure.

FIGS. 16A-16N are exemplary illustrations of exemplary embodiments of microporation derived from icosahedron pattern shapes, according to some embodiments of the present disclosure FIGS. 17A-17B, and also FIGS. 2K-18 and 2K-19 as shown above, are exemplary illustration of microporation patterns derived from icosahedron pattern shapes representing a fractal sphere and icosahedron/tetrahedron tessellations, according to some embodiments of the present disclosure.

In some embodiments, the exemplary microporation patterns, for example as illustrated in FIGS. 14A to 17B above may be pre-drilled in to contact lens or mask. FIG. 18 illustrates an exemplary contact lens/eye mask that is cooperative with a microporation pattern.

In some embodiments, the micropore pattern is described by the Vogel model or a variation of the Vogel model. The Vogel model is $\varphi=n*a$, $r=c\sqrt{n}$, where: n is the ordering number of an micropore, counting outward from the center of the micropore pattern; $\varphi$ is the angle between a reference direction and a position vector of the nth micropore (e.g., a floret) in a polar coordinate system originating at the center of the micropore pattern (e.g., a capitulum), such that the divergence angle, $\alpha$, between the position vectors of any two successive micropores is a constant angle $\alpha$; r is the distance from the center of the micropore pattern to the center of the nth micropore; and c is a constant scaling factor.

In some embodiments, all, substantially all, or a portion of the micropores of the micropore pattern will be described by (i.e., conform to) the Vogel model. In some embodiments, all the micropores of the micropore pattern may be described by the Vogel model. In some other embodiments, at least 50%, at least 60%, at least 70%, at least 80%, at least 90%, at least 95%, or at least 99% of the micropores may be described by the Vogel model.

Surface Area:

The total target tissue surface area affects the amount total tissue material removed. Typically, as the amount of total tissue surface area is increased, the amount of surface material removed is increased. In some embodiments, the total microporation surface area of the target tissue may be equal to the total potential surface of the microporation system (i.e., the microporation target area if there were no micropores) minus the total micropore area (i.e., the sum of the area of all the micropores). Thus, the amount of the total microporation surface area can range from 1% to about 99.5% of the total potential surface area, depending on the amount of desired micropore area. See FIG. 30 for exemplary surface areas, according to some embodiments of the present disclosure.

Depth:

Referring back to FIGS. 4A-5 to 4A-10, they illustrate that the total target tissue depth may affect the amount of total tissue material removed. Generally, as the amount of total tissue depth is increased, the amount of interstitial or subsurface tissue removed is increased. In some embodiments, the depth of the tissue microporation removed is equal to the total potential subsurface and interstitial tissue of the microporation system (i.e., the total interstitial and subsurface tissue if there were no micropores) minus the total micropore cubic volume (i.e., the sum of the area of all the micropores). Thus, the amount of the total microporation cubic volume can range from 1% to about 95% of the total potential subsurface and interstitial cubic volume of the microporation tissue, depending on the amount of desired micropore cubic volume.

Density of Micropores:

The density of the micropore array may influence the total amount of micropore area and the total amount of surface, subsurface, and interstitial volume removed. It also may influence the total number of micropores and micropore distribution. A plurality of exemplary density configurations, micropore size and distribution of micropores are illustrated in FIGS. 2K-1-A to 2K-1-C and through 2K-17 above. It should be noted that micropores can be delivered randomly, uniformly, or singularly.

Number of Micropores:

The number of micropores may influence the total amount of micropore area and the amount of total surface, subsurface, and interstitial volume removed. Additionally, the number of micropores may affect the density and distribution of micropore coverage on the surface of the microporation, which in turn may directly affect the total volume extraction of the microporation. In some embodiments, the number of micropores may be at least about 3, at least about 5, at least about 8, at least about 12, or at least about 15. In some other embodiments, the number of micropores may be at least about 45, at least about 96, at least about 151, or at least about 257. For other parameters, see also FIGS. 31-34, 37, 38, and 39.

In some embodiments, the number of pores can range between 36 to 10,000 pursuant to the size of the spot which can range from 1 nm-600 µm. The number of micropores can be within a range comprising any pair of the previous upper and lower limits.

Various parameters and factors may influence the microporation of the present disclosure and are illustrated in FIGS. 31-35, and also discussed below.

Divergence Angle:

In delivering the laser pulse to the target tissue, increasing or decreasing the divergence angle α may affect how the micropores are placed within the pattern and the shape of the clockwise and counter clockwise spirals. The divergence angle is equal to 360° divided by a constant or variable value, thus the divergence angle can be a constant value, or it can vary. In some embodiments, the pattern may have a divergence angle in polar co-ordinates that ranges from about 100° to about 170°. Small changes in divergence angle can significantly alter the array pattern, and may show phyllotactic patterns that differ only in the value of the divergence angle. An exemplary divergence angle may be 137.3°. The divergence angle may also be 137.5°, or 137.6°. In some embodiments, the divergence angle is at least about 30°, at least about 45°, at least about 60°; at least about 90°, or at least about 120°. In other embodiments, the divergence angle is less than 180°, such as not greater than about 150°. The divergence angle can be within a range comprising any pair of the previous upper and lower limits. In some other embodiments, the divergence angle ranges from about 90° to about 179°, about 120° to about 150°, about 130° to about 140°, or about 135° to about 139°. In some embodiments, the divergence angle is determined by dividing 360° by an irrational number. In some embodiments, the divergence angle is determined by dividing 360° by the golden ratio. In some embodiments, the divergence angle is in the range of about 137° to about 138°, such as about 137.5° to about 137.6°, such as about 137.50° to about 137.51°. In some embodiments, the divergence angle is 137.508°.

Distance to the Edge of the Microporation Array:

In some embodiments, the overall dimensions of the array pattern can be determined based on the geometry of the microporation and intended usage. The distance from the center of the pattern to the outermost micropores can extend to a distance coterminous with the edge of the microporation. Thus, the edges of the outermost micropores can extend to or intersect with the edge of the microporation. Alternatively, the distance from the center of the pattern to the outermost micropores can extend to a distance that allows a certain amount of space between the edges of the outermost micropores and the edge of the microporation to be free of micropores. The minimum distance from the edges of the outermost micropores can specified as desired. In some embodiments, the minimum distance from the edges of the outermost micropores to the outer edge of the microporation is a specific distance, identified as a discreet length or as a percentage of the length of face of the microporation upon which the array pattern appears.

Size of Micropores:

In some embodiments, the size of the micropores may be determined, at least in part, by the desired total amount of array area for the microporation. The size of the micropores can be constant throughout the pattern or it can vary within the pattern. In some embodiments, the size of the micropores is constant. In some embodiments, the size of the micropores varies with the distance of the micropores from the center of the pattern. The size of the pores can range from 1 nm-600 µm. In some other embodiments, the size is 50 µm, 100 µm 125 µm, 200 µm, 250 µm, 325 µm, 425 µm, or 600 µm.

Shape of Micropores:

Shape of micropores themselves created in connective tissue by electromagnetic irradiation may have relative consequence on the tissue reaction and wound healing. Square shapes may heal slower than round shapes. The microporation system is capable of creating a plurality of geometric individual micropore shapes. In some embodiments, the ideal shape is square.

Shape may also be impactful in the micropore array. The amount of coverage can be influenced by the shape of the micropores. The shape of the micropores can be regular or irregular. In some embodiments, the shape of the micropores can be in the form of slits, regular polygons, irregular polygons, ellipsoids, circles, arcs, spirals, channels, or combinations thereof. In some embodiments, the micropore arrays have the shape of a circle. In some embodiments, the shape of the array may be in the form of one or more geometric patterns, for example, icosahedron or tetrahedron tessellations, wherein multiple polygons intersect.

FIGS. 16A-N show examples of such shaped micropore arrays. The micropore arrays are configured such that the patterns resemble polygons, which can have slightly accurate edges. Tissue removal in these configurations effect biomechanical properties in a mathematically and geometrically balanced way producing stability to the microporation.

Design Factor:

The design factor may influence the overall placement of the microporation array or lattice in 3D tissue and relative to microporation edges with relation to the 'atmosphere' within the tissue. The design of the microporation can be adjusted depending on the inherent shape of the tissue itself or around the intended physiological anatomy or desired impact. This can be a self-dual (infinite) regular Euclidean honeycombs, dual polyhedron, 7 cube, 7 orthoplex or likewise simple lattice, Bravais lattice, or non-Bravais lattice;

Scaling Factor:

The scaling factor may influence the overall size and dimensions of the micropore array pattern. The scaling factor can be adjusted so that the edges of the outermost micropores are within a desired distance of the outer edge of the microporation. Additionally, the scaling factor can be adjusted so that the inner edges of the innermost micropores are within a desired distance of the inner edge of the microporation. Duality can be generalized to n-dimensional space and dual polytopes; in two dimension these are called dual polygons, or three dimensions or a plurality of dimensions containing vertices, array's, or likewise containing tessalations both isotropic or anisotropic.

Distance Between Nearest Adjacent Micropores:

Along with consideration for the number and size of the micropores, the distance between the centers of the nearest adjacent micropores can be determined. The distance between the centers of any two micropores may be a function of the other array design considerations. In some embodiments, the shortest distance between the center of any two micropores is never repeated (i.e., the pore-to-pore spacing is never the same exact distance). This type of spacing is also an example of controlled asymmetry. In some other embodiments, the shortest distance between the center of any two micropores is always repeated (i.e., the pore-to-pore spacing is always the same exact distance). This type of spacing is also an example of controlled symmetry. In some embodiments, the distance between two micropores are randomly arranged (i.e. the pore-to pore spacing is random). The system thus can provide controlled asymmetry which is at least partial rotational asymmetry about the center of the array design or pattern, random asymmetry which is at least partial rotational random about the center of the array design or pattern, and controlled symmetry which is at least partial rotational about the center of the array design or pattern, and random symmetry which is at least partial rotational random about the center of the array design or pattern.

In some embodiments, the rotational asymmetry may extend to at least 51% of the micropores of the pattern design. In some embodiments, the rotational asymmetry may extend to at least 20 micropores of the array pattern design. In some embodiments, the rotational symmetry may extend to at least 51% of the micropores of the pattern design. In some embodiments, the rotational symmetry may extend to at least 20 micropores of the pattern design. In some embodiments, the rotational random pattern may extend to at least 51% of the micropores of the pattern design. In some embodiments, rotational random pattern may extend to at least 20 micropores of the pattern design.

In some embodiments, the 51% of the aperture pattern may be described in polar co-ordinates by the Vogel model equation: $\varphi = n^*\alpha$, $r = c\sqrt{n}$., as described above.

Co-Operative Eye Contact Lens/Eye Mask

The co-operative Eye contact lens/Eye mask (see FIG. 27A, element 2700, and FIG. 40) can be flexible or rigid, soft or hard. It can be made of any number of various materials including those conventionally used as contact lens or eye masks such as polymers both hydrophilic, hydrophobic or soft gel or collagen or dissolvable materials or special metals. An exemplary flexible lens/mask may include a pliable hydrophilic ("water-loving") plastic.

In some embodiments, the described systems, methods and devices of the present disclosure may include method and apparatus for treatment of sclera and neighboring ocular structures and fractional microporation and resurfacing, laser eye microporation for rejuvenation or restoration of physiological eye function, and/or alleviation of dysfunction or disease. In various embodiments, the arrays may take on a plurality of geometries, densities, configurations, distributions, densities and spot sizes and depths. They may also be preplanned and performed in various time points. It can also penetrate the epi sclera, sclera substantia, or lamina *fusca* at any percentage of required poration. Electromagnetic energy applications are may also be suitable.

Hydrophobic Scleral Lens Customizable Wafer, Nano, μm Etc.:

In various embodiments, a hydrophobic scleral lens customizable wafer can have variable sizes measured generally in millimeters, micrometers or nanometers. Generally, it is a scleral contact lens that can contain a computer generated customized algorithm for a laser treatment on a patient's sclera. First, spots can be registered that are retreatable and the spots can be profiled via the mask or lens. The mask can be made of various materials including one or more hydrophobic polymers or blends of polymers that are impenetrable by the laser. This can provide an added level of protection for the surrounding tissue that is not going to be treated in addition to smart mapping technology. A corneal central contact lens can be tinted to protect the cornea from the microscope light and from the laser beam itself. In various embodiments, it can be disposable and not reusable once the pattern is on the eye. Additionally, it can be delivered prepackaged sterilized containers.

This can be created by measuring biometry, morphology, anatomy, topography, keratotomy, scleral thickness, material properties, refractions, light scatter, and other features and qualities that may be imported, uploaded or otherwise inputted into a three dimensional (3D) dynamic FEM module which may be a platform for "Virtual Eye." The system of the disclosure may process the information of both cornea and lens and may run a plurality of algorithmic tests once all of the optics and information have been inputted. The system may apply mathematical and physical scenarios aimed at enhancing accommodative power through manipulation of the scleral, and it may also give desirable Zernike profiling of the cornea which would produce maximum accommodative power in the event that there are Laser Vision Correction (LVC) plus accommodated planning. Once complete the pattern may be generated, e.g., by ISIS (a visualization and eye mapping software for analyzing and reproducing a visual mapping of the eye refractive status the corneal refractive status, e.g., both the lens refractive status and the corneal refractive status, or "dual optic") through Virtual Eye and there is a visualization of said pattern. In some embodiments, ISIS may be a servomechanism.

The wafer may also stamp coordinates at the 12 and 6 o'clock meridians for orientation on the eye by a physician. The wafer may also stamp a unique and different coordinate at the 10/2/4/7 meridians for the treatment quadrant orientation for the physician. The wafer/contact lens may be produced by a corresponding 3D printer which is connected to the mother board of ISIS. Once completed, the lens may be sterilized prior to putting on the patient's eyes.

In some exemplary operations, initially, a laser that can be coupled with or contain an eye tracker in some embodiments may be calibrated or initiated and a lens is put in place by the physician. The wafer may act as both a mask and guide for the laser.

Still in FIG. 18, the lens design is called "semiscleral-contact" (SEQ). This lens has as its starting point, a bearing edge of the sclera at the corneal 2.0 mm part consists of three curves. The SEQ lens features 10 fenestrations, which prevents the lens getting stuck. Irregular corneal surfaces can be corrected using RGP contact lenses, corneal lenses ranging in diameter from 8.0 mm to 12.0 mm. Sclera lenses may vary in diameter from 22.0 mm to 25.0 mm.

To build up the lens and final fitting, formulas may be used for the calculation and production of the lens. To narrow the whole range, it may begin with a sagitta fitting set of 2.70 mm extending to 4.10 mm. Differences in the fitting set are similar to a fitting set for RGP lenses with a different radius of 0.05 mm between a normal step.

The SEQ fitting set expires with sagittal 0.1 mm height difference. Despite the DK value of 90, and 10 times fenestration of SEQ lens, an oxygen supply problem may persist. Lenses adjusted in diameters larger than 12.0 mm have a lot of support that it is not moving and thus no tear exchange can occur.

In some exemplary operations, 1) as the laser contains an eye tracker, the lens is put in place by a physician. The wafer acts as both a mask and guide for the laser. 2) This wafer guided system is unique to the laser; the pattern is placed on the eye and through the lens itself which is perforated during the process creating a map receipt of the procedure and registering all spots by the scanner before and after the treatment. 3) ISIS retains this information for this specific patient's eye, 4) In the event that a retreatment is needed. All information (topo, etc.) is imported back into the patient's profile for ISIS to recalculate and reconfigure 'around' the existing spots for further maximization. 5) ISIS calculates COP before and predictable COP after applying the simulation which can inform the patient and surgeon of the amount of COP possible for any particular patient with and without additional LVC. 6) ISIS also demonstrates through use of the FEM virtual eye both the biomechanical functions, optical functions, as well as a vision simulation at all distances. 7) ISIS also demonstrates a post op COP, AA, Refractions, Zernike profile changes etc. and on the back end continues to capture all database information to come up with future more sophisticated and optimizing algorithms. 8) ISIS can also profile various algorithms to enhance the understand of the dual optic system and give changing scenarios based on change of scleral thickness and other biometry, geometry, optics etc. with age. The usefulness of this is infinite but a specific embodiment is that ISIS can generate an age-related treatment map from the patient's initial exam through cataract age. Therefore, ISIS can predict how many spots and what pattern should be used in advance so that the retreatment potential areas will be 'predetermined' by ISIS upon the first wafer. This means that on subsequent visits, ISIS can alert the physician when there is a critical loss of COP and retreatment can start at any time (this would be determined by the physician, patient and ISIS output). 9) ISIS may also have an audible interaction and can also alert the physician during treatment if there is a need for intervention, when it is complete and guide the physician at what exams should be evaluated for accuracy or for more attention. ISIS can make recommendations to the physician, but the physician is in control of the selection of programs ISIS will perform 10) ISIS also has a reference list and can search for papers, knowledge and recent trends as well. 11) ISIS may work like a voice assistant, e.g, Apple Siri.

Laser features for some embodiments may include a Er:YAG Ophthalmic Laser Lasing Medium, an Er:YAG laser with 2.94 µm wavelength; Pulse duration approximately 250 µsec; Rep rate may be 3, 10, 15, 20, 25, 30, 40, 50 pps.

Various net absorption curves of various tissue components can be important. At 2.94 µm, wavelength laser can be the closest wavelength in the near infrared spectrum to the peak absorption of H20 3.00 µm. This allows it to effectively evaporate H20 from the tissue (ablation mechanism) with little thermal effect. Laser Tissue Interaction @ 2.94 µm: 2.94 µm may be a great wavelength for tissue ablation; 10-20× better absorbed by water than $CO_2$ at 10.6 µm; 3× better absorbed by water than Er:YSGG at 2.79 µm; Ablation threshold for water at 2.94 µm about 1 J/cm$^2$. The ablation occurs instantly and may be a surface effect only. This provides very precise ablation with little collateral tissue damage.

Applications for Er:YAG ophthalmic systems can include a broad 510K for excision, incision, evaporation of ocular soft tissue therefore expansion of use is inevitable after it is adopted including in: Ptyerigium surgery; glaucoma surgery; ocular nerve head entrapment (posterior sclera); intra ocular capsulotomy; extra ocular soft tissue surgery; AMD; and others.

Methods and apparatuses for treatment of sclera and neighboring ocular structures and fractional microporation and resurfacing are also contemplated.

As described herein, a system and method for performing fractional resurfacing of a target area of an eye, e.g., the sclera, using electromagnetic radiation are provided. An electromagnetic radiation is generated by an electromagnetic radiation source. The electromagnetic radiation is caused to be applied to a particular portion of a target area of eye preferably the sclera. The electromagnetic radiation can be impeded from affecting another portion of the target area of the eye by a mask or scleral lens. Alternatively, the electromagnetic radiation may be applied to portions of the target area of the sclera other than the particular portion.

Additionally described herein is a method for modifying tissue with a quasi-continuous laser beam to change the optical properties of the eye comprises controllably setting the volumetric power density of the beam and selecting a desired wavelength for the beam. Tissue modification may be accomplished by focusing the beam at a preselected start point in the tissue and moving the beam's focal point in a predetermined manner relative to the start point throughout a specified volume of the tissue or along a specified path in the tissue. Depending on the selected volumetric power density, the tissue on which the focal point is incident can be modified either by photoablation or by a change in the tissue's visco-elastic properties.

Ophthalmic Laser System

In various embodiments, an ophthalmic laser system of the present disclosure may include a laser beam delivery system and an eye tracker responsive to movement of the eye operable with the laser beam delivery system for ablating scleral material of the eye both anterior and/or posterior through placement of laser beam shot on a selected area of the sclera of the eye. The shots are fired in a sequence and pattern such that no laser shots are fired at consecutive locations and no consecutive shots overlap. The pattern is moved in response to the movement of the eye. Since the sclera of the eye is 'off axis' the scanning mechanism is novel in that it does not operate by fixation of the beam over the visual axis of the eye. Referring to FIG. 20 and FIGS. 20A to 20D, rather the 'off axis' scanning mechanism may require an eye docking system 2000 utilizing goniometric mirror or guidance system to ablate opposing quadrants of the sclera outside the visual axis. A closed loop feedback system is in place internally to the scanner and also between the eye docking system in and the scanner in the form of a magnetic sensor mechanism which both locks the laser head to the eye docking system and by virtue of biofeedback positioning of the eye to trigger both eye tracking and beam delivery.

In some embodiments, the laser apparatus for rejuvenating a surface may include means to select and control the shape and size of the area irradiated by each pulse of laser energy without varying the energy density of the beam. By varying the size of the irradiated area between pulses, some regions of the surface may be eroded more than others and so the surface may be reprofiled. The method and apparatus are suitable, inter alia, for removing corneal ulcers and reprofiling the cornea to remove refractive errors and also for reprofiling optical elements. In one embodiment, the beam from the laser enters an optical system housed in an articulated arm and terminating in an eyepiece having a suction cup for attachment to an eye. The optical system may include a beam forming arrangement to correct an asymmetric beam cross-section, a first relay telescope, a beam dimensional control system and a second relay telescope. The beam dimension control system may have a stop with a shaped window or a shaped stop portion and movable axially along a converging or diverging beam portion. An alternative beam dimension control system has a stop with a shaped window and positioned between coupled zoom systems. Mirrors, adjustable slits and refractive systems may also be used. The laser can preferably be an Er:YAG laser in some embodiments. The apparatus may include a measurement device to measure the surface profile, and a feedback control system to control the laser operation in accordance with the measured and desired profiles.

In some embodiments, the method, apparatus, and system for template-controlled precision laser interventions described herein improves the accuracy speed range, reliability, versatility, safety, and efficacy of interventions such as laser microsurgery, particularly ophthalmic surgery including ability to perform such laser surgery outside of the visual axis. Turning back to FIG. 19, FIG. 19 illustrates an exemplary diagram of instrument and system 1900 which are applicable to those specialties wherein the positioning accuracy of the laser treatment is critical, wherever accurate containment of the spatial extent of the laser treatment is desirable, and/or whenever precise operations on a target or series of targets subject to the movement during the procedure are to be affected. The system 1900 thus may include the following key components: 1) a user interface, consisting of a video display, microprocessor and controls, gui interface, 2) an imaging system, which may include a surgical video microscope with zoom capability, 3) an automated 3D target acquisition and tracking system that can follow the movements of the subject issue, for example and eye, during the operation, thus allowing the surgeon user to predetermine his firing pattern based on an image which is automatically stabilized over time, 4) a laser, with which can be focused so that only the precise treatments described by the user interface are affected, 5) a diagnostic system incorporating a mapping and topography, numerical data, mathematical data, geometrical data, imaging data, by means for measuring precise surface and 3D shapes prior to, during and subsequent to a procedure, said measurements to be executed online within time scales not limited to human response times, and can be real time, and 6) fast reliable safety means, whereby the laser firing is interrupted automatically, should any conditions arise to warrant such interruption of the procedure for example a safety concern.

Figures 2, 2K, 3, 4, 5, 6, 7, 8, 9, 10, 11, 12, 13, 14, 15, 16, 17, 18, 19, 20:
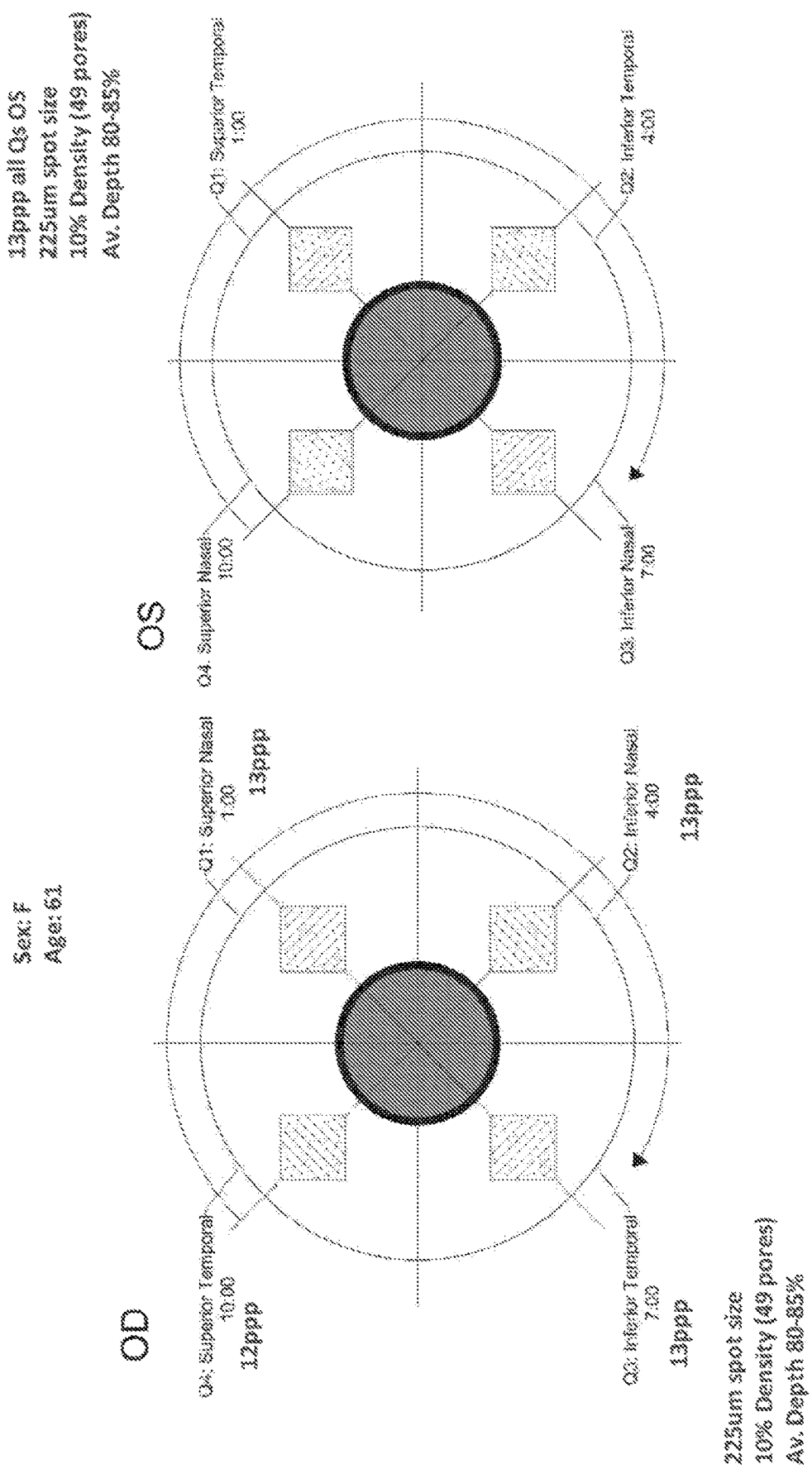

FIGS. 20(E-H) illustrate further the off-axis features of the laser system. In some embodiments, the system may provide 360-degree scanning. In some embodiments, the laser delivery may be nominally positioned perpendicular to the surface of the eye for treatment. The rotational symmetry axis is the eye fixation point. Treatment areas for the laser preferably are not hidden by eye lids and other features of the patient. Eye fixation axis and the laser beam axis have a fixed angle to expose pores in defined zones. The laser beam delivery can be rotated around the eye, β. In some embodiments, key elements may include: laser beam and scan (e.g., OCT) area are on same centerline, and scan area and focal length is matched to laser spot size and focal length. Camera is located just off laser centerline. Zoom ability is provided to see entire eye or see bottom of pore. Image provides features for eye tracking system to lock on, off axis. Color image can be provided in order to sense depth by tissue coloration. Eye fixation point is fixed angular relationship to the laser delivery beam 180° from the laser delivery beam around β. FIGS. 20G to 20I illustrate different exemplary types of off axis scanning.

Referring to FIG. 20I, another exemplary off-axis scanning, according to some embodiments of the present disclosure, is illustrated. As shown, the treatment may be angular.

In some embodiments, the system for use in ophthalmic diagnosis and analysis and for support of ophthalmic surgery may include 3D-7D mapping means for sensing locations, shapes and features on and in a patient's eye in three dimensions, and for generating data and signals representing such locations, shapes and features, display means receiving signals from the 3D-7D mapping means, for presenting to a user images representative of said locations, shapes and features of the eye, at targeted locations including display control means for enabling a user to select the target location and to display a cross section of portions of the eye in real time both during ablation and after each laser pulse, position analysis means associated with and receiving signals from the three dimensional mapping means, for recognizing the occurrence of changes of position of features of the eye, target tracking means associated with the position analysis means, for searching for a feature of target tissue and finding said features new position after such a change of position, and for generating a signal indicative of the new position, and tracking positioning means for receiving said signal from the target tracking means and for executing a change in the aim of the three dimensional mapping means to the new position of said feature of the target tissue, to thereby follow the feature and stabilize the images on the display means.

The display means can be a video display, and further including surgical microscope or digital monitor or smart device means directed at the patient's eye, for taking video microscopic images real time of target areas of the ocular tissue and for feeding video image information to the video display means to cause such video microscopic images to be displayed, assisting the user in diagnosis and analysis enabling display of different cross sections of the patient's tissue as selected by the user in real time.

The tracking positioning means may include a turning mirror under automatic control, robotic control, blue tooth control and the system may include an objective lens assembly associated with the mapping means and having a final focusing lens, with the turning mirror positioned within the objective lens assembly and movable with respect to the final focusing lens is an embodiment.

In some embodiments, the system may include a laser pulsed source for producing an infrared to near infrared light laser beam having a power capable of effecting a desired type of surgery in an eye, laser firing control means for enabling a surgeon/user to control the aim, depth, and timing of the firing of the laser to effect the desired surgery, 3D-7D mapping means directed at a patient's eye, for obtaining data representing the location and shapes of features on and inside the eye, microprocessor means for receiving data from the three dimensional mapping means and for converting the data to a format presentable on a screen and useful to the surgeon/user in precisely locating features of the eye and the aim and depth of the laser beam within those features, and display means for displaying microprocessor-generated images representing the topography of the eye and the aim and depth of the laser beam before the next pulse of the laser is fired to the surgeon/user in preparation for and during surgery, with display control means for enabling the surgeon/user to select areas of the eye for display, including images of cross sections of portions of the eye.

The infrared or near infrared pulsed, free running, or continuous or Q-Switched light laser power source may generate a laser beam capable of effecting the desired laser surgery in the patient's tissue, including within transparent tissue of the patient. The system may include an optical path means for receiving the laser beam and redirecting the laser beam and focusing it as appropriate toward a desired target in the tissue to be operated upon, The system may include a laser housing positioned to intercept and direct the optical path means, for taking images of said target along the optical path means and for feeding video image information to the video display means, and tracking for tracking movements of the subject tissue at which the system is targeted without damaging the subject tissue before the next pulse of the laser is fired and shifting the optical path accordingly before the next pulse of the laser is fired, such that information and images generated by the three dimensional mapping means and by the surgical microscope means, as well as the aiming and position of the laser beam, following changes in position of the tissue. Each image frame taken, and information is sent to the video display after each firing inside the 3D-7D micropore before and after the firing of the laser in dynamic real time and surface view. GUI may include integrated multiview system in 7 directionalities for image capture including: surface, internal pore, external pore, bottom of the micropore, whole globe eye view, target array area.

In some embodiments, 7 cube may be the preferred projection for the microprocessor: but other examples exist in dimensional sphere shape, space, and may be integrated into the GUI and microprocessor. Orthogonal projections can include examples shown in FIG. 8 above.

The system may include multi-dimensional scaling, linear discriminant analysis and linear dimensionality reduction processing as well as locally linear embedding and isometric maps (ISOMAP). Nonlinear dimensionality reduction methods may also be included.

In some embodiments, the system can allow for a 1D, 2D, 3D, or 4D, and up to 7D conversion of the topological images or fibrations. The fibration is a generalization of the notion of a fiber bundle. A fiber bundle makes precise the idea of one topological space, called a fiber, being "parameterized" by another topological space, called a base. A fibration is like a fiber bundle, except that the fibers need not be the same space, nor homeomorphic; rather, they are just homotopy equivalent. Where the fibrationsis equivalent to the technical properties of the topological space in 3, 4, 5, 6, and 7 dimensional sphere spaces a continuous mapping p: E→B satisfying the homotopy lifting property with respect to any space. Fiber bundles (over paracompact bases) constitute important examples. In homotopy theory, any mapping is 'as good as' a fibration—i.e. any map can be decomposed as a homotopy equivalence into a "mapping path space" followed by a fibration into homotopy fibers.

A laser workstation may be equipped with three programmable axes (X, Y, Z; can be expanded to 5 axes) has an automatic rotary table machine, programmable X, Y, Z-axis and a 2-station rotary table. It can include a Human Machine Interface (HMI) with Security user access level, diagnostic and data logging for validated processes and user friendly operation, as well as a sorter module adaptable for unique pulse modulation, where: hole diameter: 0.1 μm-1000 μm; drill depth max. 0.1 μm-2000 μm; Hole tolerances: >±1-20 μm Operational features can also include networked computer connection, iPad operations, joy stick operations, touch screen operations, iPhone operations, remote or Bluetooth operations, digital camera integrated operations, video integrated operations, and others.

System and Methods for Laser Assisted Ocular Drug Delivery

FIG. 20J illustrates the aqueous flow within the eye. Aqueous outflow can be regulated by active contraction of the ciliary muscle and trabecular cells. Contraction of the ciliary muscle expands the trabecular meshwork and increases outflow and decreases IOP. Contraction of trabecular cells decreases outflow and increases IOP. In some embodiments, the described systems would cause improvement in ciliary muscle dynamics would improve hydrodynamics of aqueous drainage.

The uveoscleral pathway is an alternative pathway for aqueous drainage that may account for 10-30% of all aqueous outflow. For the uveoscleral pathway, aqueous enters the ciliary body and passes between ciliary muscle fibres into supra-ciliary and suprachoroidal spaces. FIGS. 20K and 20L illustrate how in some embodiments the described systems would increase uveal outflow.

The sclera is 10 times more permeable than the cornea and half as permeable as the conjunctiva. Hence permeants can diffuse and enter the posterior segment via the transcleral route. With traditional drug delivery (such as eye drops), approximately 90% of drug is lost due to nasal lacrimal drainage, tear dilution and tear turnover leading to poor ocular bioavailability, and less than 5% of the topical drug ever reaches the aqueous humor.

In some embodiments, the described systems, methods and devices of the present disclosure may be used for laser assisted ocular drug delivery, such as methods and apparatuses for phototherapeutically treating, e.g. by ablating, coagulating, and/or phototherapeutically modulating a target tissue, e.g., scleral tissue and other intraocular tissues such as choroid, subchoroidal space, neuroretina, or others. There is disclosed a method for creating an initial permeation surface (A) in a biological membrane (1) comprising: a) creating a plurality of individual micropores ($2i$) in the biological membrane (1), each individual micropore ($2i$) having an individual permeation surface (Ai); and b) creating such a number of individual micropores ($2i$) and of such shapes, that the initial permeation surface (A), which is the sum of the individual permeation surfaces (Ai) of all individual micropores ($2i$), having a desired value. A microporator performing the method is also disclosed. Biological surface may be an eye in this case. In the case of the eye: irradiating the area of the sclera such that the therapeutic agent passes through the open area created by the laser radiation and is thereby delivered to intraocular target tissues in the anterior or posterior globe such as the choroid, neuroretina, retinal epithelium, uvea, vitreous, or aqueous.

In some embodiments, the described systems, methods and devices of the present disclosure may be used for laser assisted ocular drug delivery, such as methods and apparatuses for a smart activated polymer carrier, which could be light activated, light modified poly(acrylamide)s, or could be used to finely manipulate the pore size of nano/microporous materials and demonstrate its application for reversible color tuning of porous polymer photonic crystals based on humidity condensation.

Additionally, in some embodiments, the systems described herein can include one or more of: an eye docking station, a scleral mask/nozzle guard, nozzle, novel 360$dg$ jointed articulated arm, novel off axis scanning, drug delivery system, depth control, accessories, Fibonacci algorithms, and others. Some options may include hand held wands, fiberoptic hand pieces, scanning automated laser applicator, workstation, remote control over wireless communication, e.g., Bluetooth or others, hand held tonometer for preoperative and post-operative ocular pressure measurements, and others.

FIG. 20M illustrates an exemplary hand piece delivery system vs. articulated arm.

For delivery purposes, the eye can be considered as consisting of two segments. The anterior segment comprises the cornea, conjunctiva, sclera and anterior uvea while the posterior segment includes the retina, vitreous and choroid. There may be three main routes for delivery of drugs to the eye: topical, systemic, and intra-ocular injection. Controlled delivery systems, such as ocular inserts, minitablets and disposable lenses, can be applied to the exterior surface of the eye for treatment of conditions affecting the anterior segment of the eye. Extended residence times following topical application have the potential to improve bioavailability of the administered drug and additionally a range of strategies has been tested to improve penetration including cyclodextrins, liposomes and nanoparticles. Drug delivery strategies for treatment of diseases of the posterior segment of the eye will be discussed herein. The development of therapeutic agents that require repeated, long-term administration is a driver for the development of sustained-release drug delivery systems to result in less frequent dosing and less invasive techniques.

Drug delivery to the eye is often for two main purposes. First, to treat the exterior of the eye for periocular conditions such as conjunctivitis, blepharitis and dry eye and secondly to treat intraocular disorders such as glaucoma, diabetic retinopathy, uveitis and age-related macular degeneration (AMD), retinal pathologies, and biomechanical compression, restriction, or interference with normal physiological functions of vessels, nerves, or connective tissues under the surface of the eye tissue. Under normal conditions drugs that are administered to the eye as aqueous eye drop solutions will rapidly be diluted and washed from the eye surface by the constant flow of tear fluid. Drug dilution on the eye surface also reduces drug flow from the surface into the eye. Consequently, eye drops must be administered frequently and at high concentrations in order to achieve therapeutic levels. The successful delivery of lipophilic drugs in aqueous eye drop suspensions has led to the development of delivery systems intended to increase the residence times of drug on the surface of the eye. By maintaining high levels of drug within the tear fluid for extended times it may be possible to increase uptake into the eye. This can also be combined with strategies to improve ocular penetration. Beyond the use of conventional systems such as solutions, suspensions, creams and gels, developments have been made using devices such as inserts and viscoelastic solutions.

In some embodiments, the described systems, methods and devices of the present disclosure may be used for posterior ocular drug delivery in the posterior sclera including but not limited to the peripapillary sclera and lamina cribrosa. Currently, treatment of diseases in the posterior globe is hampered by poor efficacy of topical drugs and that there is no minimally invasive way to reach or to treat the posterior globe.

FIGS. 20N and 20O illustrate in some embodiments the treatment zones in the anterior and posterior globe, according to some embodiments of the present disclosure.

In some embodiments, the described systems, methods and devices of the present disclosure may be used for, but not limited to, the delivery of drugs, nutraceuticals, grape seed extract, stem cells, plasma rich proteins, light activated smart polymer carriers, and matrix metalloproteinases. FIGS. 20P-1 to 20P-3 illustrate, in some embodiments, the exemplary targets for choroid plexus drug and nutraceutical delivery.

It is often difficult to attain and retain effective drug concentrations at the site of action. Only about 5% of the applied dose from eye drops penetrates the cornea to reach the ocular tissues and residence times are around 2-5 minutes. Attempts to improve ocular bioavailability include extending drug residence time in the conjunctival sac and improving drug penetration across the cornea, the major pathway of drug entry into the internal eye. Delivery systems for topical administration include suspensions, gels, erodible and non-erodible inserts and rods.

Increasing the viscosity of topical formulations can improve retention in the eye and combinations of viscosity-modifying agents may prove synergistic. Such formulations are particularly useful as artificial tears and ocular lubricants but may also be utilized for the topical delivery of drugs to the eye. Polyvinyl alcohol (PVA) and celluloses such as hydroxypropyl and methylcellulose are often used as viscosity modifiers as they have a wide range of molecular weights and demonstrate compatibility with many of the topically applied active agents. Specific combinations of polymers can be selected to obtain specific viscosity or gelling characteristics. In situ gelling systems undergo a transition from a liquid phase to a solid phase forming a viscoelastic gel in response to a trigger such as change in pH, temperature of the presence of ions. Poloxamers, block copolymers of poly(oxyethylene) and poly(oxypropylene) form thermoreversible gels in the 25-35° C. range and are generally well tolerated. Cellulose acetate phthalate (CAP) undergoes a phase transition triggered by change in pH. Such systems however require high polymer concentrations, which can result in discomfort to the user. Gellan gum is an anionic polysaccharide which forms a clear gel in the presence of mono or divalent cations. Once it is gelled the first controlled release ophthalmic delivery device was launched in the mid-1970s. It comprises the active pilocarpine and alginic acid contained within a reservoir enclosed by two release-controlling membranes made of ethylene-vinyl acetate copolymer and enclosed by a white retaining. Like liposomes, polymeric microparticulate delivery systems such as microspheres and nanospheres have been investigated for topical delivery to the eye. Particles in the micrometer size range are termed microspheres whereas nanoparticles are sub-micron in diameter. FIGS. 20Q-1 to 20Q-3 illustrate how in some embodiments the described systems could of the present disclosure may be used for transcleral drug delivery and to improve drug intracellular release and penetration. They can be manufactured using a number of techniques including milling and homogenization, spray-drying, supercritical fluid technology and emulsion solvent evaporation. Incorporation of microparticles into viscous drops and gels would facilitate easier administration than aqueous suspension formulations. Microporation method may enable active drug to penetrate the sclera and reach the targeted underlying tissue. The delivery system may use synergistic mechanism to enhance penetration. Thermodynamic stable properties may allow solubilization of drug and then promote release of drug. Methods may include intraocular drug delivery via scleral vessels and aqueous. A smart activated polymer carrier may be incorporated, and may be light activated, light modified poly(acrylamide)s, or may be used to finely manipulate the pore size of nano/microporous materials and demonstrate its application for reversible color tuning of porous polymer photonic crystals based on humidity condensation.

As a result, although topical ocular and subconjunctival sites are therefore used for anterior targets, intravitreal administration is desirable for posterior targets. Local administration of the drug will decrease the likelihood of side effects, particularly with potent molecules with severe side effects such as immune-suppressants. Alone, or in combination, these can be useful for alleviating conditions associated with dry eye. Effective blood retinal barriers prevent most systemically administered drugs from achieving therapeutic levels in the vitreoretinal space and side effects experienced following systemic administration of such potent molecules limit the usefulness of the route Sustained release may prolong the duration of effective concentration at the site of action as demonstrated by the current delivery systems. Controlled release formulations proposed for sustained intravitreal delivery include liposomal formulations, biodegradable microspheres, biodegradable and non-biodegradable implants. Entrapping the drug in a nanoparticle prior to incorporation into a contact lens is a strategy that can be used to sustain the release. Providing the nanoparticle size and loading are low, then the lens should remain transparent. Particulate polymeric delivery can include microspheres or nanospheres that can be manufactured in a number of ways including spray-drying, emulsification and solvent evaporation and precipitation Microspheres may be useful for delivery to the anterior segment, to adhere to the surface of the eye and prolong release but they are also useful as sustained release injectable formulations. FIG. 20R illustrates an exemplary optha-coil, which may include a drug-loaded hydrogel embedded on a coiled wire designed to be placed in the conjunctival fornix. Following injection of nanoparticles into the vitreous, optional targeting of drug-loaded sustained release microspheres within the eye has also been explored by modifying surface of particles to alter their distribution within the eye. FIG. 20S illustrates, according to some embodiments, exemplary drug delivery carriers. FIGS. 20T-1 to 20T-3 illustrate, according to some embodiments of the present disclosure, a scleral wafer.

In some embodiments, the drug delivery system may include a drug and a lens, disposed on an eye, having a back surface comprising: a central portion (corneal) and a scleral portion having an outer rim and an inner rim and a treatment portion consisting of an outer rim, an inner room and an interlocking carrier depot which has a plurality of tissue array sizes, shapes and variations. Corneal portion may be made of silicium carbide to protect the cornea and or can be metallic. In some embodiments, silicium carbide may be preferred. It may also be opaque. The lens may be a scleral lens covering at least 18 mm in diameter. In some embodiments, the scleral portion of the lens may contact only the sclera. The treatment portion of the lens may, in some embodiments, contact only the sclera and the periphery of the cornea including the corneoscleral envelope and limbus.

In some embodiments, the haptic portion of the scleral lens may further define a channel that extends radially at least part of the distance between the outer rim and the inner rim. The drug may be selected from the group consisting of an antibiotic, an antiviral, an antifungal, an antiparasitic, a corticosteroid, a non-steroidal anti-inflammatory, a mydriatic, cycloplegic, a biologic, a drug that modifies neovascularization, a drug that increases aqueous outflow, a drug that reduces aqueous secretion, an antihistamine, a secretagogue, a mast cell stabilizer, a tear supplement, an anti-metabolite, and an immunomodulatory, VEGF, and other posterior drugs such as timoline, etc.

In some embodiments, the treated disease may include bacterial infection, viral infection, fungal infection, parasitic infection, inflammation, neovascularization, ocular surface disease, glaucoma, allergy, dry eye, dysplasia, neoplasm, and AMD.

In some embodiments, the treatment portion of the lens may be made of mesoporous silica. Photoactivated moving parts based on the photoisomerization of azobenzene derivatives have been used in conjunction with mesoporous silica. The back and forth wagging motion has been demonstrated to act as a molecular impeller that regulates the release of molecules from the pores of silica nanoparticles under "remote control" upon photoexcitation. Azobenzene-driven release, unlike that regulated by many other nanomachines, can occur in aqueous environments. Using light-activated mesostructured silica (LAMS) nanoparticles, luminescent dyes and ocular drugs are only released inside of the target tissue array (e.g. sclera) that are illuminated at the specific wavelengths that activate the impellers. The quantity of molecules released is governed by the light intensity and the irradiation time. The irradiated target tissue array is exposed to suspensions of the particles and the particles are taken up by the cells. Cells containing the particles loaded with a particular drug are released from the particles inside of the cells only when the impellers are photoexcited by a particular wavelength. The ocular drug of choice which is loaded into and released from the particles inside the cells under light excitation, and apoptosis is induced. Intracellular release of molecules may be sensitively controlled by the light intensity, irradiation time, and wavelength, and the anticancer drug delivery inside of cells is regulated under external control.

The drug delivery system may be used within the preoperative/perioperative/postoperative state for any drug delivery needed for a plurality of eye surgeries for use prophylactically or post operatively.

In some embodiments, the transcleral delivery system for treating an eye of a patient may include an apparatus for facilitating transcleral delivery of a drug through an area of the apparatus and may include an ablator that is configured to generate a microporation in the area of the sclera of the eye of the patient, and may include a drug, wherein the drug effects at least one of the biological regulation of the target tissue. The drug may be administered transclerally or intrasclerally to a site of laser poration having a predetermined permeation surface over time, wherein the predetermined permeation surface over time is effective to achieve a predetermined deposit concentration of the at least one drug to thereby treat the eye disease, further wherein the site of laser poration comprises a plurality of pores having different geometries. The drug may be transclerally or intrasclerally administered at a first location, and a plurality of drugs may be transclerally or intrasclerally administered at a different location. The drug may also be administered into the suprachoroidal space. The drug may be delivered either after or during the irradiation of the target tissue array.

Turning back to FIGS. 20, 20A-20B, the system of the disclosure may include an eye docking station 2000. The eye docking station 2000 may be positioned above the eye 2010 during a medical operation. FIG. 20C illustrates an exemplary top view of the eye docking station 2000. The eye docking station 2000 may provide a view of the four quadrants. FIG. 20D illustrates an exemplary scleral fixation component 2020 attachable to the eye docking station 2000.

In some embodiments, the laser docking station may include the female end to the laser housing unit can be accomplished using magnetic sensors between the female and male parts which are in a closed feedback loop with the laser head. These sensors will detect the spectral reflection of the tissue which is differently absorbed by Er:YAG by the nature of the Er:YAG wavelength.

Turning to FIGS. 21A-21B, embodiments of a nozzle guard 2100 and 2110 are illustrated. FIG. 22 illustrates, in some exemplary operations, the nozzle guard 2110 being attached to a nozzle 2200. FIG. 23 illustrates the nozzle 2200 being fitted with disposable insert and filter 2310.

FIG. 24 illustrates and exemplary workstation 2400 of the laser microporation system of the present disclosure, and hand piece and related apparatus 2420 for laser surgery of the eye. The workstation 2400 can include the method, apparatus and system for template-controlled precision laser interventions as described above. As described above, the method, apparatus and system may improve the accuracy, speed range, reliability, versatility, safety, and efficacy of interventions such as laser microsurgery, particularly ophthalmic surgery including ability to perform such laser surgery outside of the visual axis.

The workstation 2400 may can include GUI interface which is touch screen or remotely controlled. The graphical user interface (GUI), is a type of user interface that allows users to interact with electronic devices through graphical icons and visual indicators such as secondary notation, instead of text-based user interfaces, typed command labels or text navigation.

The workstation 2400 may include an articulating arm 2410; a laser housing unit 2500 (FIGS. 25A-25B) which may include: a CCD video camera; Galvos Scanner capable of off axis scanning; aiming beam; and others.

FIGS. 25A-25B illustrate an exemplary embodiment of the housing unit 2500 which is rotatable 360 degrees.

The workstation may include three-dimensional mapping means, at least one communicatively coupled microprocessor, power supply, and the display means include means for presenting images to the surgeon/user indicating precise current location of laser aim and depth in computer generated views which comprise generally a plan view and selected cross sectional views of the eye representing features of the eye at different depths.

The workstation may also include an optical path with a focusing lens capable of controlling the focus of the laser beam on the eye tissue, and thus the depth at which the laser beam is effective, within about 5 microns, with depth control means for the surgeon to vary the focus of said lens to control the depth at which the laser beam is effective.

The workstation may further include system program means enabling the surgeon/user to pre-program a pattern of lesions in the ocular tissue along three axes in three dimensions and to activate the laser to follow the preselected pre-programmed path of surgery automatically.

The workstation user interface can include equipment for presenting information to a surgeon/user and for enabling control of the surgical procedure by the surgeon/user, including video display means for presenting precise information, patterns and meridians of arrays to the surgeon/user relating to the location in a patient's tissue at which the system is targeted, and the three-7-dimensional topography and contours of features of the subject tissue including imaging of cross sections of tissues, scanning surfaces and areas and real time dynamic control of the firing of the surgical laser beam by the user.

The workstation may contain or include an imaging system connected to the video display means, including three-dimensional to seven-dimensional mapping means for generating, reading, and interpreting data to obtain information regarding the location in seven dimensions of significant features of the tissue to be operated upon, and including microprocessor means for interpreting the data and presenting the data to the video display means in a format useful to the surgeon/user. This also includes an anatomy locator and eraser technology which has a chromophoric sensor to sense change in color, dimension, water content, shape, spectral properties, optical properties and has a reverse scanning biofeedback feature which can outline precise 3D-7D imagery of blood vessels, veins, and any other untargeted anatomy. It is able to signal the laser to avoid this untargeted anatomy. There is also an eraser feature that the user/surgeon can manually identify on the touch screen GUI interface to guide the laser to avoid erased areas/arrays/spots/regions.

The laser workstation can be equipped with three programmable axes (X, Y, Z; can be expanded to 5 axes) has an automatic rotary table machine, programmable X, Y, Z-axis and a 2-station rotary table Includes a Human Machine Interface (HMI) with Security user access level, diagnostic and data logging for validated processes and user-friendly operation. A sorter module with adaptable operational features: unique pulse modulation; hole diameter: −1 µm-800 µm; drill depth max. 0.1 µm-2000 µm; Hole tolerances: >±0.1 µm-20 µm.

Depth Control

In most tissues, disease progression is accompanied by changes in the mechanical properties. Laser speckle rheology (LSR) is a new technique we have developed to measure the mechanical properties of tissue. By illuminating the sample with coherent laser light and calculating the speckle intensity modulations from reflected laser speckle patterns, LSR calculates $\tau$, the decay time constant of intensity decorrelation which is closely associated with tissue mechanical properties. The use of LSR technology can be validated by measuring mechanical properties of tissue. LSR measurements of $\tau$ are performed on a variety of phantom and tissue samples and compared with the complex shear modulus $G^*$, measured using a rheometer. In all cases, strong correlation is observed between $\tau$ and $G^*$ ($r=0.95$, $p<0.002$). These results demonstrate the efficacy of LSR as a non-invasive and non-contact technology for mechanical evaluation of biological samples.

It is known that disease progression in major killers such as cancer and atherosclerosis, and several other debilitating disorders including neurodegenerative disease and osteoarthritis, is accompanied by changes in tissue mechanical properties. Most available evidence on the significance of biomechanical properties in evaluation of disease can be obtained using conventional mechanical testing, ex vivo, which involves straining, stretching, or manipulating the sample. To address the need for mechanical characterization in situ, a new optical tool can include an LSR.

When a turbid sample, such as tissue, is illuminated by a coherent laser beam, rays interact with tissue particles and travel along paths of different lengths due to multiple scatterings. Self-interference of the returning light creates a pattern of dark and bright spots, known as laser speckle. Due to thermal Brownian motion of scattering particles, light paths can constantly change, and speckle pattern fluctuates with time scales corresponding to the mechanical properties of the medium surrounding the scattering centers.

Open biofeedback loops can be used in various embodiments during intraoperative procedures using chromophore and other biofeedback processes. In chromophore embodiments, saturation of color can be measured with sensitivity to micron levels of accuracy to determine correct and incorrect tissues for surgical procedures. Pulse decisions can be made based on various preset color saturation levels. This is in contrast to current systems that may use color or other metrics only for feedback to imaging equipment and not to actual laser application devices that are applying treatments.

Similarly, subsurface anatomy avoidance for predictive depth calibration can use tools to determine depth calculation in real-time to determine how close extraction or other treatment procedures are to completion, while also maintaining active monitoring for undesirable and unforeseen anatomical structures. As such, hydro- or other feature monitoring is different from older systems that may monitor surface levels for reflection but are unable to effectively measure depth in a tissue or other biological substance.

LSR exploits this concept and analyses the intensity decorrelation of backscattered rays to produce an estimate of tissue biomechanics. To this end, LSR calculates the intensity decorrelation function of speckle series, $g_2(t)$, and extracts its decay time constant, $\tau$, as a measure of biomechanical properties.

Laser Speckle Rheology Bench

In some exemplary operations, bulk mechanical properties of tissue and substrates are measured using a bench-top LSR set-up. This set-up includes a laser of a plurality of coherence laser lengths followed by a linear polarizer and a beam expander. A focal length lens and a plane mirror are used to focus the illumination spot at the target tissue site. Laser speckle patterns are imaged using a high-speed CMOS camera. The image series are processed and the correlation between each two frames is calculated to determine the intensity decorrelation function, $g_2(t)$. Temporal and spatial averaging is applied over the image series pixels to reduce statistical errors. A single exponential is fitted to the resulting $g_2(t)$ curve to extract the time constant, $\tau$.

The sclera is a viscoelastic tissue and its complex shear modulus can be adjusted accurately by reshaping with a laser or selective fibril and/or microfibril ablation thereby modifying viscoelastic modulus and reducing biomechanical stiffness. Measurement of mechanical properties through biofeedback loop during the course of the laser procedure enables evaluation of LSR sensitivity to small gradual changes in mechanical properties and therefore tittering of the desired effect. Moreover, an aspect of some embodiments of the present disclosure is the simulation through FEM (VESA) of changes in viscoelastic modulus through artificial intelligence algorithm predictions of desired patterns of reshaping and/or fibril/microfibril selective ablations.

The scleral transparency or changes in opacity/transparency can create scattering features. The final volume fraction is measured to sufficiently identify strong back-scattered signal. LSR measurements are obtained followed by a conventional mechanical frequency sweep for a specified duration time. A final time point measurement is performed on treated sclera using both LSR and AR-G2 instrument.

As used herein, chromophore relates to water absorption spectrum to quantify tissue chromophore concentration changes in near-infrared spectroscopy.

Systems and methods herein can be used for measuring the differential path length of photons in a scattering medium utilizing the spectral absorption features of water. Determination of this differential path length is a prerequisite for quantifying chromophore concentration changes measured by near-infrared spectroscopy (NIRS). The quantification of tissue chromophore concentration measurements is used to quantify depth of ablation rates yielded by water absorption and time-resolved measurements through various layers of scleral tissue as it relates to ablation rate of absorption, pulse width and energy of the laser beam.

The number of pulses can be detected by the laser as well as a video camera, e.g., a CDD camera, which can detect reflect light which is reflected differently through different colors.

In some embodiments, water can also be used as a chromophore since the sclera is made 99% of water, therefore pulses per pore lasered in scleral tissue can be feedback to the laser system and can be utilized by how many pulses per pore and at which tissue level it is at since there is tissue hierarchy in the sclera.

In some embodiments, electrical vibrations can provide biofeedback. The quantification of tissue chromophore concentration measurements may be performed through the galvos or optics comparing the differential path estimates yielded by water absorption and time-resolved measurements, pulses per pore. The sensor is also able to deliver and quantify the dynamic changes in the absorption coefficient of water as a function of incident fluence at 2.94 µm.

Chromophore concentrations, absorption and scattering properties of human in vivo sclera absorption and reduced scattering coefficients of in-vivo human connective tissue such as the sclera of the eye can provide critical information on non-invasive connective tissue (sclera) diagnoses for surgical and clinical purposes. To date, very few, if any, in-vivo scleral optical properties have been reported. As stated previously, absorption and scattering properties of in-vivo skin in the wavelength range from 650 to 1000 nm using the diffusing probe in the "modified two-layer geometry." As disclosed herein, determination of the spectra of scleral optical properties may be done continuously in the range from 500 to 1000 nm. It was found that the concentration of chromophores, such as oxy-hemoglobin, deoxy-hemoglobin, and melanin, calculated based on the absorption spectra of eighteen subjects at wavelengths above and below 600 nm were distinct because of the inherent difference in the interrogation region. The scattering power, which is related to the average scatterer's size, demonstrates a clear contrast between scleral phenotypes, scleral sites, and wavelengths. The present disclosure may use the concentrations of oxy- and deoxy-hemoglobin assessed at wavelengths above and below 600 nm to distinguish between targeted tissue (sclera) and adjacent anatomy (arteries/veins). For example, the sclera is not vascularized and would demonstrate a deoxy-hemoglobin response while the adjacent blood vessel would demonstrate an osy-hemoglobin response. The diffuse reflectance techniques with the visible and near infrared light sources can be employed to investigate the hemodynamics and optical properties of upper dermis and lower dermis.

The absorption coefficient $\mu_a$, the scattering coefficient $\mu_s'$, and chromophore concentrations of sclera are fundamental properties of tissue that can provide essential information for many surgical, therapeutic, and diagnostic applications such as monitoring of skin blood oxygenation, melanin concentration, detection of hydration with fluorescence, laser surgery, and photodynamic therapy.

Photon diffusion theory derived from the radiative transport equation is usually employed as a forward model to determine optical properties of in-vivo samples at source-detector separation longer than five mean-free-paths, where mean-free-path is defined as $1/(\mu_a+\mu_s')$. This has been proven to be a not adequate model for source-detector separations longer than five mean-free-paths, because boundary conditions and the assumption of multiple scattering in a turbid medium cannot be satisfied. In order to limit interrogation to superficial tissue volumes, such as sclera, source-detector separations shorter than five meanfree-paths may be incorporated. In-vivo techniques can employ alternative forward models to determine optical properties of sclera. To determine optical properties of in-vivo sclera the present disclosure may use visible reflectance spectroscopy with a multi-layer scleral model and an optimization algorithm predetermined by use of video camera guidance, e.g., OCT, UBM or CCD video camera guidance integrated using artificial intelligence FEM. A multi-layer skin model and a number of fitting parameters, such as layer thickness, chromophores, and scattering properties for each layer, and their corresponding ranges must be chosen carefully in advance to avoid non-uniqueness in the solution space.

A system model may be employed to extract optical properties from diffuse reflectance spectra collected from sclera in-vivo. The technique may require that all of the chromophores contributing to the measured signals are known in advance and the reduced scattering coefficient has a linear relation to the wavelength in order to separate absorption and reduced scattering coefficients from measured reflectance. All constituent chromophores are then determined, and the absorption spectra is recovered. In addition, the reduced scattering coefficient produces a linear dependence on wavelength and the empirical mathematical model will recover tissue optical properties properly.

Further embodiments herein may include the use of a probe design which has been adjusted into multiple source-detector pairs so that it can employ a white light source to obtain continuous spectra of absorption and reduced scattering coefficients. The advantages of this multi-source-detector separation probe include relative low instrument cost and self-calibration in real time in vivo for instrument response (by using the reflectance of one source detection pair as the reference and normalizing the reflectance of other source detector separation pairs to the reference). The normalized reflectance versus source-detector separation is then fit to a diffusion model by a least square minimization algorithm to determine the absorption and reduced scattering spectra. The recovered absorption spectra are fit linearly with known chromophore absorption spectra to extract chromophore concentrations, and the reduced scattering spectra are fit to a scattering power law to obtain the scattering power. The probe is used to determine the skin optical properties sclera and also extract the chromophore concentrations and the scattering power of sclera It is found that performing the "two-region chromophore fitting" to the absorption spectrum would result in the best fit with minimal residuals. Two-region chromophore fitting, as used herein, may mean that the sclera absorption spectrum is fit to a set of known chromophore absorption spectra at wavelengths between, e.g., 500 nm and 600 nm, and again fit separately between, e.g., 600 nm and 1000 nm. The rationale for performing the two-region fitting is that the sclera has very different optical properties in the visible and the NIR wavelength regions, and thus the sampling volumes at these two regions are quite different. Likewise, the best fittings for reduced scattering coefficients of skin were obtained when the reduced scattering spectra were fit in the region below and above 600 nm separately. The scattering power is not only dependent to anatomical location but also on sclera layer. These systems and methods are capable of studying in-vivo superficial tissue at different depths simultaneously. Significantly different hemoglobin concentration at the targeted scleral tissue and untargeted adjacent anatomy is also disclosed in various embodiments.

In some embodiments, the system can include a diffusing probe used with multimodal fibers for both penetration and detectors. Reflectance can be measured through multiple layers, plurality of depths and capable of simultaneous depths. Diffuse reflectance spectroscopy as a tool to measure the absorption coefficient in sclera with integrated in-vivo imaging of tissue absorption scattering and hemoglobin concentration for means of injury prevention depth control and anatomy avoidance guidance for laser surgery and observation of in vivo micropore biometry and ongoing wound healing changes in tissue.

In a laser treatment, the optical properties (absorption and scattering coefficients) are important parameters. The melanin content of a tissue influences the absorption of light in the skin. A diffuse reflectance probe consisting of a ring of six light delivery fibers and a central collecting fiber system is proposed to measure the diffused reflected light from sclera. The absorption coefficient can be calculated from these measurements. The system of the present disclosure may be capable of real-time in-vivo technique to determine the absorption coefficient of desired target tissue in the sclera over multiple layers of the sclera at multiple depths. Three sources of signals that affect the intensity of diffusely reflected light derive from characteristic of connective tissue. (1) Light scattering changes, both fast (over 10 s of milliseconds) and slow (i.e., >~0.5 s), (2) early (~0.5-2.5 s) absorption changes from alterations in chromophore redox status, i.e., the oxy/deoxy-hemoglobin ratio (known as the "initial dip" period), and (3), slower (~2-10 s) absorption changes due to blood volume increase (correlated with the fMRI BOLD signal). Light scattering changes have been attributed to interstitial volume changes resulting from cellular hydration, water content, water movement, and capillary expansion.

Quantitative diffuse optical methods such as spatially-resolved reflectance, diffuse optical spectroscopy (DOS), and tomography (DOT), and diffuse correlation spectroscopy (DCS) possess exquisite sensitivity to functional and structural alterations in connective tissue. Some embodiments can utilize the near-infrared spectral region (600-1000 nm) to separate and quantify the multispectral absorption ($\mu_a$) and reduced scattering coefficients ($\mu_s'$), providing quantitative determination of several important biological chromophores such as deoxy-hemoglobin (HbR), oxy-hemoglobin ($HbO_2$), water ($H_2O$), and lipids. Concentrations of these chromophores represent the direct metrics of tissue function such as blood volume fraction, tissue oxygenation, and hydration. Additionally, the scattering coefficient can contain important structural information about the size and density of scatterers and can be used to assess tissue composition (extracellular matrix proteins, cell nuclei, mitochondria) as well as follow the process of tissue remodeling (wound healing, etc.). The system utilizes a limited number of optical wavelengths (e.g., 2-6) and a narrow temporal bandwidth, but forms higher resolution images of subsurface structures by sampling a large number of source-detector "views." To achieve maximal spatial resolution, the ideal DOT design may employ thousands of source-detector pairs and wavelengths. The system of the present disclosure may further employ a non-contact quantitative optical imaging technology, modulated imaging which is capable of both separating and spatially-resolving optical absorption and scattering parameters, allowing wide-field quantitative mapping of tissue optical properties. It may use spatially modulated illumination for imaging of tissue constituents. Periodic illumination patterns of various spatial frequencies are projected over a large area of a sample. The diffusely reflected image is modified from the illumination pattern due to the turbidity of the sample. Sine-wave illumination patterns may be used. The demodulation of these spatially modulated waves characterizes the modulation transfer function (MTF) of the material and embodies the sample optical property information. Color coding may be incorporated into the software to allow for color assignment and viewing of overlay on the displayed 3D converted image. Artificial intelligence recognition of color assigned anatomical distinctions may be incorporated, thereby allowing for real time identification of tissue variance between targeted tissue and adjacent anatomy and incorporation of color assigned 3D integrated conversion display of image sample. Anatomy avoidance technology primarily focused on blood vessels and sub surface tissue via use of optical properties of the tissues using reflective spectroscopy, biofeedback loop and a video camera.

Referring to FIG. 26-A, an exemplary multilayer imaging platform 2600 is illustrated, according to some embodiments of the present disclosure. The platform 2600 may include: HL—Halogen Lamp; MS—Mirror system DD—digital Driver; L2—projection lens; L3—camera lens; LCTF—liquid crystal tunable filter; and CCD VC—CCD Video Camera, or other suitable video camera. FIGS. 26-B and 26-C illustrate an exemplary CCD camera with nozzle. FIG. 26-D illustrates an exemplary camera view using the CCD camera. Other suitable cameras may be used. In some embodiments, the platform may include solid state laser wavelength Er:YAG 2.94 µm, free running system with scanning and long working distance platform, procedure performed in slit lamp sitting position, physician controlled/software dependent, procedure time several minutes both eye, etc.

In some embodiments, a method for quantitatively mapping tissue absorption and scattering properties is provided, and thereby allowing local sampling of in vivo concentrations of oxy- and deoxy-hemoglobin can be used for selective identification and distinguishing of target tissues and untargeted tissues for purposes of surgical planning and laser guidance for laser surgery of the sclera. Consistent dynamic changes in both scattering and absorption highlight the importance of optical property separation for quantitative assessment of tissue hemodynamics. The systems and methods of the present disclosure may integrate general platforms of spatially modulated structured illumination using speckle correlation and fluorescence. The systems and methods may then be used in an in vivo real-time intraoperative setting to provide feedback and guidance for surgeons. 3D conversion of the reconstructed image can be viewed simultaneously by CCD video camera in color code assignments to exploit anatomy avoidance software and targeted treatments which can be modified intraoperatively. The system may be used further postoperatively in order to view microporated tissue subsurface biometry, physiology, wound healing and morphology for further guidance and treatment implications.

Use of Fluorescence: The sclera has only 25% of the total GAG's that are present in the cornea. Because the GAG's attract water, the sclera is less hydrated than the cornea (but not 75% less; due to several structures that carefully maintain a lower hydration level in the cornea). The large variation in fibril size and the irregular spacing between scleral components leads to light scattering and opacity. The color of the sclera is white when healthy, but can discolor over time or due to illness (e.g., hepatitis). Internally, the sclera merges with the choroidal tissue in the suprachoroid layer. The innermost scleral layer is called the lamina *fusca*, as described herein. All of these have a specific fluorescence, spectral property and water content.

Fluorescence and diffuse reflectance spectroscopy are powerful tools to differentiate one connective tissue to the other based on the emissions from endogenous fluorophores and diffuse reflection of absorbers such as hemoglobin, melanin, water, protein content etc. However, separate analytical methods are used for the identification of fluorophores and hemoglobin. The estimation of fluorophores and hemoglobin simultaneously using a single technique of auto fluorescence spectroscopy can be performed. The diagnostic and real time treatment selection of targeted and untargeted in vivo tissues are important technical features herein. Emissions from prominent fluorophores collagen, flavin adenine dinucleotide, phospholipids, and GAGS, Proteoglycans are analyzed a priori and can also be assigned color tags. The water concentration can also be calculated from the ratio of fluorescence emissions at 500 and 570 nm. A better classification of normal and tumor tissues is yielded for 410 nm excitation compared to 320 nm when diagnostic algorithm based on linear discriminant analysis is used. Fluorescence spectroscopy as a single entity can be used to evaluate the prominent fluorophores as well as the water concentration within gradient tissues and segregated tissue structure and components.

Fluorescence spectroscopy is a tool used to differentiate targeted and untargeted tissues based on the emission spectral profile from endogenous fluorophores. Fluorescence estimates the concentration of fluorophores using auto fluorescence spectroscopy and to utilize its diagnostic inputs on in vivo tissues of clinical importance and to utilize that information as laser guidance software code platform via a real time biofeedback loop. Fluorescence emissions of the scleral tissues are recorded at excitation wavelengths of 320 and 410 nm. The emission characteristics of fluorophores such as collagen, nicotinamide adenine dinucleotide (NADH), flavin adenine dinucleotide (FAD), phospholipids and porphyrins, proteoglycans, GAGs, Collagen extracellular matrix and melanocytes of scleral tissues and adjacent anatomical tissues such as blood vessels, veins, nerves etc. are elicited. Exact tissue classification is then carried out using the spectral intensity ratio (SIR) and multivariate principal component analysis-linear discriminant analysis (PCA-LDA). The diagnostic algorithm based on PCA-LDA can provide better classification efficiency than SIR. Moreover, the spectral data based on an excitation wavelength of 100 nm to 700 nm in particular may be more efficient in the classification than 320 nm excitation, using PCA-LDA. Better efficacy of PCA-LDA in tissue classification can be further confirmed by the receiver operator characteristic (ROC) curve method. The results of this initial data capture represent a system and method of the present disclosure for using fluorescence spectroscopy based real time tools for the discrimination of various connective tissue components in this embodiment of the scleral connective tissue of the eye from the adjacent untargeted tissue, which may present a huge challenge. This anatomy avoidance system can be reiterated using real time imaging, e.g., OCT imaging sensors as well as chromophore sensors (water, color etc.) or spectroscopy without fluorescence.

There are many biological molecules which can absorb light via electronic transitions. Such transitions are relatively energetic and hence are associated with absorption of ultraviolet, visible and near-infrared wavelengths. The molecules generally have a string of double bonds whose pi-orbital electrons act similar to the electrons in a metal in that they collectively behave as a small antenna which can "receive" the electromagnetic wave of a passing photon. If the resonance of the pi-orbital structure matches the photon's wavelength then photon absorption is possible. The systems of the disclosure described herein may utilize these electrical vibrations to give biofeedback to the laser module thereby distinguishing not only targeted and untargeted tissues but actual transitions in tissue from one chromophore to the next creating an ultrasensitive ultra-feedback loop. In addition, in the field of infrared spectroscopy studies the variety of bonds which can resonantly vibrate or twist in response to infrared wavelengths and thereby absorb such photons. Perhaps the most dominant chromophore in biology which absorbs via vibrational transitions is water. In the infrared, the absorption of water is the strongest contributor to tissue absorption and is described in this invention. All other tissues which have color chromophores such as blood vessels, veins, or melanin are also described as providing biofeedback in their own specific absorptions or vibrational transitions and further defined as tissue characteristics which are sensed by these laser modules and other systems and combinations described herein.

In some embodiments color and chromophore sensing can be used to track blood vessels and other subsurface features in the sclera and other ocular locations. Similarly, hydration sensing can also be used. The systems of the present disclosure may include a biofeedback sensor, a scanner including a galvanometer and a camera that provide biofeedback that is used to distinguish targeted and untargeted tissues in addition to the transitions within tissues from one chromophore to the next, in the form of a sensitive biofeedback loop. Such transitions are relatively energetic and hence are associated with absorption of ultraviolet, visible and near-infrared wavelengths. On the other hand, currently known systems in the art use simple image facilitated feedback for the laser module it discloses. Since many biological molecules can absorb light via electronic transitions, sensing and monitoring them can be useful generic imaging capabilities.

It should be noted that chromophore sensing and monitoring, which is the use of color differences based on inherent light absorption by different materials as a way to sense and monitor and determine boundaries within a tissue, is an advantageous improvement. Color sensing and monitoring provides an advantage in that it can identify subtle differences in tissue composition that can then be used for positional based avoidance and a higher degree of accuracy in targeting only those tissue locations desired.

In some embodiments, features of the laser system of the present disclosure can include: Flash Lamp or Solid State laser wavelength Er:YAG 2.94 µm, or other wavelengths with high water absorption near peaks, as shown in FIG. 26-2; Fiber optic delivery system, with fiber core between 50 µm and 600 µm, with a hand held probe & eye contacting; flash lamp pumped; physician dependent; no eye tracking; procedure time ~10 minutes per eye; physician/manual depth control.

An exemplary system functional diagram for a laser system of the disclosure is illustrated in FIG. 3B above.

In some embodiments the features can include: solid state laser wavelength Er:YAG 2.94 µm; free space, short focal length, optic delivery system with a hand held laser head, eye contacting; solid state laser wavelength Er:YAG 2.94 µm diode, or other wavelengths with high water absorption near peaks, as shown in FIG. 26-2; diode pumped; manual positioning; 2D scanning micro pore placement; spot 50 µm to 425 µm, scleral nozzle guard; with physician/manual depth control; performed semi-reclined; software controlled/foot pedal; monitor visualization. Exemplary system diagrams are illustrated in FIG. 3A and FIGS. 27A to 27C.

Engineering advantages of the system may include: light weight components, more "space" in the hand piece. Engineering advantages may also include: solid state laser source based in the base station, miniaturization of all components, power/energy sufficient, and others. Clinical advantages can include: easy to use, simple, less technologic, and others. Clinical challenges advantages may also include: patient eye movements tracking, depth control, means to hold eye lid open (see, e.g., speculum illustrated in FIGS. 28A to 28C and FIGS. 29A to 29B).

In some embodiments the features may include: solid state laser wavelength Er:YAG 2.94 µm; free space, short focal length, optic delivery system with manual control, eye contacting; solid state laser wavelength Er:YAG 2.94 µm diode, or other wavelengths with high water absorption near peaks, as shown in FIG. 26-2; diode pumped; manual positioning; 2D scanning micro pore placement; spot 50 µm to 425 µm, scleral nozzle guard and foot pedal; with physician/manual depth control; performed semi-reclined; software controlled/foot pedal; with visualization camera, an articulating arm with hand piece holder and camera and monitor visualization (as illustrated in FIG. 26A and FIG. 2).

Other engineering advantages may also include: light weight components, miniaturization of all components, power/energy sufficient, stability of the articulating arm, camera image zoom and resolution, and others. Clinical advantages can include: easy to use, simple, less technologic, and others.

In some embodiments the features, may include: free space, long focal length optic delivery system with automatic controls, non-patient contacting; solid state laser wavelength Er:YAG 2.94 µm, or other wavelengths with high water absorption near peaks, as shown in FIG. 26-2; diode Pumped; robotic positioning for 6 axis; 2D scanning micro pore placement; 15 to 20 cm working distance with active depth control; laser power monitor sensor and controls; performed semi-reclined; hands free/software controlled/foot pedal; eye tracking; spot 50 µm to 425 µm; eye fixation light source or LED array, ablation debris removal system and camera/monitor visualization; procedure time ~few minutes both eyes (as illustrated in FIG. 26.1).

Further engineering advantages may include: Automation of 6 axis laser positioning, depth control, eye tracking, eye fixation point, multiple treatment patterns, ablation material removal, reduced treatment times, surgeon hands free operation and others. Clinical advantages may include: easy to use, simple, faster, no patient eye contact, improved pore repeatability, automation, high accuracy beam deflection scanner, patient eye tracking, and depth control.

In some embodiments, the features of the free space optical delivery system can be combined with the features of the fiber delivery system as an additional subsystem.

Engineering advantages may include: Integration of various subsystems, controls, displays and others. Clinical advantages may include: improved camera and visualization, OCT and depth verification, expanded treatment capability using advantages of multiple beam delivery systems, and expanded controls and functionality in controls and software.

In some embodiments, the 2.94 µm Er:YAG laser may be substituted with other wavelengths that have high water absorption as shown on a wavelength vs water absorbtion plot (see FIG. 26-2) e.g., 2.0 µm and others.

In some embodiments, the 2.94 µm Er:YAG laser may be substituted with other types of diode pump solid state (DPSS) lasers with single mode emmissions and higher beam quality that could product round, square or rectangular spots.

In some embodiments, the 2.94 µm Er:YAG laser may be substituted with other types of diode pump solid state (DPSS) lasers that combine multiple sources to achive equivalent fluence.

In some embodiments, the 2.94 µm Er:YAG solid state laser may be substituted with other type of lasers with equivalent fluence specification that use shorter pulse lengths. In some embodiments the features can include: a camera that may provide both high resolution, color images; a zoom range to see entire eye or the bottom of the pore for the surgeon and allow them to monitor the treatment protocol and have the opportunity to terminate and shut off the laser if needed; an electronic signal interface to allow the system to gain image data. The camera may also provide system controls when used with internal image processing and analysis to provide eye position and automatic centering of the patient eye for treatment, input for eye tracking software, background image to super impose treatment areas on the image of the patient's eye. The Camera can be positioned off the laser axis (see FIG. 20F) to enable field of view to see the treatment area, the entire eye and to see features of the patient eye to lock eye tracking to.

Engineering advantages may include: Integration of a camera images and analysis with the eye tracking and laser beam delivery systems and controls software. These features may mitigate potential risks; keep the doctor/user in control of the treatment. Clinical advantages may include: Improved surgeon visualization and overall control of the treatment, risk mitigation of eye movement, and others.

In some embodiments the features can include: Depth control monitored by OCT and/or other technologies and may control the remaining scalar thickness below the bottom of the pore without interrupting the treatment while insuring that depth of the pore limits are not exceeded. The OCT and/or other sensor may be merged into the laser beam axis and optical may match the focal length to the laser beam delivery system so the OCT and/or other system will work as a focal sensor for the OCT and/or system and laser system. The OCT and/or other system may sample pore depth continually, the sample rate will provide verification between laser pulses or during laser pulses enabling the laser emissions to be immediately terminated (refer back to FIG. 4B-1 for an exemplary OCT system).

Engineering advantages may include: Integration of an OCT system with the laser beam delivery system and controls software. Clinical advantages may include: Reduce surgeon dependences, risk mitigation for sclera perforation, improved pore depth and repeatability, and others.

In some embodiments, a long working distance system may be preferred because 1) it gives more engineering flexibility to fully feature the procedure, including improved: eye tracking, depth control, positioning accuracy, lighting and visualization, plume evacuation, and cost advantages; 2) less invasive, no contact—ultra minimally invasive; 3) automated control, reliable, predictable outcomes; 4) user and patient safety; 5) "No Touch" procedure; and others.

In some embodiments the features can include: Robotics to position the laser beam delivery system centerline, e.g., in 6 axis position to position the centerline of the laser on the center of the eye globe, at a distance to focus the beam spot on the surface of the sclera; a means to rotate the laser beam delivery system around the eye for 360° of rotation to perform all treatment patterns comprised of individual ablated pores (See examples shown in FIGS. 20E, 20G, and 20H).

In some embodiments the features of the robotics to position the laser beam delivery system can include: long focal length optical, 10-20 cm, a galvanometer scanners to position x and y, an angular motion controls to scan in y only and then step x, an auto-focus controls to correct z, focus to an individual patient, means to ablate quadrants in sub quadrant sections with combination of x and y moves and reduced motion of the x,y scanner beam motion. The robot could control multiple axes, e.g., 6 axes similar to a coordinate measuring machine; the laser beam delivery system could be mounted to a rotary mechanism on symmetrical axis of the patient's eye controlling various axis with an x,y scanner and focus mechanism and others (See example shown in FIG. 20I).

Other features may include stability, speed, small angular precision in the x,y scanner(s), mass of the moving system. The Clinical advantages are hands off operation, limited surgeon training and manual skills, reduced treatment time, non-contact with patient and others.

In some embodiments, patient may still move eyes to required position. A fixation target may shift to each of the 4 quadrants, or sub-treatment areas (see, e.g., FIG. 2B-2) in a quadrant and robotic or joy stick position may have to track eye position, including: superior nasal; superior temporal; inferior nasal; inferior temporal. Visualization of each quadrant and laser ablation/image with hand held system may be provided. Eye fixation position may be integral to the positioning of the treatment area on the eye based on the specifics of the patient. The ability to shift the eye fixation point can provide a means for vascular avoidance in shifting the treatment area. Movements in the fixation point provide a means to move the center of the treatment position on the eye. Also included is a means to break up a large treatment pattern into smaller ablation areas, a mosaic of the full treatment area, reducing the incident angle of the beam to the surface of the eye at any point and negating the need to move the laser beam delivery system.

In some embodiments, the fixation point may be comprised of a single or multiple illumination sources; selectively illuminated based on location relative to the laser beam. The illumination sources could move with the laser delivery system or have multiple sources in predefined locations. The illumination source could be an LED or array of LED's, individually addressable. The fixation point location can be fixed or controlled as part of the eye tracking system in combination with laser beam positioning.

In some exemplary operations, zone treatment simulations may be performed, including: baseline model with sclera stiffness and attachment tightness altered in individual full zones: treated combinations of zones (with and without changing attachment): for example, individually: 0, 1, 2, 3, 4; combined: 1+2+3, 1+2+3+4, 0+1+2+3+4; effective stiffness: modulus of elasticity (E)=1.61 MPa, equivalent to ~30 years old; loose attachment between the sclera and the ciliary/choroid where values in original accommodation model are used. (See, e.g., FIG. 35).

Effect of zone treatment on ciliary deformation in accommodation may include sclera stiffness, sclera stiffness+attachment.

In some embodiments, different treatment region shapes may be applied to one sclera quadrant with reference to multiple (e.g., 3 or 5) critical zones baseline simulation: original model of healthy accommodation with "old" sclera: stiff starting sclera: modulus of elasticity (E)=2.85 MPa, equivalent to ~50 years old; tight attachment between the sclera and the ciliary/choroid, all other parameters changed (ciliary activation, stiffness of other components, etc.).

In some exemplary operations, shape treatment simulations may include: baseline model with regionally "treated" sclera stiffness: treated different area shapes (without changing attachment)→treated stiffness: modulus of elasticity (E)=1.61 MPa, equivalent to ~30 years old; effective stiffness in each zone may be determined by amount of shape area in each zone and values in original accommodation model.

Effect of shape treatment on ciliary deformation in accommodation may include sclera stiffness only.

Treated stiffness may depend on: pore volume fraction in the treated region→% sclera volume removed by treatment; pore volume fraction is varied by changing parameters of ablation holes; and others. Resultant stiffness estimated as microscale mixture: holes assumed to be parallel evenly spaced/sized within volume=volume fraction (% of total sclera volume); remaining volume is "old" sclera (E=2.85 MPa); need to remove ~43.5% of volume to change sclera stiffness in the treated area from old (e.g., 50 year-old) to young (e.g., 30 year-old); protocols (combinations of density % & depth) allow for a maximum volume fraction of 13.7%, equivalent to a new stiffness of 2.46 MPa; array size=side length of the square area of treatment (mm).

The following parameters are considered. (See also FIGS. 26-3A, 26-3A1, 26-3A2, and 36).

Exemplary model outcomes are shown in FIG. 41.

Treated surface area=surface area of sclera where treatment is applied (mm^2), where treated surface area=array squared.

Thickness=thickness of sclera in the treated area (mm), assumed uniform.

Treated volume=volume of sclera where treatment is applied (mm^2) treated volume=treated surface area*thickness=array$^2$*thickness Density %=percent of treated surface area occupied by pores (%).

Spot size=surface area of one pore (mm^2).

\# pores=number of pores in the treated region.

$$\# \text{ pores} = \frac{\text{density \%} * \text{treated surface area}}{\text{spot size} * 100}$$

$$= \frac{\text{density \%} * \text{array}^2}{\text{spot size} * 100} * \text{round to nearest whole number}$$

Total pore surface area=total area within the treated surface area occupied by pores $$\text{total pore surface area} = \text{spot size} * \text{pores}$$

$$\approx \frac{\text{density \%} * \text{treated surface area}}{100}$$

$$\approx \frac{\text{density \%} * \text{array}^2}{100}$$

Depth=depth of one pore (mm); dependent on pulse per pore (ppp) parameter depth %=percent of the thickness extended into by the pore.

$$\text{depth \%} = \frac{\text{depth}}{\text{thickness}} * 100$$

As shown in FIG. 26-3A, total pore volume=total area within the treated surface area occupied by pores Volume fraction=percent of treated volume occupied by pores (%), i.e. percent of sclera volume removed by the laser.

$$\text{volume fraction} = \frac{\text{total pore volume}}{\text{treated volume}} * 100$$

$$\approx \frac{\text{density \%} * \text{depth}}{\text{thickness}}$$

$$= \frac{\text{density \%} * \text{depth \%}}{100}$$

Relationships between treatment parameters include: input parameters of laser treatment; properties of the sclera; input to calculate new stiffness.

Calculating new stiffness of sclera in the treated region.

Volume fraction=percent of treated volume occupied by pores (%), i.e. percent of sclera volume removed by the laser.

$$\text{volume fraction} = \frac{\text{total pore volume}}{\text{treated volume}} * 100$$

$$\approx \frac{\text{density \%} * \text{depth}}{\text{thickness}}$$

$$= \frac{\text{density \%} * \text{depth \%}}{\text{thickness}}$$

Stiffness=modulus of elasticity of sclera before treatment (MPa).

Treated stiffness=modulus of elasticity of sclera after treatment (MPa); estimated from microscale mixture model.

$$\text{treated stiffness} = \left(1 - \frac{\text{volume fraction}}{100}\right) * \text{stiffness}$$

$$\approx \left(1 - \frac{\text{density \%} * \text{depth}}{\text{thickness} * 100}\right) * \text{stiffness}$$

$$= \left(1 - \frac{\text{density \%} * \text{depth}}{10000}\right) * \text{stiffness}$$

Input parameters of laser treatment: properties of the sclera, input to calculate new stiffness input to finite element model of treated zones, effect of volume fraction on ciliary deformation in accommodation: sclera stiffness only, full zone region treated (region fraction=1).

Protocols=range of possible combinations of density % and depth, sclera in all zones changed to treated stiffness corresponding with pore volume fraction.

Effect of volume fraction on ciliary deformation in accommodation: sclera stiffness+attachment, full zone region treated (region fraction=1), healthy=original accommodation model results.

Protocols=range of possible combinations of density % and depth, sclera in all zones changed to treated stiffness corresponding with pore volume fraction effect of volume fraction on ciliary deformation in accommodation: sclera stiffness+treatment area shape.

Protocols=range of possible combinations of density % and depth, sclera in all zones changed to treated stiffness corresponding with pore volume fraction and region fraction of treated area.

J/cm2 calculation: J/cm2×Hz (1/sec)×Pore size (cm2)=W; J/cm2=W/Hz/pore size. Example: spot is actually a "square", therefore the area would be based on square calculation: 7.2 J/cm2=1.1 w/300 Hz/(225 μm $10^{-4}$)$^2$.

Factors that may affect ablation depth % on living eyes in surgery include: moisture content on surface and inside the tissue, tenon or conjuntiva layer, laser firing angle, thermal damage, may consider water spray, Cryo spray/refrigerated eye drops, Cryo hydrogel cartridge in the laser disposable system (perioperative medications such as antibiotics/steroids).

In some embodiments, the described systems, methods and devices of the disclosure may include following features.

Adjustable micropore density: dose and inflammation control could be achieved thanks to a variable number of micropores created per application area. Adjustable micropore size; dose and flexible patterning of microporation. Adjustable micropore thermal profile: the system can create micropores with adjustable thermal profiles that minimize creation of a coagulation zone. Adjustable depth with depth recognition: the system creates micropores in a controlled manner and prevent too deep ablation Anatomy recognition to avoid blood vessels. (FIG. 26-4 illustrates exemplary anatomy recognition.) Laser security level: the device is a Laser Class 1c device, the system detects the eye contact and the eye pod covers the cornea. Integrated smoke evacuation and filtration: fractional ablation can be conducted without any extra need in installing a smoke evacuation system, since smoke, vapor and tissue particles will be sucked out directly by integrated systems. Laser system will have an integrated real time video camera (e.g., an endo camera, CCD camera) with biofeedback loop to laser guidance system integrated with GUI display for depth control/limit control. (See FIG. 26-4-1).

In some embodiments, the described systems, methods and devices of the disclosure may provide: Laser system biofeedback loop integrates chromophore recognition of color change using melanin content (computer integration of various micropore staging for color change; a [[. A]] prior depth information in the 3 zones of thickness; laser system capable of integrating a priori scleral thickness mapping for communication with laser guidance planning and scleral microporationl; use of OCT or UBM or 3D tomography; laser system programming release code with controlled pulses per procedure; electronically linked to reporting to a data report (calibration data, and service data, statistics etc.). Laser system components may be built in modular fashion for easy service maintenance and repair management. Self-calibrating setup as well as real time procedure calibration prior to treatment, after treatment and before subsequent treatment may be included. All calibrations may be recorded in database. Other features may include communication port for online communication (e.g., WIFI service trouble shooting, report generation, and communication to server, WIFI access to diagnostic information (error code/parts requirement), and dispense either trouble shooting repair and maintenance or dispense an order for service by service representative). Some embodiments may include spare parts service kit for service maintenance and repair for onsite repair; laser system key card integration with controlled pulses programming with time limitation included; aiming beam with flexible shape to set boundary conditions and also to trigger if the laser nozzle is on axis, level and positioning; aiming beam coincident with alignment fixation beam to trigger system Go No Go for starting treatment ablation; laser system requirements containing an eye tracking system and corresponding eye fixation system for safety of ablation to control for eye movement; laser system requirements having ability to go 'on axis' delivery through a gonio mirror system to deliver microporation on the sclera, or through a slit lamp application or free space application. These may require higher power, good beam quality as well as integration of fixation target and/or eye tracking system. Good beam quality may mean: laser system focusing down to 50 μm and up to 425 μm. The laser system may be capable of doing a quick 360 dg procedure through galvos scanning and use of robotics to change quadrant treatments within 40-45 seconds per whole eye (e.g., 4 quadrants in each eye about 10 seconds per quadrant; 1-2 seconds repositioning laser to subsequent quadrant). The laser system may be a workstation with integration of foot pedal, computer monitor; OCT; CCD video camera and/or microscope system. The laser system may include patient positioning table/chair module that is flexible from supine position; flexible angle; or seated; and motorized chair.

In some exemplary operations, the described systems, methods and devices of the disclosure may include the following medical procedure: 1) The user manual may give information about the correct handling of the system. 2) Put the eye-applicator onto the treatment area and place the applicator unit on the eye-applicator. 3) The user can set the treatment parameters. 4) The user starts the treatment procedure. 5) The user may be informed about the on-going state of the treatment. 6) The user may be informed about the calibration of the energy on the eye before and after the treatment. 7) To prevent undesired odors, ablation smoke may be prevented from spreading. 8) The user may be informed about the visualization of the eye during the treatment, between quadrants and after the treatment.

In general, the system will have low maintenance. A system service, if necessary, may be conducted as fast as possible, leading to a minimal downtime. Furthermore, service costs may be lower than with common laser systems. The applicator unit, eye-applicator and the disposable insert may be easy and hygienic to handle, especially while attaching and detaching. Software may allow data exchange between the device and a computing device.

Microporations—Exemplary Parameters

| Term | Definition | |
| --- | --- | --- |
| Procedure | full eye - 4 quadrants | |
| Treatment site and size | Procedure: average area 300 cm2 (=mean value) partial treatments: average area 50 cm2 | |
| Scenarios | Maximal utilisation case | Expected utilisation case |
| No. of treatments per day | | |
| Array size | 5 mm (Variable between 2 mm-14 mm) | 5 mm (Variable between 2 mm-14 mm) |
| "Standard" microporation (MP) parameters; based on preliminary experiments: | | |
| MP1 | 300 Hz repetition rate, 125 μs laser pulse duration, 5 pulses per pore, 5% | |
| MP2 | 200 Hz repetition rate, 175 μs laser pulse duration, 5 pulses per pore, 7% | |
| MP3 | 100 Hz repetition rate, 225 μs laser pulse duration, 7 pulses per pore, 8% | |
| MP4 | 200 Hz repetition rate, 225 μs laser pulse duration, 5 pulses per pore, 6% | |

Service requirements may include: Maximum every year or after a predetermined number of procedures, e.g., 1000, 2000, or 3000 procedures, whatever occurs first. Overall product life time: all components may be evaluated to withstand a product life time of, e.g., at least 5 years.

System operation may be through pre-approved electronic key card. Visualization required during surgery: Lighting of eye to aid visualization to be provided—either external light source or incorporated into laser adaptor fixation device, a video camera and GUI interface to computer monitor may be a required module. Patient can be in horizontal or inclined or seated position. Shielding for eye safety of patient during procedures may be needed. Operation: The system may allow activating the laser when applicator and insert are attached, on proper tissue contact and with verified user access. Pore depth monitor: maximum depth monitored by end switch (optical or equal monitored). Management of eye movement intra-procedure: Eye tracking technology with corresponding eye fixation targets may be included for fully non-contact eye procedure. Vasculature avoidance: Scan/define ocular vasculature may be provided to avoid microporation in this area. See FIGS. 4A-1 to 4A-10 which illustrate how microporation/nanoporation may be used to remove surface, subsurface and interstitial tissue and affect the surface, interstitial, biomechanical characteristics (e.g., planarity, surface porosity, tissue geometry, tissue viscoelasticity and other biomechanical and biorheological characteristics) of the ablated target surface or target tissue.

Performance requirements may include: Variable pore size, pore array size and pore location. Exemplary preparation time: 5 min from power-on of the device until start of microporation process (assuming average user reaction time). Robotics incorporation by quadrant to achieve treatment time requirements. Treatment time may be <60 s, 45 s for one procedure. Diameter of micropores: Adjustable between 50 µm-600 µm. Tissue ablation rate: adjustable between 1 to 15%. Microporation array size: Area adjustable up to between 1 mm×1 mm and up to 14×14 mm, square shaped pore custom shape array. Multiple ablation pattern capability. Short press to activate and deactivate laser: the actual microporation process may be started by pressing a foot switch only for a short amount of time, instead of pressing it during the entire microporation. Stopping the laser can be done identically. Ablated hole depth: 5% to 95% of scleral thickness. Biocompatibility: All tissue contact parts are to be constructed with materials that are in compliance with medical device requirements.

In some embodiments, the system may include: laser wavelength: 2900 nm+/−200 nm; around the mid IR absorption maximum of water. Maximum laser fluency: ≥15.0 J/cm$^2$ on the tissue ≥25.0 J/cm$^2$ on the tissue; to widen treatment possibilities 2900 nm+/−200 nm; around the mid IR absorption maximum of water. Laser setting combinations: Laser repetition rate and pulse duration may be adjustable by using pre-defined combinations in the range of 100-500 Hz and 50-225 µs. Said range may be a minimum range, e.g., ≥15.0 J/cm$^2$ on the tissue, or ≥25.0 J/cm$^2$ on the tissue, to widen treatment possibilities. Aggressive treatments number of pulses per pore: "Aggressive" settings may also be selectable to create micropores far into the dermis, e.g. with a depth >1 mm. As the depth is mainly fluence-controlled, a high number of pulses per pores should automatically lead to larger depth values. Therefore, the pulse per pore (PPP) values may be adjustable between: 1-15PPP. Shock and vibration: Device may withstand a lorry transport within the supplied single-use or multiple-use (in case of service or repair) packaging. Prevention of odour spreading:

A system to reduce the spreading of unpleasant odour to a minimum may be implemented. GUI: The user interface may be supported by a reasonable display size. Audible noise: The maximum noise generated by the system (cooling and evacuation system at 100%) may not exceed 70 dBA or 50 dBA. Shock absorbance of the unit: The unit may tolerate a fall of certain height without any major damage which causes the system to fail. System connectivity with one or more of USB, LAN, WLAN, Bluetooth, Zigbee, or other suitable technologies.

In certain embodiments, the physical requirements of the system described herein may include these exemplary parameters: Laser System may be incorporated into a "Cart" type workstation unit with lockable wheels and counter balanced/articulated arm as to prevent tipping of the cart during use or transport (See FIGS. 24 and 26-5). No Tilt requirement. Weight: Weight (Cart+counter balance/articulated arm): <100 kg. Ancillary equipment: video monitoring system, e.g. used in conjunction with standard oculars, etc. Temperature and Relative humidity specifications for shipment and use: Humidity: <70% RH, non-condensing; Operating temperature: 18 to 35° C.; Humidity: <70% RH, non-condensing; Storage and transport temperature: −10 to 60° C.

Design and Usability: The usability of the design may fulfill the general needs of the targeted user groups, including lead users, doctors, and medical staff. Weight balance: The weight balance of the unit may achieve market acceptance. Shape of applicator unit: The shape of the unit may be optimized. Radius of action: The connection between the table-top unit and the hand-held unit may allow an action radius of at least 1.2 m. Good view to see proper positioning of the eye: The user may be able to verify the proper positioning of the laser on the eye tissue. Convenient handling of applicator and insert: Applicator and insert may be easily attachable and detachable.

Permitted application areas on human body: Generally, the device may be applied to the eyes. Biocompatibility: All tissue contact parts are to be constructed with materials that are in compliance with medical device requirements.

Accessories may include: Applicator insert (disposable part): A disposable part to collect ablated tissue which establishes a hygienic interface between device and tissue. Eye pod (optional): The applicator may be reusable, easy to clean, bio-compatible, and sterilisable. Foot Switch: Foot switch operation for standard laser delivery.

In some embodiments, the systems described in the present disclosure may include construction of a system that uses a pulsed, 2.94 µm Er:YAG laser, along with a handheld probe, to ablate holes in the sclera, to modify the plasticity of a region of the sclera, in the treatment of presbyopia and other eye dysfunctions.

In some embodiments, the system may include parts of a PLEASE™ Platform and additionally a 3Mikron™ Class IV Er:YAG fractional laser system. The main parts may be: a laser module (e.g., module 2610 illustrated in FIG. 26-1), a spherical shaped application (e.g. Saucer) module including: 3Mikron™ DPM-2 (Er:YAG), Scanning unit & eye tracking, a robotic stage for positioning, touchscreen control display, camera system, microscope, suction system, depth detection system, lighting and laminar air flow, aiming beam. A mobile cart module can include: power supply, touchscreen control display for non-surgical personal, control and cooling unit, DriCon™ Platform, wireless foot pedal, and others.

In some embodiments, some or all of the system can be easily positioned over the patients face. The laser module (see, e.g., module 2610 illustrated in FIG. 26-1) may allow establishing a local sterile environment utilizing laminar airflow inside. The laser module may cover most or all relevant parts of the treatment procedure, such as the mechatronic motion system, that moves the laser with high precision to the selected treatment area on the sclera.

The system may include ability to assure control of ablation depth and warning/control feature that can reliably detect the depth of the tissue ablation and ultimately the interface between the sclera and choroid and effectively prevent ablation beyond the sclera, ability of the system to be ergonomically and clinically practical as well as acceptable for use by the physician, high reliability and controls to assure patient safety and re-producibility of the procedure, ability to scan with a larger working distance in order to produce a fast procedure.

In some embodiments, the system includes a display which included in the laser module (such as module 2610 in FIG. 26-1) to view the tissue area (doctors display), control & safety (see also below) which includes laser supply, electronics and motion control platform as well as safety, direct interface to a base station (e.g., base station 2620 illustrated in FIG. 26-1). The system may also include motion stage: Translation stage to position the laser & optics & scanner in the specific area, laser and optics: 3mikron module and beam forming optics, depth control system to avoid too deep ablation, eye tracking module, suction and laminar flow for operator safety. Beam deflection synchronized with eye tracking for micropore array generation. Other components and features include: camera unit for vision. The base station may be an intelligent moveable base station that may include operator display for control and safety, distribution of power to different modules, water cooling of laser system, optional foot pedal, communication interface with external world, debug, updates, and other features, and main supply for wide range power supply for international operation.

As mentioned above, in some embodiments, the described systems, methods and devices of the disclosure may include creating a finite element model of the accommodative mechanism that includes seven major zonule pathways and three ciliary muscle sections, calibrating and validating the model through comparison to previously published experimental measurements of ciliary muscle and lens motion during accommodation, and using the model to investigate the influence of zonular anatomy and ciliary muscle architecture on healthy accommodative function. The model may include geometry of the lens and extra-lenticular structures and simulations utilized novel zonular tensioning and muscle contraction driven accommodation.

In some embodiments, the described systems, methods and devices of the disclosure may include a method to change the biomechanical properties of biological tissue using a complex of matrix formations consisting of perforations on said tissue where the configuration is based on a mathematical algorithm. The change in biomechanical properties of biological tissue is related to elasticity, shock absorption, resilience, mechanical dampening, pliability, stiffness, rigidity, configuration, alignment, deformation, mobility and/or volume of said tissue. The matrix formations of perforations may allow for a non-monotonic force deformation relationship on said tissue with the range of isotropic elastic constant across the medium. Each matrix formation may create a linear algebraic relationship between row length and column length with each perforation of said tissue having continuous linear vector spaces with derivatives up to N. Where N is an infinite number. The complex may create a total surface area wherein each perforation has a proportional relationship to the total surface area of said tissue. The complex can also be arranged to achieve equilibrium of forces, stress and strain and reduce shearing effect the between the matrix formations and the perforation. Each perforation may be excised volume of tissue which defines a point lattice on said tissue where the preferred shape of excised volume is cylindrical. The matrix formation consists of tessellations with or without a repeating pattern wherein the tessellations are Euclidian, Non-Euclidean, regular, semi-regular, hyperbolic, parabolic, spherical, or elliptical and any variation therein. Each perforation may have a linear relationship with the other perforations within each matrix formation and the complex of matrices individually. The tessellations directly or indirectly relate to stress and shear strain atomic relationships between tissues by computing the mathematical array of position vectors between perforations. The atomic relationship is a predictable relationship of the volume removed by each perforation to the change in biomechanical properties seen as an element of the mathematical algorithm. The predictable relationship of the removed volume may be mutually exclusive. The tessellations may be a square which can be subdivided into a tessellation of equiangular polygons to derivative of n. In some embodiments, the mathematical algorithm uses a factor $\Phi$ or Phi to find the most efficient placement of matrices to alter the biomechanical properties of said tissue. The factor $\Phi$ or Phi may be 1.618 (4 significant digits) representing any fraction of a set of spanning vectors in a lattice having the shortest length relative to all other vectors' length. In some embodiments, the mathematical algorithm of claim 1 includes a nonlinear hyperbolic relationship between planes of biological tissue and at any boundary or partition of neighboring tissues, planes and spaces in and outside of the matrix.

In some embodiments, the described systems, methods and devices of the disclosure may include a protection lens 2700 as illustrated in FIGS. 27A to 27C.

In some embodiments, the described systems, methods and devices of the disclosure may include speculum 2810/2820/2830 as illustrated in various embodiments in FIGS. 28A to 28C. FIGS. 29A and 29B illustrate an exemplary operation using the speculum 2830.

One or more of the components, processes, features, and/or functions illustrated in the figures may be rearranged and/or combined into a single component, block, feature or function or embodied in several components, steps, or functions. Additional elements, components, processes, and/or functions may also be added without departing from the disclosure. The apparatus, devices, and/or components illustrated in the Figures may be configured to perform one or more of the methods, features, or processes described in the Figures. The algorithms described herein may also be efficiently implemented in software and/or embedded in hardware.

Note that the aspects of the present disclosure may be described herein as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The enablements described above are considered novel over the prior art and are considered critical to the operation of at least one aspect of the disclosure and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus, if an element can be understood in the context of this specification as including more than one meaning, then its use must be understood as being generic to all possible meanings supported by the specification and by the word or words describing the element.

The definitions of the words or drawing elements described above are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

In the foregoing description and in the figures, like elements are identified with like reference numerals. The use of "e.g.," "etc," and "or" indicates non-exclusive alternatives without limitation, unless otherwise noted. The use of "including" or "includes" means "including, but not limited to," or "includes, but not limited to," unless otherwise noted.

As used above, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, processes, operations, values, and the like.

It should be noted that where a discrete value or range of values is set forth herein (e.g., 5, 6, 10, 100, etc.), it is noted that the value or range of values may be claimed more broadly than as a discrete number or range of numbers, unless indicated otherwise. Any discrete values mentioned herein are merely provided as examples.

Terms as used above may have the following definitions.

Cornea and sclera tissues have collagen building blocks, where most of the sclera and cornea are primarily connective tissue. Collagen is made up of 3 single strands of alpha and/or beta chains to form a triple helix. Collagen fibrils are 25-230 nm in diameter and are arranged into bundles of fibrils that are highly disorganized and variable in size in the scleral stroma, and very organized and uniform in size in the corneal stroma. Type 1 is the most common collagen found in the cornea and sclera. The random arrangement and the amount of interweaving in the scleral stroma probably contribute to strength and flexibility of the eye.

The intertwined helices in a collage molecule have non-helical portions on the ends of the strand. The individual molecules from natural linkages, creating long assemblies of parallel molecules that are the collagen fibrils. The structure of collagen fibrils is created through intermolecular cross-linking.

The collagen in the cornea and sclera is associated w/ polysaccharide molecules called glycosaminoglycans (GAGs). A proteoglycan is a core protein to which many GAGs are attached, and they form a matrix around the collagen fibrils. The dominant GAGs in the cornea and sclera are dermatan sulfate and keratan sulfate. The collagen fibrils in the cornea and sclera are then surrounded by and embedded in proteoglycans.

GAGs are rather large molecules. They also have a very negative charge and, therefore, attract positively charged molecules such as sodium. Sodium comes along with water, so tissues with large amounts of GAGs will take up considerable water if left to their own devices. The combination of $H_2O$ creates a gel around the collagen fibrils creating the ground substance. The corneal stroma has a higher affinity for water, whereas the cornea has very narrow limits because it must remain transparent. In cornea spacing of collagen is key to its transparency. Water content needs to be maintained at a steady level to keep spacing of collagen regular.

In general, a sclera functions to maintain the shape of the eye and resists deforming forces both internal (TOP) and external. The sclera also provides attachment points for extraocular muscles and the optic nerve. The opacity of the sclera is due to many factors including the number of GAG's (glycosaminoglycans—complex sugars that attach covalently to collagen, the amount of water present, and the size and distribution of the collagen fibrils.

The sclera has only 25% of the total GAG's that are present in the cornea. Because the GAG's attract water, the sclera is less hydrated than the cornea (but not 75% less; due to several structures that carefully maintain a lower hydration level in the cornea). The large variation in fibril size and the irregular spacing between scleral components leads to light scattering and opacity. The color of the sclera is white when healthy, but can discolor over time or due to illness (e.g. hepatitis). Internally, the sclera merges with the choroidal tissue in the suprachoroid layer. The innermost scleral layer is called the lamina *fusca*.

The sclera contains a number of holes where structures pass through or interrupt the expansion of the sclera. At the posterior pole of the eye the optic nerve passes through the posterior scleral layer. This area is bridged by a network of scleral tissue called the lamina cribosa. The lamina cribosa is the weakest part of the sclera. Elevated TOP could lead to a bulging out at the optic nerve and subsequent tissue damage. The scleral blood supply is very limited, the tissue is largely avascular. It contains no capillary beds, only a few small branches from the episclera and choroid, and branches of the long posterior ciliary arteries. Scleral thickness varies from 1.0 mm at the posterior pole to 0.3 mm behind rectus muscle insertions. The sclera covers ~⅚ of the entire eye (about 85%).

The sclera consists of 3 layers: (1) episclera, consists of loose vascularized connective tissue. Branches of the anterior ciliary arteries form a capillary network anterior to the rectus muscle insertions. Surrounds the peripheral cornea and is physically linked to Tenon's capsule (see Orbit study guide) by connective tissue strands. The sclera thins towards the back of the eye. (2) scleral stroma thick dense connective tissue layer that is continuous with the corneal stroma at the limbus. (3) lamina *fusca* refers to the few pigmented cells that remain adherent to sclera after removal of choroids.

Tear layer consists of three layers that together are 7 µm thick. The outer or most anterior layer (1) is a lipid layer, the middle layer (2) is an aqueous layer that originates from the lacrimal gland. The mucous layer (3) is in contact with squamous cells (posterior layer).

The cornea functions as the eye's primary refractive element. Most important feature is transparency. The cornea generally comprises about ⅙ of the outer layer of the eye. Radius of curvature of ~8 mm; overall the cornea is 0.52-0.53 mm thick at the center and 0.71 mm at the periphery. Posterior side (inner surface) of cornea has smaller radius of curvature than anterior.

The cornea is the major refractive component of the eye contributing over 40 diopters. It is avascular and transparent transmitting light very well. The anterior portion of the cornea is covered with tear film (see above). Optical zone is the circular region of the cornea that is 4 mm around the corneal apex. Central radius of curvature and refractive power: Air/tear interface +43.6 D; Tear/cornea +5.3 D; Cornea/aqueous −5.8 D; total central refractive power=43.1 D.

The cornea consists of five layers. From anterior to posterior they are: 1) Epithelial; 2) bowman's; 3) stroma; 4) Decemet's; 5) endothelium.

Epithelial layer is the first corneal layer and most complex. The epithelial cell layer is made up of ~6-8 rows of cells. The epithelial layer is about 50 µm thick. The entire cornea is about 500-700 microns (µm) thick (0.5 to 0.7 mm). Surface layer (anterior) consists of squamous cells that are non-pigmented and have a flattened appearance. The surface of these cells consists of many microvilli that serve to increase the surface area and stabilize the tear film 'layer." The squamous cells are connected through tight junctions i.e. Zonulae Occludens. This creates an effective barrier to exclude foreign material that might cause damage. As the surface cells get older their attachments are lost and the cell is sloughed off in the tear film. New cells migrate outward from the more internal rows of epithelial cells (bowman's) toward the tear film layer.

The cornea epithelium is subdivided into 3 parts: 1) The squamous cell layers at the surface of the cornea, 2) wing cells that have an appearance of a wing, and 3) columnar basal cells. All the 3 cell types originally derive from the columnar basal cells. So, cells are continually being renewed along the basal surface and will ultimately (in about 10 days) turnover an entire new cell layer. Basal cells communicate through gap junctions. The middle layer of wing cells is 2-3 layers thick. These cells are polyhedral and have convex anterior surfaces and concave posterior surfaces. The most posterior cell layer consists of a single row of columnar basal cells. Cells transform from columnar to cuboidal to squamous. [Programmed cell death is called apoptosis. This process occurs throughout the body including corneal epithelium cells.] The cells are connected to adjacent cells by desmosomes and the basement membrane by hemidesmosomes. The basement membrane (Bowman's) is formed with secretions from the basal epithelial cells. Newly born epithelial cells are formed at the corneal periphery and then they migrate toward the center of the cornea. There are 325,000 nerve endings in epithelial layer of the cornea. These nerve endings arise from about 2000 nerves which arise from the medial and lateral long ciliary nerves.

Bowman's layer (formerly Bowman's membrane) is the second corneal layer. This layer of cornea is about 10 µm thick. It is a dense, acellular fibrous sheet of interwoven collagen fibers that are randomly arranged. Fibrils are 20-25 µm in diameter. Bowman's layer is a transition layer between the basal epithelium and the stroma. This layer is produced by the epithelium; It does regenerate, but very slowly. Corneal nerves pass through the layer losing their Schwann cell covering and passing into overlying epithelium as unmyelinated fibers. The Bowman's layer ends at the corneal periphery.

The corneal stroma layer is the third layer, also known as substantia propria. It is 500 to 700 microns thick representing about 90% of the total cornea thickness. It is comprised of collagen fibrils and fibroblasts. The fibroblasts in the corneal stroma are often called keratocytes [old name, corneal corpuscles] and are specialized fibroblasts that produce collagen fibrils during development and maintain the connective tissue in the mature eye. Collagen fibrils of the cornea are 25-35 nm in diameter and are grouped into flat bundles called lamellae. There are 200-300 lamellae distributed throughout the corneal stroma. All the lamellae run parallel to the surface of the cornea. These stacked fibers account for 90% of the thickness and volume of the cornea. Adjacent lamellae lie at angles to one another; each lamellae extends across the entire cornea; each fibril runs from limbus to limbus. In the anterior ⅓ of stroma lamellae are 5-30 µm wide and 0.2-1.2 µm thick. Posterior ⅔ of the stroma is more regular and larger (100-200 µm). In the innermost layer, adjacent to the next corneal layer Descemet's membrane the collagen fibrils interlace to form a dense but thin collagenous sheet which contributes to the maintenance of the attachment between the stroma & Descemet's membrane. Keratocytes in the stroma produce fibrils that make up the lamellae. In between the fibrils is the ground substance that contains proteoglycans (protein with the carbohydrate glycosaminoglycan (GAG). The GAGs are hydrophilic negatively charged that are located around specific sites around each collagen fibril. The hydrophilic nature of the GAGs serves to keep the stroma well hydrated which helps to maintain the spatial arrangement of the fibrils. Corneal hydration and the regular arrangement of the fibrils contributes to corneal transparency. So, proper hydration is critical to maintain transparency. Proper hydration is maintained by the actions of the epithelium and endothelium to maintain a balance (primarily by pumping water out of the cornea).

The fourth corneal layer is Descemet's membrane layer. It's Its function is as a structure and tough resistant barrier to perforation of the cornea. Secreted by endothelium. It has 5 types of collagen with Type VIII dominant. It is considered to be the basement membrane of the endothelium. The layer is constitutively adding new material so it becomes thicker with age; it is approximately 10 microns thick. It has an anterior portion that exhibits a banded appearance like a latticework of collagen fibrils. The posterior of Descemet's membrane is non-banded and is secreted by the endothelial cells throughout life.

Some terms may have definitions that vary in part or wholly from this document. For example, constrict has been defined to mean: to make narrow or draw together <constrict the pupil of the eye>; to subject (as a body part) to compression <constrict a nerve>; to become constricted; to become tighter and narrower, or to make something become tighter and narrower, e.g. the drug causes the blood vessels to constrict.

Contracture has been variously defined to mean: a permanent shortening (as of muscle, tendon, or scar tissue) producing deformity or distortion; to shorten; to become reduced in size; in the case of muscle, either to shorten or to undergo an increase in tension; to acquire by contagion or infection; an explicit bilateral commitment by psychotherapist and patient to a defined course of action to attain the goal of the psychotherapy; To straighten a limb, to diminish or extinguish the angle formed by flexion; to place the distal segment of a limb in such a position that its axis is continuous with that of the proximal segment.

Extension has been defined to mean: additional piece, a piece that has been or can be added, or that can be pulled out, to enlarge or lengthen something.

Expansion has been defined in various circumstances as meaning: the act or process of expanding; the quality or state of being expanded; to increase in size, number or importance, or to make something increase in this way, process of becoming enlarged: the process of increasing, or increasing something, in size, extent, scope, or number.

Perforate has been defined in various forms to mean: to make a hole or holes in something; pierced with one or more holes.

In diagnostic or therapeutic radiology, a plate made of one or more metals such as aluminum and copper which, placed in the x- or gamma ray beam, permits passage of a greater proportion of higher-energy radiation and attenuation of lower-energy and less desirable radiation, raising the average energy or hardening the beam. A device used in spectrophotometric analysis to isolate a segment of the spectrum. A mathematical algorithm applied to image data for the purpose of enhancing image quality, usually by suppression or enhancement of high spatial frequencies. A passive electronic circuit or device that selectively permits the passage of certain electrical signals. A device placed in the inferior vena cava to prevent pulmonary embolism from low extremity clot. There are many variants.

Puncture is defined as to make a hole or holes in something; make holes for tearing: to make a line of small holes in paper to make tearing it easier; penetrate something: penetrate or pass through something; biology with small holes: dotted with small holes; biology with transparent spots: dotted with transparent spots.

Perforate: to drill, bore, drill, drive, hole, honeycomb, penetrate, permeate, pierce, pit, probe, punch, puncture, slit, stab, burrow, gouge, mine, penetrate, perforate, pierce, pit, prick, punch, puncture, ream, riddle, sink, tunnel Crenellate has been defined as: to indent; to notch; as, a crenelated leaf; having repeated square indentations like those in a battlement; "a crenelated molding."

Compression: reduction in size, the reduction of the volume or mass of something by applying pressure, or the state of having been treated in this way.

Decompression: pressure decrease: a decrease in surrounding or inherent pressure, especially the controlled decrease in pressure that divers undergo to prevent decompression sickness; to reduce pressure in organ: a surgical procedure to reduce pressure in an organ or part of the body caused, for example, by fluid on the brain, or to reduce the pressure of tissues on a nerve; computing data expansion: the expansion to full size of compressed computer data.

Flexible: susceptible to being led or directed; "fictile masses of people ripe for propaganda" able to adjust readily to different conditions; "an adaptable person"; "a flexible personality"; "an elastic clause in a contract" [elastic, flexible, pliant]; "a flexible wire"; "a pliant young tree" [bendable, pliant]; [ductile, malleable, pliant, tensile, tractile]

Pliable: capable of being bent or flexed or twisted without breaking; capable of being shaped or bent or drawn out; "ductile copper"; "malleable metals such as gold"; "they soaked the leather to made it pliable"; "pliant molten glass"; "made of highly tensile steel alloy".

Diaphragm: muscular membranous partition separating the abdominal and thoracic cavities and functioning in respiration; also called midriff; a thin disk, especially in a microphone or telephone receiver, that vibrates in response to sound waves to produce electric signals, or that vibrates in response to electric signals to produce sound waves; a musculo-membranous partition separating the abdominal and thoracic cavities and functioning in respiration.

Pore as used herein means minute opening in tissue, as in the skin of a human or an animal, serving for example as an outlet for perspiration.

Nuclear pores Openings in the membrane of a cell's nuclear envelope that allow the exchange of materials between the nucleus and the cytoplasm.

The invention claimed is:

1. A system for delivering microporation medical treatments to improve biomechanics, the system comprising:
   a laser for generating a beam of laser radiation on a treatment-axis not aligned with a patient's visual-axis, operable for use in subsurface ablative medical treatments to create an array pattern of micropores that improves biomechanics;
   a housing;
   a controller within the housing, in communication with the laser and operable to control dosimetry of the beam of laser radiation in application to a target tissue;
   a lens operable to focus the beam of laser radiation onto a target tissue;
   an automated off-axis subsurface anatomy tracking, measuring, and avoidance system; and
   wherein the array pattern of micropores is at least one of a radial pattern, a spiral pattern, a phyllotactic pattern, or an asymmetric pattern, and wherein the array pattern of micropores has a controlled asymmetry which is an at least partial rotational asymmetry about the center of the array pattern and extends to at least 51 percent of the micropores of the array pattern.

2. The system of claim 1, wherein the array pattern of micropores is a spiral pattern of an Archimedean spiral, a Euler spiral, a Fermat's spiral, a hyperbolic spiral, a lituus, a logarithmic spiral, a Fibonacci spiral, a golden spiral, or combinations thereof.

3. The system of claim 1, wherein the array pattern has a number of clockwise spirals and a number of counter-clockwise spirals.

4. The system of claim 3, wherein the number of clockwise spirals and the number of counterclockwise spirals are Fibonacci numbers or multiples of Fibonacci numbers.

5. The system of claim 3, wherein the number of clockwise spirals and the number of counterclockwise spirals are in a ratio that converges on the golden ratio.

6. The system of claim 1, wherein the at least partial rotational asymmetry extends to at least 20 micropores of the array pattern.

7. The system of claim 1, wherein the array pattern of micropores has a random asymmetry.

8. The system of claim 1, wherein the array pattern of micropores has a random symmetry.

9. A method of delivering microporation medical treatments to improve biomechanics comprising:
  generating, by a laser, a treatment beam on a treatment-axis not aligned with a patient's visual-axis in a subsurface ablative medical treatment to create an array of micropores that improves biomechanics;
  controlling, by a controller in electrical communication with the laser, dosimetry of the treatment beam in application to a target tissue;
  focusing, by a lens, the treatment beam onto the target tissue;
  monitoring, by an automated off-axis subsurface anatomy tracking, measuring, and avoidance system, an eye position for application of the treatment beam; and
  wherein the array pattern of micropores is at least one of a radial pattern, a spiral pattern, a phyllotactic pattern, or an asymmetric pattern, and wherein the array pattern of micropores has a controlled asymmetry which is an at least partial rotational asymmetry about the center of the array pattern and extends to at least 51 percent of the micropores of the array pattern.

10. The method of claim 9, wherein the array pattern of micropores is a spiral pattern of an Archimedean spiral, a Euler spiral, a Fermat's spiral, a hyperbolic spiral, a lituus, a logarithmic spiral, a Fibonacci spiral, a golden spiral, or combinations thereof.

11. The method of claim 9, wherein the array pattern has a number of clockwise spirals and a number of counter-clockwise spirals.

12. The method of claim 11, wherein the number of clockwise spirals and the number of counterclockwise spirals are Fibonacci numbers or multiples of Fibonacci numbers.

13. The method of claim 11, wherein the number of clockwise spirals and the number of counterclockwise spirals are in a ratio that converges on the golden ratio.

14. The method of claim 9, wherein the at least partial rotational asymmetry extends to at least 20 micropores of the array pattern.

15. The method of claim 9, wherein the array pattern of micropores has a random asymmetry.

* * * * *